US008546376B2

(12) United States Patent
Bell et al.

(10) Patent No.: US 8,546,376 B2
(45) Date of Patent: Oct. 1, 2013

(54) PHARMACEUTICAL COMPOUNDS

(75) Inventors: Mark Peter Bell, Craigavon (GB); Timothy Harrison, Craigavon (GB); Sumita Bhattacharyya, Craigavon (GB); James Samuel Shane Rountree, Craigavon (GB); Frank Burkamp, Craigavon (GB); Stephen Price, Harlow (GB); Calum MacLeod, Harlow (GB); Richard Leonard Elliott, Harlow (GB); Phillip Smith, Harlow (GB); Toby Jonathan Blench, Harlow (GB); Colin Roderick O'Dowd, Craigavon (GB); Lixin Zhang, Craigavon (GB); Graham Peter Trevitt, Craigavon (GB); Hazel Joan Dyke, Harlow (GB)

(73) Assignee: Almac Discovery Limited, Craigavon, Northern Ireland (GB)

( * ) Notice: Subject to any disclaimer, the term of this patent is extended or adjusted under 35 U.S.C. 154(b) by 0 days.

(21) Appl. No.: 13/496,287

(22) PCT Filed: Sep. 17, 2010

(86) PCT No.: PCT/GB2010/001746
§ 371 (c)(1),
(2), (4) Date: Jun. 4, 2012

(87) PCT Pub. No.: WO2011/033265
PCT Pub. Date: Mar. 24, 2011

(65) Prior Publication Data
US 2012/0238541 A1    Sep. 20, 2012

(30) Foreign Application Priority Data

Sep. 18, 2009 (GB) .................................. 0916458.3
Apr. 6, 2010 (GB) .................................. 1005734.7

(51) Int. Cl.
| | | |
|---|---|---|
| A61K 31/4188 | (2006.01) |
| A61K 31/352 | (2006.01) |
| A61K 31/357 | (2006.01) |
| A61K 31/397 | (2006.01) |
| A61K 31/4155 | (2006.01) |
| A61K 31/4162 | (2006.01) |
| A61K 31/4178 | (2006.01) |
| A61K 31/4192 | (2006.01) |
| A61K 31/422 | (2006.01) |
| A61K 31/436 | (2006.01) |
| A61K 31/437 | (2006.01) |
| A61K 31/496 | (2006.01) |
| A61K 31/5377 | (2006.01) |
| A61K 31/5383 | (2006.01) |
| A61P 35/00 | (2006.01) |
| C07C 225/20 | (2006.01) |
| C07D 311/26 | (2006.01) |
| C07D 405/10 | (2006.01) |
| C07D 413/10 | (2006.01) |
| C07D 491/052 | (2006.01) |
| C07D 491/147 | (2006.01) |
| C07D 493/04 | (2006.01) |
| C07D 498/04 | (2006.01) |

(52) U.S. Cl.
USPC ............... 514/210.19; 514/229.8; 514/233.5; 514/254.11; 514/293; 514/302; 514/359; 514/375; 514/378; 514/394; 514/397; 514/406; 514/455; 514/456; 544/101; 544/151; 544/376; 546/83; 546/116; 548/218; 548/247; 548/256; 548/302.1; 548/311.4; 548/349.5; 548/364.4; 549/387; 549/403; 564/308

(58) Field of Classification Search
None
See application file for complete search history.

(56) References Cited

U.S. PATENT DOCUMENTS

2012/0309739 A1    12/2012   Bell et al.

FOREIGN PATENT DOCUMENTS

| WO | WO 2006/135627 A2 | 12/2006 |
| WO | WO 2008/070016 A2 | 6/2008 |
| WO | WO 2008/070134 A1 | 6/2008 |

OTHER PUBLICATIONS

International Search Report & Written Opinion from PCT/GB2010/001746, dated Jan. 25, 2011.

*Primary Examiner* — Janet Andres
*Assistant Examiner* — Timothy R Rozof
(74) *Attorney, Agent, or Firm* — Lathrop & Gage LLP; Brian C. Trinque

(57) ABSTRACT

The invention relates to a series of compounds with particular activity as inhibitors of the serine-threonine kinase AKT. Also provided are pharmaceutical compositions comprising same as well as methods for treating cancer.

16 Claims, No Drawings

PHARMACEUTICAL COMPOUNDS

RELATED APPLICATIONS

This application is a 35 U.S.C. §371 filing of International Patent Application No: PCT/GB2010/001746, which was filed on Sep. 17, 2010, and which claims priority to Great Britain Patent Application No: 0916458.3, which was filed on Sep. 18, 2009 and Great Britain Patent Application No: 1005734.7, which was filed on Apr. 6, 2010. The entire contents of the aforementioned applications are hereby incorporated herein by reference.

The present invention relates to compounds that are useful as inhibitors of the activity of one or more isoforms of the serine/threonine kinase, AKT. The present invention also relates to pharmaceutical compositions comprising these compounds and to methods of using these compounds in the treatment of cancer.

BACKGROUND TO THE INVENTION

The AKT protein family, also known as protein kinases B (PKB), is known to be involved in a wide variety of biological processes including cell proliferation, differentiation, apoptosis, tumourigenesis, as well as glycogen synthesis and glucose uptake. These enzymes are members of the serine/threonine-specific protein kinase family.

The PKB/AKT pathway has been identified as an important regulator of cell survival signalling and apoptosis in cells. Signalling is thought to occur through a range of growth factor receptors including platelet derived growth factor, insulin growth factor and nerve growth factor, resulting in activation of phosphatidylinositol 3-OH kinase (PI-3K). This activation in turn leads to the generation of phosphatidylinositol(3,4,5)triphosphate (PIP3). Activated PIP3 binds to and in turn phosphorylates the enzyme PDK-1, the main activator of AKT, through its pleckstrin homology domain. Activated PDK-1 is responsible for a phosphorylation event at Thr308 of AKT, which induces a conformational change that facilitates further phosphorylation of AKT at Ser 473 by PDK-2.

PDK-1 phosphorylation of downstream kinases is not unique to AKT, as it has been reported to activate p70 S6 kinase and protein kinase C.

The activation of AKT influences multiple events within the cell including the inhibition of apoptosis, the progression of the cell cycle, cellular survival, metabolism, angiogenesis and hormone resistance.

Presently three family members of AKT have been identified, AKT 1, AKT 2 and AKT 3 (also known as PKBα, PKBβ and PKBγ). The family members share 80% amino acid sequence homology and all retain similar regional structure. They possess a C-terminal pleckstrin homology domain, a catalytic domain, a short q helical linker region and a carboxyl terminal domain. The PH domain permits binding of proteins to the cell membrane through a phospholipid interaction. The catalytic domain of AKT family members contains two residues essential for kinase activation, namely Thr308 and Ser 473. In turn AKT can phosphorylate any protein containing the RXRXXS/T-B motif where X represents any amino acid and B represents bulky hydrophobic residues.

Turning to the cellular function of AKT, hyperactivation of AKT has been linked to the inhibition of cellular apoptosis due to phosphorylation and negative regulation of the forkhead family of transcription factors which regulate various genes responsible for instigating death processes including FKHR, FKHRL1 and AFX. Conversely, AKT has been reported to up-regulate genes which are known to be anti-apoptotic including IKK and CREB. It is this mixture of positive and negative regulation which highlights the importance of AKT in regulating apoptosis. AKT promotes unwanted cell survival through its phosphorylation of several key apoptotic proteins including Bad and Pro-caspase 9, thus rendering them inactive and preventing signalling through this pathway. AKT activates and inhibits multiple mechanisms which have a major role in the progression of the cell cycle, ultimately leading to cell proliferation. The best characterised cell cycle regulator and tumour suppressor proteins p53 can be dysregulated via AKT phosphorylation and activation of the main p53 negative regulator MDM2. Phosphorylated MDM2 translocates to the nucleus where it prevents p53 transcription. The inhibition of p53 allows aberrant proliferation of the cell and progression towards a benign state.

In a similar fashion, AKT can also phosphorylate p27kip1 and p21; two main inhibitors of cycle progression, leading to loss of function, resulting in unchecked cell cycle progress and excessive proliferation.

AKT activation causes an increase in the rate of glycolysis by increasing the rate of glucose metabolism. It has also been reported that activated AKT stimulates the transport of amino acids and supports mTOR dependent increases in protein translation. Proangiogenic factors, such as vascular endothelial growth factor (VEGF), have been reported to activate AKT, ultimately resulting in inhibition of endothelial apoptosis, as well as activating endothelial nitric oxide synthase (eNOS). The sum result of this is rapid neovascularisation and cell migration.

Hypoxia driven angiogenesis, primarily mediated by hypoxia inducible factor (HIF 1α) can lead to the induction of multiple proteins including VEGF. Increased activated AKT has been reported to increase HIF-1α expression leading to an increase in angiogenesis independent of a hypoxic environment. Recent data has shown that HIF-1α activity in invasive breast cancer is correlated with increased activated AKT-1 phosphorylation.

Estrogen receptor (ER) and androgen receptor (AR) inhibitors, designed to inhibit cell signalling and induce apoptosis, are vital tools in cancer therapies. Incidence of resistance to these drugs arises rapidly in cancers including prostate, breast and ovarian. AKT has been reported to phosphorylate androgen receptors, leading to inhibition of AR activity and blockade of normal apoptotic signalling in prostate cancer induced by androgens.

In a similar manner, activation of AKT leads to phosphorylation of ERα resulting in an inhibition of tamoxifen mediated apoptosis or tumour regression, coupled with the creation of an estrogen independent signalling pathway. Activated AKT-2 has been identified as a promoter of ERα transcription in the presence or absence of estrogen increasing the rate of proliferation of breast cancer cells.

Hyperactivated AKT has been reported in a range of cancers compared to normal tissues including breast, lung, prostate, gastric, ovary, pancreas, thyroid, glioblastoma and haemological cancers. Phosphorylation of AKT has also been associated with clinical characteristics including increased stage and grade of tumour and increased poor prognosis. The activation of AKT can arise from a number of different genetic mutations in the AKT/PI-3K pathway.

Somatic mutations in the PI-3KCA gene have been widely reported in a large variety of tumours including breast, prostate and head and neck. A large number of these mutations will increase copy number of the gene leading to an increase in PI-3K activity. A recent study has identified a PI-3K mutation which selectively phosphorylates AKT in colon cancer which results in increase cell proliferation and invasion).

Any mutation which increases the activity of the PI-3K pathway will ultimately result in an increased activation of AKT. Gene amplifications are common occurrences in cancer. Amplifications of AKT-2 have been reported in ovarian, pancreatic, breast and head and neck squamous cell carcinoma. No amplifications or mutations in AKT-3 have been reported to date although deletion mutations leading to hyperactivation and amplification mutations have been reported associated with AKT-1. One mutation; E17K, results in pathological localization of AKT-1 to the cell membrane, inducing its activation and resulting in downstream signalling and cellular transformation. In vivo, this mutation has been shown to induce leukaemia in mice.

Phosphatase and tensin homolog deleted on chromosome 10 (PTEN) is a tumour suppressor gene known to negatively regulate AKT function. In cancer, loss of PTEN function results in constitutive phosphorylation of AKT and other downstream effectors of the PI-3K pathway. Loss of PTEN, due to deletion mutations or promoter methylation, has been reported in a number of different cancers including glioblastoma, endometrial, lung, breast, prostate and thyroid. This loss is commonly associated with hyperactivation of AKT. Recent studies have shown that loss of heterozygosity (LOH) at the PTEN gene was directly correlated to increased AKT activation and chemoresistance in gastric carcinomas and decreased progesterone receptor expression in breast carcinomas.

AKT activation is commonly initiated at the cell surface through a signalling event at a receptor, usually one of the tyrosine kinase family. Two tyrosine kinase receptors commonly amplified or overexpressed in cancer are HER2 and EGFR. In HER2 overexpressing tumours there is often a hyperactivation of AKT, this has been reported in ovarian, stomach and bladder cancer. Similarly in EGFR overexpressing tumours, particularly those with the EGFRvIII activating mutation, selective activation of AKT has been reported in a range of cancers including non-small cell lung cancers, breast, ovarian and most commonly high grade gliomas.

Examples of AKT inhibitors are provided in WO 2008/070134, WO 2008/070016 and WO 2008/070041. These documents provide specific naphthyridine compounds substituted with a five membered heterocycle.

SUMMARY OF THE INVENTION

The present invention provides a compound according to Formula (I):

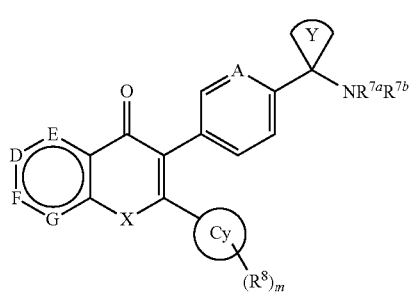

wherein:
0, 1 or 2 of D, E, F and G are independently selected from N, NH and $NR^1$ and the others are independently selected from CH and $CR^2$, wherein each $R^1$ is independently selected from aryl, C1-C10 alkyl, $CONHR^3$, $CONR^{3a}R^{3b}$, $COR^3$ and $CO_2R^3$ and each $R^2$ is independently selected from aryl, C1-C10 alkyl, CN, CHO, $CO_2H$, $CONH_2$, $CONHR^3$, $CONR^{3a}R^{3b}$, $COR^3$, $CO_2R^3$, $NH_2$, $NHR^3$, $NR^{3a}R^{3b}$, oxo, OH, $OR^3$, SH, $SR^3$, $SOR^3$, $SO_2R^3$, $SO_2NHR^3$, $SO_2NR^{3a}R^{3b}$, F, Cl, Br and I, wherein each $R^3$, $R^{3a}$ and $R^{3b}$ is independently selected from optionally substituted C1-C10 alkyl and optionally substituted C1-C10 aryl, including wherein $R^{3a}$ and $R^{3b}$ are joined to one another to form a heterocycle that includes the nitrogen to which they are attached, wherein A is N or CH;

wherein at least D or G is NH or $NR^1$ if E or F is CO and at least E or F is NH or $NR^1$ if D or G is CO, wherein separate $R^1$ and/or $R^2$ groups may be joined to one another to form a heterocycle that includes the C and/or N atoms to which they are attached if the separate $R^1$ and/or $R^2$ groups are contained on D and E and/or F and G, or D and F and the separate $R^2$ groups are selected from $OR^3$, $SR^3$, $SOR^3$, $SO_2R^3$, $SO_2NHR^3$, $SO_2NR^{3a}R^{3b}$, $NHR^3$, $NR^{3a}R^{3b}$, $CO_2R^3$, $CONHR^3$ and $CONR^{3a}R^3$, and/or wherein separate $R^1$ and/or $R^2$ groups on F and G may be joined to form the structure:

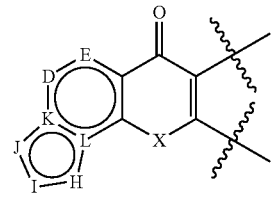

where 0 or 1 of K and L are N and the other(s) is/are C, and wherein H, I and J are independently selected from O, S, NH, $NR^4$, N, CH and $CR^5$, wherein each $R^4$ is independently selected from aryl, C1-C10 alkyl, $CONHR^6$, $CONR^{6a}R^{6b}$, $COR^6$ and $CO_2R^6$ and each $R^5$ is independently selected from aryl, C1-C10 alkyl, CN, CHO, $CO_2H$, $CONH_2$, $CONHR^6$, $CONR^{6a}R^{6b}$, $COR^6$, $CO_2R^6$, oxo, $NH_2$, $NHR^6$, $NR^{6a}R^{6b}$, OH, $OR^6$, SH, $SR^6$, $SOR^6$, $SO_2R^6$, $SO_2NHR^6$, $SO_2NR^{6a}R^{6b}$, F, Cl, Br and I, wherein each $R^6$, $R^{6a}$ and $R^{6b}$ is independently selected from C1-C10 alkyl, including wherein $R^{6a}$ and $R^{6b}$ are joined to one another to form a heterocycle that includes the nitrogen to which they are attached, X is selected from O, S, SO, $SO_2$ or a carbon-carbon bond;

$R^{7a}$ and $R^{7b}$ are independently selected from H and alkyl, including wherein $R^{7a}$ and $R^{7b}$ are joined to one another to form a heterocycle that includes the nitrogen to which they are attached; and

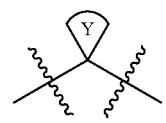

is selected from:

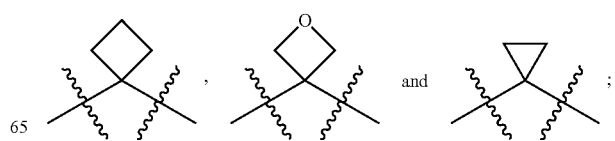

or where the $R^{7a}$ and $R^{7b}$ groups are absent as is the nitrogen to which they are bound and Y is geminal dimethyl so that the moiety bound is

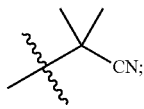 [SMILES: *C(C)(C)C#N]

ring Cy is selected from ($C_3$ to $C_8$)cycloalkyl and aryl, wherein m is 0, 1, 2, 3, 4 or 5, and each $R^8$ is independently selected from alkyl, CN, CHO $CO_2H$, $CONH_2$, $CONHR^9$, $CONHR^{9a}R^{9b}$, $COR^9$, $CO_2R^9$, $NH_2$, $NHR^9$, $NR^{9a}R^{9b}$, OH, $OR^9$, SH, $SR^9$, F, Cl, Br and I, wherein each $R^9$, $R^{98}$ and $R^{9b}$ is independently selected from alkyl, including wherein $R^{9a}$ and $R^{9b}$ form a heterocycle that includes the nitrogen to which they are attached;

or where the ketone carboxyl oxygen opposite X is replaced with a sulphur atom to give a thioketone or with a group comprising nitrogen to give an imine or optionally lower alkyl substituted oxime;

and pharmaceutically acceptable salts, stereoisomers and tautomers thereof.

DETAILED DESCRIPTION OF THE INVENTION

The term "alkyl group" refers to an aliphatic group containing at least carbon and hydrogen and containing 1 to 15 carbon atoms, such as 1 to 10 carbon atoms. Attachment to the alkyl group occurs through a carbon atom.

A "$C_n$ alkyl" group refers to an aliphatic group containing n carbon atoms. For example, a $C_1$-$C_{10}$ alkyl group contains 1, 2, 3, 4, 5, 6, 7, 8, 9 or 10 carbon atoms.

An alkyl group may be straight chained or it may be branched.

An alkyl group may contain no ring structures or it may contain one or more rings.

For example, a "cycloalkyl" group contains at least one ring. It is understood that attachment to a cycloalkyl group is via a ring of the cycloalkyl group. Each ring may contain 3 to 10 atoms, such as 4 to 8 or 5 to 7 atoms. Each ring may be independently selected to contain just carbon atoms or to contain both carbon atoms and from 1 to 4 heteroatoms selected from O, N and S. For cyclo-heteroalkyl groups (i.e. cycloalkyl groups that contain one or more heteroatoms), attachment to the cycloalkyl group may occur either through a carbon atom or, if one or more heteroatoms are contained in a ring, attachment may also occur through a heteroatom contained in a ring.

For example, a cycloalkyl group may be mono-cyclic or bi-cyclic.

Thus, a "$C_n$ cycloalkyl" group contains n carbon atoms. All n carbon atoms may be contained in the ring(s) of the cycloalkyl group or one or more of the carbons may not be contained in the ring(s) and may instead form one or more chains branching from the ring.

If a $C_n$ alkyl group is joined to a separate $C_m$ alkyl group containing m carbon atoms to form, for example, a heterocycle, the two alkyl groups contain a total number of m+n carbon atoms.

An alkyl group may be saturated or unsaturated. Thus, the alkyl group may be an alkenyl group (i.e. contain a carbon-carbon double bond) and/or an alkynyl group (i.e. contain a carbon-carbon triple bond). If the alkyl group is unsaturated, it may contain at least 2 carbon atoms. It is understood that any unsaturated portions of an alkyl group are non-aromatic (aromatic groups fall within the scope of the definition of "aryl". Any part of the alkyl group may be unsaturated, for example the straight, branched or cyclic portion of an alkyl group may contain a carbon-carbon double bond or a carbon-carbon triple bond. Attachment to an unsaturated alky group may occur through the unsaturated part of the alkyl group or may occur through the unsaturated part of the group.

For example, an unsaturated alkyl group may contain 1 to 4 carbon-carbon double bonds or 1 to 3 carbon-carbon triple bonds or 1 to 4 of a combination of carbon-carbon double bonds and carbon-carbon triple bonds.

An alkyl group may be substituted with one or more heteroatoms or it may be unsubstituted (i.e. not contain any heteroatoms). If more than one hetero-substituent is present, the substituents are independently selected from one another unless they form a part of a particular functional group (e.g. an amide group).

The heteroatom substituents may in turn be substituted with further carbon-containing groups. In this case, the $C_n$ or $C_m$ prefix that defines the substituted alkyl group refers to the total number of carbons contained in the group, i.e. including the carbon atoms contained in any substituted heteroatomic groups, and the total alkyl group contains 1 to 15 carbon atoms as defined previously.

Accordingly, if the alkyl group is substituted, it may, for example, contain one or more of CN, $CO_2H$, $CONH_2$, CONHR, $CONR^aR^b$, $CO_2R$, $NH_2$, NHR, $NR^aR^b$, OH, OR, SH, SR, F, Cl, Br and I, wherein each R, $R^a$ and $R^b$ are independently selected groups (e.g. alkyl/aryl groups) attached to the atom to which the group joins through a carbon atom of each group, including wherein $R^a$ and $R^b$ form a heterocycle that includes the heteroatom to which they are attached. A group containing two $C_m$-$C_n$ alkyl moieties that form a cycle that includes, for example, the heteroatom to which they are attached may contain from $C_{2m}$ to $C_{2n}$ carbon atoms.

Examples of unsubstituted saturated alkyl groups containing no cyclic structures include methyl, ethyl, n-propyl, sec-propyl, n-butyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched).

Examples of unsubstituted saturated cyclic alkyl groups include cyclopropyl, cyclobutyl, cyclopentyl and cyclohexyl.

Examples of unsaturated alkyl groups include ethenyl, propenyl, butenyl, 2-methylbutenyl and cyclohexenyl.

The term "aryl group" refers to a group containing at least one ring that is aromatic and containing 1 to 15 carbon atoms, such as 1 to 10 carbon atoms. Where an aryl group is stated as being substituted at a particular position, attachment of the position to the aryl group is onto the aromatic ring of the aryl group itself rather than the position being joined to the aryl group through any non-aromatic side-chain of the aryl group. For example, when $R^1$ is an aryl group in $CR^1$, the C is attached to the aromatic part of the aryl group.

Each ring of the aryl group has 3 to 10 atoms in the ring, such as 4 to 8 or 5 to 7 atoms. Each ring may be independently selected to contain only carbon atoms or to contain both carbon atoms and from 1 to 4 heteroatoms selected from O, N and S. For heteroaryl groups (i.e. aryl groups that contain one or more heteroatoms), attachment to the aryl group may occur either through a carbon atom or, if one or more heteroatoms are contained in a ring, attachment may also occur through a heteroatom contained in a ring.

It is noted that the heteroatoms contained in a ring of a heteroaryl group may be substituted, for example forming an N-oxide.

For example, the aromatic group may be mono-cyclic or bi-cyclic, wherein one or both of the rings of a bi-cyclic system is aromatic.

Examples of aryl groups include acridinyl, phenyl, carbazolyl, cinnolinyl, quinoxalinyl, pyrrazolyl, indolyl, benzotriazolyl, furanyl, naphthyl, thienyl, thiazolyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline, benzimidazolyl and melaminyl.

It is noted that the term "heterocycle" includes within its scope both cycloalkyl groups containing one or more heteroatoms within the ring system and aryl groups containing one or more heteroatoms within the ring system.

The term "halo" refers to a group selected from chlorine, fluorine, bromine and iodine.

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect, the present invention provides the compound of the invention in which

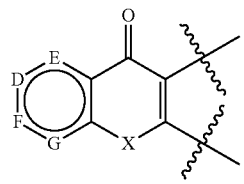

is selected from:

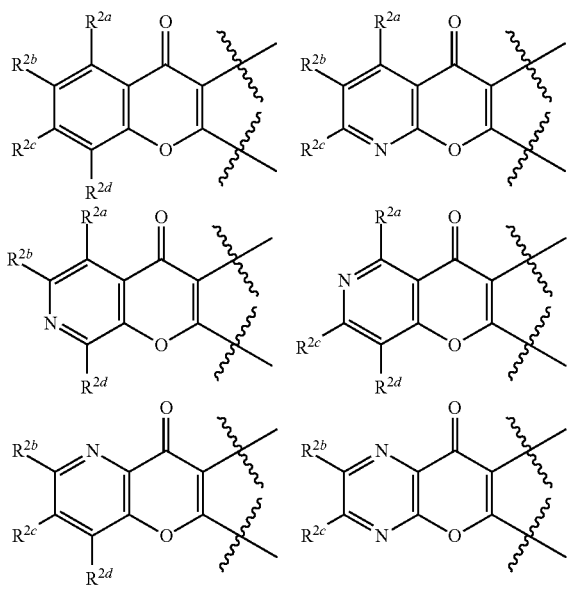

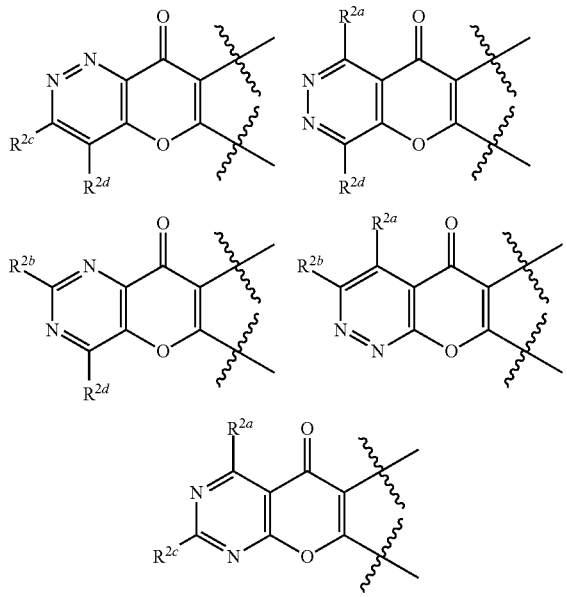

wherein $R^{2a}$, $R^{2b}$, $R^{2c}$ and $R^{2d}$ are independently selected from $R^2$ and H, where $R^2$ is defined herein.

For completeness, it is noted that separate $R^1$, $R^2$, $R^3$, $R^4$, $R^5$, $R^6$ and $R^7$ groups may not be joined to one another unless they meet the conditions positively recited herein.

For completeness, it is also noted that certain chemical formulae used herein define delocalized systems. This definition is known in the art as a definition of aromaticity and may indicate the presence of, for example, a mono-, di- or tri-cyclic system that contains (4n+2) electrons where n is an integer. In other words, these systems may display Hückel aromaticity.

The first aspect of the invention may also provide the compound of the invention in which

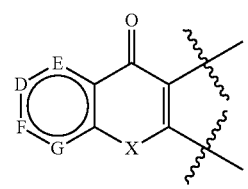

is selected from:

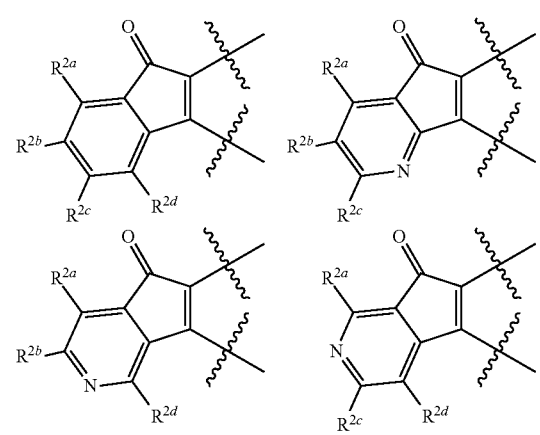

-continued

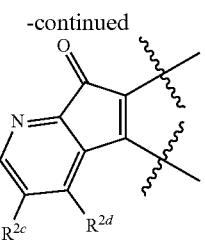

wherein $R^{2a}$, $R^{2b}$, $R^{2c}$ and $R^{2d}$ are independently selected from $R^2$ and H, where $R^2$ is defined herein.

Accordingly, these formulae are examples of structures where X=a carbon-carbon bond.

The first aspect of the invention may also provide a compound of the invention in which

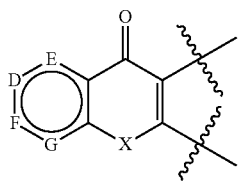

is selected from:

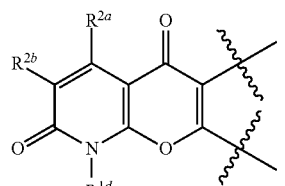 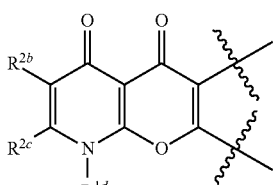

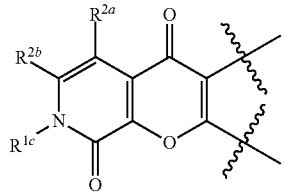 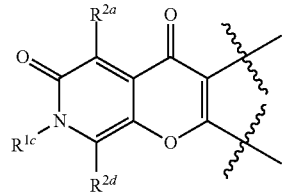

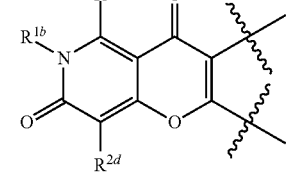 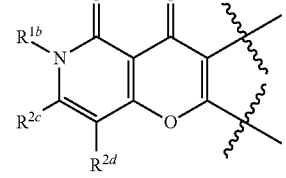

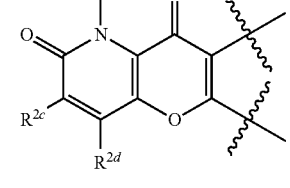 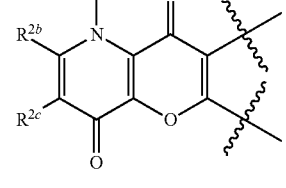

wherein $R^{1a}$, $R^{1b}$, $R^{1c}$ and $R^{1d}$ are independently selected from $R^1$ and H and $R^{2a}$, $R^{2b}$, $R^{2c}$ and $R^{2d}$ are independently selected from $R^2$ and H, where $R^1$ and $R^2$ are defined herein.

The first aspect of the invention may also provide a compound of the invention in which

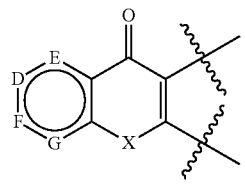

is selected from:

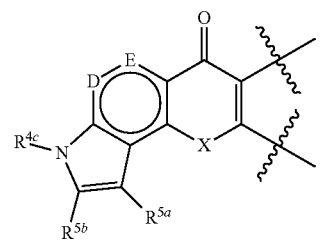

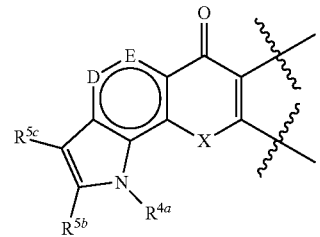

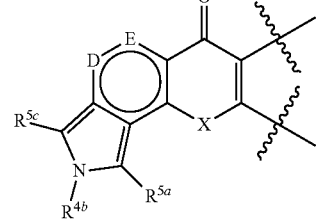

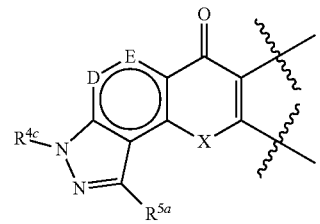

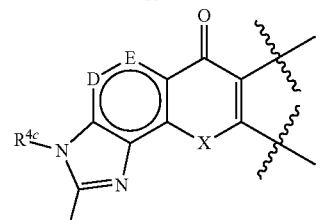

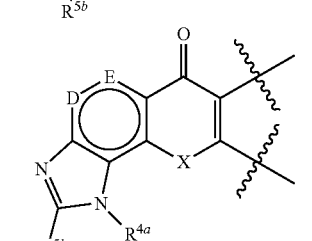

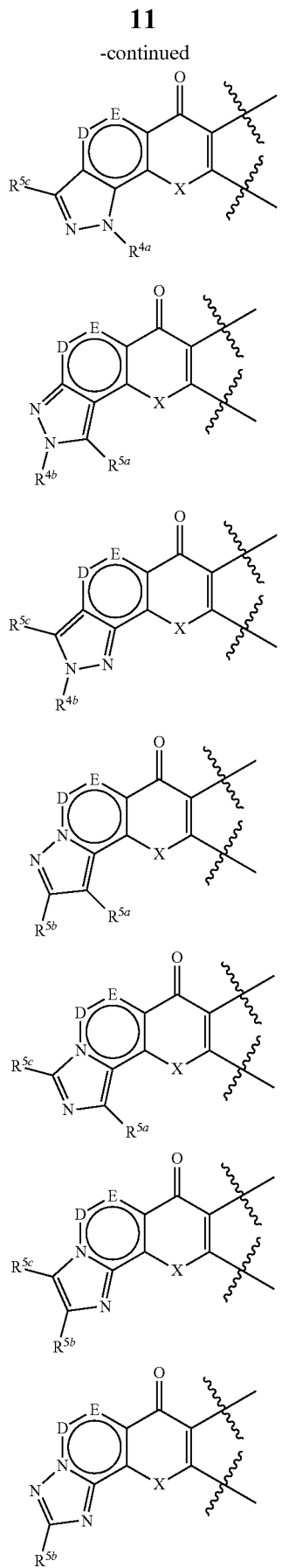
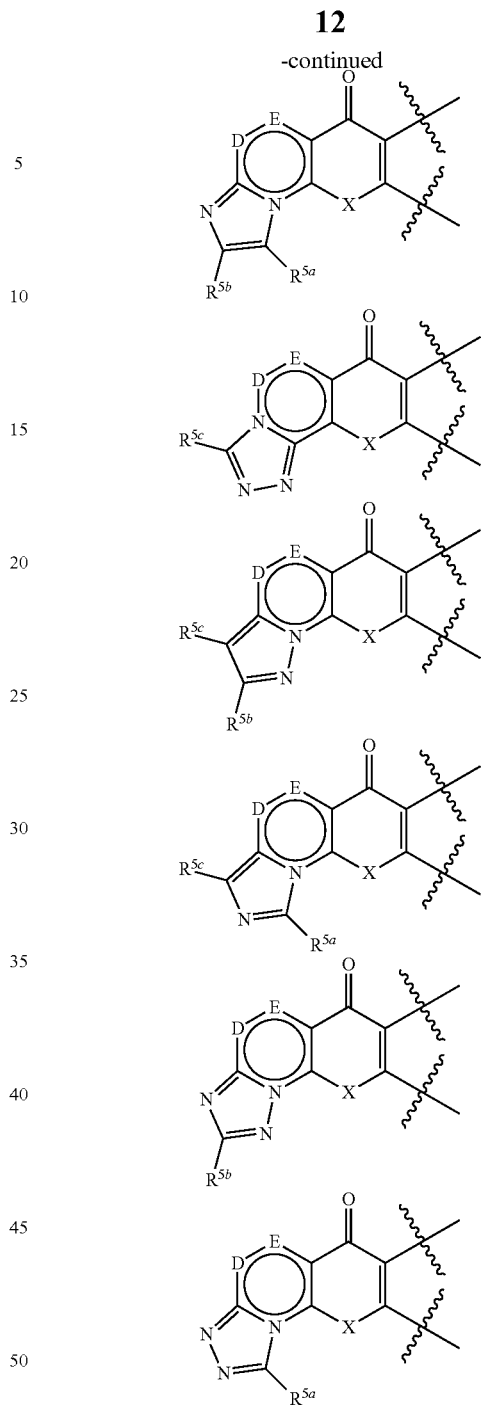
wherein $R^{4a}$, $R^{4b}$ and $R^{4c}$ are independently selected from $R^4$ and H and $R^{5a}$, $R^{5b}$ and $R^{5c}$ are independently selected from $R^5$ and H, wherein $R^4$, $R^5$, D, E and X are as defined herein. For example, X may be O.
The first aspect of the invention may also provide a compound of the invention in which
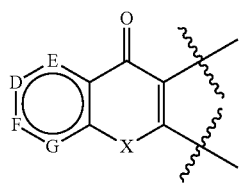

is selected from:

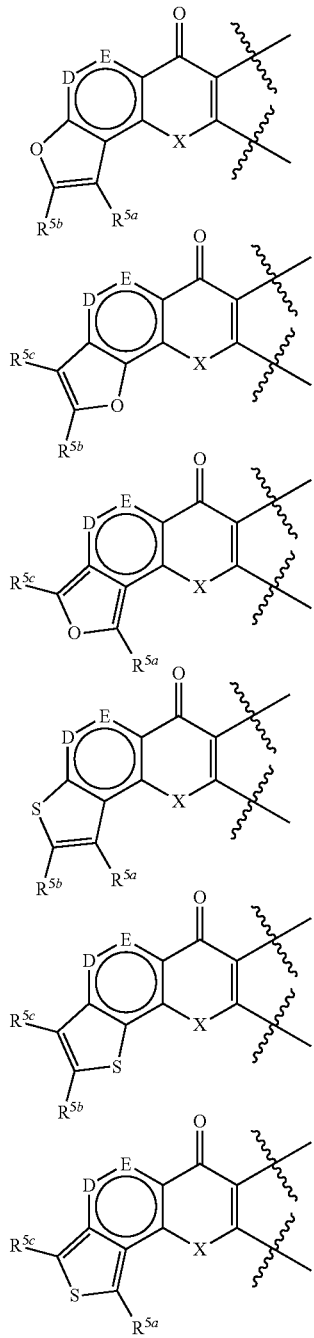

wherein $R^{5a}$, $R^{5b}$ and $R^{5c}$ are independently selected from $R^5$ and H, wherein $R^5$, D, E and X are as defined herein. For example, X may be O.

The first aspect of the invention may also provide a compound of the invention in which

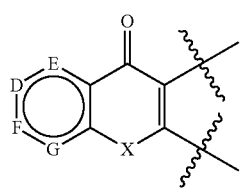

is selected from:

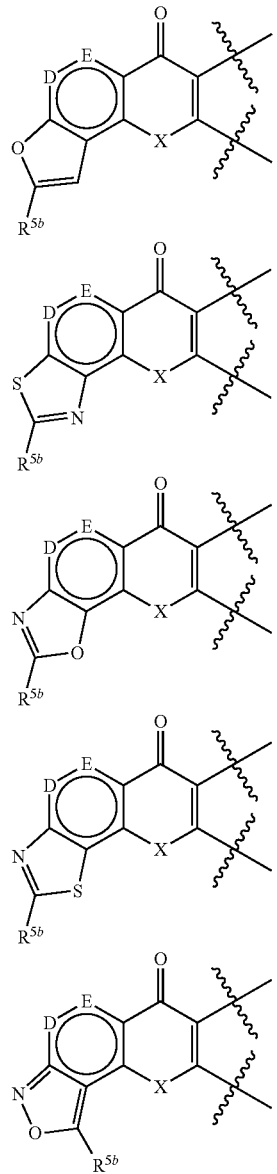

wherein $R^{5b}$ is $R^5$ or H, wherein $R^5$, D, E and X are as defined herein. For example, X may be O.

The first aspect of the invention may also provide a compound of the invention in which

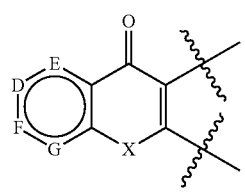

is selected from:

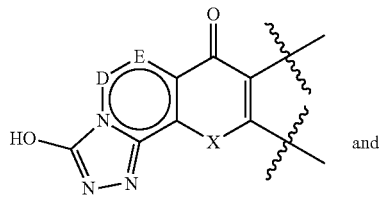
and

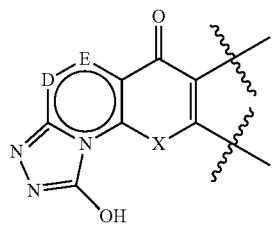

The first aspect of the invention may also provide a compound of the invention in which:

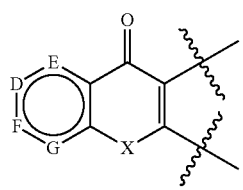

is selected from:

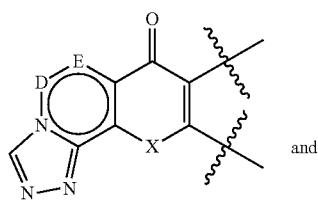
and

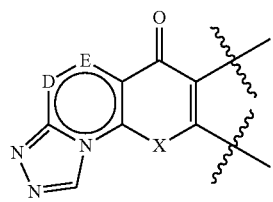

For example, X is O in the following structures:

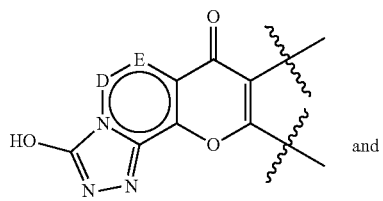
and

-continued

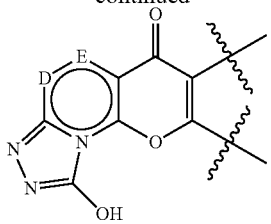

and also:

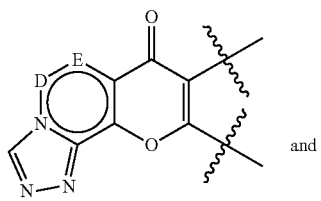
and

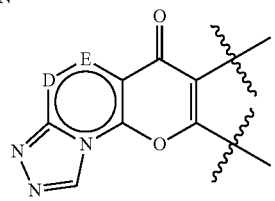

In one embodiment, D and E may be independently selected from N, CH and CR$^1$. For example, 0 or 1 of D and E may be selected to be N. For example, D and E may both be independently selected from CH and CR$^1$. For example, D and E may both be CH.

In one embodiment,

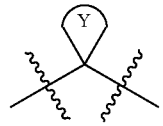

is chosen to be

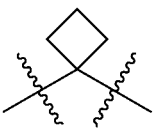

In one embodiment, ring Cy may be a six-membered aromatic ring. For example, Cy may be phenyl.

Accordingly, the first aspect may provide a compound having the formula:

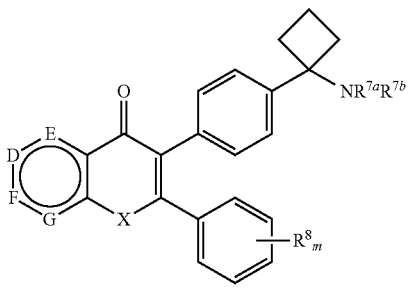

In one embodiment, m may be 0, 1 or 2. For example, m may be 0.

For example, Cy may be phenyl and m may be 0, 1 or 2, such as 0. Accordingly, the first aspect may provide a compound having the formula:

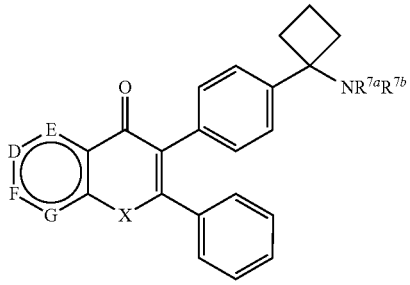

In one embodiment, $R^{7a}$ and $R^{7b}$ are independently chosen from a physiological hydrolyzable amide and H. For example, $R^{7a}$ and $R^{7b}$ may be chosen to both be H. Thus, for example, the present invention may provide a compound having the formula:

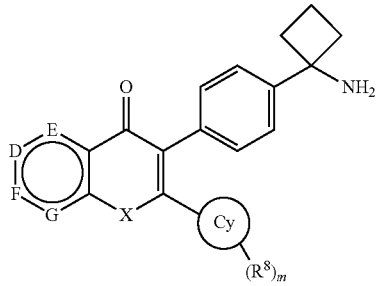

In a second aspect, the present invention provides a compound selected from:

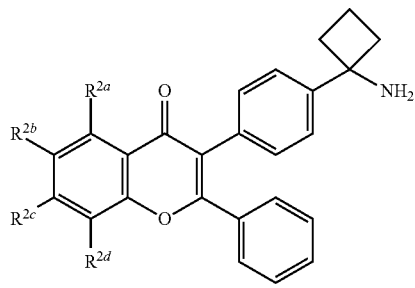

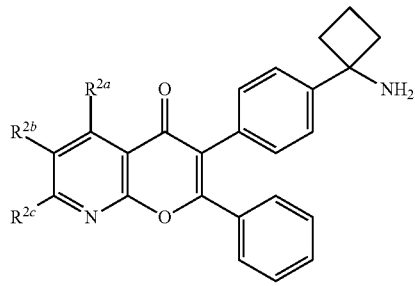

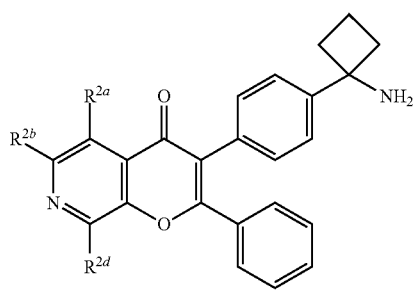

wherein $R^{2a}$, $R^{2b}$, $R^{2c}$ and $R^{2d}$ are independently selected from $R^2$ and H, wherein $R^2$ is as defined herein.

The compound may also be selected from:

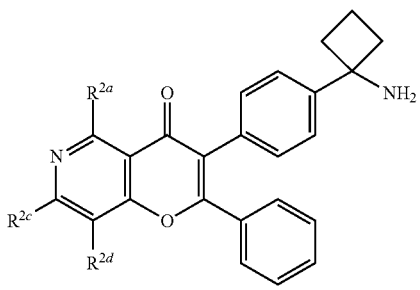

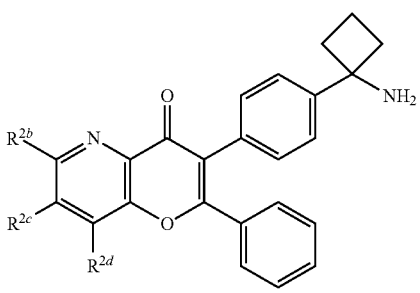

wherein $R^{2a}$, $R^{2b}$, $R^{2c}$ and $R^{2d}$ are independently selected from $R^2$ and H, wherein $R^2$ is as defined herein.

The compound may also be selected from:

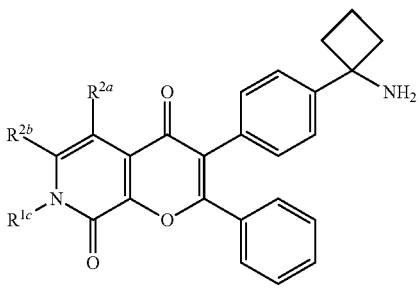

-continued

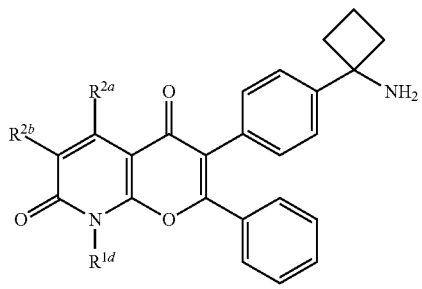

wherein $R^{1c}$ and $R^{1d}$ are independently selected from $R^1$ and H and $R^{2a}$ and $R^{2b}$ are independently selected from $R^2$ and H, wherein $R^1$ and $R^2$ are as defined herein.

The compound may also be selected from:

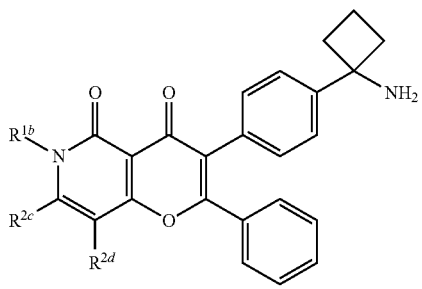

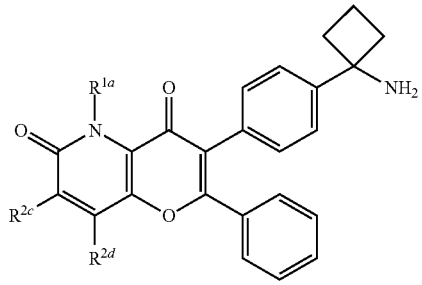

wherein $R^{1a}$ and $R^{1b}$ are independently selected from $R^1$ and H and $R^{2c}$ and $R^{2d}$ are independently selected from $R^2$ and H, wherein $R^1$ and $R^2$ are as defined herein.

The compound may also have the structure:

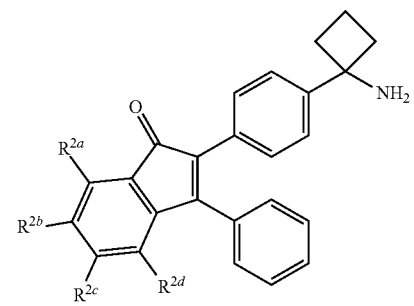

wherein $R^{2a}$, $R^{2b}$, $R^{2c}$ and $R^{2d}$ are independently selected from $R^2$ and H, wherein $R^2$, $R^{2a}$ and $R^{2b}$ are as defined herein.

The compound may also be selected from:

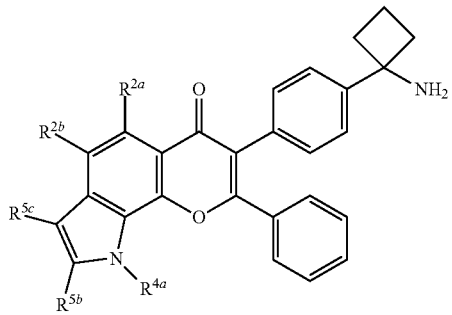

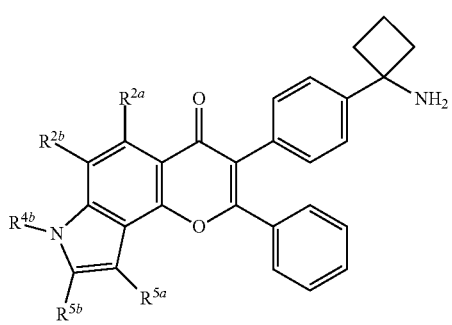

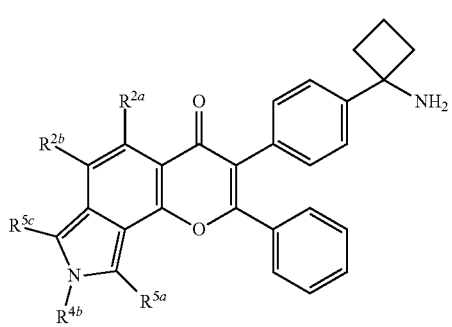

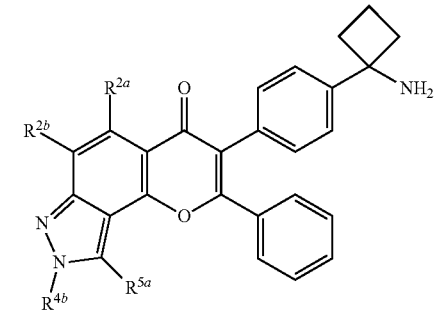

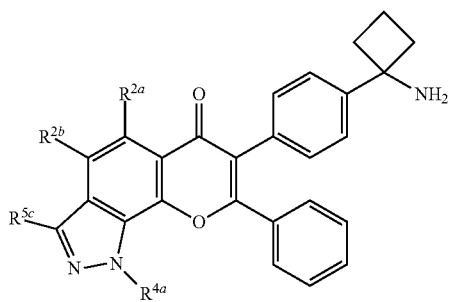

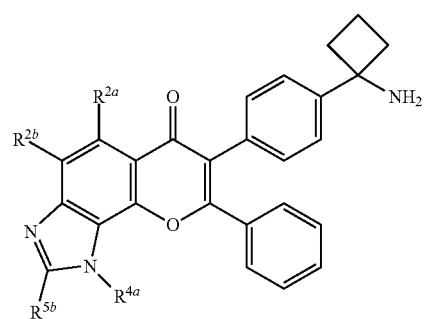
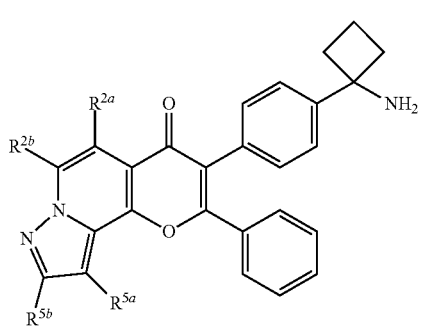
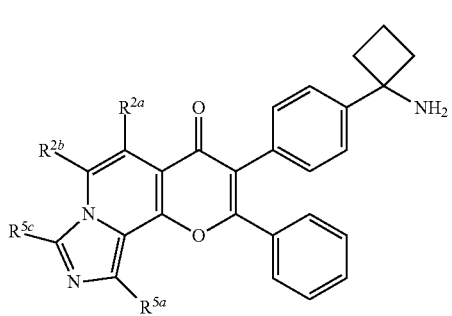
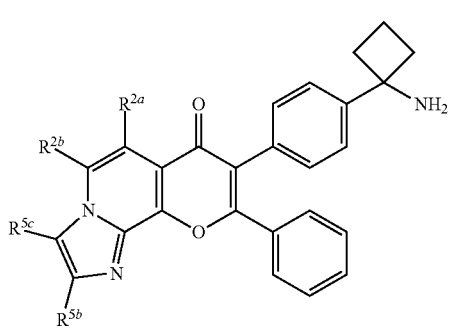
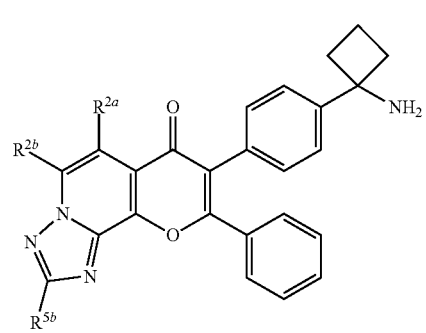
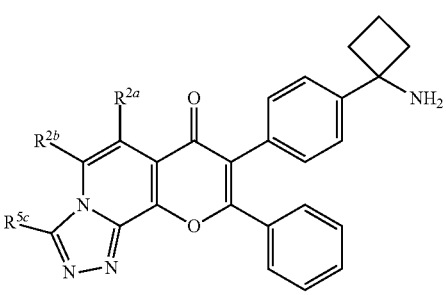
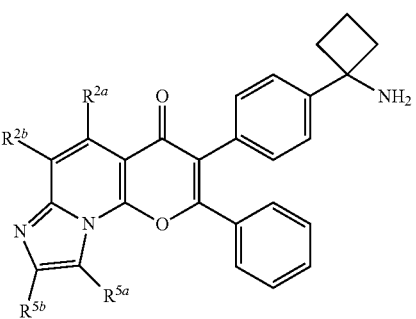
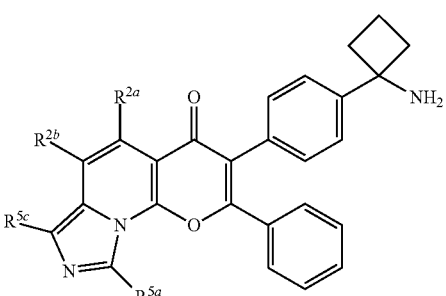
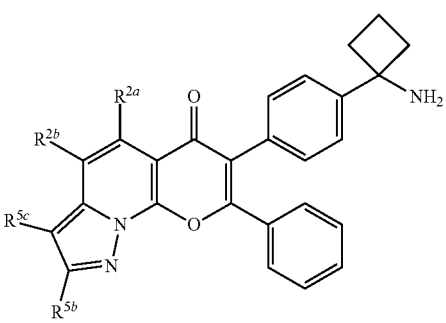
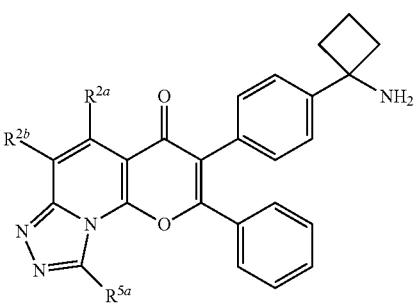

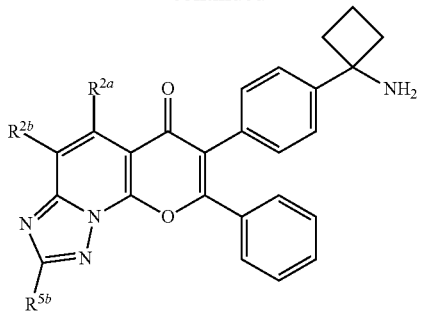

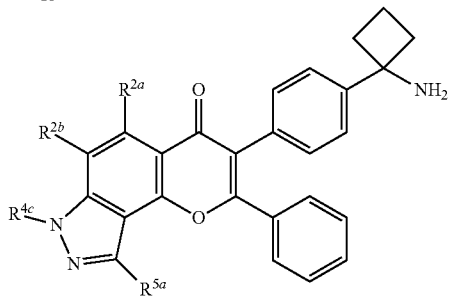

wherein $R^{2a}$ and $R^{2b}$ are independently selected from $R^2$ and H, $R^{4a}$, $R^{4b}$ and $R^{4c}$ are independently selected from $R^4$ and H and $R^{5a}$, $R^{5b}$ and $R^{5c}$ are independently selected from H and $R^5$, wherein $R^2$, $R^4$ and $R^5$ are as defined herein.

For example, the compound may be:

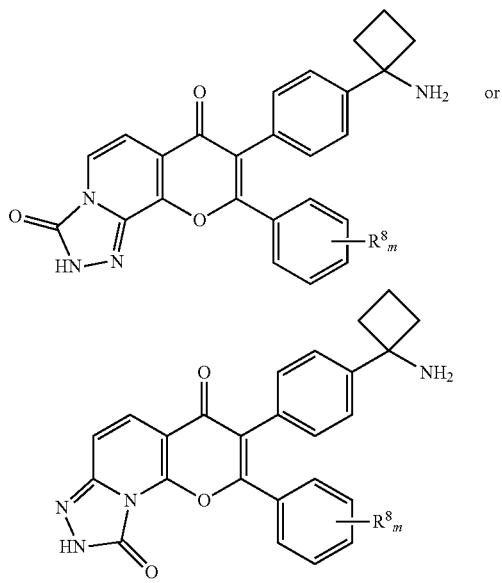

For example, the compound may be:

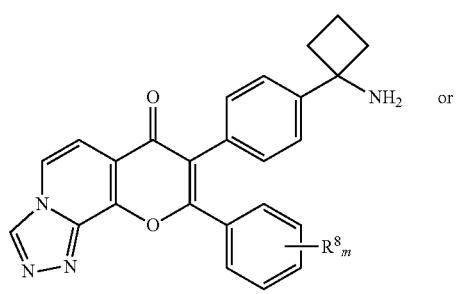

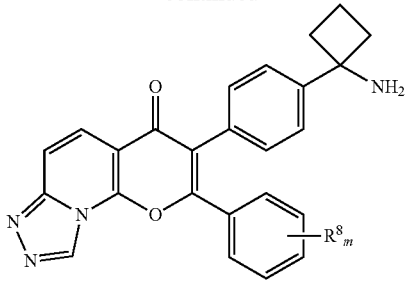

In a third aspect, the present invention provides a compound selected from the group of compounds whose syntheses are described in the examples.

In a preferred embodiment the compound of the invention is selected from:

7-[4-(1-Amino-cyclobutyl)-phenyl]-8-phenyl-2H-9-oxa-1,2,3a-triaza-cyclopenta[a]naphthalene-3,6-dione hydrochloride;

7-[4-(1-Amino-cyclobutyl)-phenyl]-2-methyl-8-phenyl-2H-9-oxa-1,2,3a-triaza-cyclopenta[a ]naphthalene-3,6-dione hydrochloride;

or pharmaceutically acceptable salts, stereoisomers and tautomers thereof.

Preferred compounds are also preferred as active agents in medicaments according to further aspects of the invention.

In a fourth aspect (which for the avoidance of doubt may be freely combined with Formula (I), the first aspect, the second aspect or the third aspect), the present invention provides a compound in which $R^1$ is selected from $C_1$-$C_6$ alkyl and H. For example, each $R^1$ may be chosen to be H.

The fourth aspect also provides a compound in which $R^2$ is selected from $C_2$-$C_6$ alkyl, aryl containing a five- or six-membered aromatic ring, CN, CHO, $CONH_2$, $CH_aHal_bY_c$ (wherein a is 0, 1, 2 or 3 and b is 3, 2, 1 or 0, each Hal is an independently selected halogen and c is 0 or 1 and Y is OH or $NH_2$ and a+b+c is 3), $NH_2$, $NHR^3$, $NR^{3a}R^{3b}$, oxo, OH, $OR^3$, F, Cl, Br and I, wherein each $R^{3a}$ and $R^{3b}$ is independently selected from C1-C6 alkyl, including wherein $R^{3a}$ and $R^{3b}$ join one another to form a heterocycle that includes the nitrogen to which they are attached.

The fourth aspect also provides a compound in which $R^4$ is selected from H, C2-C6 alkyl $CH_aHal_bY_c$ (wherein a is 0, 1, 2 or 3 and b is 3, 2, 1 or 0, each Hal is an independently selected halogen and c is 0 or 1 and Y is OH or $NH_2$ and a+b+c is 3). For example, $R^4$ may be H.

The fourth aspect also provides a compound in which $R^5$ is selected from $C_2$-$C_6$ alkyl, $CH_aHal_bY_c$ (wherein a is 0, 1, 2 or 3 and b is 3, 2, 1 or 0, each Hal is an independently selected halogen and c is 0 or 1 and Y is OH or $NH_2$ and a+b+c is 3), OH, O(C1-C6 alkyl), F, Cl, Br and I.

The fourth aspect also provides for a C1 to Cn alkyl may to be chosen to be from a C2 to Cn alkyl. A C1 alkyl may also be chosen to be CN, CHO, $CO_2H$, $CONH_2$ or $CH_aHal_bY_c$ (wherein a is 0, 1, 2 or 3 and b is 3, 2, 1 or 0, each Hal is an independently selected halogen and c is 0 or 1 and Y is OH or $NH_2$ and a+b+c is 3). An example of a C1 alkyl is methyl.

For example, each $R^1$ may be independently selected from aryl, C2-C10 alkyl and $CH_aHal_b$ (wherein a is 0, 1, 2 or 3 and b is 3, 2, 1 or 0, each Hal is an independently selected halogen and a+b is 3) and each $R^2$ is independently selected from aryl, C2-C10 alkyl, CN, CHO, $CO_2H$, $CONH_2$, $CH_aHal_bY_c$ (wherein a is 0, 1, 2 or 3 and b is 3, 2, 1 or 0, each Hal is an independently selected halogen and c is 0 or 1 and Y is OH or NH$_2$ and a+b+c is 3), NH$_2$, NHR$^3$, NR$^{3a}$R$^{3b}$, oxo, OH, OR$^3$, SH, SR$^3$, SOR$^3$, SO$_2$R$^3$, SO$_2$NHR$^3$, SO$_2$NR$^{3a}$R$^{3b}$, F, Cl, Br and I, wherein each R$^3$, R$^{3a}$ and R$^{3b}$ is independently selected from C1-C10 alkyl, including wherein R$^{3a}$ and R$^{3b}$ are joined to one another to form a heterocycle that includes the nitrogen to which they are attached, and each R$^4$ may be independently selected from aryl, C2-C10 alkyl and CH$_a$Hal$_b$ (wherein a is 0, 1, 2 or 3 and b is 3, 2, 1 or 0, each Hal is an independently selected halogen and a+b is 3) and each R$^5$ is independently selected from aryl, C2-C10 alkyl, CN, CHO, CO$_2$H, CONH$_2$, oxo, CH$_a$Hal$_b$Y$_c$ (wherein a is 0, 1, 2 or 3 and b is 3, 2, 1 or 0, each Hal is an independently selected halogen and c is 0 or 1 and Y is OH or NH$_2$ and a+b+c is 3), NH$_2$, NHR$^6$, NR$^{6a}$R$^{6b}$, OH, OR$^6$, SH, SR$^6$, SOR$^6$, SO$_2$R$^6$, SO$_2$NHR$^6$, SO$_2$NR$^{6a}$R$^{6b}$, F, Cl, Br and I, wherein each R$^6$, R$^{6a}$ and R$^{6b}$ is independently selected from C1-C10 alkyl, including wherein R$^{6a}$ and R$^{6b}$ are joined to one another to form a heterocycle that includes the nitrogen to which they are attached.

For example, an alkyl group may be substituted or unsubstituted. For example, the alkyl group may be methyl. The alkyl group may be substituted with one or more halogen atoms such as F, such as completely substituted with halogen atoms such as F (as in CF$_3$).

For example, the aryl group may contain a five- or six-membered heterocycle. For example, the aryl group may be a five-membered heterocycle containing 1 or 2 carbon atoms. Examples of suitable aryl groups include:

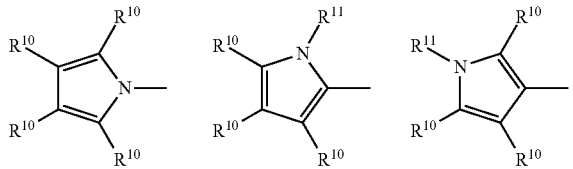

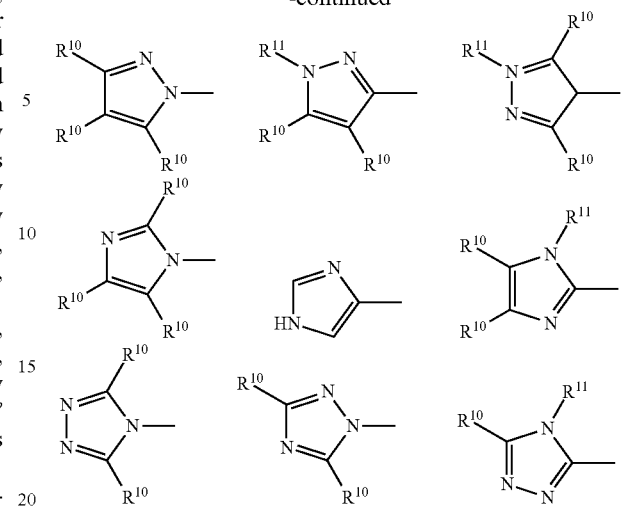

wherein each R$^{10}$ is independently selected from H or R$^2$ as defined herein and R$^{11}$ is independently selected from H or R$^1$ as defined herein. For example, any or all of R$^{10}$ and R$^{11}$ may be H.

For example, D and/or F may contain an aryl group.

In whatever aspect, the compounds of the present invention may possess some aspect of stereochemistry. For example, the compounds may possess chiral centres and/or planes and/or axes. As such, the compounds may be provided as single stereoisomers, single diastereomers, mixtures of stereoisomers or as racemic mixtures. Stereoisomers are known in the art to be molecules that have the same molecular formula and sequence of bonded atoms, but which differ in their spatial orientations of their atoms and/or groups.

In addition, the compounds of the present invention may possess tautomerism. For example, the following heterocyclic groups may exist in different tautomers:

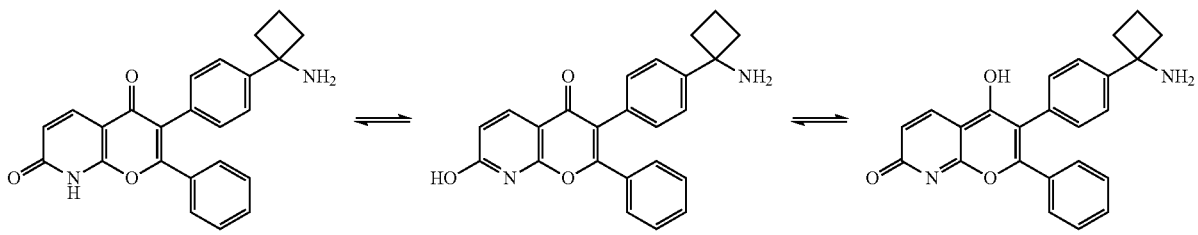

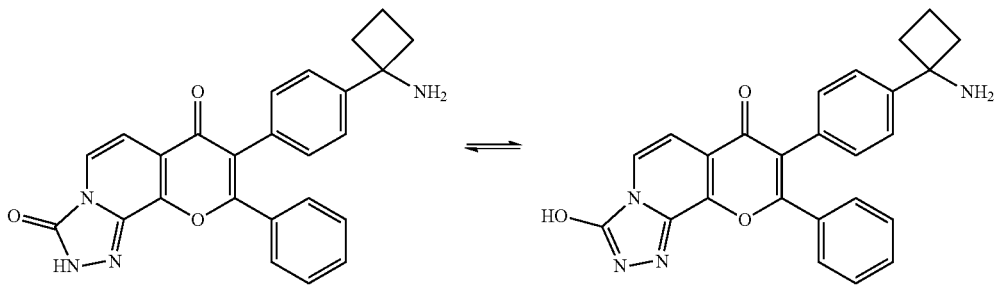

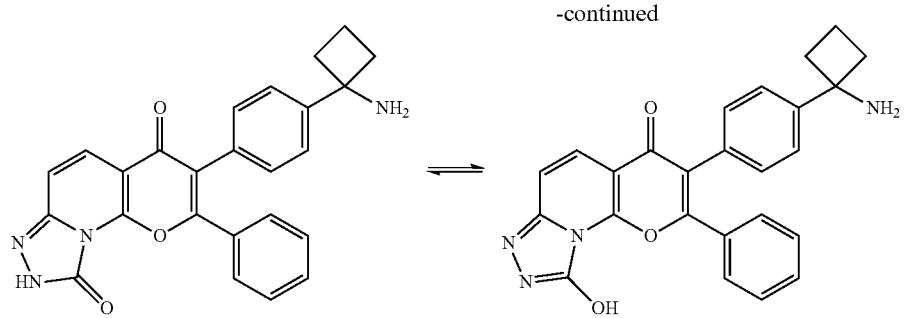

Each tautomeric form is intended to fall within the scope of the invention.

In addition, the compounds of the present invention may be provided as a pro-drug. Pro-drugs are transformed, generally in vivo, from one form to the active forms of the drugs described herein. For example, a prodrug may be formed by protecting the amine appending the cyclobutane as a physiological hydrolyzable amide. Alternatively or additionally, if D, E, F and/or G is NH, one or more of these may be protected as a physiological hydrolyzable amide.

In addition, the compounds of the present invention may be provided in the form of their pharmaceutically acceptable salts or as co-crystals. For example, the compounds may be provided having protonated amine groups.

The term "pharmaceutically acceptable salt" refers to ionic compounds formed by the addition of an acid to a base. The term refers to such salts that are considered in the art as being suitable for use in contact with a patient, for example in vivo and pharmaceutically acceptable salts are generally chosen for their non-toxic, non-irritant characteristics.

The term "co-crystal" refers to a multi-component molecular crystal, which may comprise non-ionic interactions.

Pharmaceutically acceptable salts and co-crystals may be prepared by ion exchange chromatography or by reacting the free base or acidic form of a compound with stoichiometric amounts or with an excess of the desired salt-forming inorganic or organic acid or base in one or more suitable solvents.

Salts known in the art to be generally suitable for use in contact with a patient include salts derived from inorganic and/or organic acids, including the hydrobromide, hydrochloride, sulphate, bisulphate, nitrate, acetate, oxalate, oleate, palmitate, stearate, laurate, benzoate, lactate, phosphate, tosylate, citrate, maleate, fumarate, succinate and tartrate. These may include cations based on the alkali and alkaline earth metals, such as sodium, potassium, calcium and magnesium, as well as ammonium, tetramethylammonium, tetraethylammonium. Further reference is made to the number of literature sources that survey suitable pharmaceutically acceptable salts, for example the Handbook of pharmaceutical salts published by IUPAC.

In addition, the compounds of the present invention may sometimes exist as zwitterions, which are considered as part of the invention.

The compounds of the present invention are useful in the treatment of medical conditions associated with disordered cell growth, including, but not restricted to, cancer, in particular cancers associated with overactivity of AKT occurring either from a direct change within the kinase itself such as may occur following a mutation within any of its subunits or from increased upstream activity including but not restricted to increased PI3K or PDK activity. Increased PI3K activity may have occurred through loss of the tumor suppressor PTEN. In a further aspect the present invention provides a method of treating cancer comprising administering a compound of the invention to a patient in need thereof.

For example, cancers include cardiac cancers, lung cancers, gastrointestinal cancers, genitourinary tract cancers, liver cancers, bone cancers, nervous system cancers, gynecological cancers, hematologic cancers, skin cancers and adrenal gland cancers:

For example, cancers include adrenal tumors, bile duct, bladder, blood, bone and connective tissue, brain and central nervous system, breast, cervical, colon and rectal (colorectal), endometrial, esophageal, gallbladder, head and neck, Hodgkin's Lymphoma, hypopharangeal, kidney, laryngeal, leukemias, liver, lung, lymphoma, mediastinal tumors, melanoma (malignant melanoma), mesothelioma, multiple myeloma, nasal cavity, nasopharyngeal, neuroendocrine tumors, non-Hodgkin's lymphoma, oral, oesophagus, oropharyngeal, ovarian, pancreas, paranasal sinus, parathyroid, penis, pituitary tumors, prostate, salivary gland, sarcoma, skin, spine, stomach, testicular, thyroid, urethra, uterine, vaginal and vulvar.

The compounds of the present invention are also useful in preparing a medicament that is useful in treating the diseases described above, in particular cancer.

The compounds of the present invention may selectively inhibit one or two of the AKT protein family over the other AKT isoform(s). For example, the compounds may selectively inhibit one or two of AKT1, AKT2 or AKT3 over the other isoform(s) of AKT.

For example, the compounds of the present invention may inhibit at least AKT1 and/or AKT2. For example, the compounds may selectively inhibit AKT1 and/or AKT2 over AKT3.

The present invention is further directed to a method of inhibiting AKT activity which comprises administering to a mammal in need thereof a pharmaceutically effective amount of the compound of the present invention.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The present invention also includes within its scope the use of the compounds of the present invention in combination with a second drug in the treatment of cancer. The second drug may be a drug that is already known in the art in the treatment of cancer. The present invention also includes the use of the compounds of the invention in a regime including the step of radiotherapy.

In particular, cancers often become resistant to therapy. The development of resistance may be delayed or overcome by the administration of a combination of drugs that includes the compounds of the present invention.

For example, drugs that may be used in combination with the compounds of the present invention may target the same or a similar biological pathway to that targeted by the compounds of the present invention or may act on a different or unrelated pathway.

Depending on the disease to be treated, a variety of combination partners may be coadministered with the compounds of the present invention. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including vinca alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; protein kinase inhibitors, including imatinib, gefitinib, sorafenib, sunitinib, erlotinib, dasatinib, and lapatinib; proteosome inhibitors, including bortezomib; histone deacetylase inhibitors, including valproate and SAHA; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (Flutamide, Biclutamide) and Luteinisng Hormone Analogues or antagonists.

With regard to combination therapy the compounds of the present invention may be administered separately, sequentially, simultaneously, concurrently or may be chronologically staggered with one or more standard therapeutics such as any of those mentioned above.

The present invention also provides a pharmaceutical composition suitable for clinical use. In particular, a pharmaceutical composition may comprise a pharmaceutical carrier and, dispersed therein, a therapeutically effective amount of the compounds of the invention.

The composition may be solid or liquid. The pharmaceutical carrier is generally chosen based on the type of administration being used and the pharmaceutical carrier may for example be solid or liquid. The compounds of the invention may be in the same phase or in a different phase than the pharmaceutical carrier.

Pharmaceutical compositions may be formulated according to their particular use and purpose by mixing, for example, excipient, binding agent, lubricant, disintegrating agent, coating material, emulsifier, suspending agent, solvent, stabilizer, absorption enhancer and/or ointment base. The composition may be suitable for oral, injectable, rectal or topical administration.

For example, the pharmaceutical composition may be administered orally, such as in the form of tablets, coated tablets, hard or soft gelatine capsules, solutions, emulsions, or suspensions. Administration can also be carried out rectally, for example using suppositories, locally or percutaneously, for example using ointments, creams, gels or solution, or paenterally, for example using injectable solutions.

For the preparation of tablets, coated tablets or hard gelatine capsules, the compounds of the present invention may be admixed with pharmaceutically inert, inorganic or organic excipients. Examples of suitable excipients include lactose, mize starch or derivatives thereof, talc or stearic acid or salts thereof. Suitable excipients for use with soft gelatine capsules include, for example, vegetable oils, waxes, fats and semi-solid or liquid polyols.

For the preparation of solutions and syrups, excipients include, for example, water, polyols, saccharose, invert sugar and glucose.

For injectable solutions, excipients include, for example, water, alcohols, polyols, glycerine and vegetable oil.

For suppositories and for local and percutaneous application, excipients include, for example, natural or hardened oils, waxes, fats and semi-solid or liquid polyols.

The pharmaceutical compositions may also contain preserving agents, solublizing agents, stabilizing agents, wetting agents, emulsifiers, sweeteners, colorants, odorants, buffers, coating agents and/or antioxidants.

For combination therapies, the second drug may be provided in pharmaceutical composition with the present invention or may be provided separately.

Thus, a pharmaceutical formulation for oral administration may, for example, be granule, tablet, sugar coated tablet, capsule, pill, suspension or emulsion. For parenteral injection for, for example, intravenous, intramuscular or subcutaneous use, a sterile aqueous solution may be provided that may contain other substances including, for example, salts and/or glucose to make to solution isotonic. The anti-cancer agent may also be administered in the form of a suppository or pessary, or may be applied topically in the form of a lotion, solution, cream, ointment or dusting powder.

EXAMPLES

The present invention will now be described in relation to several examples.

Examples 1 to 108 were synthesised according to the methods described subsequently. Their $IC_{50}$ values were determined as described below and are represented in the following table, in which the compound numbers correspond to the numbers in the examples.

| Example Number | $IC_{50}$ in IMAP assay vs AKT1 | $IC_{50}$ in IMAP assay vs AKT2 | $IC_{50}$ in IMAP assay vs AKT3 |
|---|---|---|---|
| 1 | ++ | ++ | + |
| 2 | +++ | ++ | + |
| 3 | ++ | ++ | + |
| 4 | ++ | +++ | + |
| 5 | ++ | ++ | + |
| 6 | + | ++ | + |
| 7 | ++ | ++ | + |
| 8 | ++ | ++ | + |
| 9 | +++ | +++ | ++ |
| 10 | ++ | +++ | ++ |
| 11 | ++ | ++ | + |
| 12 | ++ | +++ | ++ |
| 13 | ++ | ++ | + |
| 14 | ++ | ++ | + |
| 15 | ++ | +++ | ++ |

| Example Number | IC50 in IMAP assay vs AKT1 | IC50 in IMAP assay vs AKT2 | IC50 in IMAP assay vs AKT3 |
|---|---|---|---|
| 16 | ++ | ++ | ++ |
| 17 | + | ++ | + |
| 18 | + | ++ | + |

| # | | | |
|---|---|---|---|
| 19 | ++ | ++ | ++ |
| 20 | ++ | +++ | + |
| 21 | ++ | ++ | + |
| 22 | ++ | ++ | + |
| 23 | ++ | ++ | + |
| 24 | + | ++ | + |
| 25 | + | ++ | + |
| 26 | + | ++ | + |
| 27 | + | ++ | + |
| 28 | + | ++ | + |
| 29 | ++ | +++ | + |
| 30 | + | ++ | ++ |
| 31 | + | ++ | ++ |
| 32 | ++ | +++ | ++ |
| 33 | +++ | +++ | +++ |
| 34 | ++ | ++ | + |
| 35 | ++ | ++ | ++ |
| 36 | ++ | ++ | + |
| 37 | +++ | ++ | ++ |
| 38 | ++ | ++ | + |
| 39 | +++ | +++ | ++ |
| 40 | +++ | +++ | ++ |
| 41 | + | ++ | + |
| 42 | +++ | +++ | ++ |
| 43 | + | + | + |
| 44 | +++ | +++ | +++ |
| 45 | ++ | +++ | ++ |
| 47 | ++ | ++ | + |
| 48 | ++ | ++ | ++ |
| 49 | +++ | + | + |
| 50 | +++ | ++ | ++ |
| 51 | +++ | +++ | +++ |
| 52 | +++ | +++ | +++ |
| 53 | +++ | +++ | ++ |
| 54 | +++ | +++ | ++ |
| 55 | +++ | +++ | ++ |
| 56 | +++ | +++ | ++ |
| 57 | +++ | +++ | ++ |
| 58 | +++ | +++ | ++ |
| 59 | +++ | +++ | ++ |
| 60 | +++ | +++ | ++ |
| 61 | +++ | +++ | ++ |
| 62 | +++ | +++ | +++ |
| 63 | +++ | +++ | +++ |
| 64 | +++ | +++ | +++ |
| 65 | ++ | ++ | ++ |
| 66 | +++ | ++ | + |
| 67 | +++ | + | + |
| 68 | +++ | ++ | + |
| 69 | +++ | ++ | + |
| 70 | +++ | + | + |
| 71 | +++ | + | + |
| 72 | +++ | ++ | + |
| 73 | +++ | +++ | ++ |
| 74 | +++ | +++ | ++ |
| 75 | +++ | +++ | ++ |
| 76 | +++ | ++ | ++ |
| 77 | +++ | ++ | ++ |
| 78 | ++ | ++ | ++ |
| 79 | +++ | +++ | +++ |
| 80 | +++ | +++ | +++ |
| 81 | +++ | +++ | ++ |
| 82 | +++ | +++ | + |
| 83 | +++ | +++ | ++ |
| 84 | +++ | +++ | ++ |
| 85 | +++ | +++ | ++ |
| 86 | +++ | +++ | ++ |
| 87 | +++ | +++ | + |
| 88 | +++ | +++ | + |
| 89 | +++ | +++ | ++ |
| 90 | +++ | +++ | +++ |
| 91 | +++ | +++ | + |
| 92 | +++ | +++ | ++ |
| 93 | +++ | ++ | + |
| 94 | +++ | ++ | + |
| 95 | +++ | +++ | ++ |
| 96 | +++ | +++ | +++ |
| 97 | +++ | ++ | + |
| 98 | +++ | +++ | ++ |
| 99 | +++ | ++ | ++ |
| 100 | +++ | ++ | ++ |
| 101 | +++ | +++ | +++ |
| 102 | +++ | ++ | + |
| 103 | +++ | ++ | + |
| 104 | ++ | + | + |
| 105 | +++ | ++ | ++ |
| 106 | +++ | +++ | +++ |
| 107 | ++ | + | + |
| 108 | ++ | +++ | + |
| 109 | +++ | ++ | ++ |
| 110 | +++ | ++ | ++ |
| 111 | +++ | ++ | ++ |
| 112 | +++ | +++ | ++ |
| 113 | +++ | + | + |
| 114 | +++ | ++ | + |
| 115 | + | ++ | + |
| 116 | +++ | ++ | ++ |
| 117 | +++ | +++ | ++ |
| 118 | +++ | ++ | ++ |
| 119 | ++ | ++ | + |
| 120 | ++ | ++ | + |
| 121 | ++ | + | + |
| 122 | +++ | +++ | + |
| 123 | +++ | +++ | ++ |
| 124 | +++ | ++ | ++ |
| 125 | +++ | ++ | + |
| 126 | +++ | ++ | + |
| 127 | +++ | ++ | + |
| 128 | +++ | ++ | + |
| 129 | +++ | +++ | ++ |

Key
+ $IC_{50} > 10$ μM
++ $1$ μM $< IC_{50} \leq 10$ μM
+++ $IC_{50} \leq 1$ μM In addition, the phosphorylation status of various members of the AKT/PI3K pathway was investigated via western blotting. Representative examples (e.g. 20 and 40) show inhibition of AKT phosphorylation for 48 h at 10 μM.

It can be seen from the Table that several examples exhibit selectivity for one or more AKT isoforms over the other isoform(s). For example, a greater activity for AKT1 and/or AKT2 is observed compared to AKT3.

In addition, the activity of compounds in in vitro cell proliferation assays was investigated. Representative examples (e.g. 4, 40 and 44) show inhibition of proliferation of PC3 and/or LnCaP cell lines with an $IC_{50} < 10$ μM.

Abbreviations

AcOH: Acetic acid; nBuLi: n-Butyllithium; BINAP: 2,2'-bis(diphenylphosphino)-1,1'-binaphthyl; DBU: 1,8-Diazabicyclo[5.4.0]undec-7-ene; DCM: Dichloromethane; DIBAL Diisobutylaluminium hydride; DIPEA: Diisopropylethylamine; DMA: N,N-Dimethyl acetamide; DMAP: 4-Dimethylaminopyridine; DME: Dimethyl ether; DMF: N,N-Dimethylformamide; DMSO: Dimethylsulfoxide; EDCI: 1-Ethyl-3-(3'-dimethylaminopropyl)carbodiimide; EtOAc: Ethyl acetate; h: Hour: HATU: O-(7-Azabenzotriazol-1-yl)-N,N,N',N'-tetramethyluronium hexafluorophosphate; HCl: Hydrochloric acid; HOBt: 1-Hydroxybenzotriazole; HPLC: High Pressure Liquid Chromatography; t-Bu: Tertiary butyl; IMS: Industrial methylated spirits: M: Molar; MeOH: Methanol; NMP: N-Methyl-2-pyrrolidone; NMR: Nuclear Magnetic Resonance; Min: Minutes; RT: Room temperature; SCX: SCX—strong cation exchange; TBAF: Tetra-n-butylammonium fluoride; TEA: Triethylamine; TFA: Trifluoroacetic acid; THF: Tetrahydrofuran; TMSCl: Trimethylsilyl chloride General Experimental Conditions $^1$H NMR spectra were recorded at ambient temperature using a Varian Unity Inova (400 MHz) spectrometer with a triple resonance 5 mm probe, a Bruker Avance DRX (400

MHz) with a 5 mm inverse detection triple resonance TXI probe, a Bruker Avance (500 MHz) spectrometer with a 5 mm QNP probe or a Bruker Avance DPX (300 MHz) spectrometer with a standard 5 mm dual frequency probe. Chemical shifts are expressed in ppm relative to tetramethylsilane.

High Pressure Liquid Chromatography—Mass Spectrometry (LCMS) experiments to determine retention times ($R_T$) and associated mass ions were performed using one of the following methods.

Method A: The system consists of a Waters Platform LC quadrupole mass spectrometer linked to a Hewlett Packard HP1100 LC system with diode array detector and 100 position autosampler. The spectrometer has an electrospray source operating in positive and negative ion mode. Additional detection is achieved using a Sedex 85 evaporative light scattering detector.

An LC-MS experiment is performed on each sample submitted using the following conditions: LC Column—Phenomenex Luna 3 micron C18(2) 30×4.6 mm or equivalent; Mobile phase—A) Water 0.1% Formic Acid B) Methanol 0.1% Formic Acid.

| Gradient - Time | flow | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Split—200 µl/min split to the ESI source with inline HP1100 DAD detection
Detection—MS, ELS, UV
MS ionisation method—Electrospray (positive and negative ion)
Total experiment time—6 mins (approx)

Method B: The system consists of a Waters ZMD quadrupole mass spectrometer linked to a Waters 1525 LC system with Waters 996 diode array detector. Sample injection is done by a Waters 2700 autosampler. The spectrometer has an electrospray source operating in positive and negative ion mode. Additional detection is achieved using a Sedex 85 evaporative light scattering detector.

An LC-MS experiment is performed on each sample submitted using the following conditions: LC Column—Phenomenex Luna 3 micron C18(2) 30×4.6 mm or equivalent. Mobile phase—A) Water 0.1% Formic Acid B) Methanol 0.1% Formic Acid.

| Gradient - Time | flow | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Split—200 µl/min split to the ESI source with inline Waters 996 DAD detection
Detection—MS, ELS, UV
MS ionisation method—Electrospray (positive and negative ion)
Total experiment time—6 mins (approx)

Method C: The system consists of a Finnigan AQA single quadrupole mass spectrometer linked to a Hewlett Packard 1050 LC system with UV diode array detector and autosampler. The spectrometer has an electrospray source operating in positive ion mode. Additional detection is achieved using a Sedex 65 evaporative light scattering detector. An LC-MS experiment is performed on each sample submitted using the following conditions: LC Column—Phenomenex Luna 3 micron C18(2) 30×4.6 mm or equivalent. Mobile phase—A) Water 0.1% Formic Acid B) Methanol 0.1% Formic Acid.

| Gradient - Time | flow | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Split—2041/min split to the ESI source
Detection—MS, ELS, UV
MS ionisation method—Electrospray (positive ion)
Total experiment time—6 mins (approx)

Method D: The system consists of a Waters Micromass ZQ2000 quadrupole mass spectrometer linked to a Hewlett Packard HP1100 LC system with a DAD UV detector. Sample injection is by a CTC HTS PAL autosampler. The spectrometer has an electrospray source operating in positive and negative ion mode. Additional detection was achieved using a Sedex 85 evaporative light scattering detector.

An LC-MS experiment is performed on each sample submitted using the following conditions: LC Column—Higgins Clipeus 5 micron C18 100×3.0 mm, maintained at 40° C. Mobile phase—A) Water 0.1% Formic Acid B) Methanol 0.1% Formic Acid.

| Gradient - Time | flow ml/min | % A | % B |
| --- | --- | --- | --- |
| 0.00 | 1.0 | 85 | 15 |
| 1.00 | 1.0 | 85 | 15 |
| 13.00 | 1.0 | 5 | 95 |
| 20.00 | 1.0 | 5 | 95 |
| 22.00 | 1.0 | 85 | 15 |
| 25.00 | 1.0 | 85 | 15 |

Detection—MS, ELS, UV (100 µl split to MS with in-line UV DAD detector)
MS ionisation method—Electrospray (positive/negative ion)
Method D*: The method used was the same as Method D only with: Mobile phase—A) Water 0.1% Formic Acid B) Acetonitrile 0.1% Formic Acid.

| Gradient - Time | flow ml/min | % A | % B |
| --- | --- | --- | --- |
| 0.00 | 1.0 | 95 | 5 |
| 1.00 | 1.0 | 95 | 5 |
| 15.00 | 1.0 | 5 | 95 |
| 20.00 | 1.0 | 5 | 95 |
| 22.00 | 1.0 | 95 | 5 |
| 25.00 | 1.0 | 95 | 5 |

Detection—MS, ELS, UV (100 µl split to MS with in-line UV DAD detector)
MS ionisation method—Electrospray (positive/negative ion)
Method E: The system consists of a Waters Micromass ZQ2000 quadrupole mass spectrometer linked to a Waters Acquity HPLC system with a PDA UV detector. The spectrometer has an electrospray source operating in positive and negative ion mode. An LC-MS experiment is performed on each sample submitted using the following conditions: LC Column—Acquity BEH C18 1.7 μm 100×2.1 mm, maintained at 40° C. or Acquity BEH Shield RP18 1.7 um 100×2.1 mm, maintained at 40° C. Mobile phase—A) Water 0.1% Formic Acid B) Acetonitrile 0.1% Formic Acid.

| Gradient - Time | flow ml/min | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA
MS ionisation method—Electrospray (positive/negative ion)

Method F: The system consists of a Waters Quattro Micro triple quadrupole mass spectrometer linked to a Hewlett Packard HP1100 LC system with a DAD UV detector. Sample injection is done by a CTC HTS PAL autosampler. The spectrometer has an electrospray source operating in positive and negative ion mode. Additional detection is achieved using a Sedex 85 evaporative light scattering detector. An LC-MS experiment is performed on each sample submitted using the following conditions: LC Column—Higgins Clipeus 5 micron C18 100×3.0 mm, maintained at 40° C. Mobile phase—A) Water 0.1% Formic Acid B) Methanol 0.1% Formic Acid.

| Gradient - Time | flow ml/min | % A | % B |
| --- | --- | --- | --- |
| 0.00 | 1.0 | 85 | 15 |
| 1.00 | 1.0 | 85 | 15 |
| 13.00 | 1.0 | 5 | 95 |
| 20.00 | 1.0 | 5 | 95 |
| 22.00 | 1.0 | 85 | 15 |
| 25.00 | 1.0 | 85 | 15 |

Detection—MS, ELS, UV (100 μl split to MS with in-line UV DAD detector)
MS ionisation method—Electrospray (positive/negative ion)

Method G: The system consists of a Waters ZMD quadrupole mass spectrometer linked to a Waters 1525 LC system with Waters 996 diode array detector. Sample injection is done by a Waters 2700 autosampler. The spectrometer has an electrospray source operating in positive and negative ion mode. Additional detection is achieved using a Sedex 85 evaporative light scattering detector.

An LC-MS experiment is performed on each sample submitted using the following conditions: LC Column—Luna 3 micron C18(2) 30×4.6 mm or equivalent. Mobile phase—A) Water 0.1% Formic Acid B) Acetonitrile 0.1% Formic Acid.

| Gradient - Time | flow | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Split—200 μl/min split to the ESI source with inline Waters 996 DAD detection
Detection—MS, ELS, UV
MS ionisation method—Electrospray (positive and negative ion)
Total experiment time—6 mins (approx)

Method H: The system consists of a Waters Platform LC quadrupole mass spectrometer linked to a Hewlett Packard HP1100 LC system with diode array detector and 100 position autosampler. The spectrometer has an electrospray source operating in positive and negative ion mode. Additional detection is achieved using a Sedex 85 evaporative light scattering detector.

An LC-MS experiment is performed on each sample submitted using the following conditions: LC Column—Phenomenex Luna 3 micron C18(2) 30×4.6 mm or equivalent; Mobile phase—A) Water 0.1% Formic Acid B) Acetonitrile 0.1% Formic Acid.

| Gradient - Time | flow | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Split—200 μl/min split to the ESI source with inline HP1100 DAD detection
Detection—MS, ELS, UV
MS ionisation method—Electrospray (positive and negative ion)
Total experiment time—6 mins (approx)

Method I: The system consists of ThermoFinnigan LCQ Advantage Mass Spectrometer with the Surveyor LC system and 200 position autosampler. The spectrometer has an electrospray source operating in positive and negative ion mode. An LC-MS experiment is performed on each sample submitted using the following conditions: LC Column—Luna 3 micron C18 50×2 mm; Mobile phase—A) Water 0.1% Formic Acid B) Acetonitrile 0.1% Formic Acid.

| Gradient - Time | flow | % A | % B |
| --- | --- | --- | --- |
| 0.00 | 0.6 | 95 | 5 |
| 7.00 | 0.6 | 5 | 95 |
| 8.00 | 0.6 | 5 | 95 |
| 8.20 | 0.6 | 95 | 5 |
| 11.00 | 0.6 | 95 | 5 |

Split—100 μl/min split to the ESI source with inline Surveyor DAD detection
Detection—MS, UV
MS ionisation method—Electrospray (positive and negative ion)
Total experiment time—11 mins (approx)

Method J: The system consists of a Agilent Technologies 6140 single quadrupole mass spectrometer linked to a Agilent Technologies 1290 Infinity LC system with UV diode array detector and autosampler. The spectrometer has a multimode ionization source (electrospray and atmospheric pressure chemical ionizations) operating in positive and negative ion mode. An LC-MS experiment is performed on each sample submitted using the following conditions: LC Column—Zorbax Eclipse Plus C18 RRHD 1.8 micron 50×2.1 mm maintained at 40° C. Mobile phase—A) Water 0.1% Formic Acid B) Acetonitrile 0.1% Formic Acid.

| Gradient - Time | Flow mL/min | % A | % B |
|---|---|---|---|
| 0.00 | 1.0 | 95 | 5 |
| 1.80 | 1.0 | 0 | 100 |
| 2.20 | 1.0 | 0 | 100 |
| 2.21 | 1.0 | 95 | 5 |
| 2.50 | 1.0 | 95 | 5 |

Detection—MS, UV
MS ionisation method—Multimode (positive and negative ion)
Total experiment time—2.50 mins (approx)

Microwave experiments were carried out using a Biotage Initiator™ Sixty, which uses a single-mode resonator and dynamic field tuning, both of which give reproducibility and control. Temperature from 60-250° C. can be achieved, and pressures of up to 20 bar can be reached.

Unless otherwise indicated, the nomenclature of structures was assigned using MDL Autonom 2000 software or CambridgeSoft ChemBioDraw Ultra 11.0 or 12.0 using "convert structure to name" function.

Example 1

3-[4-(1-Amino-cyclobutyl)-phenyl]-6-fluoro-2-phenyl-chromen-4-one

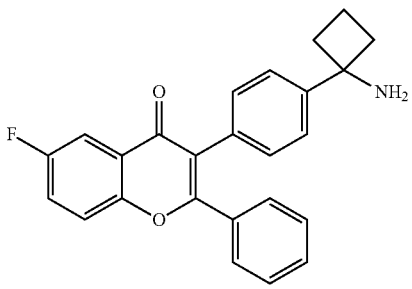

Step 1: 1-(5-Fluoro-2-methoxy-phenyl)-3-phenyl-prop-2-yn-1-ol: To a stirred solution of 5-fluoro-2-methoxybenzaldehyde (933 mg, 6.05 mmol) in anhydrous THF (15 mL) at 0° C. was added phenylethynyl magnesium bromide solution (1M in THF, 9.0 mL, 9.08 mmol). The temperature was allowed to increase to RT over the course of the reaction. After 18 h, the reaction mixture was quenched with saturated aqueous ammonium chloride solution and extracted with EtOAc (20 mL). The organic extracts were washed with brine, dried ($Na_2SO_4$), filtered and concentrated in vacuo. The resultant residue was subjected to flash chromatography ($SiO_2$, gradient 0 to 30% EtOAc in cyclohexane) to afford the title compound (1.19 g, 77%). $^1$H NMR (400 MHz, DMSO-d6): δ 7.42-7.32 (m, 6H), 7.16-7.09 (m, 1H), 7.06-7.02 (m, 1H), 6.16-6.13 (d, 1H), 5.78-5.75 (d, 1H), 3.83 (s, 3H).

Step 2: 1-(5-Fluoro-2-methoxy-phenyl)-3-phenyl-propynone: To a solution of 1-(5-fluoro-2-methoxy-phenyl)-3-phenyl-prop-2-yn-1-ol (1.19 g, 4.64 mmol) in DCM (25 mL) was added manganese dioxide (4.03 g, 46.4 mmol) and the reaction stirred at RT. After 18 h, the mixture was filtered through Celite® and the eluent concentrated in vacuo to afford the title compound (1.10 g, 93%). $^1$H NMR (400 MHz, DMSO-d6): δ 7.74-7.68 (m, 2H), 7.65-7.48 (m, 5H), 7.32-7.27 (m, 1H), 3.95 (s, 3H).

Step 3: 6-Fluoro-3-iodo-2-phenyl-chromen-4-one: A solution of 1-(5-fluoro-2-methoxy-phenyl)-3-phenyl-propynone (550 mg, 2.16 mmol) in DCM (10 mL) was cooled to −78° C. A solution of iodine monochloride (1M in DCM, 3.24 mL, 3.24 mmol) was added dropwise over 5 min. The reaction mixture was allowed to reach RT with stirring. After 3 h, the mixture was diluted using DCM (10 mL), washed with 10% aqueous sodium thiosulphate solution (20 mL), water (20 mL), brine (20 mL), dried ($Na_2SO_4$), filtered and concentrated in vacuo to afford the title compound (765 mg, 97%). $^1$H NMR (400 MHz, DMSO-d6): δ 7.84-7.73 (m, 5H), 7.62-7.55 (m, 3H).

Step 4: {1-[4-(6-Fluoro-4-oxo-2-phenyl-4H-chromen-3-yl)-phenyl]-cyclobutyl}-carbamic acid tert-butyl ester: To a microwave vial were added 6-fluoro-3-iodo-2-phenyl-chromen-4-one (55 mg, 0.15 mmol), {1-[4-(4,4,5,5-tetramethyl-[1,3,2]dioxaborolan-2-yl)-phenyl]-cyclobutyl}-carbamic acid tert-butyl ester (62 mg, 0.165 mmol, prepared as described in WO2008/070016), sodium carbonate solution (2M in water, 0.26 mL, 0.53 mmol), tetrakis(triphenylphosphine)palladium(0) (17 mg, 0.015 mmol) and DME (3 mL). The reaction mixture was purged using argon and heated in a microwave reactor to 125° C. for 30 min. The mixture was partitioned between water (2 mL) and EtOAc (3 mL). The aqueous phase was extracted with ethyl acetate (3 mL). The combined organic extracts were washed with brine (5 mL), dried ($Na_2SO_4$), filtered and concentrated in vacuo. The resultant residue was subjected to flash chromatography ($SiO_2$, gradient 0 to 30% ethyl acetate in cyclohexane) to afford the title compound (22 mg, 30%). $^1$H NMR (400 MHz, $CDCl_3$): δ 7.95-7.90 (m, 1H), 7.57-7.52 (m, 1H), 7.46-7.30 (m, 6H), 7.28-7.22 (m, 2H), 7.21-7.16 (m, 2H), 5.03 (s, 1H), 2.64-2.31 (m, 4H), 2.14-2.00 (m, 1H), 1.89-1.77 (m, 1H), 1.48-1.18 (m, 9H).

Step 5: 3-[4-(1-Amino-cyclobutyl)-phenyl]-6-fluoro-2-phenyl-chromen-4-one: To a solution of {1-[4-(6-fluoro-4-oxo-2-phenyl-4H-chromen-3-yl)-phenyl]-cyclobutyl}-carbamic acid tert-butyl ester (22 mg, 0.045 mmol) in DCM (4 mL) was added TFA (1 mL). The mixture was stirred at RT for 1 h and then directly loaded onto an SCX cartridge (2 g, pre-wet using DCM). Impurities were removed by eluting with MeOH:DCM (1:1) and product eluted using $NH_3$ solution (2M in MeOH):DCM (1:1) to give the title compound (14 mg, 82%). LCMS (Method F): $R_T$=9.03 min, $[M+H]^+$=386. $^1$H NMR (400 MHz, $CDCl_3$): δ 7.92 (dd, J=8.3 and 3.2 Hz, 1H), 7.55 (dd, J=9.5 and 4.7 Hz, 1H), 7.47-7.32 (m, 6H), 7.29 (d, J=7.9 Hz, 2H), 7.19 (d, J=8.3 Hz, 2H), 2.61-2.50 (m, 2H), 2.22-2.00 (m, 3H), 1.82-1.69 (m, 1H).

Example 2

3-[4-(1-Amino-cyclobutyl)-phenyl]-8-fluoro-2-phenyl-chromen-4-one

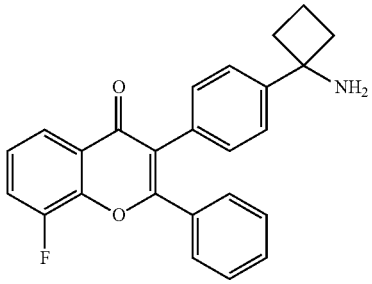 [SMILES: NC1(c2ccc(-c3c(-c4ccccc4)oc4c(F)cccc4c3=O)cc2)CCC1]

Step 1: 3-Fluoro-2,N-dimethoxy-N-methyl-benzamide: Following the procedure used to prepare N-dimethoxy-N-methyl-nicotinamide, 3-fluoro-2-methoxybenzaldehyde (1.00 g, 5.88 mmol) was reacted to give the title compound (1.00 g, 80%). $^1$H NMR (400 MHz, DMSO-d6): $^1$H NMR (400 MHz, DMSO-d□): δ 7.39-7.28 (m, 1H), 7.20-7.08 (m, 2H), 3.85 (s, 3H), 3.54-3.38 (m, 3H), 3.34-3.15 (m, 3H).

Step 2: 1-(3-Fluoro-2-methoxy-phenyl)-3-phenyl-propynone: Following the procedure used to prepare 1-(2-methoxy-pyridin-3-yl)-3-phenyl-propynone, 3-fluoro-2,N-dimethoxy-N-methyl-benzamide (1.00 g, 4.69 mmol) was reacted to give the title compound (0.55 g, 46%). $^1$H NMR (400 MHz, DMSO-d6): δ 7.77-7.71 (m, 3H), 7.67-7.57 (m, 2H), 7.56-7.50 (m, 2H), 7.34-7.26 (m, 1H), 4.01-3.99 (d, 3H).

Step 3: 8-Fluoro-3-iodo-2-phenyl-chromen-4-one: Following the procedure used to prepare 6-fluoro-3-iodo-2-phenyl-chromen-4-one, 1-(3-Fluoro-2-methoxy-phenyl)-3-phenyl-propynone (0.55 g, 2.16 mmol) was reacted to give the title compound (765 mg, 97%). $^1$H NMR (400 MHz, DMSO-d6): δ 7.93-7.88 (m, 1H), 7.86-7.78 (m, 3H), 7.63-7.57 (m, 3H), 7.56-7.49 (m, 1H).

Step 4: {1-[4-(8-Fluoro-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 8-fluoro-3-iodo-2-phenyl-chromen-4-one (55 mg, 0.15 mmol) was reacted to give the title compound (36 mg, 49%). LCMS (Method A): $R_T$=4.91 min, [M+H]$^+$=486.

Step 5: 3-[4-(1-Amino-cyclobutyl)-phenyl]-8-fluoro-2-phenyl-chromen-4-one: Following the procedure used to prepare 3-[4-(1-amino-cyclobutyl)-phenyl]-6-fluoro-2-phenyl-chromen-4-one, {1-[4-(8-fluoro-4-oxo-2-phenyl-4H-chromen-3-yl)-phenyl]-cyclobutyl}-carbamic acid tert-butyl ester (35 mg, 0.072 mmol) was reacted to give the title compound (22 mg, 79%). LCMS (Method F): $R_T$=9.24 min, [M+H]$^+$=386. $^1$H NMR (400 MHz, CDCl$_3$): δ 8.01 (d, J=8.6 Hz, 1H), 7.49-7.29 (m, 7H), 7.26 (d, J=8.1 Hz, 2H), 7.17 (d, J=8.1 Hz, 2H), 2.58-2.48 (m, 2H), 2.24-1.97 (m, 3H), 1.79-1.68 (m, 1H).

Example 3

3-[4-(1-Amino-cyclobutyl)-phenyl]-5-fluoro-2-phenyl-chromen-4-one

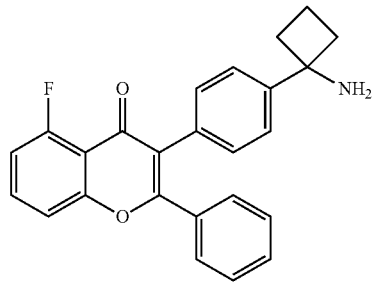 [SMILES: NC1(c2ccc(-c3c(-c4ccccc4)oc4cccc(F)c4c3=O)cc2)CCC1]

Step 1: 1-(2-Fluoro-6-methoxy-phenyl)-3-phenyl-prop-2-yn-1-ol: Following the procedure used to prepare 1-(5-fluoro-2-methoxy-phenyl)-3-phenyl-prop-2-yn-1-ol, 2-fluoro-6-methoxy-benzaldehyde (947 mg, 6.14 mmol) was reacted to give the title compound (1.21 g, 77%). $^1$H NMR (400 MHz, DMSO-d6): δ 7.41-7.30 (m, 6H), 6.91-6.79 (m, 2H), 5.97-5.94 (m, 1H), 5.90-5.87 (d, 1H), 3.86 (s, 3H).

Step 2: 1-(2-Fluoro-6-methoxy-phenyl)-3-phenyl-propynone: Following the procedure used to prepare 1-(5-fluoro-2-methoxy-phenyl)-3-phenyl-propynone, 1-(2-fluoro-6-methoxy-phenyl)-3-phenyl-prop-2-yn-1-ol (1.21 g, 4.72 mmol) was reacted to give the title compound (1.16 g, 97%). $^1$H NMR (400 MHz, DMSO-d6): δ 7.69-7.64 (m, 2H), 7.61-7.47 (m, 4H), 7.08-7.04 (m, 1H), 6.98-6.92 (m, 1H), 3.91 (s, 3H).

Step 3: 5-Fluoro-3-iodo-2-phenyl-chromen-4-one: Following the procedure used to prepare 6-fluoro-3-iodo-2-phenyl-chromen-4-one, 1-(2-fluoro-6-methoxy-phenyl)-3-phenyl-propynone (1.16 g, 4.56 mmol) was reacted to give the title compound (1.38 g, 83%). $^1$H NMR (400 MHz, DMSO-d6): δ 7.87-7.77 (m, 3H), 7.62-7.55 (m, 3H), 7.54-7.50 (m, 1H), 7.36-7.29 (m, 1H).

Step 4: {1-[4-(5-Fluoro-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 5-fluoro-3-iodo-2-phenyl-chromen-4-one (55 mg, 0.15 mmol) was reacted to give the title compound (19 mg, 26%). $^1$H NMR (400 MHz, CDCl$_3$): δ 7.65-7.57 (m, 1H), 7.41-7.29 (m, 6H), 7.28-7.22 (m, 2H), 7.21-7.16 (m, 2H), 7.09-7.03 (m, 1H), 5.03 (s, 1H), 2.61-2.29 (m, 4H), 2.21-2.00 (m, 1H), 1.88-1.74 (m, 1H), 1.48-1.18 (m, 9H).

Step 5: 3-[4-(1-Amino-cyclobutyl)-phenyl]-5-fluoro-2-phenyl-chromen-4-one: Following the procedure used to prepare 3-[4-(1-amino-cyclobutyl)-phenyl]-6-fluoro-2-phenyl-chromen-4-one, {1-[4-(5-fluoro-4-oxo-2-phenyl-4H-chromen-3-yl)-phenyl]-cyclobutyl}-carbamic acid tert-butyl ester (19 mg, 0.039 mmol) was reacted to give the title compound (11 mg, 73%). LCMS (Method F): $R_T$=8.60 min, [M+H]$^+$=386. $^1$H NMR (400 MHz, CDCl$_3$): δ 7.63-7.54 (m, 1H), 7.38-7.27 (m, 6H), 7.27-7.20 (m, 2H), 7.15 (d, J=8.6 Hz, 2H), 7.03 (t, J=8.6 Hz, 1H), 2.57-2.47 (m, 2H), 2.24-2.12 (m, 2H), 2.12-1.99 (m, 1H), 1.78-1.66 (m, 1H).

Example 4

3-[4-(1-Amino-cyclobutyl)-phenyl]-7,8-dimethoxy-2-phenyl-chromen-4-one

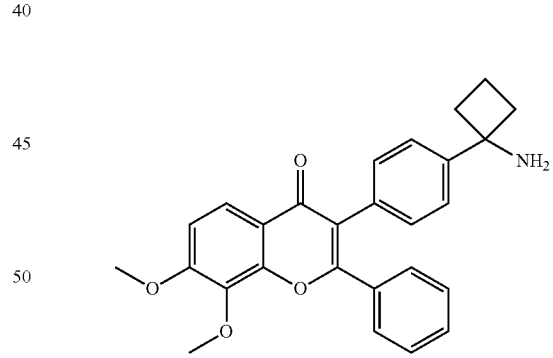

Step 1: 3-Phenyl-1-(2,3,4-trimethoxy-phenyl)-prop-2-yn-1-ol: Following the procedure used to prepare 1-(5-fluoro-2-methoxy-phenyl)-3-phenyl-prop-2-yn-1-ol, 2,3,4-trimethoxybenzaldehyde (1.00 g, 5.10 mmol) was reacted to give the title compound (1.50 g, 99%). $^1$H NMR (400 MHz, DMSO-d6): δ 7.45-7.28 (m, 6H), 6.88-6.83 (m, 1H), 5.97-5.92 (d, 1H), 5.73-5.68 (d, 1H), 3.85 (s, 3H), 3.80 (s, 3H), 3.76 (s, 3H).

Step 2: 3-Phenyl-1-(2,3,4-trimethoxy-phenyl)-propynone: Following the procedure used to prepare 1-(5-fluoro-2-methoxy-phenyl)-3-phenyl-propynone, 3-phenyl-1-(2,3,4-trimethoxy-phenyl)-prop-2-yn-1-ol (1.50 g, 5.03 mmol) was reacted to give the title compound (1.35 g, 91%). $^1$H NMR (400 MHz, DMSO-d6): δ 7.78-7.70 (m, 3H), 7.61-7.49 (m, 3H), 7.03-7.00 (d, 1H), 3.93 (s, 3H), 3.91 (s, 3H), 3.79 (s, 3H).

Step 3: 3-Iodo-7,8-dimethoxy-2-phenyl-chromen-4-one: Following the procedure used to prepare 6-fluoro-3-iodo-2-phenyl-chromen-4-one, 3-phenyl-1-(2,3,4-trimethoxy-phenyl)-propynone (1.35 g, 4.56 mmol) was reacted to give the title compound (1.52 g, 82%). $^1$H NMR (400 MHz, DMSO-d6): δ 7.86-7.78 (m, 3H), 7.62-7.57 (m, 3H), 7.35-7.32 (d, 1H), 3.97 (s, 3H), 3.83 (s, 3H).

Step 4: {1-[4-(7,8-Dimethoxy-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-7,8-dimethoxy-2-phenyl-chromen-4-one (82 mg, 0.20 mmol) was reacted to give the title compound (41 mg, 41%). $^1$H NMR (400 MHz, CDCl$_3$): δ 7.56-7.52 (d, 1H), 6.99-6.68 (m, 9H), 6.61-6.56 (d, 1H), 4.61-4.54 (m, 1H), 3.57-3.53 (m, 6H), 2.12-2.00 (m, 4H), 1.65-1.28 (m, 2H), 1.00-0.72 (m, 9H).

Step 5: 3-[4-(1-Amino-cyclobutyl)-phenyl]-7,8-dimethoxy-2-phenyl-chromen-4-one: Following the procedure used to prepare 3-[4-(1-amino-cyclobutyl)-phenyl]-6-fluoro-2-phenyl-chromen-4-one, {1-[4-(7,8-dimethoxy-4-oxo-2-phenyl-4H-chromen-3-yl)-phenyl]-cyclobutyl}-carbamic acid tert-butyl ester (41 mg, 0.078 mmol) was reacted to give the title compound (27 mg, 82%). LCMS (Method E): R$_T$=3.55 min, [M+H]$^+$=428. $^1$H NMR (400 MHz, DMSO-d6): δ 7.79 (d, J=9.2 Hz, 1H), 7.40-7.24 (m, 8H), 7.06 (d, J=8.8 Hz, 2H), 3.93 (s, 3H), 3.86 (s, 3H), 2.36-2.17 (m, 4H), 2.07-1.87 (m, 3H), 1.64-1.53 (m, 1H).

Example 5

3-[4-(1-Amino-cyclobutyl)-phenyl]-6-methoxy-2-phenyl-chromen-4-one

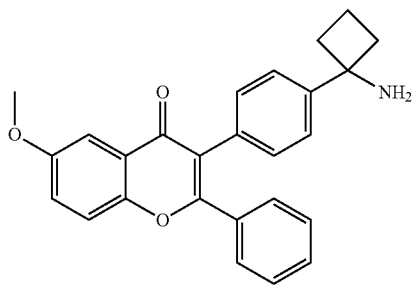 [SMILES: COc1ccc2oc(-c3ccccc3)c(-c3ccc(C4(N)CCC4)cc3)c(=O)c2c1]

Step 1: 1-(2,5-Dimethoxy-phenyl)-3-phenyl-prop-2-yn-1-ol: Following the procedure used to prepare 1-(5-fluoro-2-methoxy-phenyl)-3-phenyl-prop-2-yn-1-ol, 2,5-dimethoxy-benzaldehyde (1.00 g, 6.02 mmol) was reacted to give the title compound (1.50 g, 93%). $^1$H NMR (400 MHz, DMSO-d6): δ 7.42-7.34 (m, 5H), 7.18-7.15 (d, 1H), 6.97-6.94 (d, 1H), 6.87-6.83 (m, 1H), 6.03-6.01 (d, 1H), 5.77-5.74 (d, 1H), 3.78 (s, 3H), 3.72 (s, 3H).

Step 2: 1-(2,5-Dimethoxy-phenyl)-3-phenyl-propynone: Following the procedure used to prepare 1-(5-fluoro-2-methoxy-phenyl)-3-phenyl-propynone, 1-(2,5-dimethoxy-phenyl)-3-phenyl-prop-2-yn-1-ol (1.50 g, 5.59 mmol) was reacted to give the title compound (1.33 g, 89%). $^1$H NMR (400 MHz, DMSO-d6): δ 7.73-7.68 (m, 2H), 7.62-7.49 (m, 3H), 7.39-7.36 (d, 1H), 7.29-7.20 (m, 2H), 3.90 (s, 3H), 3.78 (s, 3H).

Step 3: 3-Iodo-6-methoxy-2-phenyl-chromen-4-one: Following the procedure used to prepare 6-fluoro-3-iodo-2-phenyl-chromen-4-one, 1-(2,5-dimethoxy-phenyl)-3-phenyl-propynone (1.33 g, 4.99 mmol) was reacted to give the title compound (1.31 g, 69%). $^1$H NMR (400 MHz, DMSO-d6): δ 7.80-7.77 (m, 2H), 7.69-7.65 (m, 1H), 7.61-7.55 (m, 3H), 7.48-7.43 (m, 2H), 3.89 (s, 3H).

Step 4: {1-[4-(6-Methoxy-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-6-methoxy-2-phenyl-chromen-4-one (76 mg, 0.20 mmol) was reacted to give the title compound (42 mg, 44%). $^1$H NMR (400 MHz, CDCl$_3$): δ 7.68-7.64 (d, 1H), 7.51-7.16 (m, 11H), 5.05 (s, 1H), 3.92 (s, 3H), 2.61-2.45 (m, 4H), 2.16-1.75 (m, 2H), 1.52-1.00 (m, 9H).

Step 5: 3-[4-(1-Amino-cyclobutyl)-phenyl]-6-methoxy-2-phenyl-chromen-4-one: Following the procedure used to prepare 3-[4-(1-amino-cyclobutyl)-phenyl]-6-fluoro-2-phenyl-chromen-4-one, {1-[4-(6-methoxy-4-oxo-2-phenyl-4H-chromen-3-yl)-phenyl]-cyclobutyl}-carbamic acid tert-butyl ester (42 mg, 0.084 mmol) was reacted to give the title compound (27 mg, 82%). LCMS (Method E): R$_T$=3.70 min, [M+H]$^+$=399. $^1$H NMR (400 MHz, DMSO-d6): δ 7.65 (d, J=8.7 Hz, 1H), 7.44-7.25 (m, 9H), 7.09-7.04 (m, 2H), 7.83 (s, 3H), 2.35-2.26 (m, 2H), 2.17 (bs, 2H), 2.06-1.87 (m, 3H), 1.64-1.53 (m, 1H).

Example 6

3-[4-(1-Amino-cyclobutyl)-phenyl]-6-methoxy-7-methyl-2-phenyl-chromen-4-one

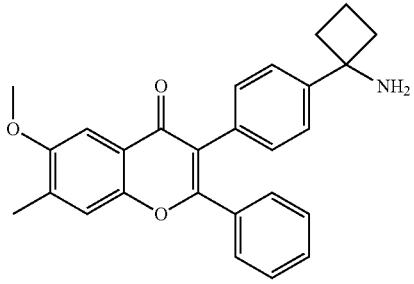 [SMILES: COc1cc2c(=O)c(-c3ccc(C4(N)CCC4)cc3)c(-c3ccccc3)oc2cc1C]

Step 1: 1-(2,5-Dimethoxy-4-methyl-phenyl)-3-phenyl-prop-2-yn-1-ol: Following the procedure used to prepare 1-(5-fluoro-2-methoxy-phenyl)-3-phenyl-prop-2-yn-1-ol, 2,5-dimethoxy-4-methyl-benzaldehyde (1.00 g, 5.55 mmol) was reacted to give the title compound (1.54 g, 98%). $^1$H NMR (400 MHz, DMSO-d6): δ 7.42-7.34 (m, 5H), 7.16 (s, 1H), 6.86 (s, 1H), 5.98-5.94 (d, 1H), 5.77-5.74 (d, 1H), 3.77 (s, 3H), 3.76 (s, 3H), 2.16 (s, 3H).

Step 2: 1-(2,5-Dimethoxy-4-methyl-phenyl)-3-phenyl-propynone: Following the procedure used to prepare 1-(5-fluoro-2-methoxy-phenyl)-3-phenyl-propynone, 1-(2,5-dimethoxy-4-methyl-phenyl)-3-phenyl-prop-2-yn-1-ol (1.54 g, 5.45 mmol) was reacted to give the title compound (1.32 g, 86%). $^1$H NMR (400 MHz, DMSO-d6): δ 7.72-7.68 (m, 2H), 7.60-7.49 (m, 3H), 7.36 (s, 1H), 7.14 (s, 1H), 3.91 (s, 3H), 3.81 (s, 3H), 2.25 (s, 3H).

Step 3: 3-Iodo-6-methoxy-7-methyl-2-phenyl-chromen-4-one: Following the procedure used to prepare 6-fluoro-3-iodo-2-phenyl-chromen-4-one, 1-(2,5-dimethoxy-4-methylphenyl)-3-phenyl-propynone (1.32 g, 4.71 mmol) was reacted to give the title compound (1.47 g, 80%). ¹H NMR (400 MHz, DMSO-d6): δ 7.79-7.75 (m, 2H), 7.61-7.55 (m, 4H), 7.40 (s, 1H), 3.92 (s, 3H), 2.31-2.29 (m, 3H).

Step 4: {1-[4-(6-Methoxy-7-methyl-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-6-methoxy-7-methyl-2-phenyl-chromen-4-one (78 mg, 0.20 mmol) was reacted to give the title compound (40 mg, 41%). ¹H NMR (400 MHz, CDCl₃): δ 7.56 (s, 1H), 7.41-7.17 (m, 10H), 5.04 (s, 1H), 3.94 (s, 3H), 2.60-2.46 (m, 4H), 2.39-2.35 (m, 3H), 2.13-2.00 (m, 1H), 1.90-1.76 (m, 1H), 1.48-1.10 (m, 9H).

Step 5: 3-[4-(1-Amino-cyclobutyl)-phenyl]-6-methoxy-7-methyl-2-phenyl-chromen-4-one: Following the procedure used to prepare 3-[4-(1-amino-cyclobutyl)-phenyl]-6-fluoro-2-phenyl-chromen-4-one, {1-[4-(6-methoxy-7-methyl-4-oxo-2-phenyl-4H-chromen-3-yl)-phenyl]-cyclobutyl}-carbamic acid tert-butyl ester (40 mg, 0.078 mmol) was reacted to give the title compound (28 mg, 88%). LCMS (Method E): R_T=3.99 min, [M+H]⁺=412. ¹H NMR (400 MHz, DMSO-d6): δ 7.55 (s, 1H), 7.37-7.24 (m, 8H), 7.06 (d, J=7.8 Hz, 2H), 3.86 (s, 3H), 2.35-2.16 (m, 7H), 2.07-1.87 (m, 3H), 1.64-1.53 (m, 1H).

Example 7

3-[4-(1-Amino-cyclobutyl)-phenyl]-7-methoxy-6-methyl-2-phenyl-chromen-4-one

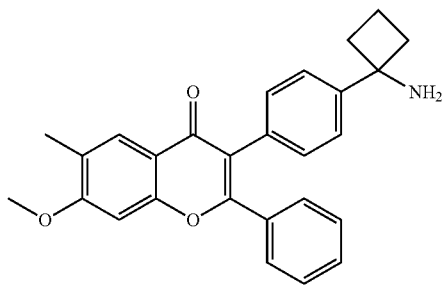 [SMILES: COc1cc2oc(-c3ccccc3)c(-c3ccc(C4(N)CCC4)cc3)c(=O)c2cc1C]

Step 1: 1-(2,4-Dimethoxy-5-methyl-phenyl)-3-phenyl-prop-2-yn-1-ol: Following the procedure used to prepare 1-(5-fluoro-2-methoxy-phenyl)-3-phenyl-prop-2-yn-1-ol, 2,4-dimethoxy-5-methyl-benzaldehyde (1.00 g, 5.55 mmol) was reacted to give the title compound (1.39 g, 89%). ¹H NMR (400 MHz, DMSO-d6): δ 7.43-7.30 (m, 6H), 6.61 (s, 1H), 5.79-5.70 (m, 2H), 3.83 (s, 3H), 3.82 (s, 3H), 2.09 (s, 3H).

Step 2: 1-(2,4-Dimethoxy-5-methyl-phenyl)-3-phenyl-propynone: Following the procedure used to prepare 1-(5-fluoro-2-methoxy-phenyl)-3-phenyl-propynone, 1-(2,4-dimethoxy-5-methyl-phenyl)-3-phenyl-prop-2-yn-1-ol (1.39 g, 4.92 mmol) was reacted to give the title compound (1.21 g, 88%). ¹H NMR (400 MHz, DMSO-d6): δ 7.76-7.74 (m, 1H), 7.71-7.67 (m, 2H), 7.59-7.48 (m, 3H), 6.73 (s, 1H), 3.97 (s, 3H), 3.95 (s, 3H), 2.14-2.11 (m, 3H).

Step 3: 3-Iodo-7-methoxy-6-methyl-2-phenyl-chromen-4-one: Following the procedure used to prepare 6-fluoro-3-iodo-2-phenyl-chromen-4-one, 1-(2,4-dimethoxy-5-methyl-phenyl)-3-phenyl-propynone (1.21 g, 4.32 mmol) was reacted to give the title compound (1.27 g, 75%). ¹H NMR (400 MHz, DMSO-d6): δ 7.85-7.83 (m, 1H), 7.80-7.75 (m, 2H), 7.60-7.56 (m, 3H), 7.20 (s, 1H), 3.92 (s, 3H), 2.27-2.25 (m, 3H).

Step 4: {1-[4-(7-Methoxy-6-methyl-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-7-methoxy-6-methyl-2-phenyl-chromen-4-one (78 mg, 0.20 mmol) was reacted to give the title compound (46 mg, 47%). ¹H NMR (400 MHz, CDCl₃): δ 8.20-7.98 (m, 1H), 7.44-7.15 (m, 9H), 6.86 (s, 1H), 5.05 (s, 1H), 3.94 (s, 3H), 2.61-2.44 (m, 4H), 2.33-2.28 (m, 3H), 2.14-1.98 (m, 1H), 1.91-1.75 (m, 1H), 1.49-1.12 (m, 9H).

Step 5: 3-[4-(1-Amino-cyclobutyl)-phenyl]-7-methoxy-6-methyl-2-phenyl-chromen-4-one: Following the procedure used to prepare 3-[4-(1-amino-cyclobutyl)-phenyl]-6-fluoro-2-phenyl-chromen-4-one, {1-[4-(7-methoxy-6-methyl-4-oxo-2-phenyl-4H-chromen-3-yl)-phenyl]-cyclobutyl}-carbamic acid tert-butyl ester (46 mg, 0.090 mmol) was reacted to give the title compound (34 mg, 92%). LCMS (Method E): R_T=3.85 min, [M+H]⁺=412. ¹H NMR (400 MHz, DMSO-d6): δ 7.80 (s, 1H), 7.38-7.25 (m, 7H), 7.18 (s, 1H), 7.05 (d, J=9.6 Hz, 2H), 3.90 (s, 3H), 2.35-2.26 (m, 2H), 2.25-2.10 (m, 5H), 2.06-1.87 (m, 3H), 1.64-1.53 (m, 1H).

Example 8

7-[4-(1-Amino-cyclobutyl)-phenyl]-6-Phenyl-2,3-dihydro-1,4,5-trioxa-anthracen-8-one

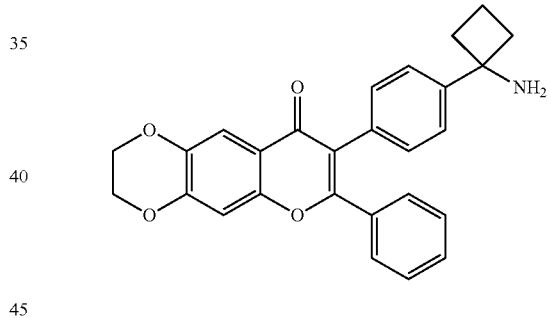

Step 1: 1-(7-Methoxy-2,3-dihydro-benzo[1,4]dioxin-6-yl)-3-phenyl-prop-2-yn-1-ol: Following the procedure used to prepare 1-(5-fluoro-2-methoxy-phenyl)-3-phenyl-prop-2-yn-1-ol, 7-methoxy-2,3-dihydro-benzo[1,4],dioxine-6-carbaldehyde (1.03 g, 5.32 mmol) was reacted to give the title compound (1.40 g, 89%). ¹H NMR (400 MHz, DMSO-d6): δ 7.43-7.34 (m, 5H), 7.05 (s, 1H), 6.54 (s, 1H), 5.86-5.83 (d, 1H), 5.70-5.66 (d, 1H), 4.25-4.16 (m, 4H), 3.73 (s, 3H).

Step 2: 1-(7-Methoxy-2,3-dihydro-benzo[1,4]clioxin-6-yl)-3-phenyl-propynone: Following the procedure used to prepare 1-(5-fluoro-2-methoxy-phenyl)-3-phenyl-propynone, 1-(7-methoxy-2,3-dihydro-benzo[1,4]dioxin-6-yl)-3-phenyl-prop-2-yn-1-ol (1.40 g, 4.72 mmol) was reacted to give the title compound (1.25 g, 90%). ¹H NMR (400 MHz, DMSO-d6): δ 7.70-7.65 (m, 2H), 7.59-7.74 (m, 3H), 7.42 (s, 1H), 6.73 (s, 1H), 4.38-4.34 (m, 2H), 4.27-4.23 (m, 2H), 3.86 (s, 3H).

Step 3: 7-Iodo-6-phenyl-2,3-dihydro-1,4,5-trioxa-anthracen-8-one: Following the procedure used to prepare 6-fluoro-3-iodo-2-phenyl-chromen-4-one, 1-(7-methoxy-2,3-dihydro-benzo[1,4]dioxin-6-yl)-3-phenyl-propynone (1.25 g, 4.25 mmol) was reacted to give the title compound (1.57 g, 91%). $^1$H NMR (400 MHz, DMSO-d6): δ 7.80-7.73 (m, 2H), 7.62-7.55 (m, 3H), 7.42 (s, 1H), 7.22 (s, 1H), 4.46-4.32 (m, 4H).

Step 4: {1-[4-(8-Oxo-6-phenyl-2,3-dihydro-8H-1,4,5-trioxa-anthracen-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-iodo-6-phenyl-2,3-dihydro-1,4,5-trioxa-anthracen-8-one (91 mg, 0.225 mmol) was reacted to give the title compound (65 mg, 55%). $^1$H NMR (400 MHz, CDCl$_3$): δ 7.72 (s, 1H), 7.43-7.14 (m, 9H), 7.00 (s, 1H), 5.03 (s, 1H), 4.43-4.30 (m, 4H), 2.64-2.43 (m, 4H), 2.14-1.98 (m, 1H), 1.91-1.63 (m, 1H), 1.50-1.14 (m, 9H).

Step 5: 7-[4-(1-Amino-cyclobutyl)-phenyl]-6-phenyl-2,3-dihydro-1,4,5-trioxa-anthracen-8-one: Following the procedure used to prepare 3-[4-(1-amino-cyclobutyl)-6-fluoro-2-phenyl-chromen-4-one, {1-[4-(8-oxo-6-phenyl-2,3-dihydro-8H-1,4,5-trioxa-anthracen-7-yl)-phenyl]-cyclobutyl}-carbamic acid tert-butyl ester (65 mg, 0.124 mmol) was reacted to give the title compound (27 mg, 51%). LCMS (Method E): R$_T$=3.62 min, [M+H]$^+$=426. $^1$H NMR (400 MHz, DMSO-d6): δ 7.38 (s, 1H), 7.36-7.23 (m, 7H), 7.19 (s, 1H), 7.04 (d, J=8.6 Hz, 2H), 4.39-4.34 (m, 2H), 4.33-4.28 (m, 2H), 2.36-2.13 (m, 4H), 2.06-1.87 (m, 3H), 1.64-1.53 (m, 1H).

Example 9

3-[4-(1-Amino-cyclobutyl)-phenyl]-8-bromo-7-methoxy-2-phenyl-chromen-4-one

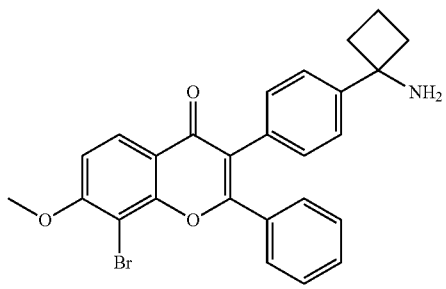 [SMILES: COc1ccc2c(=O)c(-c3ccc(C4(N)CCC4)cc3)c(-c3ccccc3)oc2c1Br]

Step 1: 1-(3-Bromo-2,4-dimethoxy-phenyl)-3-phenyl-prop-2-yn-1-ol: Following the procedure used to prepare 1-(5-fluoro-2-methoxy-phenyl)-3-phenyl-prop-2-yn-1-ol, 3-bromo-2,4-dimethoxy-benzaldehyde (0.80 g, 3.26 mmol) [prepared as described in Helv. Chim, Acta, 1990, 73, 48], was reacted to give the title compound (0.67 g, 59%). $^1$H NMR (400 MHz, DMSO-d6): δ 7.67-7.62 (d, 1H), 7.45-7.35 (m, 5H), 7.01-6.96 (d, 1H), 6.14-6.11 (d, 1H), 5.78-5.74 (d, 1H), 3.88-3.84 (m, 6H).

Step 2: 1-(3-Bromo-2,4-dimethoxy-phenyl)-3-phenyl-propynone: Following the procedure used to prepare 1-(5-fluoro-2-methoxy-phenyl)-3-phenyl-propynone, 1-(3-bromo-2,4-dimethoxy-phenyl)-3-phenyl-prop-2-yn-1-ol (0.67 g, 1.93 mmol) was reacted to give the title compound (0.67 g, 100%). $^1$H NMR (400 MHz, DMSO-d6): δ 8.17-8.13 (d, 1H), 7.77-7.72 (m, 2H), 7.62-7.50 (m, 3H), 7.15-7.11 (d, 1H), 3.98 (s, 3H), 3.88 (s, 3H).

Step 3: 8-Bromo-3-iodo-7-methoxy-2-phenyl-chromen-4-one: Following the procedure used to prepare 6-fluoro-3-iodo-2-phenyl-chromen-4-one, 1-(3-bromo-2,4-dimethoxy-phenyl)-3-phenyl-propynone (0.67 g, 1.93 mmol) was reacted to give the title compound (0.80 g, 90%). $^1$H NMR (400 MHz, DMSO-d6): 8.13-8.09 (1H, d), 7.89-7.83 (2H, m), 7.65-7.57 (3H, m), 7.40-7.36 (1H, d), 4.03 (3H, s).

Step 4: {1-[4-(8-Bromo-7-methoxy-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 8-bromo-3-iodo-7-methoxy-2-phenyl-chromen-4-one (198 mg, 0.434 mmol) was reacted to give the title compound (100 mg, 40%). $^1$H NMR (400 MHz, CDCl$_3$): δ 8.27-8.22 (d, 1H), 7.53-7.19 (m, 9H), 7.08-7.03 (d, 1H), 5.06 (s, 1H), 4.06 (s, 3H), 2.58-1.76 (m, 6H), 1.46-1.18 (m, 9H).

Step 5: 3-[4-(1-Amino-cyclobutyl)-phenyl]-8-bromo-7-methoxy-2-phenyl-chromen-4-one: Following the procedure used to prepare 3-[4-(1-amino-cyclobutyl)-phenyl]-6-fluoro-2-phenyl-chromen-4-one, {1-[4-(8-bromo-7-methoxy-4-oxo-2-phenyl-4H-chromen-3-yl)-phenyl]-cyclobutyl}-carbamic acid tert-butyl ester (20 mg, 0.035 mmol) was reacted to give the title compound (13 mg, 78%). LCMS (Method E): R$_T$=3.93 min, [M+H]$^+$=476/478. $^1$H NMR (400 MHz, DMSO-d6): δ 8.05 (d, J=8.7 Hz, 1H), 7.42-7.26 (m, 8H), 7.09 (d, J=7.8 Hz, 2H), 3.99 (s, 3H), 2.56 (bs, 2H), 2.37-2.25 (m, 2H), 2.10-1.87 (m, 3H), 1.66-1.53 (m, 1H).

Example 10

3-[4-(1-Amino-cyclobutyl)-phenyl]-7-methoxy-4-oxo-2-phenyl-4H-chromene-6-carboxylic acid amide

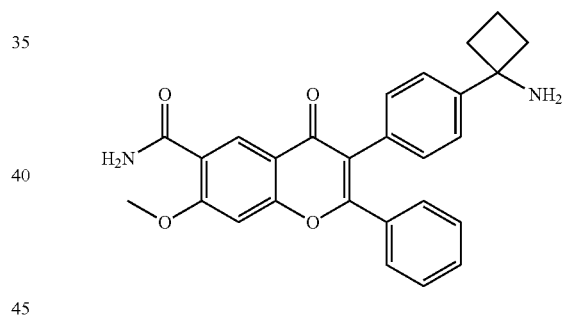

Step 1: {1-[4-(6-Carbamoyl-7-methoxy-4-oxo-2-phenyl-4H-chromen-3-yl)-phenyl]-cyclobutyl}-carbamic acid tert-butylester: Following the procedure used to prepare 3-[4-(1-amino-cyclobutyl)-phenyl]-4-oxo-2-phenyl-4H-chromene-7-carboxylic acid amide, {1-[4-(6-bromo-7-methoxy-4-oxo-2-phenyl-4H-chromen-3-yl)-phenyl]-cyclobutyl}-carbamic acid tert-butyl ester (115 mg, 0.20 mmol) was reacted to give the title compound (40 mg, 37%). LCMS (Method B): R$_T$=4.58 min, [M+H]$^+$=541.

Step 2: 3-[4-(1-Amino-cyclobutyl)-phenyl]-7-methoxy-4-oxo-2-phenyl-4H-chromene-6-carboxylic acid amide: Following the procedure used to prepare 3-[4-(1-amino-cyclobutyl)-phenyl]-6-fluoro-2-phenyl-chromen-4-one, {1-[4-(6-carbamoyl-7-methoxy-4-oxo-2-phenyl-4H-chromen-3-yl)-phenyl]-cyclobutyl}-carbamic acid tert-butylester (40 mg, 0.074 mmol) was reacted to give the title compound (19 mg, 58%). LCMS (Method E): R$_T$=3.15 min, [M+H]$^+$=441. $^1$H NMR (400 MHz, DMSO-d6): δ 8.44 (s, 1H), 7.68 (d, J=7.7 Hz, 2H), 7.41-7.26 (m, 8H), 7.10 (d, J=8.3 Hz, 2H), 3.98 (s, 3H), 3.27 (s, 2H), 2.39-2.29 (m, 2H), 2.11-2.02 (m, 2H), 2.00-1.89 (m, 1H), 1.67-1.55 (m, 1H).

Example 11

3-[4-(1-Amino-cyclobutyl)-phenyl]-7-methoxy-4-oxo-2-phenyl-4H-chromene-6-carbonitrile

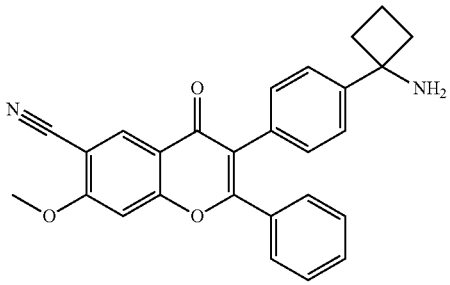 [SMILES: COc1cc2oc(-c3ccccc3)c(-c3ccc(C4(N)CCC4)cc3)c(=O)c2cc1C#N]

Step 1: {1-[4-(6-Cyano-7-methoxy-4-oxo-2-phenyl-4H-chromen-3-yl)-phenyl]-cyclobutyl}-carbamic acid tert-butyl ester: Following the procedure used to prepare {1-[4-(6-cyano-4-oxo-2-phenyl-4H-chromen-3-yl)-phenyl]-cyclobutyl}-carbamic acid tert-butyl ester, {1-[4-(6-bromo-7-methoxy-4-oxo-2-phenyl-4H-chromen-3-yl)-phenyl]-cyclobutyl}-carbamic acid tert-butyl ester (115 mg, 0.20 mmol) was reacted to give the title compound (81 mg, 77%). $^1$H NMR (400 MHz, CDCl$_3$): δ 8.53 (s, 1H), 7.45-7.14 (m, 9H), 7.00 (s, 1H), 5.05 (s, 1H), 4.05 (s, 3H), 2.60-2.39 (m, 4H), 2.16-2.00 (m, 1H), 1.92-1.77 (m, 1H), 1.56-1.14 (m, 9H).

Step 2: 3-[4-(1-Amino-cyclobutyl)-phenyl]-7-methoxy-4-oxo-2-phenyl-4H-chromene-6-carbonitrile: Following the procedure used to prepare 3-[4-(1-amino-cyclobutyl)-phenyl]-6-fluoro-2-phenyl-chromen-4-one, {1-[4-(6-cyano-7-methoxy-4-oxo-2-phenyl-4H-chromen-3-yl)-phenyl]-cyclobutyl}-carbamic acid tert-butyl ester (81 mg, 0.155 mmol) was reacted to give the title compound (39 mg, 60%). LCMS (Method E): R$_T$=3.57 min, [M+H]$^+$=423. $^1$H NMR (400 MHz, DMSO-d6): δ 8.36 (s, 1H), 7.53 (s, 1H), 7.41-7.26 (m, 7H), 7.09 (d, J=8.1 Hz, 2H), 4.01 (s, 3H), 2.85 (bs, 2H), 2.37-2.27 (m, 2H), 2.10-1.88 (m, 3H), 1.66-1.54 (m, 1H).

Example 12

3-[4-(1-Amino-cyclobutyl)-phenyl]-7-methoxy-4-oxo-2-phenyl-4H-chromene-8-carbonitrile

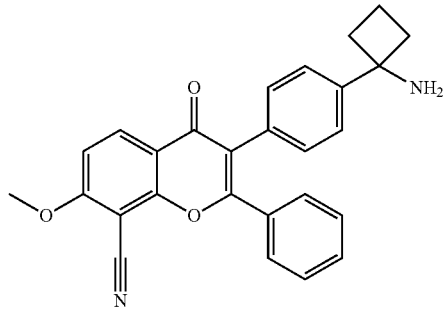 [SMILES: COc1ccc2c(=O)c(-c3ccc(C4(N)CCC4)cc3)c(-c3ccccc3)oc2c1C#N]

Step 1: {1-[4-(8-Cyano-7-methoxy-4-oxo-2-phenyl-4H-chromen-3-yl)-phenyl]-cyclobutyl}-carbamic acid tert-butyl ester: Following the procedure used to prepare {1-[4-(6-cyano-4-oxo-2-phenyl-4H-chromen-3-yl)-phenyl]-cyclobutyl}-carbamic acid tert-butyl ester, {1-[4-(8-bromo-7-methoxy-4-oxo-2-phenyl-4H-chromen-3-yl)-phenyl]-cyclobutyl}-carbamic acid tert-butyl ester (150 mg, 0.0867 mmol) was reacted to give the title compound (15 mg, 33%). LCMS (Method B): R$_T$=4.79 min, [M+H]$^+$=523.

Step 2: 3-[4-(1-Amino-cyclobutyl)-phenyl]-7-methoxy-4-oxo-2-phenyl-4H-chromene-8-carbonitrile: Following the procedure used to prepare 3-[4-(1-amino-cyclobutyl)-phenyl]-6-fluoro-2-phenyl-chromen-4-one, {1-[4-(8-cyano-7-methoxy-4-oxo-2-phenyl-4H-chromen-3-yl)-phenyl]-cyclobutyl}-carbamic acid tert-butyl ester (15 mg, 0.0287 mmol) was reacted to give the title compound (5.2 mg, 43%). LCMS (Method E): R$_T$=3.47 min, M+H$^+$=423. $^1$H NMR (400 MHz, CDCl$_3$): δ 8.43 (d, J=9.3 Hz, 1H), 7.49-7.44 (m, 2H), 7.41-7.33 (m, 3H), 7.29 (d, J=7.4 Hz, 2H), 7.20 (d, J=7.4 Hz, 2H), 7.08 (d, J=9.0 Hz, 2H), 4.11 (s, 3H), 2.61-2.51 (m, 2H), 2.23-2.02 (m, 3H), 1.83-1.64 (m, 1H).

Example 13

3-[4-(1-Amino-cyclobutyl)-phenyl]-2-phenyl-7-bromo-chromen-4-one

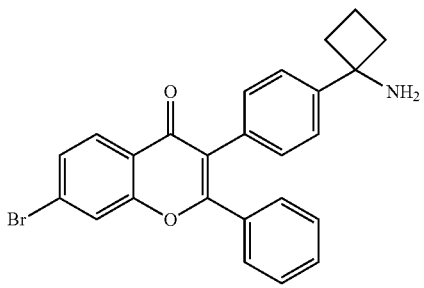 [SMILES: NC1(c2ccc(-c3c(-c4ccccc4)oc4cc(Br)ccc4c3=O)cc2)CCC1]

Step 1: 1-(4-Bromo-2-methoxy-phenyl)-3-phenyl-prop-2-yn-1-ol: Following the procedure used to prepare 1-(5-fluoro-2-methoxy-phenyl)-3-phenyl-prop-2-yn-1-ol, 2-methoxy-4-bromobenzaldehyde was reacted to give the title compound as a pale yellow oil (1.43 g, 96%). LCMS (Method B): R$_T$=4.53 min, [M+H]$^+$=299/301.

Step 2: 1-(4-Bromo-2-methoxy-phenyl)-3-phenyl-propynone: Following the procedure used to prepare 1-(5-fluoro-2-methoxy-phenyl)-3-phenyl-propynone, 1-(4-bromo-2-methoxy-phenyl)-3-phenyl-prop-2-yn-1-ol was reacted to give the title compound as a pale yellow oil (1.25 g, 88%). LCMS (Method B): R$_T$=4.65 min, [M+H]$^+$=315/317.

Step 3: 7-Bromo-3-iodo-2-phenyl-chromen-4-one: Following the procedure used to prepare 6-fluoro-3-iodo-2-phenyl-chromen-4-one, 1-(4-bromo-2-methoxy-phenyl)-3-phenyl-propynone was reacted to give the title compound as an off-white solid (1.58 g, 95%). LCMS (Method B): R$_T$=4.73 min, [M+H]$^+$=427/429.

Step 4: {1-[4-(7-Bromo-4-oxo-2-phenyl-4H-chromen-3-yl)-phenyl]-cyclobutyl}-carbamic acid tert-butyl ester: 7-Bromo-3-iodo-2-phenyl-chromen-4-one (320 mg, 0.75 mmol), {1-[4-(4,4,5,5-tetramethyl-[1,3,2]dioxaborolan-2-yl)-phenyl]-cyclobutyl}-carbamic acid tert-butyl ester (295 mg, 0.8 mmol), tetrakis(triphenyphosphine)palladium (0) (87 mg, 0.075 mmol) and sodium carbonate (159 mg, 1.5 mmol) were suspended in DME (10 mL) and water (5 mL) in a microwave vial. The vial was sealed, evacuated and flushed twice with nitrogen. The reaction mixture was heated in a microwave at 125° C. for 15 min. The resulting mixture was partitioned between ethyl acetate (40 mL) and water (20 mL) and the phases separated. The organic layer was washed with brine (20 mL), dried (Na$_2$SO$_4$), filtered and concentrated in vacuo. The resulting residue was subjected to flash chromatography (SiO$_2$, 20% ethyl acetate in cyclohexane) to give the title compound as a pale yellow foam (200 mg, 49%). LCMS (Method A): R$_T$=5.45 min, [M+H]$^+$=546/548.

Step 5: 3-[4-(1-Amino-cyclobutyl)-phenyl]-2-phenyl-7-bromo-chromen-4-one: 3-[4-(1-Following the procedure used to prepare 3-[4-(1-amino-cyclobutyl)-phenyl]-6-fluoro- 2-phenyl-chromen-4-one, {1-[4-(7-bromo-4-oxo-2-phenyl-4H-chromen-3-yl)-phenyl]-cyclobutyl}-carbamic acid tert-butyl ester was reacted to give the title compound as a pale yellow solid (22 mg, 77%). $^1$H NMR (400 MHz, DMSO-d6): δ 8.09 (d, J=2 Hz, 1H), 8.03 (d, J=8 Hz, 1H), 7.71 (dd, J=2 and 8 Hz, 1H), 7.45-31 (m, 7H), 7.15-7.11 (m, 2H), 2.40-2.32 (m, 2H), 2.12-2.04 (m, 2H), 2.04-1.94 (m, 1H), 1.69-1.60 (m, 1H). LCMS (Method F): $R_T$=10.10 min, [M+H]$^+$=446/448.

Example 14

3-[4-(1-Amino-cyclobutyp-phenyl]-7-methoxy-2-phenyl-chromen-4-one

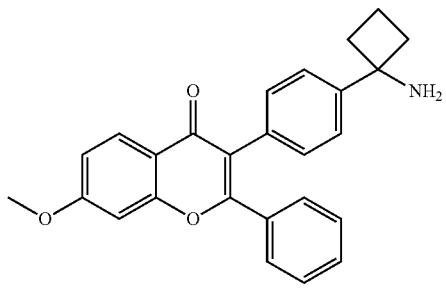 [SMILES: COc1ccc2c(=O)c(-c3ccc(C4(N)CCC4)cc3)c(-c3ccccc3)oc2c1]

Step 1: {1-[4-(7-Methoxy-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-7-methoxy-2-phenyl-chromen-4-one was reacted to give the title compound (80 mg, 100%) as a colourless oil. LCMS (Method A) $R_T$=4.88 min, [M+H]$^+$=498.

Step 2: 3-[4-(1-Amino-cyclobutyl)-phenyl]-7-methoxy-2-phenyl-chromen-4-one: Following the procedure used to prepare 3-[4-(1-amino-cyclobutyl)-phenyl]-6-fluoro-2-phenyl-chromen-4-one, {1-[4-(7-methoxy-4-oxo-2-phenyl-4H-chromen-3-yl)-phenyl]-cyclobutyl}-carbamic acid tert-butyl ester was reacted to give the title compound as an off-white solid (50 mg, 84%). $^1$H NMR (400 MHz, CDCl$_3$): δ 8.19 (d, J=9 Hz, 1H), 7.41-7.38 (m, 2H), 7.36-7.31 (m, 3H), 7.29-7.24 (m, 2H), 7.21-7.17 (m, 2H), 7.00 (dd, J=2 and 9 Hz, 1H), 6.93 (d, J=2 Hz, 1H), 3.93 (s, 3H), 2.59-2.51 (m, 2H), 2.20-2.10 (m, 2H), 2.10-2.01 (m, 1H), 1.80-1.70 (m, 1H). LCMS (Method F): $R_T$=9.26 min, [M+H]$^+$=398.

Example 15

3-[4-(1-Amino-cyclobutyl)-phenyl]-6,7-dimethoxy-2-phenyl-chromen-4-one

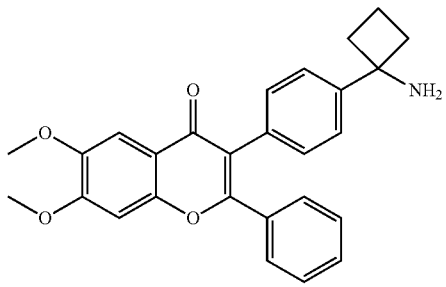 [SMILES: COc1cc2oc(-c3ccccc3)c(-c3ccc(C4(N)CCC4)cc3)c(=O)c2cc1OC]

Step 1: 3-Phenyl-1-(2,4,5-trimethoxy-phenyl)-prop-2-yn-1-ol: Following the procedure used to prepare 1-(5-fluoro-2-methoxy-phenyl)-3-phenyl-prop-2-yn-1-ol, 2,4,5-trimethoxybenzaldehyde was reacted to give the title compound as an off-white solid (535 mg, 90%). LCMS (Method B): $R_T$=3.99 min, [M+Na]$^+$=321.

Step 2: 3-Phenyl-1-(2,4,5-trimethoxy-phenyl)-propynone: Following the procedure used to prepare 1-(5-fluoro-2-methoxy-phenyl)-3-phenyl-propynone, 3-phenyl-1-(2,4,5-trimethoxy-phenyl)-prop-2-yn-1-ol was reacted to give the title compound as a yellow solid (503 mg, 95%). LCMS (Method B): $R_T$=3.68 min, [M+Na]$^+$=297.

Step 3: 3-Iodo-6,7-dimethoxy-2-phenyl-chromen-4-one: Following the procedure used to prepare 6-fluoro-3-iodo-2-phenyl-chromen-4-one, 3-phenyl-1-(2,4,5-trimethoxy-phenyl)-propynone was reacted to give the title compound as an off-white solid (597 mg, 87%). LCMS (Method B): $R_T$=3.86 min, [M+H]$^+$=409.

Step 4: {1-[4-(6,7-Dimethoxy-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-6,7-dimethoxy-2-phenyl-chromen-4-one was reacted to give the title compound as a white solid (68 mg, 86%). LCMS (Method B): $R_T$=4.81 min, [M+H]$^+$=528.

Step 5: 3-[4-(1-Amino-cyclobutyl)-phenyl]-6,7-dimethoxy-2-phenyl-chromen-4-one: Following the procedure used to prepare 3-[4-(1-amino-cyclobutyl)-phenyl]-6-fluoro-2-phenyl-chromen-4-one, {1-[4-(6,7-dimethoxy-4-oxo-2-phenyl-4H-chromen-3-yl)-phenyl]-cyclobutyl}-carbamic acid tert-butyl ester was reacted to give the title compound as a white solid (48 mg, 94%). $^1$H NMR (400 MHz, DMSO-d6): δ 7.42-7.29 (m, 9H), 7.13-7.09 (m, 2H), 3.93 (s, 3H), 3.88 (s, 3H), 2.40-2.33 (m, 2H), 2.11-2.02 (m, 2H), 2.02-1.95 (m, 1H), 1.69-1.60 (m, 1H). LCMS (Method F): $R_T$=8.99 min, [M+H]$^+$=428.

Example 16

3-[4-(1-Amino-cyclobutyl)-phenyl]-8-methoxy-2-phenyl-chromen-4-one

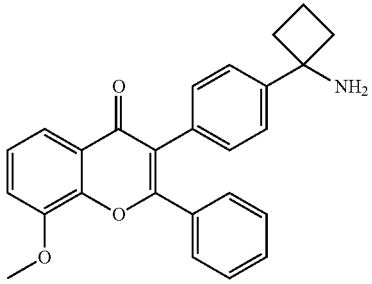 [SMILES: COc1cccc2c(=O)c(-c3ccc(C4(N)CCC4)cc3)c(-c3ccccc3)oc12]

Step 1: 3-Phenyl-1-(2,3-dimethoxy-phenyl)-prop-2-yn-1-ol: Following the procedure used to prepare 1-(5-fluoro-2-methoxy-phenyl)-3-phenyl-prop-2-yn-1-ol, 2,3-dimethoxybenzaldehyde was reacted to give the title compound as a colourless oil (352 mg, 66%). LCMS (Method B): $R_T$=4.09 min, [M+Na]$^+$=291.

Step 2: 3-Phenyl-1-(2,3-dimethoxy-phenyl)-propynone: Following the procedure used to prepare 1-(5-fluoro-2-methoxy-phenyl)-3-phenyl-propynone, 3-phenyl-1-(2,3-dimethoxy-phenyl)-prop-2-yn-1-ol was reacted to give the title compound as a yellow oil (334 mg, 97%). LCMS (Method B): $R_T$=4.31 min, [M+Na]$^+$=289.

Step 3: 3-Iodo-8-methoxy-2-phenyl-chromen-4-one: Following the procedure used to prepare 6-fluoro-3-iodo-2-phenyl-chromen-4-one, 3-phenyl-1-(2,3-dimethoxy-phenyl)-propynone was reacted to give the title compound as a pale yellow solid (365 mg, 78%). LCMS (Method B): $R_T$=4.35 min, [M+H]$^+$=379.

Step 4: {1-[4-(8-Methoxy-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-8-methoxy-2-phenyl-chromen-4-one was reacted to give the title compound as a white solid (73 mg, 98%). LCMS (Method B): $R_T$=4.84 min, [M+H]$^+$=498.

Step 5: 3-[4-(1-Amino-cyclobutyl)-phenyl]-8-methoxy-2-phenyl-chromen-4-one: Following the procedure used to prepare 3-[4-(1-amino-cyclobutyl)-phenyl]-6-fluoro-2-phenyl-chromen-4-one, {1-[4-(8-methoxy-4-oxo-2-phenyl-4H-chromen-3-yl)-phenyl]-cyclobutyl}-carbamic acid tert-butyl ester was reacted to give the title compound as a white solid (46 mg, 83%). $^1$H NMR (400 MHz, DMSO-d6): δ 7.64 (dd, J=2 and 8 Hz, 1H), 7.50-7.32 (m, 9H), 7.14-7.11 (m, 2H), 3.98 (s, 3H), 2.40-2.32 (m, 2H), 2.11-2.03 (m, 2H), 2.03-1.94 (m, 1H), 1.69-1.60 (m, 1H). LCMS (Method F): $R_T$=8.94 min, [M+H]$^+$=398.

Example 17

3-[4-(1-Amino-cyclobutyl)-phenyl]-2-phenyl-7-(2H-pyrazol-3-ylchromen-4-one

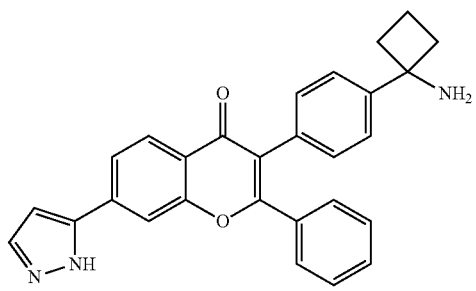 [SMILES: NC1(c2ccc(-c3c(-c4ccccc4)oc4cc(-c5ccn[nH]5)ccc4c3=O)cc2)CCC1]

Step 1: (1-{4-[4-oxo-2-phenyl-7-(2H-pyrazol-3-yl)-4H-chromen-3-yl]-phenyl}-cyclobutyl)-carbamic acid tert-butyl ester: {1-[4-(7-Bromo-4-oxo-2-phenyl-4H-chromen-3-yl)-phenyl]-cyclobutyl}-carbamic acid tert-butyl ester (81 mg, 0.15 mmol), 1H-pyrazole-5-boronic acid (22 mg, 0.2 mmol), tetrakis(triphenylphosphine)palladium (0) (17 mg, 0.015 mmol) and sodium carbonate (32 mg, 0.30 mmol) were suspended in DME (2 mL) and water (1 mL) in a microwave vial. The vial was sealed, evacuated and flushed twice with nitrogen. The mixture was heated in a microwave at 150° C. for 25 min. The resulting mixture was partitioned between ethyl acetate (40 mL) and water (20 mL) and the phases were separated. The organic layer was washed with brine (20 mL), dried (Na$_2$SO$_4$), filtered and concentrated in vacuo. The resulting residue was subjected to flash chromatography (SiO$_2$, 40% ethyl acetate in cyclohexane) to give the title compound as a pale brown oil (36 mg, 45%). LCMS (Method B): $R_T$=4.82 min, [M+H]$^+$=534.

Step 2: 3-[4-(1-Amino-cyclobutyl)-phenyl]-2-phenyl-7-(2H-pyrazol-3-yl)-chromen-4-one: Following the procedure used to prepare 3-[4-(1-amino-cyclobutyl)-phenyl]-6-fluoro-2-phenyl-chromen-4-one, (1-{-4-[4-oxo-2-phenyl-7-(2H-pyrazol-3-yl)-4H-chromen-3-yl]-phenyl}-cyclobutyl)-carbamic acid tert-butyl ester was reacted to give the title compound as a cream solid (27 mg, 92%). $^1$H NMR (400 MHz, DMSO-d6): δ 13.36-13.12 (br s, 1H), 8.14-8.11 (m, 2H), 8.05-8.00 (m, 1H), 7.90-7.83 (br s, 1H), 7.48-7.33 (m, 7H), 7.21-7.17 (m, 2H), 7.00 (d, J=3 Hz, 1H), 2.47-2.39 (m, 2H), 2.24-2.15 (m, 2H), 2.08-1.97 (m, 1H), 1.73-1.64 (m, 1H). LCMS (Method F): $R_T$=8.99 min, [M+H]$^+$=434.

Example 18

3-[4-(1-Amino-cyclobutyl)-phenyl]-4-oxo-2-phenyl-4H-chromene-7-carboxylic acid amide

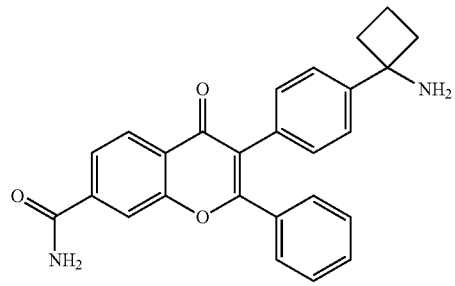 [SMILES: NC(=O)c1ccc2c(=O)c(-c3ccc(C4(N)CCC4)cc3)c(-c3ccccc3)oc2c1]

Step 1: {1-[4-(7-Carbamoyl-4-oxo-2-phenyl-4H-chromen-3-yl)-phenyl]-cyclobutyl}-carbamic acid tert-butyl ester: To a solution of {1-[4-(7-bromo-4-oxo-2-phenyl-4H-chromen-3-yl)-phenyl]-cyclobutyl}-carbamic acid tert-butyl ester (81 mg, 0.15 mmol) in 1,4-dioxane (3.0 mL) in a microwave vial was added hydroxylamine hydrochloride (21 mg, 0.3 mmol), molybdenum hexacarbonyl (20 mg, 0.075 mmol), Herrmann's catalyst (7 mg, 0.0075 mmol) and tri-tert-butylphosphine tetrafluoroborate (4 mg, 0.015 mmol), followed by DBU (22 μL, 0.15 mmol) and DIPEA (51 μL, 0.30 mmol). The vial was sealed, evacuated and flushed twice with nitrogen. The mixture was heated in a microwave at 150° C. for 30 min. The resulting mixture was partitioned between ethyl acetate (40 mL) and water (20 mL) and the phases were separated. The organic layer was washed with brine (20 mL), dried (Na$_2$SO$_4$), filtered and concentrated in vacuo. The resulting residue was subjected to flash chromatography (SiO$_2$, gradient 50-60% ethyl acetate in cyclohexane) to afford the title compound as a white solid (46 mg, 60%). LCMS (Method B): $R_T$=4.57 min, [M+H]$^+$=511.

Step 2: 3-[4-(1-Amino-cyclobutyl)-phenyl]-4-oxo-2-phenyl-4H-chromene-7-carboxylic acid Amide: Following the procedure used to prepare 3-[4-(1-amino-cyclobutyl)-phenyl]-6-fluoro-2-phenyl-chromen-4-one, {1-[4-(7-carbamoyl-4-oxo-2-phenyl-4H-chromen-3-yl)-phenyl]-cyclobutyl}-carbamic acid tert-butyl ester was reacted to give the title compound as a cream solid (26 mg, 70%). $^1$H NMR (400 MHz, DMSO-d6): δ 8.30-8.26 (br s, 1H), 8.21 (d, J=2 Hz, 1H), 8.17 (d, J=8 Hz, 1H), 7.98 (dd, J=2 and 8 Hz, 1H), 7.74-7.71 (br s, 1H), 7.47-7.33 (m, 7H), 7.19-7.15 (m, 2H), 2.44-2.36 (m, 2H), 2.19-2.11 (m, 2H), 2.07-1.96 (m, 1H), 1.72-1.62 (m, 1H). LCMS (Method F): $R_T$=8.99 min, [M+H]$^+$=434.

Example 19

3-[4-(1-Amino-cyclobutyl)-phenyl]-6-bromo-2-phenyl-chromen-4-one

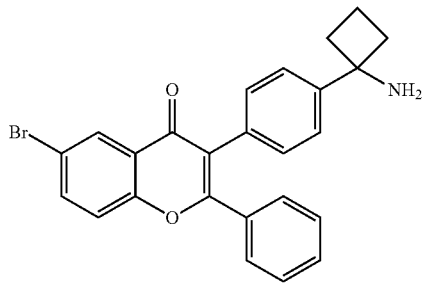 [SMILES: NC1(c2ccc(-c3c(-c4ccccc4)oc4ccc(Br)cc4c3=O)cc2)CCC1]

Step 1: 1-(5-Bromo-2-methoxy-phenyl)-3-phenyl-prop-2-yn-1-ol: Following the procedure used to prepare 1-(5-fluoro-2-methoxy-phenyl)-3-phenyl-prop-2-yn-1-ol, 2-methoxy-5-bromobenzaldehyde was reacted to give the title compound as a colourless oil (440 mg, 69%). LCMS (Method B): $R_T$=4.47 min, [M−OH+H]$^+$=299/301.

Step 2: 1-(5-Bromo-2-methoxy-phenyl)-3-phenyl-propynone: Following the procedure used to prepare 1-(5-fluoro-2-methoxy-phenyl)-3-phenyl-propynone, 1-(5-bromo-2-methoxy-phenyl)-3-phenyl-prop-2-yn-1-ol was reacted to give the title compound as a pale yellow solid (411 mg, 95%). LCMS (Method B): $R_T$=4.20 min, [M+Na]$^+$=337/339.

Step 3: 6-Bromo-3-iodo-2-phenyl-chromen-4-one: Following the procedure used to prepare 6-fluoro-3-iodo-2-phenyl-chromen-4-one, 1-(5-bromo-2-methoxy-phenyl)-3-phenyl-propynone was reacted to give the title compound as an off-white solid (520 mg, 94%). LCMS (Method B): $R_T$=4.24 min, [M+H]$^+$=427/429.

Step 4: {1-[4-(6-Bromo-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 6-bromo-3-iodo-2-phenyl-chromen-4-one was reacted to give the title compound as a pale yellow foam (303 mg, 74%). LCMS (Method A) $R_T$=5.02 min, [M+H]$^+$=546/548.

Step 5: 3-[4-(1-Amino-cyclobutyl)-phenyl]-2-phenyl-6-bromo-chromen-4-one: Following the procedure used to prepare 3-[4-(1-amino-cyclobutyl)-phenyl]-6-fluoro-2-phenyl-chromen-4-one, {1-[4-(6-bromo-4-oxo-2-phenyl-4H-chromen-3-yl)-phenyl]-cyclobutyl}-carbamic acid tert-butyl ester was reacted to give the title compound as a pale yellow solid (26 mg, 80%). $^1$H NMR (400 MHz, DMSO-d6): δ 8.18 (d, J=2 Hz, 1H), 8.02 (dd, J=2 and 9 Hz, 1H), 7.75 (d, J=9 Hz, 1H), 7.45-7.31 (m, 7H), 7.17-7.12 (m, 2H), 2.44-2.34 (m, 2H), 2.17-2.07 (m, 2H), 2.05-1.95 (m, 1H), 1.71-1.61 (m, 1H). LCMS (Method F): $R_T$=9.86 min, [M+H]$^+$=446/448.

Example 20

3-[4-(1-Amino-cyclobutyl)-phenyl]-6-(4-methyl-piperazin-1-yl)-2-phenyl-chromen-4-one

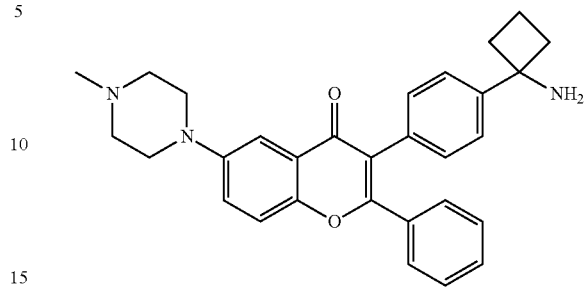

Step 1: (1-{4-[6-(4-Methyl-piperazin-1-yl)-4-oxo-2-phenyl-4H-chromen-3-yl]-phenyl}-cyclobutyl)-carbamic acid tert-butyl ester: {1-[4-(6-Bromo-4-oxo-2-phenyl-4H-chromen-3-yl)-phenyl]-cyclobutyl}-carbamic acid tert-butyl ester (55 mg, 0.1 mmol), 1-methylpiperazine (13 µL, 0.12 mmol), tris(dibenzylideneacetone)dipalladium(0) (5 mg, 0.005 mmol), (S)-BINAP (9 mg, 0.015 mmol) and cesium carbonate (46 mg, 0.14 mmol) were suspended in toluene (1.0 mL) in a microwave vial. The vial was sealed, evacuated and flushed twice with nitrogen. The mixture was heated in a microwave at 150° C. for 30 min. Further tris(dibenzylideneacetone)dipalladium(0) (5 mg, 0.005 mmol) and (S)-BINAP (9 mg, 0.015 mmol) were added to the vial and the mixture heated conventionally at 110° C. for 24 hours. The mixture was cooled to RT, dissolved in methanol and loaded onto an SCX-2 cartridge. The cartridge was washed repeatedly with methanol before eluting with 2M ammonia in methanol solution. The eluent was collected and concentrated in vacuo. The resulting residue was subjected to flash chromatography (SiO$_2$, gradient 3%-4% 2M ammonia in methanol/DCM) to afford the title compound as a yellow oil (15 mg, 27%). LCMS (Method B): $R_T$=3.74 min, M+H$^+$=566.

Step 2: 3-[4-(1-Amino-cyclobutyl)-phenyl]-6-(4-methyl-piperazin-1-yl)-2-phenyl-chromen-4-one: Following the procedure used to prepare 3-[4-(1-amino-cyclobutyl)-phenyl]-6-fluoro-2-phenyl-chromen-4-one, (1-{4-[6-(4-methyl-piperazin-1-yl)-4-oxo-2-phenyl-4H-chromen-3-yl]-phenyl}-cyclobutyl)-carbamic acid tert-butyl ester was reacted to give the title compound as a yellow solid (12 mg, 96%). $^1$H NMR (400 MHz, DMSO-d6): as 7.63-7.56 (m, 2H), 7.41-7.29 (m, 8H), 7.13-7.09 (m, 2H), 3.25-3.20 (m, 4H), 2.52-2.47 (m, 4H), 2.41-2.32 (m, 2H), 2.24 (s, 3H), 2.12-2.04 (m, 2H), 2.04-1.94 (m, 1H), 1.69-1.60 (m, 1H). LCMS (Method F): $R_T$=6.39 min, [M+H]$^+$=466.

Example 21

3-[4-(1-Amino-cyclobutyl)-phenyl]-4-oxo-2-phenyl-4H-chromene-6-carbonitrile

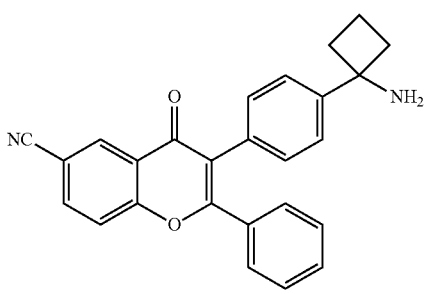 [SMILES: N#Cc1ccc2oc(-c3ccccc3)c(-c3ccc(C4(N)CCC4)cc3)c(=O)c2c1]

Step 1: {1-[4-(6-Cyano-4-oxo-2-phenyl-4H-chromen-3-yl)-phenyl]-cyclobutyl}-carbamic acid tert-butyl ester: {1-[4-(6-Bromo-4-oxo-2-phenyl-4H-chromen-3-yl)-phenyl]- cyclobutyl}-carbamic acid tert-butyl ester (92 mg, 0.17 mmol), zinc (II) cyanide (40 mg, 0.34 mmol) and tetrakis (triphenyphosphine)palladium(0) (20 mg, 0.017 mmol) were suspended in DMA (2 mL) in a microwave vial. The vial was sealed, evacuated and flushed twice with nitrogen. The mixture was heated in a microwave at 150° C. for 30 min. The resulting mixture was allowed to cool to RT, partitioned between ethyl acetate (40 mL) and water (20 mL) and the phases separated. The organic layer was washed with brine (20 mL), dried (Na₂SO₄), filtered and concentrated in vacuo. The resulting residue was subjected to flash chromatography (SiO₂, 20% ethyl acetate in cyclohexane) to afford the title compound as a white solid (45 mg, 54%). LCMS (Method B): $R_T$=4.76 min, [M+Na]⁺=515.

Step 2: 3-[4-(1-Amino-cyclobutyl)-phenyl]-4-oxo-2-phenyl-4H-chromene-6-carbonitrile: Following the procedure used to prepare 3-[4-(1-amino-cyclobutyl)-phenyl]-6-fluoro-2-phenyl-chromen-4-one, {1-[4-(6-cyano-4-oxo-2-phenyl-4H-chromen-3-yl)-phenyl]-cyclobutyl}-carbamic acid tert-butyl ester was reacted to give the title compound as a yellow solid (33 mg, 94%). ¹H NMR (400 MHz, DMSO-d6): δ 8.51 (d, J=2 Hz, 1H), 8.27 (dd, J=2 and 8 Hz, 1H), 7.95 (d, J=8 Hz, 1H), 7.46-7.33 (m, 7H), 7.18-7.14 (m, 2H), 2.44-2.36 (m, 2H), 2.20-2.12 (m, 2H), 2.07-1.97 (m, 1H), 1.73-1.63 (m, 1H). LCMS (Method F): $R_T$=8.47 min, [M+H]⁺=393.

Example 22

3-[4-(1-Amino-cyclobutyl)-phenyl]-6-imidazol-1-yl-2-phenyl-chromen-4-one

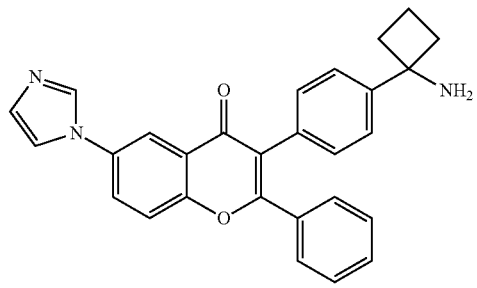 [SMILES: NC1(c2ccc(-c3c(-c4ccccc4)oc4ccc(-n5ccnc5)cc4c3=O)cc2)CCC1]

{1-[4-(6-Bromo-4-oxo-2-phenyl-4H-chromen-3-yl)-phenyl]-cyclobutyl}-carbamic acid tert-butyl ester (55 mg, 0.1 mmol), imidazole (9 mg, 0.12 mmol), cesium carbonate (49 mg, 0.15 mmol) and copper (I)thiophene-2-carboxylate (4 mg, 0.02 mmol) were suspended in NMP (1.0 mL) in a microwave vial. The vial was sealed, evacuated and flushed twice with nitrogen. The mixture was heated conventionally at 110° C. for 24 hours. Due to incomplete reaction, the temperature was increased to 130° C. After a further 24 hours, the reaction mixture was allowed to cool to RT, dissolved in methanol and loaded onto an SCX-2 cartridge. The cartridge was washed repeatedly with methanol before eluting with 2 M ammonia in methanol solution. The eluent was collected and concentrated in vacuo. The resulting residue was dissolved in DCM (2 mL) and TFA (500 μL) and stirred at RT for 1.5 hours. The mixture was dissolved in methanol and loaded onto an SCX-2 cartridge. The cartridge was washed repeatedly with methanol before eluting with 2 M ammonia in methanol solution. The eluent was collected and concentrated in vacuo. The resulting residue was purified on reverse phase HPLC (gradient 5% 20 mM TEA in acetonitrile/20 mM TEA in water to 98% 20 mM TEA in acetonitrile/20 mM TEA in water) to give the title compound as a white solid (6 mg, 14%). ¹H NMR (400 MHz, DMSO-d6): δ 8.43-8.42 (m, 1H), 8.23 (d, J=3 Hz, 1H), 8.18 (dd, J=3 and 9 Hz, 1H), 7.94 (d, J=9 Hz, 1H), 7.93-7.92 (m, 1H), 7.47-7.33 (m, 7H), 7.16-7.13 (m, 3H), 2.40-2.32 (m, 2H), 2.11-2.02 (m, 2H), 2.02-1.95 (m, 1H), 1.70-1.61 (m, 1H). LCMS (Method F): $R_T$=6.40 min, [M+H]⁺=434.

Example 23

3-[4-(1-Amino-cyclobutyl)-phenyl]-6,7-difluoro-2-phenyl-chromen-4-one

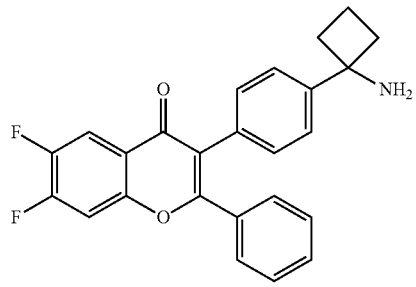

Step 1: 3-Phenyl-1-(2-methoxy-4,5-difluoro-phenyl)-prop-2-yn-1-ol: Following the procedure used to prepare 1-(5-fluoro-2-methoxy-phenyl)-3-phenyl-prop-2-yn-1-ol, 2-methoxy-4,5-difluorobenzaldehyde was reacted to give the title compound as a colourless oil (531 mg, 97%). LCMS (Method B): $R_T$=3.90 min, [M−H₂O+H]⁺=257.

Step 2: 3-Phenyl-1-(2-methoxy-4,5-difluoro-phenyl)-propynone: Following the procedure used to prepare 1-(5-fluoro-2-methoxy-phenyl)-3-phenyl-propynone, 3-phenyl-1-(2-methoxy-4,5-difluoro-phenyl)-prop-2-yn-1-ol was reacted to give the title compound as a white solid (495 mg, 94%). LCMS (Method B): $R_T$=4.56 min, [M+H]⁺=273.

Step 3: 6,7-Difluoro-3-iodo-2-phenyl-chromen-4-one: Following the procedure used to prepare 6-fluoro-3-iodo-2-phenyl-chromen-4-one, 3-phenyl-1-(2-methoxy-4,5-difluoro-phenyl)-propynone was reacted to give the title compound as an off-white solid (587 mg, 90%). LCMS (Method B): $R_T$=4.05 min, [M+H]⁺=385.

Step 4: {1-[4-(6,7-Difluoro-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 6,7-difluoro-3-iodo-2-phenyl-chromen-4-one was reacted to give the title compound as a pale yellow oil (91 mg, 90%). LCMS (Method B): $R_T$=5.01 min, [M+Na]⁺=526.

Step 5: 3-[4-(1-Amino-cyclobutyl)-phenyl]-6,7-difluoro-2-phenyl-chromen-4-one: Following the procedure used to prepare 3-[4-(1-amino-cyclobutyl)-phenyl]-6-fluoro-2-phenyl-chromen-4-one, {1-[4-(6,7-difluoro-4-oxo-2-phenyl-4H-chromen-3-yl)-phenyl]-cyclobutyl}-carbamic acid tert-butyl ester was reacted to give the title compound as a white solid (67 mg, 92%). ¹H NMR (400 MHz, DMSO-d6): δ 8.08-7.99 (m, 2H), 7.43-7.32 (m, 7H), 7.16-7.13 (m, 2H), 2.43-2.35 (m, 2H), 2.20-2.11 (m, 2H), 2.07-1.96 (m, 1H), 1.72-1.61 (m, 1H). LCMS (Method E): $R_T$=3.75 min, [M+H]⁺=404.

Example 24

3-[4-(1-Amino-cyclobutyl)-phenyl]-2-phenyl-7-trifluoromethoxy-chromen-4-one

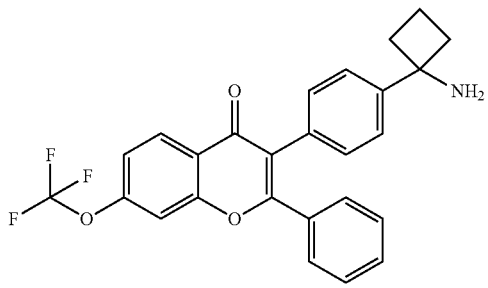 [SMILES: NC1(c2ccc(-c3c(-c4ccccc4)oc4cc(OC(F)(F)F)ccc4c3=O)cc2)CCC1]

Step 1: 1-(2-Methoxy-4-trifluoromethoxy-phenyl)-3-phenyl-prop-2-yn-1-ol: Following the procedure used to prepare 1-(5-fluoro-2-methoxy-phenyl)-3-phenyl-prop-2-yn-1-ol, 2-methoxy-4-trifluoromethoxy-benzaldehyde was reacted to give the title compound as a pale yellow oil (650 mg, 100%). LCMS (Method B): $R_T$=4.13 min, $[M-H_2O+H]^+$=305.

Step 2: 1-(2-Methoxy-4-trifluoromethoxy-phenyl)-3-phenyl-propynone: Following the procedure used to prepare 1-(5-fluoro-2-methoxy-phenyl)-3-phenyl-propynone, 1-(2-methoxy-4-trifluoromethoxy-phenyl)-3-phenyl-prop-2-yn-1-ol was reacted to give the title compound as a pale yellow oil (604 mg, 94%). LCMS (Method B): $R_T$=4.74 min, $[M+Na]^+$=343.

Step 3: 3-Iodo-2-phenyl-7-trifluoromethoxy-chromen-4-one: Following the procedure used to prepare 6-fluoro-3-iodo-2-phenyl-chromen-4-one, 1-(2-methoxy-4-trifluoromethoxy-phenyl)-3-phenyl-propynone was reacted to give the title compound as an off-white solid (781 mg, 98%). LCMS (Method B): $R_T$=4.82 min, $[M+H]^+$=433.

Step 4: {1-[4-(4-oxo-2-phenyl-7-trifluoromethoxy-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-2-phenyl-7-trifluoromethoxy-chromen-4-one was reacted to give the title compound as a beige solid (83 mg, 100%). LCMS (Method B): $R_T$=5.11 min, $[M+Na]^+$=574.

Step 5: 3-[4-(1-Amino-cyclobutyl)-phenyl]-2-phenyl-7-trifluoromethoxy-chromen-4-one: Following the procedure used to prepare 3-[4-(1-amino-cyclobutyl)-phenyl]-6-fluoro-2-phenyl-chromen-4-one, {1-[4-(4-oxo-2-phenyl-7-trifluoromethoxy-4H-chromen-3-yl)-phenyl]-cyclobutyl}-carbamic acid tert-butyl ester was reacted to give the title compound as a white solid (54 mg, 86%). $^1$H NMR (400 MHz, CDCl$_3$): δ 8.30 (d, J=8 Hz, 1H), 7.41-7.33 (m, 6H), 7.30-7.25 (m, 3H), 7.19-7.16 (m, 2H), 2.61-2.52 (m, 2H), 2.33-2.24 (m, 2H), 2.16-2.06 (m, 1H), 1.81-1.71 (m, 1H). LCMS (Method E): $R_T$=4.15 min, $[M+H]^+$=452.

Example 25

3-[4-(1-Amino-cyclobutyl)-phenyl]-2-phenyl-6-trifluoromethoxy-chromen-4-one

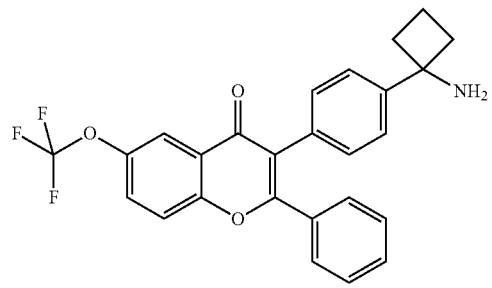 [SMILES: NC1(c2ccc(-c3c(-c4ccccc4)oc4ccc(OC(F)(F)F)cc4c3=O)cc2)CCC1]

Step 1: 1-(2-Methoxy-5-trifluoromethoxy-phenyl)-3-phenyl-prop-2-yn-1-ol: Following the procedure used to prepare 1-(5-fluoro-2-methoxy-phenyl)-3-phenyl-prop-2-yn-1-ol, 2-methoxy-5-trifluoromethoxy-benzaldehyde was reacted to give the title compound as a pale yellow oil (642 mg, 99%). LCMS (Method B): $R_T$=4.55 min, $[M-H_2O+H]^+$=305.

Step 2: 1-(2-Methoxy-5-trifluoromethoxy-phenyl)-3-phenyl-propynone: Following the procedure used to prepare 1-(5-fluoro-2-methoxy-phenyl)-3-phenyl-propynone, 1-(2-methoxy-5-trifluoromethoxy-phenyl)-3-phenyl-prop-2-yn-1-ol was reacted to give the title compound as an off-white solid (604 mg, 95%). LCMS (Method B): $R_T$=4.72 min, $[M+Na]^+$=343.

Step 3: 3-Iodo-2-phenyl-6-trifluoromethoxy-chromen-4-one: Following the procedure used to prepare 6-fluoro-3-iodo-2-phenyl-chromen-4-one, 1-(2-methoxy-5-trifluoromethoxy-phenyl)-3-phenyl-propynone was reacted to give the title compound as a pale yellow solid (757 mg, 94%). LCMS (Method B): $R_T$=4.72 min, $[M+H]^+$=433.

Step 4: {1-[4-(4-Oxo-2-phenyl-6-trifluoromethoxy-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-2-phenyl-6-trifluoromethoxy-chromen-4-one was reacted to give the title compound as a pale yellow oil (90 mg, 100%). LCMS (Method B): $R_T$=5.07 min, $[M+Na]^+$=574.

Step 5: 3-[4-(1-Amino-cyclobutyl)-phenyl]-2-phenyl-6-trifluoromethoxy-chromen-4-one: Following the procedure used to prepare 3-[4-(1-amino-cyclobutyl)-phenyl]-6-fluoro-2-phenyl-chromen-4-one, {1-[4-(4-oxo-2-phenyl-6-trifluoromethoxy-4H-chromen-3-yl)-phenyl]-cyclobutyl}-carbamic acid tert-butyl ester was reacted to give the title compound as a white solid (54 mg, 80%). $^1$H NMR (400 MHz, DMSO-d6): δ 7.97-7.87 (m, 3H), 7.45-7.32 (m, 7H), 7.16-7.12 (m, 2H), 2.42-2.33 (m, 2H), 2.15-2.05 (m, 2H), 2.05-1.94 (m, 1H), 1.70-1.60 (m, 1H). LCMS (Method E): $R_T$=4.06 min, $[M+H]^+$=452.

Example 26

3-[4-(1-Amino-cyclobutyl)-phenyl]-7-bromo-6-methoxy-2-phenyl-chromen-4-one

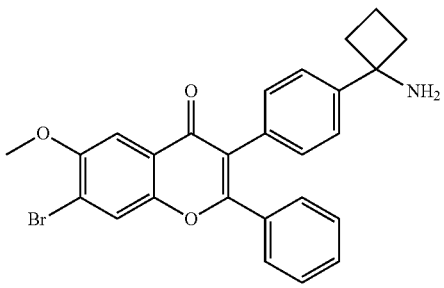 [SMILES: COc1cc2c(=O)c(-c3ccc(C4(N)CCC4)cc3)c(-c3ccccc3)oc2cc1Br]

Step 1: 1-(4-Bromo-2,5-dimethoxy-phenyl)-3-phenyl-prop-2-yn-1-ol: Following the procedure used to prepare 1-(5-fluoro-2-methoxy-phenyl)-3-phenyl-prop-2-yn-1-ol, 2,5-dimethoxy-4-bromobenzaldehyde was reacted to give the title compound as a colourless oil (1.45 g, 100%). LCMS (Method B): $R_T$=4.49 min, [M+Na]$^+$=369/371.

Step 2: 1-(4-Bromo-2,5-dimethoxy-phenyl)-3-phenyl-propynone: Following the procedure used to prepare 1-(5-fluoro-2-methoxy-phenyl)-3-phenyl-propynone, 1-(4-bromo-2,5-dimethoxy-phenyl)-3-phenyl-prop-2-yn-1-ol was reacted to give the title compound as a bright yellow solid (1.28 g, 93%). LCMS (Method B): $R_T$=4.17 min, [M+Na]$^+$=367/369.

Step 3: 7-Bromo-3-iodo-6-methoxy-2-phenyl-chromen-4-one: Following the procedure used to prepare 6-fluoro-3-iodo-2-phenyl-chromen-4-one, 1-(4-bromo-2,5-dimethoxy-phenyl)-3-phenyl-propynone was reacted to give the title compound as an off-white solid (1.65 g, 98%). LCMS (Method B): $R_T$=4.81 min, [M+Na]$^+$=479/481.

Step 4: {1-[4-(7-Bromo-6-methoxy-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-bromo-3-iodo-6-methoxy-2-phenyl-chromen-4-one was reacted to give the title compound as a pale yellow foam (302 mg, 52%). LCMS (Method B): $R_T$=5.02 min, [M+Na]$^+$=598/600.

Step 5: 3-[4-(1-Amino-cyclobutyl)-phenyl]-7-bromo-6-methoxy-2-phenyl-chromen-4-one: Following the procedure used to prepare 3-[4-(1-amino-cyclobutyl)-phenyl]-6-fluoro-2-phenyl-chromen-4-one, {1-[4-(7-bromo-6-methoxy-4-oxo-2-phenyl-4H-chromen-3-yl)-phenyl]-cyclobutyl}-carbamic acid tert-butyl ester was reacted to give the title compound as a white solid (29 mg, 81%). $^1$H NMR (400 MHz, DMSO-d6): δ 8.19 (s, 1H), 7.46 (s, 1H), 7.44-7.31 (m, 7H), 7.14-7.10 (m, 2H), 4.02 (s, 3H), 2.40-2.32 (m, 2H), 2.13-2.03 (m, 2H), 2.03-1.94 (m, 1H), 1.70-1.60 (m, 1H). LCMS (Method E): $R_T$=3.87 min, [M+H]$^+$=476/478.

Example 27

3-[4-(1-Amino-cyclobutyl)-phenyl]-6-bromo-7-methoxy-2-phenyl-chromen-4-one

Step 1: 1-(5-Bromo-2,4-dimethoxy-phenyl)-3-phenyl-prop-2-yn-1-ol: Following the procedure used to prepare 1-(5-fluoro-2-methoxy-phenyl)-3-phenyl-prop-2-yn-1-ol, 2,4-dimethoxy-5-bromobenzaldehyde was reacted to give the title compound as a yellow foam (1.43 g, 100%). LCMS (Method B): $R_T$=4.99 min, [M+Na]$^+$=369/371.

Step 2: 1-(5-Bromo-2,4-dimethoxy-phenyl)-3-phenyl-propynone: Following the procedure used to prepare 1-(5-fluoro-2-methoxy-phenyl)-3-phenyl-propynone, 1-(5-bromo-2,4-dimethoxy-phenyl)-3-phenyl-prop-2-yn-1-ol was reacted to give the title compound as an off-white solid (1.30 g, 94%). LCMS (Method B): $R_T$=4.14 min, [M+Na]$^+$=367/369.

Step 3: 6-Bromo-3-iodo-7-methoxy-2-phenyl-chromen-4-one: Following the procedure used to prepare 6-fluoro-3-iodo-2-phenyl-chromen-4-one, 1-(5-bromo-2,4-dimethoxy-phenyl)-3-phenyl-propynone was reacted to give the title compound as an off-white solid (1.65 g, 98%). LCMS (Method B): $R_T$=4.81 min, [M+Na]$^+$=479/481.

Step 4: {1-[4-(6-Bromo-7-methoxy-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 6-bromo-3-iodo-7-methoxy-2-phenyl-chromen-4-one was reacted to give the title compound as a pale yellow foam (434 mg, 75%). LCMS (Method B): $R_T$=5.04 min, [M+Na]$^+$=598/600.

Step 5: 3-[4-(1-Amino-cyclobutyl)-phenyl]-6-bromo-7-methoxy-2-phenyl-chromen-4-one: Following the procedure used to prepare 3-[4-(1-amino-cyclobutyl)-phenyl]-6-fluoro-2-phenyl-chromen-4-one, {1-[4-(6-bromo-7-methoxy-4-oxo-2-phenyl-4H-chromen-3-yl)-phenyl]-cyclobutyl}-carbamic acid tert-butyl ester was reacted to give the title compound as a white solid (27 mg, 76%). $^1$H NMR (400 MHz, DMSO-d6): δ 8.19 (s, 1H), 7.46 (s, 1H), 7.44-7.31 (m, 7H), 7.14-7.10 (m, 2H), 4.02 (s, 3H), 2.40-2.32 (m, 2H), 2.12-2.04 (m, 2H), 2.04-1.94 (m, 1H), 1.69-1.60 (m, 1H). LCMS (Method E): $R_T$=3.87 min, [M+H]$^+$=476/478.

Example 28

3-[4-(1-Amino-cyclobutyl)-phenyl]-6-methoxy-2-phenyl-7-(2H-pyrazol-3-yl)-chromen-4-one

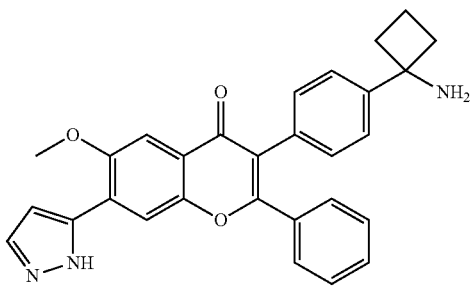 [SMILES: COc1cc2c(=O)c(-c3ccc(C4(N)CCC4)cc3)c(-c3ccccc3)oc2cc1-c1ccn[nH]1]

Step 1: (1-{4-[6-Methoxy-4-oxo-2-phenyl-7-(2H-pyrazol-3-yl)-4H-chromen-3-yl]-phenyl}-cyclobutyl)-carbamic acid tert-butyl ester: Following the procedure used to prepare (1-{4-[4-oxo-2-phenyl-7-(2H-pyrazol-3-yl)-4H-chromen-3-yl]-phenyl}-cyclobutyl)-carbamic acid tert-butyl ester, {1-[4-(7-bromo-6-methoxy-4-oxo-2-phenyl-4H-chromen-3-yl)-phenyl]-cyclobutyl}-carbamic acid tert-butyl ester was reacted to give the title compound as a colourless oil (55 mg, 65%). LCMS (Method B): $R_T$=4.90 min, $[M+H]^+$=564.

Step 2: 3-[4-(1-Amino-cyclobutyl)-phenyl]-6-methoxy-2-phenyl-7-(2H-pyrazol-3-yl)-chromen-4-one: Following the procedure used to prepare 3-[4-(1-amino-cyclobutyl)-phenyl]-6-fluoro-2-phenyl-chromen-4-one, (1-{4-[6-methoxy-4-oxo-2-phenyl-7-(2H-pyrazol-3-yl)-4H-chromen-3-yl]-phenyl}-cyclobutyl)-carbamic acid tert-butyl ester was reacted to give the title compound as a pale yellow solid (34 mg, 75%). $^1$H NMR (400 MHz, DMSO-d6): δ 13.32-13.18 (br s, 1H), 8.21 (s, 1H), 7.88-7.72 (br s, 1H), 7.60-7.56 (br s, 1H), 7.44-7.30 (m, 7H), 7.19-7.14 (m, 2H), 6.97 (s, 1H), 4.01 (s, 3H), 2.45-2.36 (m, 2H), 2.20-2.10 (m, 2H), 2.08-1.97 (m, 1H), 1.72-1.61 (m, 1H). LCMS (Method E): $R_T$=3.39 min, $[M+H]^+$=464.

Example 29

3-[4-(1-Amino-cyclobutyl)-phenyl]-6-methoxy-4-oxo-2-phenyl-4H-chromene-7-carboxylic acid amide

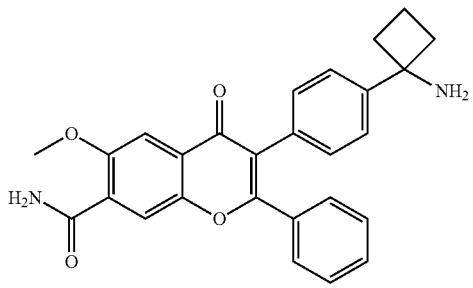 [SMILES: COc1cc2c(=O)c(-c3ccc(C4(N)CCC4)cc3)c(-c3ccccc3)oc2cc1C(N)=O]

Step 1: {1-[4-(7-Carbamoyl-6-methoxy-4-oxo-2-phenyl-4H-chromen-3-yl)-phenyl]-cyclobutyl}-carbamic acid tert-butyl ester: Following the procedure used to prepare 3-[4-(1-amino-cyclobutyl)-phenyl]-4-oxo-2-phenyl-4H-chromene-7-carboxylic acid amide, {1-[4-(7-bromo-6-methoxy-4-oxo-2-phenyl-4H-chromen-3-yl)-phenyl]-cyclobutyl}-carbamic acid tert-butyl ester was reacted to give the title compound as a colourless oil (22 mg, 27%). LCMS (Method B): $R_T$=4.17 min, $[M+H]^+$=541.

Step 2: 3-[4-(1-Amino-cyclobutyl)-phenyl]-6-methoxy-4-oxo-2-phenyl-4H-chromene-7-carboxylic acid amide: Following the procedure used to prepare 3-[4-(1-amino-cyclobutyl)-phenyl]-6-fluoro-2-phenyl-chromen-4-one, {1-[4-(7-carbamoyl-6-methoxy-4-oxo-2-phenyl-4H-chromen-3-yl)-phenyl]-cyclobutyl}-carbamic acid tert-butyl ester was reacted to give the title compound as a pale yellow solid (17 mg, 93%). $^1$H NMR (400 MHz, DMSO-d6): δ 7.99 (s, 1H), 7.91-7.88 (br s, 1H), 7.85-7.81 (br s, 1H), 7.59 (s, 1H), 7.45-7.31 (m, 7H), 7.16-7.11 (m, 2H), 3.98 (s, 3H), 2.41-2.33 (m, 2H), 2.13-2.04 (m, 2H), 2.04-1.94 (m, 1H), 1.70-1.60 (m, 1H). LCMS (Method E): $R_T$=2.99 min, $[M+H]^+$=441.

Example 30

3-[4-(1-Amino-cyclobutyl)-phenyl]-6-methoxy-4-oxo-2-phenyl-4H-chromene-7-carbonitrile

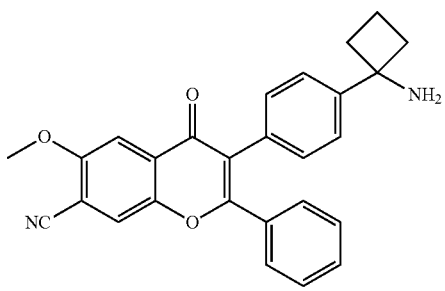 [SMILES: COc1cc2c(=O)c(-c3ccc(C4(N)CCC4)cc3)c(-c3ccccc3)oc2cc1C#N]

Step 1: {1-[4-(7-Cyano-6-methoxy-4-oxo-2-phenyl-4H-chromen-3-yl)-phenyl]-cyclobutyl}-carbamic acid tert-butyl ester: Following the procedure used to prepare {1-[4-(6-cyano-4-oxo-2-phenyl-4H-chromen-3-yl)-phenyl]-cyclobutyl}-carbamic acid tert-butyl ester, {1-[4-(7-bromo-6-methoxy-4-oxo-2-phenyl-4H-chromen-3-yl)-phenyl]-cyclobutyl}-carbamic acid tert-butyl ester was reacted to give the title compound as a white solid (42 mg, 57%). LCMS (Method A): $R_T$=4.84 min, $[M+H]^+$=523.

Step 2: 3-[4-(1-Amino-cyclobutyl)-phenyl]-6-methoxy-4-oxo-2-phenyl-4H-chromene-7-carbonitrile: Following the procedure used to prepare 3-[4-(1-amino-cyclobutyl)-phenyl]-6-fluoro-2-phenyl-chromen-4-one, {1-[4-(7-cyano-6-methoxy-4-oxo-2-phenyl-4H-chromen-3-yl)-phenyl]-cyclobutyl}-carbamic acid tert-butyl ester was reacted to give the title compound as a pale yellow solid (23 mg, 71%). $^1$H NMR (400 MHz, DMSO-d6): δ 8.41 (s, 1H), 7.65 (s, 1H), 7.43-7.32 (m, 7H), 7.16-7.12 (m, 2H), 4.02 (s, 3H), 2.42-2.35 (m, 2H), 2.17-2.09 (m, 2H), 2.06-1.96 (m, 1H), 1.72-1.62 (m, 1H). LCMS (Method E): $R_T$=3.67 min, $[M+H]^+$=423.

Example 31

3-[4-(1-Amino-cyclobutyl)-phenyl]-7-(2-methoxy-ethyl)-2-phenyl-7H-pyrano[2,3-c]pyridine-4,8-dione

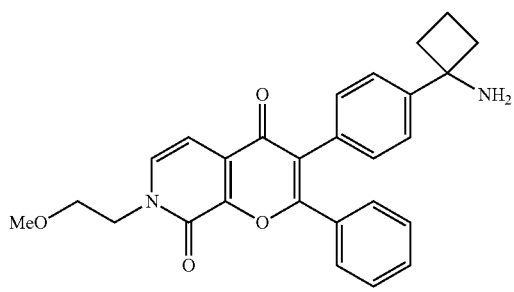 [SMILES: COCCn1ccc2c(=O)c(-c3ccc(C4(N)CCC4)cc3)c(-c3ccccc3)oc2c1=O]

Step 1: 3-Iodo-7-(2-methoxy-ethyl)-2-phenyl-7H-pyrano[2,3-c]pyridine-4,8-dione: To a solution of 3-iodo-2-phenyl-7H-pyrano[2,3-c]pyridine-4,8-dione (100 mg, 0.27 mmol) in DMF (3 mL) was added potassium carbonate (55 mg, 0.40 mmol), followed by 2-bromoethyl methyl ether (28 µL, 0.37 mmol). The reaction mixture was stirred at RT for 24 hours. The resulting mixture was partitioned between ethyl acetate (40 mL) and water (20 mL) and the phases were separated. The organic layer was washed with brine (20 mL), dried (Na$_2$SO$_4$), filtered and concentrated in vacuo. The resulting residue was subjected to flash chromatography (SiO$_2$, 60% ethyl acetate in cyclohexane) to give the title compound as a white solid (67 mg, 59%). LCMS (Method B): R$_T$=3.94 min, [M+H]$^+$=424.

Step 2: (1-{4-[7-(2-Methoxy-ethyl)-4,8-dioxo-2-phenyl-7,8-dihydro-4H-pyrano[2,3-c]pyridin-3-yl]-phenyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-7-(2-methoxy-ethyl)-2-phenyl-7H-pyrano[2,3-c]pyridine-4,8-dione was reacted to give the title compound as a colourless oil (82 mg, 100%). LCMS (Method B): R$_T$=4.63 min, [M+H]$^+$=543.

Step 3: 3-[4-(1-Amino-cyclobutyl)-phenyl]-7-(2-methoxy-ethyl)-2-phenyl-7H-pyrano[2,3-c]pyridine-4,8-dione: Following the procedure used to prepare 3-[4-(1-amino-cyclobutyl)-phenyl]-6-fluoro-2-phenyl-chromen-4-one, (1-{4-[7-(2-methoxy-ethyl)-4,8-dioxo-2-phenyl-7,8-dihydro-4H-pyrano[2,3-c]pyridin-3-yl]-phenyl}-cyclobutyl)-carbamic acid tert-butyl ester was reacted to give the title compound as an off-white solid (48 mg, 72%). $^1$H NMR (400 MHz, DMSO-d6): δ 7.64 (d, J=7 Hz, 1H), 7.42-7.32 (m, 7H), 7.16-7.12 (m, 2H), 6.67 (d, J=7 Hz, 1H), 4.22 (t, J=5 Hz, 2H), 3.65 (t, J=5 Hz, 2H), 3.26 (s, 3H), 2.42-2.35 (m, 2H), 2.18-2.10 (m, 2H), 2.06-1.96 (m, 2H). LCMS (Method E): R$_T$=2.93 min, [M+H]$^+$=443.

Example 32

3-[4-(1-Amino-cyclobutyl)-phenyl]-8-difluoromethoxy-2-phenyl-pyrano[2,3-c]pyridin-4-one

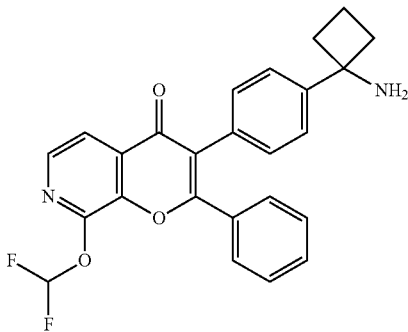 [SMILES: NC1(c2ccc(-c3c(-c4ccccc4)oc4c(OC(F)F)nccc4c3=O)cc2)CCC1]

Step 1: 8-Difluoromethoxy-3-iodo-2-phenyl-pyrano[2,3-c]pyridin-4-one: Chlorodifluoromethane was bubbled into a solution of 3-iodo-2-phenyl-7H-pyrano[2,3-c]pyridine-4,8-dione (100 mg, 0.27 mmol) and potassium carbonate (55 mg, 0.40 mmol) in DMF (3.0 mL) over 2 min. The reaction mixture was stirred at 40° C., for 2 days under a chlorodifluoromethane balloon. The resulting mixture was partitioned between ethyl acetate (40 mL) and water (20 mL) and the phases were separated. The organic layer was washed with brine (20 mL), dried (Na$_2$SO$_4$), filtered and concentrated in vacuo. The resulting residue was subjected to flash chromatography (SiO$_2$, 20% ethyl acetate in cyclohexane) to give the title compound as a white solid (33 mg, 29%). LCMS (Method B): R$_T$=4.46 min, [M+H]$^+$=416.

Step 2: {1-[4-(8-Difluoromethoxy-4-oxo-2-phenyl-4H-pyrano[2,3-c]pyridin-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 8-difluoromethoxy-3-iodo-2-phenyl-pyrano[2,3-c]pyridin-4-one was reacted to give the title compound as a colourless oil (24 mg, 56%). LCMS (Method A): R$_T$=4.85 min, [M+H]$^+$=535.

Step 3: 3-[4-(1-Amino-cyclobutyl)-phenyl]-8-difluoromethoxy-2-phenyl-pyrano[2,3-c]pyridin-4-one: Following the procedure used to prepare 3-[4-(1-amino-cyclobutyl)-phenyl]-6-fluoro-2-phenyl-chromen-4-one, {1-[4-(8-difluoromethoxy-4-oxo-2-phenyl-4H-pyrano[2,3-c]pyridin-3-yl)-phenyl]-cyclobutyl}-carbamic acid tert-butyl ester was reacted to give the title compound as a pale orange solid (9 mg, 46%). $^1$H NMR (400 MHz, DMSO-d6): δ 8.26 (d, J=5 Hz, 1H), 7.90 (t, J=72 Hz, 1H), 7.80 (d, J=5 Hz, 1H), 7.44-7.35 (m, 7H), 7.16-7.13 (m, 2H), 2.40-2.32 (m, 2H), 2.12-2.04 (m, 2H), 2.04-1.95 (m, 1H), 1.70-1.61 (m, 1H). LCMS (Method E): R$_T$=3.74 min, [M+Na]$^+$=457.

Example 33

3-[4-(1-Amino-cyclobutyl)-phenyl]-2-phenyl-7H-pyrano[2,3-c]indazol-4-one

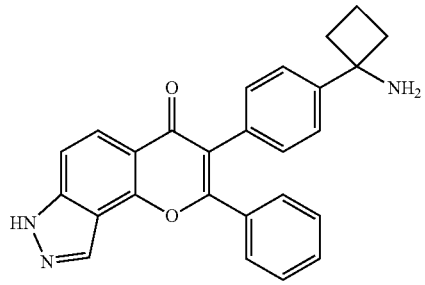 [SMILES: NC1(c2ccc(-c3c(-c4ccccc4)oc4c(ccc5[nH]ncc54)c3=O)cc2)CCC1]

Step 1: 5-Bromo-4-methoxy-1-(2-trimethylsilanyl-ethoxymethyl)-1H-indazole: To a stirred solution of 5-bromo-4-methoxy-1H-indazole (1.33 g, 5.9 mmol) in THF (20 mL) at 0° C., under a nitrogen atmosphere, was added sodium hydride (280 mg, 7 mmol) portionwise. After 5 min, (2-chloromethoxy-ethyl)-trimethylsilane (1.36 mL, 7.7 mmol) was added dropwise. After 3 hours, the reaction mixture was quenched with water (20 mL). The resulting biphasic mixture was separated, extracted with ethyl acetate (2×50 mL) and the combined organic layers were washed with brine (30 mL), dried (Na$_2$SO$_4$), filtered and concentrated in vacuo. The resulting residue was subjected to flash chromatography (SiO$_2$, gradient 10-20% ethyl acetate in cyclohexane) to give the title compound as a yellow oil (1.19 g, 56%). LCMS (Method B): R$_T$=4.91 min, [M+H]$^+$=357.

Step 2: 4-Methoxy-1-(2-trimethylsilanyl-ethoxymethyl)-indazole-5-carbaldehyde: To a stirred solution of 5-bromo-4-methoxy-1-(2-trimethylsilanyl-ethoxymethyl)-indazole (179 mg, 0.50 mmol) in THF (5.0 mL) at −78° C. under a nitrogen atmosphere was added n-butyl lithium (2.5 M in hexanes, 220 µL, 0.55 mmol) dropwise. The mixture was stirred at −78° C. for 1 hour and then DMF (78 µL, 1.0 mmol) was added. The mixture was stirred at −78° C. for 30 min, then allowed to reach RT and stirred for a further 1 hour. The reaction mixture was quenched with water (5 mL), separated and extracted with ethyl acetate (2×20 mL). The combined organic layers were washed with brine (20 mL), dried (Na$_2$SO$_4$), filtered and concentrated in vacuo. The resulting residue was subjected to flash chromatography (SiO$_2$, 20% ethyl acetate in cyclohexane) to give the title compound as a yellow oil (78 mg, 51%). LCMS (Method B): R$_T$=4.55 min, [M+H]$^+$=307.

Step 3: 1-[4-Methoxy-1-(2-trimethylsilanyl-ethoxymethyl)-1H-indazol-5-yl]-3-phenyl-prop-2-yn-1-ol: Following the procedure used to prepare 1-(5-fluoro-2-methoxy-phenyl)-3-phenyl-prop-2-yn-1-ol, 4-methoxy-1-(2-trimethylsilanyl-ethoxymethyl)-1H-indazole-5-carbaldehyde was reacted to give the title compound as a colourless oil (100 mg, 98%). LCMS (Method B): R$_T$=4.84 min, [M+Na]$^+$=431.

Step 4: 1-[4-Methoxy-1-(2-trimethylsilanyl-ethoxymethyl)-1H-indazol-5-yl]-3-phenyl-propynone: Following the procedure used to prepare 1-(5-fluoro-2-methoxy-phenyl)-3-phenyl-propynone, 1-[4-methoxy-1-(2-trimethylsilanyl-ethoxymethyl)-1H-indazol-5-yl]-3-phenyl-prop-2-yn-1-ol was reacted to give the title compound as a pale yellow oil (85 mg, 87%). LCMS (Method B): R$_T$=4.95 min, [M+H]$^+$=407.

Step 5: 3-Iodo-2-phenyl-7-(2-trimethylsilanyl-ethoxymethyl)-7H-pyrano[2,3-c]indazol-4-one: Following the procedure used to prepare 6-fluoro-3-iodo-2-phenyl-chromen-4-one, 1-[4-methoxy-1-(2-trimethylsilanyl-ethoxymethyl)-1H-indazol-5-yl]-3-phenyl-propynone was reacted to give the title compound as an orange oil (106 mg, 97%). LCMS (Method B): R$_T$=5.11 min, [M+H]$^+$=519.

Step 6: (1-{-4-[4-Oxo-2-phenyl-7-(2-trimethylsilanyl-ethoxymethyl)-4,7-dihydro-pyrano[2,3-c]indazol-3-yl]-phenyl}-cyclobutyl)-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-2-phenyl-7-(2-trimethylsilanyl-ethoxymethyl)-7H-pyrano[2,3-e]indazol-4-one was reacted to give the title compound as a yellow oil (102 mg, 80%). LCMS (Method B): R$_T$=5.36 min, [M+H]$^+$=638.

Step 7: {1-[4-(4-oxo-2-phenyl-4,7-dihydro-pyrano[2,3-e]indazol-3-yl)-phenyl]-cyclobutyl}-carbamic acid tert-butyl ester: (1-{-4-[4-oxo-2-phenyl-7-(2-trimethylsilanyl-ethoxymethyl)-4,7-dihydro-pyrano[2,3-c]indazol-3-yl)-phenyl}-cyclobutyl)-carbamic acid tert-butyl ester (100 mg, 0.16 mmol) was dissolved in 1 M TBAF in THF (3 mL, 3 mmol) under a nitrogen atmosphere and heated at 50° C. After 2.5 hours, the mixture was cooled to RT, partitioned between ethyl acetate (40 mL) and water (20 mL) and the phases were separated. The combined organic phase was washed with brine (20 mL), dried (Na$_2$SO$_4$), filtered and concentrated in vacuo. The resulting residue was subjected to flash chromatography (SiO$_2$, 60% ethyl acetate in cyclohexane) to give the title compound as an off-white solid (68 mg, 85%). LCMS (Method B): R$_T$=4.80 min, [M+H]$^+$=508.

Step 8: 3-[4-(1-Amino-cyclobutyl)-phenyl]-2-phenyl-7H-pyrano[2,3-e]indazol-4-one: To a solution of (1-{-4-[4-oxo-2-phenyl-7-(2-trimethylsilanyl-ethoxymethyl)-4,7-dihydro-pyrano[2,3-e]indazol-3-yl]-phenyl}-cyclobutyl)-carbamic acid tert-butyl ester (67 mg, 0.13 mmol) in DCM (2.0 mL), was added TFA (500 µL, 6.7 mmol). The reaction mixture was stirred at RT for 1 hour. The solution was diluted with methanol (10 mL) and loaded onto an SCX-2 cartridge. The cartridge was washed repeatedly with methanol before elution with 2 M ammonia in methanol. The eluent was collected and concentrated in vacuo. The resulting residue was subjected to flash chromatography (SiO$_2$, gradient 7-10% methanol in DCM) to give the title compound as a light pink solid (25 mg, 47%). $^1$H NMR (400 MHz, DMSO-d6): δ 8.54 (d, J=1 Hz, 1H), 8.00 (d, J=9 Hz, 1H), 7.63 (dd, J=1 and 9 Hz, 1H), 7.52-7.49 (m, 2H), 7.44-7.34 (m, 5H), 7.17-7.14 (m, 2H), 2.41-2.33 (m, 2H), 2.11-2.03 (m, 2H), 2.03-1.92 (m, 1H), 1.70-1.60 (m, 1H). LCMS (Method E): R$_T$=3.09 min, [M+H]$^+$=407.

Example 34

3-[4-(1-Amino-cyclobutyl)-phenyl]-2-phenyl-pyrano[2,3-b]pyridin-4-one

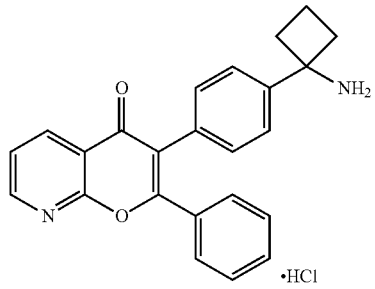 [SMILES: NC1(c2ccc(-c3c(-c4ccccc4)oc4ncccc4c3=O)cc2)CCC1 ; Cl]

Step 1: 2, N-Dimethoxy-N-methyl-nicotinamide: To a stirred ice-cooled mixture of 2-methoxy-nicotinic acid (1.43 g, 9.31 mmol) and O,N-dimethyl-hydroxylamine hydrochloride (1.0 g, 10.3 mmol) in DCM (50 mL) was added DIPEA (6.4 mL, 37.3 mmol). EDCI (2.14 g, 11.1 mmol) was added portionwise over 5 minutes. After 18 hours, the reaction mixture was washed successively with saturated sodium bicarbonate and water. The organic layer was dried (Na$_2$SO$_4$), filtered and concentrated in vacuo. The resultant residue was subjected to flash chromatography (SiO$_2$, gradient 50 to 75% EtOAc in cyclohexane) to afford the title compound (0.92 g, 51%) as a colourless oil. LCMS (Method A): R$_T$=2.48 min, [M+H]$^+$=197.

Step 2: 1-(2-Methoxy-pyridin-3-yl)-3-phenyl-propynone: To a solution of phenylacetylene (0.28 mL, 2.55 mmol) in dry THF (5 mL), cooled to −78° C., was added 2.5 M nBuLi in hexanes (1.02 mL, 2.55 mmol). The mixture was stirred for 5 minutes at −78° C., followed by addition of a solution of N-dimethoxy-N-methyl-nicotinamide (0.50 g, 2.55 mmol) in THF (5 mL) over 5 minutes. The reaction mixture was allowed to warm to 0° C. and stirred in an ice bath for 1 hour. Saturated aqueous ammonium chloride solution was added and the mixture extracted twice with ethyl acetate. The combined organic extracts were washed with brine, dried (Na$_2$SO$_4$), filtered and concentrated in vacuo. The resultant residue was subjected to flash chromatography (SiO$_2$, gradient 10 to 40% ethyl acetate in cyclohexane) to afford the title compound (0.52 g, 85%) as a colourless solid. LCMS (Method B): R$_T$=3.77 min, [M+H]$^+$=238.

Step 3: 3-Iodo-2-phenyl-pyrano[2,3-b]pyridin-4-one: Following the procedure used to prepare 6-fluoro-3-iodo-2-phenyl-chromen-4-one, 1-(2-methoxy-pyridin-3-yl)-3-phenyl-propynone was reacted to give the title compound (122 mg, 77%) as a white solid. LCMS (Method A): R$_T$=3.99 min, [M+H]$^+$=350.

Step 4: {1-[4-(4-oxo-2-phenyl-4H-pyrano[2,3-b]pyridin-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-2-phenyl-pyrano[2,3-b]

pyridin-4-one was reacted to give the title compound (46.7 mg, 66%) as a colourless gum. LCMS (Method A): $R_T$=4.65 min, [M+Na]$^+$=491.

Step 5: 3-[4-(1-Amino-cyclobutyl)-phenyl]-2-phenyl-pyrano[2,3-b]pyridin-4-one Hydrochloride: Following the procedure used to prepare 3-[4-(1-amino-cyclobutyl)-phenyl]-6-fluoro-2-phenyl-chromen-4-one, {1-[4-(4-oxo-2-phenyl-4H-pyrano[2,3-b]pyridin-3-yl)-phenyl]-cyclobutyl}-carbamic acid tert-butyl ester was reacted to give the title compound as the free base. The residue was dissolved in a mixture of MeOH (3 mL), water (7 mL) and 1 M HCl (0.3 mL) and chromatographed on a 5 g C18 cartridge {gradient 30 to 50% MeOH in water+1M HCl (0.06 mL in each 10 mL of eluent)} to give the title compound (29 mg, 73%) as a white solid. $^1$H NMR (400 MHz, CD$_3$OD): δ 8.80 (dd, J=4.8 and 2.1 Hz, 1H), 8.68 (dd, J=8.0 and 2.1 Hz, 1H), 7.65 (dd, J=7.9 and 4.8 Hz, 1H), 7.51-7.30 (m, 9H), 2.81-2.74 (m, 2H), 2.64-2.56 (m, 2H), 2.30-2.19 (m, 1H), 2.02-1.91 (m, 1H). LCMS (Method F): $R_T$=7.61 min, [M+H]$^+$=369.

Example 35

3-[4-(1-Amino-cyclobutyl)-phenyl]-7-methoxy-2-phenyl-pyrano[2,3-b]pyridin-4-one hydrochloride

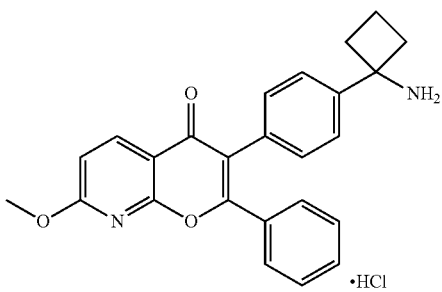 [SMILES: COc1ccc2c(=O)c(-c3ccc(C4(N)CCC4)cc3)c(-c3ccccc3)oc2n1 ; Cl]

Step 1: 1-(2,6-Dimethoxy-pyridin-3-yl)-3-phenyl-prop-2-yn-1-ol: To a solution of phenylacetylene (0.61 g, 5.98 mmol) in dry THF (10 mL), cooled to −78° C., was added 2.5 M nBuLi in hexanes (2.4 mL, 6.0 mmol). The mixture was stirred for 15 min at −78° C., followed by addition of a solution of 2,6-dimethoxypyridine-3-carbaldehyde (1.0 g, 6.0 mmol) in THF (10 mL) was added over 5 minutes. The reaction mixture was allowed to warm to 0° C. and saturated ammonium chloride was added. The resultant biphasic mixture was separated and extracted twice with ethyl acetate. The combined organic phase was washed with brine, dried (Na$_2$SO$_4$), filtered and concentrated in vacuo. The resultant residue was subjected to flash chromatography (SiO$_2$, gradient 10 to 30% ethyl acetate in cyclohexane) to afford the title compound (1.60 g, 99%) as a colourless gum. LCMS (Method B): $R_T$=4.38 min, [M+H]$^+$=270.

Step 2: 1-(2,6-Dimethoxy-pyridin-3-yl)-3-phenyl-propynone: Following the procedure used to prepare 1-(5-fluoro-2-methoxy-phenyl)-3-phenyl-propynone, 1-(2,6-dimethoxy-pyridin-3-yl)-3-phenyl-prop-2-yn-1-ol was reacted to give the title compound (119 mg, 94%) as a white solid. LCMS (Method B): $R_T$=4.53 min, [M+Na]$^+$=290.

Step 3: 3-Iodo-7-methoxy-2-phenyl-pyrano[2,3-b]pyridin-4-one: Following the procedure used to prepare 6-fluoro-3-iodo-2-phenyl-chromen-4-one, 1-(2,6-dimethoxy-pyridin-3-yl)-3-phenyl-propynone was reacted to give the title compound (146 mg, 91%) as a white solid. LCMS (Method A): $R_T$=4.43 min, [M+H]$^+$=380.

Step 4: {1-[4-(7-Methoxy-4-oxo-2-phenyl-4H-pyrano[2,3-b]pyridin-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-7-methoxy-2-phenyl-pyrano[2,3-b]pyridin-4-one was reacted to give the title compound (57 mg, 76%) as a colourless gum. LCMS (Method A): $R_T$=4.88 min, [M+H]$^+$=499.

Step 5: 3-[4-(1-Amino-cyclobutyl)-phenyl]-7-methoxy-2-phenyl-pyrano[2,3-b]pyridin-4-one hydrochloride: Following the procedure used to prepare 3-[4-(1-amino-cyclobutyl)-phenyl]-6-fluoro-2-phenyl-chromen-4-one, {1-[4-(4-oxo-2-phenyl-4H-pyrano[2,3-b]pyridin-3-yl)-phenyl]-cyclobutyl}-carbamic acid tert-butyl ester was reacted to give the title compound as the free base. The residue was dissolved in a mixture of MeOH (7 mL), water (7 mL) and 1 M HCl (0.6 mL) and then chromatographed on a 5 g C18 cartridge {gradient 50 to 70% MeOH in water+1M HCl (60 µL in each 10 mL of eluent)} to give the title compound (36.6 mg, 74%) as a white solid. $^1$H NMR (400 MHz, CD$_3$OD): δ 8.45 (d, J=8.3 Hz, 1H), 7.47-7.30 (m, 9H), 6.99 (d, J=8.3 Hz, 1H), 4.09 (s, 3H), 2.81-2.73 (m, 2H), 2.62-2.55 (m, 2H), 2.29-2.18 (m, 1H), 2.01-1.91 (m, 1H). LCMS (Method F): $R_T$=9.11 min, [M+H]$^+$=399.

Example 36

3-[4-(1-Amino-cyclobutyl)-phenyl]-2-phenyl-8H-pyrano[2,3-b]pyridine-4,7-dione hydrochloride

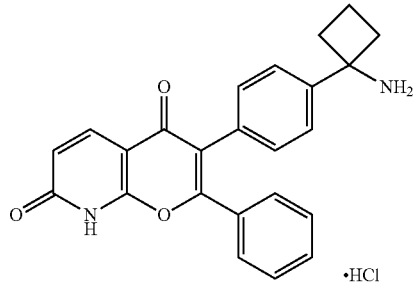 [SMILES: NC1(c2ccc(-c3c(-c4ccccc4)oc4[nH]c(=O)ccc4c3=O)cc2)CCC1 ; Cl]

A solution of 3-[4-(1-amino-cyclobutyl)-phenyl]-7-methoxy-2-phenyl-pyrano[2,3-b]pyridin-4-one hydrochloride (20 mg, 0.046 mmol) in 33% hydrogen bromide solution in AcOH (0.5 mL) was heated in a microwave oven at 100° C. for 30 minutes. The reaction mixture was added to a mixture of MeOH (10 mL) and water (5 mL) and the resultant solution passed through a 2 g SCX cartridge. The product was not retained by the cartridge. The washings containing the product were concentrated, the pH of the mixture was adjusted to ~4 by addition of aqueous sodium hydroxide solution, and chromatographed on a 5 g C18 cartridge {gradient 20 to 70% MeOH in water+1M HCl (0.12 mL in each 10 mL of eluent)}. Fractions containing product were combined and concentrated in vacuo. The resulting residue was chromatographed on a 2 g C18 cartridge {gradient 20 to 60% MeOH in water+1M HCl (0.06 mL in each 5 mL of eluent)} to give the title compound (17.7 mg, 91%) as a white solid. $^1$H NMR (400 MHz, CD$_3$OD): δ 8.30 (d, J=9.2 Hz, 1H), 7.50-7.47 (m, 2H), 7.45-7.38 (m, 3H), 7.34-7.29 (m, 4H), 6.73 (d, J=9.0 Hz, 1H), 2.80-2.73 (m, 2H), 2.66-2.59 (m, 2H), 2.31-2.20 (m, 1H), 2.01-1.90 (m, 1H). LCMS (Method F): $R_T$=6.97 min, $[M-H]^+$=383.

Example 37

3-[4-(1-Amino-cyclobutyl)-phenyl]-7-fluoro-2-phenyl-chromen-4-one hydrochloride

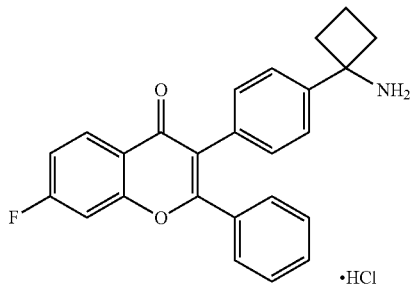 [SMILES: NC1(c2ccc(-c3c(-c4ccccc4)oc4cc(F)ccc4c3=O)cc2)CCC1 ; Cl]

Step 1: 1-(4-Fluoro-2-methoxy-phenyl)-3-phenyl-prop-2-yn-1-ol: Following the procedure used to prepare 1-(2,6-dimethoxy-pyridin-3-yl)-3-phenyl-prop-2-yn-1-ol, 4-fluoro-2-methoxy-benzaldehyde was reacted to give the title compound (1.60 g, 96%) as a colourless oil. LCMS (Method A): $R_T$=4.30 min, $[M+Na]^+$=279.

Step 2: 1-(4-Fluoro-2-methoxy-phenyl)-3-phenyl-propynone: Following the procedure used to prepare 1-(5-fluoro-2-methoxy-phenyl)-3-phenyl-propynone, 1-(4-fluoro-2-methoxy-phenyl)-3-phenyl-prop-2-yn-1-ol was reacted to give the title compound (1.31 g, 85%) as a colourless oil. LCMS (Method A): $R_T$=4.40 min, $[M+H]^+$=255.

Step 3: 7-Fluoro-3-iodo-2-phenyl-chromen-4-one: Following the procedure used to prepare 6-fluoro-3-iodo-2-phenyl-chromen-4-one, 1-(4-fluoro-2-methoxy-phenyl)-3-phenyl-propynone was reacted to give the title compound (0.83 g, 95%) as a white solid. LCMS (Method A): $R_T$=4.50 min, $[M+H]^+$=367.

Step 4: {1-[4-(7-Fluoro-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-fluoro-3-iodo-2-phenyl-chromen-4-one was reacted to give the title compound (46 mg, 95%) as a colourless solid. LCMS (Method A): $R_T$=4.91 min, $[M+H]^+$=486.

Step 5: 3-[4-(1-Amino-cyclobutyl)-phenyl]-7-fluoro-2-phenyl-chromen-4-one Hydrochloride: Following the procedure used to prepare 3-[4-(1-amino-cyclobutyl)-phenyl]-6-fluoro-2-phenyl-chromen-4-one, {1-[4-(7-fluoro-4-oxo-2-phenyl-4H-chromen-3-yl)-phenyl]-cyclobutyl}-carbamic acid tert-butyl ester was reacted to give the title compound as the free base. The residue was dissolved in a mixture of MeOH (3 mL), water (7 mL) and chromatographed on a 5 g C18 cartridge {gradient 30 to 60% MeOH in water+1M HCl (60 µL in each 10 mL of eluent)} to give the title compound (31.8 mg, 80%) as a white solid. $^1$H NMR (400 MHz, CD$_3$OD): δ 8.27 (dd, J=9.0 and 6.3 Hz, 1H), 7.51-7.29 (m, 11H), 2.81-2.74 (m, 2H), 2.64-2.56 (m, 2H), 2.30-2.19 (m, 1H), 2.02-1.91 (m, 1H). LCMS (Method F): $R_T$=9.31 min, $[M+H]^+$=386.

Example 38

3-[4-(1-Amino-cyclobutyl)-phenyl]-7-chloro-2-phenyl-pyrano[2,3-b]pyridin-4

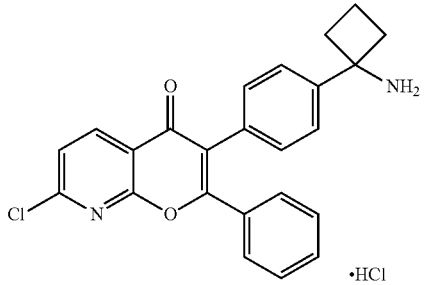 [SMILES: NC1(c2ccc(-c3c(-c4ccccc4)oc4nc(Cl)ccc4c3=O)cc2)CCC1 ; Cl]

Step 1: 3-Iodo-2-phenyl-8H-pyrano[2,3-b]pyridine-4,7-dione: A suspension of 3-iodo-7-methoxy-2-phenyl-pyrano[2,3-b]pyridin-4-one (0.25 g, 0.66 mmol) in 33% hydrogen bromide solution in AcOH (3.5 mL) was heated in a microwave oven at 60° C. for 50 min. The resultant solution was evaporated to dryness. Toluene was added to the residual solid and evaporated. The orange solid was used without further purification. LCMS (Method B): $R_T$=3.85 min, $[M+H]^+$=366.

Step 2: 7-Chloro-3-iodo-2-phenyl-pyrano[2,3-b]pyridin-4-one: To a suspension of 3-iodo-2-phenyl-8H-pyrano[2,3-b]pyridine-4,7-dione (13 mg, 0.036 mmol) in DCM (3 mL) was added DMF (0.03 mL) and thionyl chloride (0.1 mL). The mixture was heated under reflux for 3 hours, followed by standing at RT for 6 days. Upon evaporation, the residue was subjected to flash chromatography (SiO$_2$, gradient 10 to 25% ethyl acetate in cyclohexane) to afford the title compound (10 mg, 74%) as a colourless gum. LCMS (Method B): $R_T$=4.35 min, $[M+H]^+$=384/386.

Step 3: {1-[4-(7-Chloro-4-oxo-2-phenyl-4H-pyrano[2,3-b]pyridin-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-chloro-3-iodo-2-phenyl-pyrano[2,3-b]pyridin-4-one was reacted to give the title compound (8.4 mg, 64%) as a colourless gum. LCMS (Method B): $R_T$=4.42 min, $[M+Na]^+$=525/527.

Step 4: 3-[4-(1-Amino-cyclobutyl)-phenyl]-7-chloro-2-phenyl-pyrano[2,3-b]pyridin-4-one Hydrochloride: Following the procedure used to prepare 3-[4-(1-amino-cyclobutyl)-phenyl]-6-fluoro-2-phenyl-chromen-4-one, {1-[4-(7-chloro-4-oxo-2-phenyl-4H-pyrano[2,3-b]pyridin-3-yl)-phenyl]-cyclobutyl}-carbamic acid tert-butyl ester was reacted to give the title compound as the free base. The residue was dissolved in a mixture of MeOH (1 mL), water (4 mL) and 1 M HCl (0.15 mL) and chromatographed on a 2 g C18 cartridge {gradient 30 to 90% MeOH in water+1 M HCl (60 µL in each 5 mL of eluent)} to give the title compound (3.7 mg, 50%) as a white solid. $^1$H NMR (400 MHz, CD$_3$OD): δ 8.61 (d, J=8.3 Hz, 1H), 7.67 (d, J=8.0 Hz, 1H), 7.49-7.47 (m, 4H), 7.43-7.30 (m, 5H), 2.81-2.74 (m, 2H), 2.63-2.56 (m, 2H), 2.29-2.19 (m, 1H), 2.02-1.91 (m, 1H). LCMS (Method F): $R_T$=8.90 min, $[M+Na]^+$=418/420.

Example 39

3-[4-(1-Amino-cyclobutyl)-phenyl]-8-methoxy-2-phenyl-pyrano[2,3-c]pyridin-4-one hydrochloride

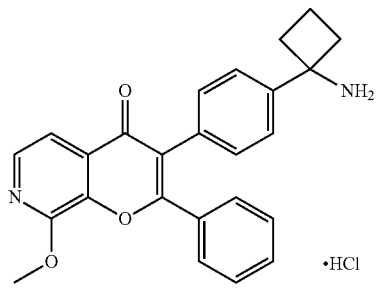 [SMILES: COc1nccc2c(=O)c(-c3ccc(C4(N)CCC4)cc3)c(-c3ccccc3)oc12 ; Cl]

Step 1: 2,3-Dimethoxy-pyridine-4-carbaldehyde: To a solution of 2,3-dimethoxypyridine (1.0 g, 7.19 mmol) in dry THF (30 mL), cooled to −78° C., was added 2.5 M nBuLi in hexanes (6.33 mL, 15.8 mmol). The mixture was allowed to warm to 0° C. and stirred for 1 hour, before cooling to −78° C. A solution of DMF (2.4 mL, 31.5 mmol) in THF (5 mL) was added. The reaction mixture was allowed to warm to 0° C. and saturated aqueous ammonium chloride solution was added. The resultant biphasic mixture separated and extracted twice with diethyl ether. The combined organic phase was washed with water, and brine, dried ($Na_2SO_4$), filtered, and concentrated in vacuo. The resultant residue was subjected to flash chromatography ($SiO_2$, gradient 15 to 20% ethyl acetate in cyclohexane) to afford the title compound (0.79 g, 65%) as a white solid. LCMS (Method B): $R_T$=2.71 min, [M+H]$^+$=168.

Step 2: 1-(2,3-Dimethoxy-pyridin-4-yl)-3-phenyl-prop-2-yn-1-ol: Following the procedure used to prepare 1-(2,6-dimethoxy-pyridin-3-yl)-3-phenyl-prop-2-yn-1-ol, 2,3-dimethoxy-pyridine-4-carbaldehyde was reacted to give the title compound (1.08 g, 86%) as a white solid. LCMS (Method A): $R_T$=4.11 min, [M+H]$^+$=270.

Step 3: 1-(2,3-Dimethoxy-pyridin-4-yl)-3-phenyl-propynone: Following the procedure used to prepare 1-(5-fluoro-2-methoxy-phenyl)-3-phenyl-propynone, 1-(2,3-dimethoxy-pyridin-4-yl)-3-phenyl-prop-2-yn-1-ol was reacted to give the title compound (1.00 g, 94%) as a pale yellow oil. LCMS (Method A): $R_T$=4.48 min, [M+H]$^+$=268.

Step 4: 3-Iodo-8-methoxy-2-phenyl-pyrano[1,3-c]pyridin-4-one: Following the procedure used to prepare 6-fluoro-3-iodo-2-phenyl-chromen-4-one, 1-(2,3-dimethoxy-pyridin-4-yl)-3-phenyl-propynone was reacted to give the title compound (1.34 g, 94%) as a pale yellow solid. LCMS (Method A): $R_T$=4.46 min, [M+H]$^+$=380.

Step 5: {1-[4-(8-Methoxy-4-oxo-2-phenyl-4H-pyrano[2,3-c]pyridin-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-8-methoxy-2-phenyl-pyrano[2,3-c]pyridin-4-one was reacted to give the title compound (53.4 mg, 71%) as a white solid. LCMS (Method A): $R_T$=4.91 min, [M+H]$^+$=499.

Step 6: 3-[4-(1-Amino-cyclobutyl)-phenyl]-8-methoxy-2-phenyl-pyrano[2,3-c]pyridin-4-one hydrochloride: Following the procedure used to prepare 3-[4-(1-amino-cyclobutyl)-phenyl]-6-fluoro-2-phenyl-chromen-4-one, {1-[4-(8-methoxy-4-oxo-2-phenyl-4H-pyrano[2,3-c]pyridin-3-yl)-phenyl]-cyclobutyl}-carbamic acid tert-butyl ester was reacted to give the title compound as the free base. The residue was dissolved in a mixture of MeOH (4 mL), water (6 mL) and 1 M HCl (0.3 mL) and then chromatographed on a 5 g C18 cartridge {gradient 40 to 70% MeOH in water+1M HCl (60 μL in each 10 mL of eluent)} to give the title compound (33 mg, 74%) as a white solid. $^1$H NMR (400 MHz, $CD_3OD$): δ 8.14 (d, J=5.5 Hz, 1H), 7.55 (d, J=5.3 Hz, 1H), 7.49-7.44 (m, 4H), 7.43-7.38 (m, 1H), 7.37-7.29 (m, 4H), 4.17 (s, 3H), 2.81-2.74 (m, 2H), 2.63-2.55 (m, 2H), 2.29-2.18 (m, 1H), 2.02-1.91 (m, 1H). LCMS (Method F): $R_T$=8.97 min, [M+H]$^+$=399.

Example 40

3-[4-(1-Amino-cyclobutyl)-phenyl]-2-phenyl-7H-pyrano[2,3-c]pyridine-4,8-dione hydrochloride

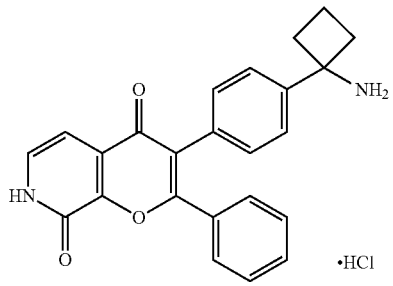 [SMILES: NC1(c2ccc(-c3c(-c4ccccc4)oc4c(=O)[nH]ccc4c3=O)cc2)CCC1 ; Cl]

A solution of 3-[4-(1-amino-cyclobutyl)-phenyl]-8-methoxy-2-phenyl-pyrano[2,3-c]pyridin-4-one hydrochloride (22 mg, 0.051 mmol) in 33% hydrogen bromide solution in AcOH (0.5 mL) was heated in a microwave oven at 100° C. for 30 min. The reaction mixture was added to a mixture of MeOH (3 mL) and water (3 mL), the pH adjusted to ~4 by addition of aqueous sodium hydroxide, and chromatographed on a 5 g C18 cartridge {gradient 35 to 70% MeOH in water+1 M HCl (0.12 mL in each 10 mL of eluent)}. Fractions containing product were concentrated in vacuo. The resultant residue was chromatographed on a 5 g C18 cartridge {gradient 35 to 70% MeOH in water+1 M HCl (0.06 mL in each 5 mL of eluent)} to give the title compound (15.1 mg, 71%) as a white solid. $^1$H NMR (400 MHz, DMSO-d6): δ 12.33 (br s, 1H), 8.51 (br s, 3H), 7.48-7.33 (m, 8H), 7.28-7.26 (m, 2H), 6.61 (d, J=6.7 Hz, 1H), 2.60-2.49 (m, 4H), 2.23-2.12 (m, 1H), 1.85-1.74 (m, 1H). LCMS (Method F): $R_T$=6.59 min, [M−H]$^−$=383.

Example 41

3-[4-(1-Amino-cyclobutyl)-phenyl]-7-methyl-2-phenyl-7H-pyrano[2,3-c]pyridine-4,8-dione hydrochloride

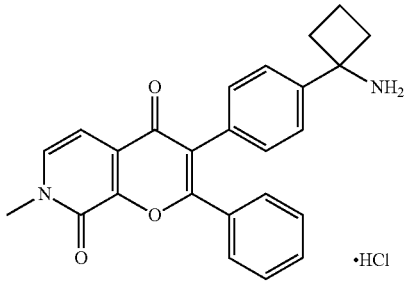 [SMILES: Cn1ccc2c(=O)c(-c3ccc(C4(N)CCC4)cc3)c(-c3ccccc3)oc2c1=O ; Cl]

Step 1: 3-Iodo-2-phenyl-7H-pyrano[2,3-c]pyridine-4,8-dione: A suspension of 3-iodo-8-methoxy-2-phenyl-pyrano[2,3-c]pyridin-4-one (0.30 g, 0.791 mmol) in 33% hydrogen bromide solution in AcOH (3 mL) was heated in a microwave oven at 60° C. for 40 minutes. After coiling to RT, the reaction mixture was added to rapidly stirred ice-cold water (30 mL). After stirring for 10 min, the solid was collected by filtration, washed with water and dried in vacuo at 50° C. to give the title compound (0.28 g, 97%) as a white solid. LCMS (Method A): $R_T$=3.74 min, [M+H]$^+$=366.

Step 2: 3-Iodo-7-methyl-2-phenyl-7H-pyrano[2,3-c]pyridine-4,8-dione: To a mixture of 3-iodo-2-phenyl-7H-pyrano[2,3-c]pyridine-4,8-dione (50 mg, 0.137 mmol) and potassium carbonate (76 mg, 0.548 mmol) in DMF (2 mL) was added iodomethane (26 µL, 0.411 mmol) at RT. After 3 days, the reaction mixture was partitioned between ethyl acetate and water. The resultant biphasic mixture was separated, the aqueous layer was extracted with ethyl acetate and the combined organic extracts were washed with water and brine, dried (Na$_2$SO$_4$), filtered, and concentrated in vacuo. The resultant residue was crystallised from ethyl acetate to give the title compound (31.8 mg, 61%) as a cream solid. The mother liquors were evaporated, the residue was dissolved in DCM and subjected to flash chromatography (SiO$_2$, gradient 70 to 100% ethyl acetate in cyclohexane) to afford a further quantity of the title compound (17.6 mg, 34%). LCMS (Method A): $R_T$=3.78 min, [M+H]$^+$=380.

Step 3: {1-[4-(7-Methyl-4,8-dioxo-2-phenyl-7,8-dihydro-4H-pyrano[2,3-c]pyridin-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-7-methyl-2-phenyl-7H-pyrano[2,3-c]pyridine-4,8-dione was reacted to give the title compound (25.2 mg, 41%) as a colourless gum. LCMS (Method B): $R_T$=4.49 min, [M+H]$^+$=521.

Step 4: 3-[4-(1-Amino-cyclobutyl)-phenyl]-7-methyl-2-phenyl-7H-pyrano[2,3-c]pyridine-4,8-dione hydrochloride: Following the procedure used to prepare 3-[4-(1-amino-cyclobutyl)-phenyl]-6-fluoro-2-phenyl-chromen-4-one, {1-[4-(7-methyl-4,8-dioxo-2-phenyl-7,8-dihydro-4H-pyrano[2,3-c]pyridin-3-yl)-phenyl]-cyclobutyl}-carbamic acid tert-butyl ester was reacted to give the title compound as the free base. The residue was dissolved in a mixture of MeOH (1 mL), water (3 mL) and 1 M HCl (0.2 mL) and chromatographed on a 5 g C18 cartridge {gradient 25 to 55% MeOH in water+1 M HCl (0.06 mL in each 5 mL of eluent)}. Fractions containing product concentrated in vacuo. The resultant residue was chromatographed on a 5 g C18 cartridge {gradient 5 to 55% MeOH in water+1 M HCl (60 µL in each 5 mL of eluent)} to give the title compound (10.1 mg, 46%) as a white solid. $^1$H NMR (400 MHz, CD$_3$OD): δ 7.63 (d, J=7.3 Hz, 1H), 7.48-7.46 (m, 4H), 7.42-7.27 (m, 5H), 6.86 (d, J=7.2 Hz, 1H), 3.71 (s, 3H), 2.81-2.73 (m, 2H), 2.63-2.55 (m, 2H), 2.29-2.18 (m, 1H), 2.02-1.91 (m, 1H). LCMS (Method E): $R_T$=2.76 min, [M+H]$^+$=399.

Example 42

3-[4-(1-Amino-cyclobutyl)-phenyl]-8-chloro-2-phenyl-pyrano[2,3-c]pyridin-4-one hydrochloride

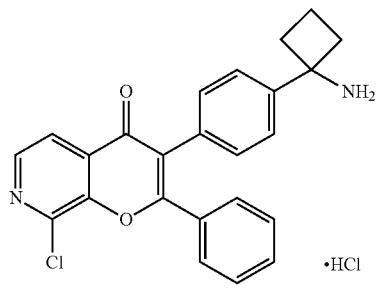 [SMILES: NC1(c2ccc(-c3c(-c4ccccc4)oc4c(Cl)nccc4c3=O)cc2)CCC1 ; Cl]

Step 1: 2-Chloro-3-methoxy-pyridine-4-carbaldehyde: To a stirred solution of 2-chloro-3-methoxypyridine (1.55 g, 10.8 mmol, prepared as described in WO2007/123995) in dry THF (30 mL), cooled to −78° C., was added 2.5 M nBuLi in hexanes (4.75 mL, 11.9 mmol). After 1 hour, a solution of DMF (2.5 mL, 32.4 mmol) in THF (5 mL) was added. After a further 2.5 hours, a saturated aqueous ammonium chloride solution was added and the reaction mixture was allowed to warm to RT. The resultant biphasic mixture was separated and extracted twice with diethyl ether. The combined organic phase was washed with water and brine, dried (Na$_2$SO$_4$), filtered, and concentrated in vacuo. The resultant residue was subjected to flash chromatography (SiO$_2$, gradient 20 to 25% ethyl acetate in cyclohexane) to afford the title compound (1.42 g, 77%) as a white solid. $^1$H NMR (300 MHz, CDCl$_3$): δ 10.44 (d, J=0.8 Hz, 1H), 8.34 (dd, J=4.9 and 0.8 Hz, 1H), 7.60 (d, J=4.9 Hz, 1H), 4.08 (s, 3H). LCMS (Method A): $R_T$=2.84 min, [M+H]$^+$=172/174.

Step 2: 1-(2-Chloro-3-methoxy-pyridin-4-yl)-3-phenyl-prop-2-yn-1-ol: Following the procedure used to prepare 1-(2,6-dimethoxy-pyridin-3-yl)-3-phenyl-prop-2-yn-1-ol, 2-chloro-3-methoxy-pyridine-4-carbaldehyde was reacted to give the title compound (1.60 g, 100%) as a colourless solid, LCMS (Method A): $R_T$=4.14 min, [M+H]$^+$=274/276.

Step 3: 1-(2-Chloro-3-methoxy-pyridin-4-yl)-3-phenyl-propynone: Following the procedure used to prepare 1-(5-fluoro-2-methoxy-phenyl)-3-phenyl-propynone, 1-(2-chloro-3-methoxy-pyridin-4-yl)-3-phenyl-prop-2-yn-1-ol was reacted to give the title compound (0.43 g, 88%) as a pale yellow solid. LCMS (Method A): $R_T$=4.41 min, [M+H]$^+$=272/274.

Step 4: 8-Chloro-3-iodo-2-phenyl-pyrano[2,3-c]pyridin-4-one: Following the procedure used to prepare 6-fluoro-3-iodo-2-phenyl-chromen-4-one, 1-(2-chloro-3-methoxy-pyridin-4-yl)-3-phenyl-propynone was reacted to give the title compound (0.351 g, 60%) as a yellow solid. $^1$H NMR (300 MHz, CDCl$_3$): δ 8.47 (d, J=5.1 Hz, 1H), 8.02 (d, J=5.1 Hz, 1H), 7.92-7.89 (m, 2H), 7.62-7.55 (m, 3H).

Step 5: {1-[4-(8-Chloro-4-oxo-2-phenyl-4H-pyrano[2,3-c]pyridin-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 8-chloro-3-iodo-2-phenyl-pyrano[2,3-c]pyridin-4-one was reacted to give the title compound (30 mg, 20%) as a white solid. LCMS (Method A): $R_T$=4.88 min, [M+Na]$^+$=525/527.

Step 6: 3-[4-(1-Amino-cyclobutyl)-phenyl]-8-chloro-2-phenyl-pyrano[2,3-c]pyridin-4-one Hydrochloride: Following the procedure of 3-[4-(1-amino-cyclobutyl)-phenyl]-6-fluoro-2-phenyl-chromen-4-one, {1-[4-(8-chloro-4-oxo-2-phenyl-4H-pyrano[2,3-c]pyridin-3-yl)-phenyl]-cyclobutyl}-carbamic acid tert-butyl ester was reacted to give the title compound as the free base. The residue was dissolved in a mixture of MeOH (2 mL), water (3 mL) and 1 M HCl (0.1 mL) and then chromatographed on a 5 g C18 cartridge {gradient 40 to 70% MeOH in water+1 M HCl (60 µL in each 10 mL of eluent)} to give the title compound (12.5 mg, 75%) as a white solid. $^1$H NMR (400 MHz, CD$_3$OD): δ 8.45 (d, J=5.1 Hz, 1H), 8.02 (d, J=5.1 Hz, 1H), 7.53-7.48 (m, 4H), 7.46-7.41 (m, 1H), 7.39-7.32 (m, 4H), 2.82-2.75 (m, 2H), 2.63-2.55 (m, 2H), 2.30-2.19 (m, 1H), 2.03-1.92 (m, 1H). LCMS (Method E): $R_T$=3.54 min, [M−NH$_2$]$^-$=386/388.

Example 43

3-[4-(1-Amino-cyclobutyl)-phenyl]-7-(2-hydroxy-ethyl)-2-phenyl-7H-pyrano[2,3-c]pyridine-4,8-dione hydrochloride

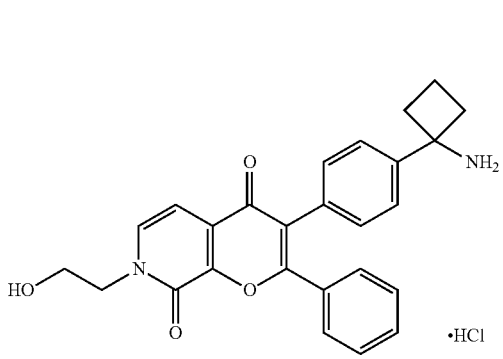 [SMILES: NC1(c2ccc(-c3c(-c4ccccc4)oc4c(=O)n(CCO)ccc4c3=O)cc2)CCC1 ; Cl]

Step 1: 7-(2-Hydroxy-ethyl)-3-iodo-2-phenyl-7H-pyrano[2,3-c]pyridine-4,8-dione: Following the procedure used to prepare 3-iodo-7-methyl-2-phenyl-7H-pyrano[2,3-c]pyridine-4,8-dione, 3-iodo-2-phenyl-7H-pyrano[2,3-c]pyridine-4,8-dione was reacted with 2-bromoethanol to give the title compound (45.2 mg, 81%) as a white solid. $^1$H NMR (400 MHz, DMSO-d6): δ 7.76-7.73 (m, 2H), 7.65 (d, J=7.3 Hz, 1H), 7.62-7.58 (m, 3H), 6.64 (d, J=7.3 Hz, 1H), 4.93 (t, J=5.5 Hz, 1H), 4.06 (t, J=5.4 Hz, 2H), 3.67 (q, J=5.4 Hz, 211).

Step 2: (1-{4-[7-(2-Hydroxy-ethyl)-4,8-dioxo-2-phenyl-7,8-dihydro-4H-pyrano[2,3-c]pyridin-3-yl]-phenyl}-cyclobutyl)-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-(2-hydroxy-ethyl)-3-iodo-2-phenyl-7H-pyrano[2,3-c]pyridine-4,8-dione was reacted to give the title compound (56 mg, 96%) as a colourless solid. LCMS (Method A): $R_T$=4.41 min, [M+H]$^+$=529.

Step 3: 3-[4-(1-Amino-cyclobutyl)-phenyl]-7-(2-hydroxy-ethyl)-2-phenyl-7H-pyrano[2,3-c]pyridine-4,8-dione hydrochloride: Following the procedure used to prepare 3-[4-(1-amino-cyclobutyl)-phenyl]-6-fluoro-2-phenyl-chromen-4-one, (1-{4-[7-(2-hydroxy-ethyl)-4,8-dioxo-2-phenyl-7,8-dihydro-4H-pyrano[2,3-c]pyridin-3-yl]-phenyl}-cyclobutyl)-carbamic acid tert-butyl ester was reacted to give the title compound as the free base. The residue was dissolved in a mixture of MeOH (4 mL), water (10 mL) and 1 M HCl (0.2 mL) and then chromatographed on a 10 g C18 cartridge {gradient 35 to 50% MeOH in water+1 M HCl (60 μL in each 10 mL of eluent)} to give the title compound (33.7 mg, 68%) as a white solid. $^1$H NMR (400 MHz, CD$_3$OD): δ 7.61 (d, J=7.3 Hz, 1H), 7.49-7.46 (m, 4H), 7.42-7.38 (m, 1H), 7.36-7.28 (m, 4H), 6.87 (d, J=7.2 Hz, 1H), 4.25 (t, J=5.2 Hz, 2H), 3.91 (t, J=5.2 Hz, 2H), 2.81-2.74 (m, 2H), 2.62-2.54 (m, 2H), 2.29-2.18 (m, 1H), 2.02-1.91 (m, 1H). LCMS (Method E): $R_T$=2.62 min, [M+H]$^+$=429.

Example 44

7-[4-(1-Amino-cyclobutyl)-phenyl]-4-chloro-8-phenyl-1H-chromeno[7,8-d]imidazol-6-one

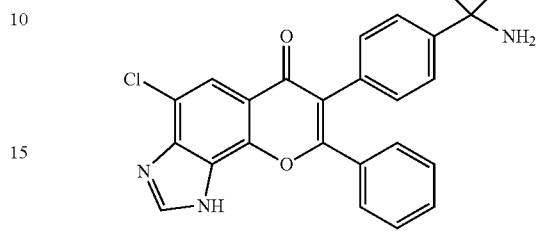

Step 1: 7-Chloro-4-methoxy-3H-benzoimidazole-5-carboxylic acid methyl ester: To a solution of 4-amino-5-chloro-2-methoxy-3-nitro-benzoic acid methyl ester (1.00 g, 3.84 mmol, prepared as described in J. Med. Chem., 2006, 49, 4762-4766) in formic acid (10.5 mL), was added tin(II) chloride dihydrate (2.6 g, 11.5 mmol). The reaction mixture was heated at 130° C. in the microwave for 10 min. Upon cooling to RT, water was added (50 mL) and the pH of the resultant mixture was adjusted to ~7 by careful addition of 5 M sodium hydroxide. The resultant mixture was filtered through a Celite® and sand filter cake, washing with EtOAc (5×30 mL). The organic layer was separated, dried (Na$_2$SO$_4$), filtered and concentrated in vacuo. The resultant residue was subjected to flash chromatography (SiO$_2$, gradient 0 to 100% EtOAc in pentane) to afford the title compound as an off-white solid (0.29 g, 31%). LCMS (Method A): $R_T$=3.40 min, [M+H]$^+$=241/243.

Step 2: 7-Chloro-4-methoxy-3-(2-trimethylsilanyl-ethoxymethyl)-3H-benzoimidazole-5-carboxylic acid methyl ester and 7-chloro-4-methoxy-1-(2-trimethylsilanyl-ethoxymethyl)-1H-benzoimidazole-5-carboxylic acid methyl ester: To a stirred solution of 7-chloro-4-methoxy-3H-benzoimidazole-5-carboxylic acid methyl ester (0.34 g, 1.41 mmol) in DMF (14 mL) at 0° C., under an argon atmosphere, was added sodium hydride (68 mg, 1.70 mmol) portionwise. After 10 min, (2-chloromethoxy-ethyl)-trimethylsilane (0.30 mL, 1.70 mmol) was added dropwise. The reaction mixture was stirred at 0° C. for 2.5 hours before being quenched into ice/water (40 mL). The resultant biphasic mixture was separated and extracted with ethyl acetate (2×40 mL). The combined organic phase was washed with brine (40 mL), dried (Na$_2$SO$_4$), filtered and concentrated in vacuo. The resulting residue was subjected to flash chromatography (SiO$_2$, gradient 0 to 60% EtOAc in pentane) to give a mixture of the title compounds as a yellow oil (0.46 g, 88%). LCMS (Method A): $R_T$=4.69 min, [M+H]$^+$=371/379 and $R_T$=4.74 min, [M+H]$^+$=371/379.

Step 3: 7-Chloro-4-methoxy-3-(2-trimethylsilanyl-ethoxymethyl)-3H-benzoimidazole-5-carboxylic acid and 7-chloro-4-methoxy-1-(2-trimethylsilanyl-ethoxymethyl)-1H-benzoimidazole-5-carboxylic acid: To a stirred suspension of a mixture of 7-chloro-4-methoxy-3-(2-trimethylsilanyl-ethoxymethyl)-3H-benzoimidazole-5-carboxylic acid and 7-chloro-4-methoxy-1-(2-trimethylsilanyl-ethoxymethyl)-1H-benzoimidazole-5-carboxylic acid (0.46 g, 1.24 mmol) in MeOH (4.0 mL) and water (4.0 mL), was added sodium hydroxide (0.24 g, 6.20 mmol) portionwise. The reaction mixture was stirred at 75° C. for 1 hour. Upon cooling to RT, water (30 mL) was added and the pH of the resultant mixture was adjusted to ~7 by careful addition of 12 M aqueous HCl solution. The resulting suspension was extracted with EtOAc (3×50 mL). The combined organic extracts were dried (Na$_2$SO$_4$), filtered and concentrated in vacuo, to yield a mixture of the title compounds as an off-white glass (0.44 g, 100%). LCMS (Method A): R$_T$=4.44 min, [M+H]$^+$=357/359 and R$_T$=4.51 min, [M+H]$^+$=357/359.

Step 4: 7-Chloro-4-methoxy-3-(2-trimethylsilanyl-ethoxymethyl)-3H-benzoimidazole-5-carboxylic acid methoxy-methyl-amide and 7-chloro-4-methoxy-1-(2-trimethylsilanyl-ethoxymethyl)-1H-benzoimidazole-5-carboxylic acid methoxy-methyl-amide: Following the procedure used to prepare N-dimethoxy-N-methyl-nicotinamide, a mixture of 7-chloro-4-methoxy-3-(2-trimethylsilanyl-ethoxymethyl)-3H-benzoimidazole-5-carboxylic acid and 7-chloro-4-methoxy-1-(2-trimethylsilanyl-ethoxymethyl)-1H-benzoimidazole-5-carboxylic acid (0.44 g, 5.88 mmol) were reacted to give a mixture of the title compounds as an oil (0.40 g, 81%). LCMS (Method A): R$_T$=4.27 min, [M+H]$^+$=400/402 and R$_T$ 4.40 min, [M+H]$^+$=400/402.

Step 5: 1-[7-Chloro-4-methoxy-3-(2-trimethylsilanyl-ethoxymethyl)-3H-benzoimidazol-5-yl]-3-phenyl-propynone and 1-[7-chloro-4-methoxy-1-(2-trimethylsilanyl-ethoxymethyl)-1H-benzoimidazol-5-yl]-3-phenyl-propynone: To a solution of a mixture of 7-chloro-4-methoxy-3-(2-trimethylsilanyl-ethoxymethyl)-3H-benzoimidazole-5-carboxylic acid methoxy-methyl-amide and 7-chloro-4-methoxy-1-(2-trimethylsilanyl-ethoxymethyl)-1H-benzoimidazole-5-carboxylic acid methoxy-methyl-amide (110 mg, 0.275 mmol) in anhydrous THF (2.0 mL) at 0° C., was added phenylethynyl magnesium bromide solution (1 M in THF, 0.41 mL, 0.41 mmol). The reaction mixture was allowed to warm to RT.

After 18 h, the reaction mixture was cooled to 0° C. and further phenylethynyl magnesium bromide solution (1 M in THF, 0.41 mL, 0.41 mmol) was added and the reaction was allowed to warm to RT. After a further 24 h, the reaction mixture was quenched with saturated aqueous ammonium chloride solution. The resultant biphasic mixture was extracted with EtOAc (2×20 mL). The combined organic extracts were dried (Na$_2$SO$_4$), filtered and concentrated in vacuo. The resultant residue was subjected to flash chromatography (SiO$_2$, gradient 0 to 50% EtOAc in pentane) to afford a mixture of the title compounds (0.11 g, 64%). LCMS (Method A): R$_T$=4.81 min, [M+H]$^+$=441/443 and R$_T$=5.04 min, [M+H]$^+$=441/443.

Step 6: 4-Chloro-7-iodo-8-phenyl-1-(2-trimethylsilanyl-ethoxymethyl)-1H-chromeno[7,8-d]imidazol-6-one and 4-chloro-7-iodo-8-phenyl-3-(2-trimethylsilanyl-ethoxymethyl)-3H-chromeno[7,8-d]imidazol-6-one: Following the procedure used to prepare 6-fluoro-3-iodo-2-phenyl-chromen-4-one, a mixture of 1-[7-chloro-4-methoxy-3-(2-trimethylsilanyl-ethoxymethyl)-3H-benzoimidazol-5-yl]-3-phenyl-propynone and 1-[7-chloro-4-methoxy-1-(2-trimethylsilanyl-ethoxymethyl)-1H-benzoimidazol-5-yl]-3-phenyl-propynone (64 mg, 0.145 mmol) were reacted to furnish a mixture of the title compounds (54 mg, 80%). LCMS (Method A): R$_T$=4.75 min, [M+H]$^+$=553/555 and R$_T$=4.96 min, [M+H]$^+$=553/555.

Step 7: (1-{4-[4-Chloro-6-oxo-8-phenyl-1-(2-trimethylsilanyl-ethoxymethyl)-1,6-dihydro-chromeno[7,8-d]imidazol-7-yl]-phenyl}-cyclobutyl)-carbamic acid tert-butyl ester and (1-{4-[4-chloro-6-oxo-8-phenyl-3-(4-trimethylsilanyl-butyl)-3,6-dihydro-chromeno[7,8-d]imidazol-7-yl]-phenyl}-cyclobutyl)-carbamic acid tert-butyl ester: Following the procedure for {1-[4-(6-fluoro-4-oxo-2-phenyl-4H-chromen-3-yl)-phenyl]-cyclobutyl}-carbamic acid tert-butyl ester, a mixture of 4-chloro-7-iodo-8-phenyl-1-(2-trimethylsilanyl-ethoxymethyl)-1H-chromeno[7,8-d]imidazol-6-one and 4-chloro-7-iodo-8-phenyl-3-(2-trimethylsilanyl-ethoxymethyl)-3H-chromeno[7,8-d]imidazol-6-one (54 mg, 0.10 mmol) were reacted to give a mixture of the title compounds (46 mg, 68%). LCMS (Method A): R$_T$=5.09 min, [M+H]$^+$=672/674 and R$_T$=5.14 min, [M+H]$^+$=672/674.

Step 8: 7-[4-(1-Amino-cyclobutyl)-phenyl]-4-chloro-8-phenyl-1H-chromeno[7,8-d]imidazol-6-one: Following the procedure for 3-[4-(1-amino-cyclobutyl)-phenyl]-6-fluoro-2-phenyl-chromen-4-one, a mixture of (1-{4-[4-chloro-6-oxo-8-phenyl-1-(2-trimethylsilanyl-ethoxymethyl)-1,6-dihydro-chromeno[7,8-d]imidazol-7-yl]-phenyl}-cyclobutyl)-carbamic acid tert-butyl ester and (1-{4-[4-chloro-6-oxo-8-phenyl-3-(4-trimethylsilanyl-butyl)-3,6-dihydro-chromeno[7,8-d]imidazol-7-yl]-phenyl}-cyclobutyl)-carbamic acid tert-butyl ester (46 mg, 0.07 mmol) were reacted to give crude product. This residue was subjected to flash chromatography [SiO$_2$, gradient 0 to 15% MeOH (2 M NH$_3$) in DCM] to furnish the title compound as a white solid (15 mg, 48%). LCMS (Method E): R$_T$=2.96 min, [M+H]*=442/444. $^1$H NMR (400 MHz, DMSO-d6): 8.33 (s, 1H), 7.87 (s, 1H), 7.45-7.41 (m, 2H), 7.39-7.35 (m, 2H), 7.32-7.27 (m, 1H), 7.22-7.16 (m, 4H), 2.59-2.50 (m, 2H), 2.31-2.22 (m, 2H), 2.12-2.00 (m, 1H), 1.80-1.69 (m, 1H).

Example 45

7-[4-(1-Amino-cyclobutyl)-phenyl]-8-phenyl-1H-chromeno[7,8-d]imidazol-6-one.TFA

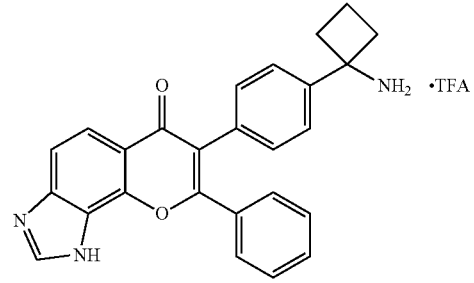 [SMILES: NC1(c2ccc(-c3c(-c4ccccc4)oc4c(ccc5nc[nH]c54)c3=O)cc2)CCC1]

Step 1: (1-{-4-[6-oxo-8-phenyl-1-(2-trimethylsilanyl-ethoxymethyl)-1,6-dihydro-chromeno[7,8-d]imidazol-7-yl]-phenyl}-cyclobutyl)-carbamic acid tert-butyl ester and (1-{4-[6-oxo-8-phenyl-3-(2-trimethylsilanyl-ethoxymethyl)-3,6-dihydro-chromeno[7,8-d]imidazol-7-yl]-phenyl}-cyclobutyl)-carbamic acid tert-butyl ester: To a mixture of (1-{4-[4-chloro-6-oxo-8-phenyl-1-(2-trimethylsilanyl-ethoxymethyl)-1,6-dihydro-chromeno[7,8-d]imidazol-7-yl]-phenyl}-cyclobutyl)-carbamic acid tert-butyl ester and (1-{-4-[4-chloro-6-oxo-8-phenyl-3-(4-trimethylsilanyl-butyl)-3,6-dihydro-chromeno[7,8-d]imidazol-7-yl]-phenyl}-cyclobutyl)-carbamic acid tert-butyl ester (46 mg, 0.07 mmol), TEA (15 uL, 0.1 mmol) in IMS (1.0 mL), was added palladium hydroxide (8 mg, 20 weight % on carbon). The reaction mixture was flushed with hydrogen and stirred at RT under a positive pressure of hydrogen (maintained by balloon) for 12 days. The reaction mixture was filtered through Celite®, washing with DCM:MeOH (1:1) and the washings were concentrated in vacuo. The resultant residue was subjected to flash chromatography (SiO$_2$, gradient 0 to 80% EtOAc in pentane) to afford a mixture of title compounds as an oil (11 mg, 25%). LCMS (Method A): $R_T$=5.05 min, [M+H]$^+$=638 and $R_T$=5.20 min, [M+H]$^+$=638.

Step 2: 7-[4-(1-Amino-cyclobutyl)-phenyl]-8-phenyl-1H-chromeno[7,8-d]imidazol-6-one: To a solution, containing a mixture of (1-{-4-[6-oxo-8-phenyl-1-(2-trimethylsilanyl-ethoxymethyl)-1,6-dihydro-chromeno[7,8-d]imidazol-7-yl]-phenyl}-cyclobutyl)-carbamic acid tert-butyl ester and (1-{4-[6-oxo-8-phenyl-3-(2-trimethylsilanyl-ethoxymethyl)-3,6-dihydro-chromeno[7,8-d]imidazol-7-yl]-phenyl}-cyclobutyl)-carbamic acid tert-butyl ester (11 mg, 0.017 mmol), in DCM (1.0 mL) was added TFA (0.25 mL). The reaction mixture was stirred at RT for 18 h. After this time the reaction mixture was concentrated in vacuo. The resultant residue was triturated with DCM (×2) and dried in vacuo to furnish the title compound (7.4 mg, 84%). LCMS (Method E): $R_T$=2.76 min, [M+]$^+$=408. $^1$H NMR (400 MHz, DMSO-d6): 8.69 (s, 1H), 8.67 (br s, 1H), 8.12 (d, J=8.6 Hz, 1H), 7.89 (d, J=8.7 Hz, 1H), 7.71-7.61 (m, 5H), 7.59-7.51 (m, 4H), 2.84-2.75 (m, 2H), 2.74-2.64 (m, 2H), 2.40-2.28 (m, 1H), 2.07-1.95 (m, 1H).

Example 46

3-[4-(1-Amino-cyclobutyl)-phenyl]-2-phenyl-1-benzopyran-4-one.TFA

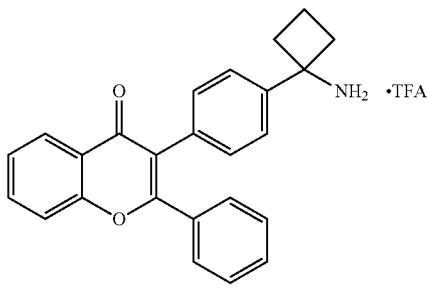 [SMILES: NC1(c2ccc(-c3c(-c4ccccc4)oc4ccccc4c3=O)cc2)CCC1]

Step 1: 3-Bromo-2-phenyl-1-benzopyran-4-one

To a round-bottom flask was added 2-phenyl-chromen-4-one (0.94 g, 4.23 mmol), acetic acid (40 mL) and N-bromosuccinimide (0.83 g, 4.65 mmol). The reaction mixture was heated to 100° C. using a hot oil bath with a water cooled reflux condenser, while stirring for 1 hour. The reaction mixture was cooled to RT and the solvents were removed in vacuo. The residue was suspended in ethyl acetate, washed with a saturated aqueous sodium hydrogen carbonate solution, dried (MgSO$_4$), filtered, and concentrated in vacuo. The resulting residue was purified by silica gel chromatography (10:1 hexane:EtOAc) to give a white solid (527 mg, 41%). $^1$H-NMR (400 MHz, CDCl$_3$) δ 8.31 (d, 1H), 7.75 (d, 2H), 7.72 (dd, 1H), 7.45-7.56 (m, 5H).

Step 2: {1-[4-(4-oxo-2-phenyl-4H-1-benzopyran-3-yl)-phenyl]-cyclobutyl}-carbamic acid tert-butyl ester: To a round-bottom flask was added 3-bromo-2-phenyl-1-benzopyran-4-one (27.1 mg, 0.09 mmol) and {1-[4-(4,4,5,5-tetramethyl-1,3,2-dioxaborolan-2-yl)-phenyl]-cyclobutyl}-carbamic acid tert-butyl ester (50.4 mg, 0.135 mmol) in toluene:ethanol (4:1, 2.5 mL) and 2 M aqueous sodium carbonate (1 mL). The solution was degassed for 20 minutes, after which time, tetrakis(triphenylphosphine) palladium (5.2 mg, 5 mol %) was added. The reaction mixture was heated to 80° C. using an oil bath with a water cooled reflux condenser, while stirring for 21 hours. The reaction mixture cooled to RT, suspended in ethyl acetate and washed with brine, dried (MgSO$_4$), filtered, and concentrated in vacuo. The resulting residue was purified by silica gel chromatography (10:1 to 5:1 hexane:EtOAc gradient) to give a white solid (12.2 mg, 94%). $^1$H-NMR (400 MHz, CDCl$_3$) δ 8.30 (d, 1H), 7.66 (dd, 1H), 7.53 (dd, 1H), 7.38-7.45 (m, 3H), 7.30-7.36 (m, 3H), 7.27 (d, 2H), 7.19 (d, 2H), 5.11 (bs, 1H), 2.35-2.58 (m, 4H), 1.91-2.09 (m, 1H), 1.77-1.88 (m, 1H), 1.38 (bs, 9H).

Step 3: 3-[4-(1-Amino-cyclobutyl)-phenyl]-2-phenyl-1-benzopyran-4-one.TFA: To a solution of {1-[4-(7-amino-4-oxo-2-phenyl-4H-1-benzopyran-3-yl)-phenyl]-cyclobutyl}-carbamic acid tert-butyl ester (12.2 mg, 0.03 mmol) in dichloromethane (1 mL) was added TFA (1 mL) and the mixture was stirred at RT for 1 hour. The reaction mixture was concentrated in vacuo to give a white solid (16.0 mg, 100%). $^1$H-NMR (400 MHz, D$_2$O) δ 8.02 (d, 1H), 7.76 (dd, 2H), 7.55 (d, 2H), 7.42 (dd, 2H), 7.28-7.34 (m, 3H), 7.17-7.22 (m, 3H) 2.60-2.67 (m, 2H), 2.44-2.52 (m, 2H), 2.04-2.08 (m, 1H), 1.80-1.83 (m, 1H). LCMS (Method I): $R_T$=4.50 min, [M+H]$^+$=368

Example 47

7-Amino-3-[4-(1-amino-cyclobutyl)-phenyl]-2-phenyl-1-benzopyran-4-one.TFA

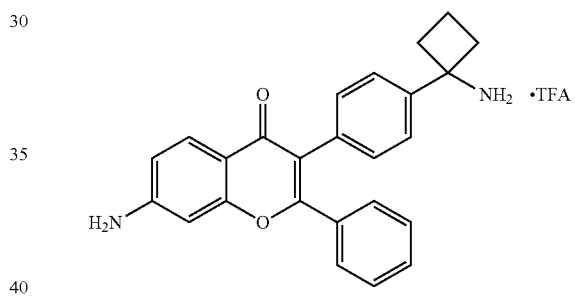

Step 1: 7-Amino-3-bromo-2-phenyl-1-benzopyran-4-one: Following the procedure for 3-bromo-2-phenyl-1-benzopyran-4-one, 7-amino-2-phenyl-1-benzopyran-4-one (1.08 g, 4.55 mmol) was reacted to give the title compound as a yellow solid (1.15 g, 80%). $^1$H-NMR (400 MHz, CDCl$_3$) δ 7.97-8.02 (m, 3H), 7.53-7.56 (m, 3H), 6.79-6.82 (m, 2H), 4.77 (bs, 2H).

Step 2: {1-[4-(7-Amino-4-oxo-2-phenyl-4H-1-benzopyran-3-yl)-phenyl]-cyclobutyl}-carbamic acid tert-butyl ester: Following the procedure used for {1-[4-(4-oxo-2-phenyl-4H-1-benzopyran-3-yl)phenyl]-cyclobutyl}-carbamic acid tert-butyl ester, 7-amino-3-bromo-2-phenyl-1-benzopyran-4-one (28.4 mg, 0.09 mmol) was reacted to give the title compound as a yellow solid (6.3 mg, 19%). $^1$H-NMR (400 MHz, CDCl$_3$) δ 8.05 (d, 1H), 7.64 (d, 2H), 7.50 (d, 2H), 7.45 (d, 2H), 7.35 (dd, 1H), 7.31 (dd, 2H), 6.82 (d, 1H), 6.74 (s, 1H), 5.28 (bs, 1H), 4.11 (bs, 2H), 2.62-2.65 (m, 4H), 2.15-2.19 (m, 1H), 1.90-1.97 (m, 1H) 1.33 (bs, 9H).

Step 3: 7-Amino-3-[4-(1-amino-cyclobutyl)-phenyl]-2-phenyl-1-benzopyran-4-one.TFA: Following the procedure used to make 3-[4-(1-amino-cyclobutyl)-phenyl]-2-phenyl-1-benzopyran-4-one, {1-[4-(7-amino-4-oxo-2-phenyl-4H-1-benzopyran-3-yl)-phenyl]-cyclobutyl}-carbamic acid tert-butyl ester (6.3 mg, 0.017 mmol) was reacted to give the title compound as a yellow solid (10.2 mg, 100%). $^1$H-NMR (400 MHz, D$_2$O) δ 7.30 (d, 1H), 7.05-7.18 (m, 4H), 6.85 (dd, 2H), 6.59-6.65 (m, 4H) 5.65 (s, 1H) 2.33-2.47 (m, 4H), 1.95-2.02 (m, 1H), 1.52-1.59 (m, 1H). LCMS (Method I): $R_T$=3.97 min, [M+H]$^+$=384.

Example 48

2-(4-(1-aminocyclobutyl)phenyl)-3-phenyl-1H-inden-1-one hydrochloride

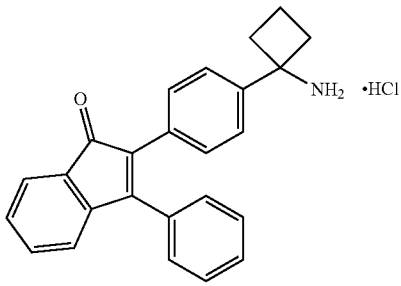 [SMILES: NC1(c2ccc(C3=C(c4ccccc4)c4ccccc4C3=O)cc2)CCC1 ; Cl]

Step 1: tert-butyl 1-(4-(phenylethynyl)phenyl)cyclobutylcarbamate: A mixture of tert-butyl 1-(4-bromophenyl)cyclobutylcarbamate (1.53 g, 4.7 mmol), ethynylbenzene (2.5 mL, 22.6 mmol), copper iodide (36 mg, 0.24 mmol) and diisopropylamine (3.2 mL, 22.6 mmol) in dioxane (3 mL) was degassed for 30 min, followed by the addition of bis(tri-tert-butylphosphine)palladium (144 mg, 0.36 mmol). The resulting mixture was heated at 90° C. for 16 h, after cooled down to RT, concentrated to dryness. The crude residue was purified by column chromatography (eluting with 10% DCM in heptane) to give the title compound (0.85 g, 52%). $^1$H NMR (500 MHz, CDCl$_3$): 7.58-7.54 (m, 4H), 7.48-7.43 (m, 2H), 7.39-7.20 (m, 3H), 2.55-2.40 (m, 4H), 2.15-2.10 (m, 1H), 1.93-1.84 (m, 1H), 1.45-1.20 (br s, 9H).

Step 2: tert-butyl 1-(4-(1-oxo-3-phenyl-1H-inden-2-yl)phenyl)cyclobutylcarbamate: A mixture of 2-bromobenzaldehyde (92.5 mg, 0.5 mmol), tert-butyl 1-(4-(phenylethynyl)phenyl)cyclobutylcarbamate (347 mg, 1.0 mmol), sodium acetate (164 mg, 2.0 mmol), tetrabutylammonium chloride hydrate (147.7 mg, 0.50 mmol) and palladium acetate (5.6 mg, 0.025 mmol) in DMF (10 mL) was heated at 100° C. for 48 h. The reaction mixture was concentrated to dryness and was partitioned between ethyl acetate (30 mL) and water (30 mL). The organic phase was washed with water (30 mL), brine (20 mL), dried (Na$_2$SO$_4$), filtered and concentrated in vacuo. The crude residue was purified by column chromatography (eluting with 10% ethyl acetate in hexane) to give title compound (14 mg, 6.2%). $^1$H NMR (500 MHz, CDCl$_3$): 7.50 (d, 1H), 7.45-7.05 (m, 12H), 2.55-2.25 (m, 4H), 2.15-1.95 (m, 1H), 1.85-1.70 (m, 1H), 1.40-1.10 (br s, 9H).

Step 3: 2-(4-(1-aminocyclobutyl)phenyl)-3-phenyl-1H-inden-1-one hydrochloride: To a solution of tert-butyl 1-(4-(1-oxo-3-phenyl-1H-inden-2-yl)phenyl)cyclobutylcarbamate (6 mg, 0.0133 mmol) in DCM (1.0 mL) was added 2 M HCl in ether (2.0 mL). The reaction mixture was stirred at RT for 24 h and concentrated in vacuo to give the title compound (3 mg, 64%). $^1$H NMR (500 MHz, CD$_3$OD): 7.65-7.10 (m, 13H), 2.75-2.60 (m, 2H), 2.55-2.45 (m, 2H), 2.20-2.05 (m, 1H), 1.95-1.80 (m, 1H). LCMS (Method I): [M+H]$^+$=353.

Example 49

7-Amino-3-[4-(1-amino-cyclobutyl)-phenyl]-6-bromo-2-phenyl-chromen-4-one. TFA

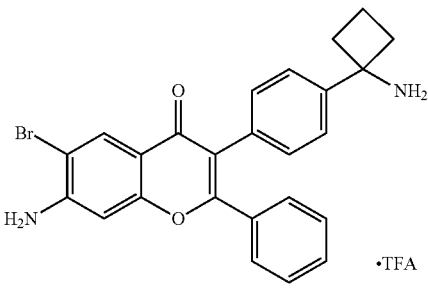 [SMILES: Nc1cc2oc(-c3ccccc3)c(-c3ccc(C4(N)CCC4)cc3)c(=O)c2cc1Br ; "·TFA"]

Step 1: {1-[4-(7-Amino-6-bromo-4-oxo-2-phenyl-4H-chromen-3-yl)-phenyl]-cyclobutyl}-carbamic acid tert-butyl ester: To a suspension of {1-[4-(7-amino-4-oxo-2-phenyl-4H-1-benzopyran-3-yl)-phenyl]-cyclobutyl}-carbamic acid tert-butyl ester (48 mg, 0.10 mmol) in chloroform (1.0 mL), was added N-bromosuccinimide (18 mg, 0.10 mmol) and the reaction mixture was stirred at RT for 1 hour. After this time, the mixture was poured into water and extracted with EtOAc (×2). The combined organic extracts were washed with brine, dried (Na$_2$SO$_4$), filtered and concentrated in vacuo. The crude residue was purified by flash chromatography (SiO$_2$, gradient 0 to 80% EtOAc in pentane) to yield the title compound as a yellow solid (34 mg, 61%). LCMS (Method B): $R_T$=4.96 min, [M+H]$^+$=561/563.

Step 2: 7-Amino-3-[4-(1-amino-cyclobutyl)-phenyl]-6-bromo-2-phenyl-chromen-4-one. TFA: Following the procedure of 3-[4-(1-amino-cyclobutyl)-phenyl]-2-phenyl-1-benzopyran-4-one, {1-[4-(7-amino-4-oxo-2-phenyl-4H-1-benzopyran-3-yl)-phenyl]-cyclobutyl}-carbamic acid tert-butyl ester (9.0 mg, 0.016 mmol) was reacted to give the title compound as a yellow solid (10 mg, 100%). LCMS (Method E): $R_T$=3.30 min, [M+H]$^+$=461/463. $^1$H NMR (300 MHz, DMSO-d6): δ 8.63 (s, 3H), 8.08 (s, 1H), 7.77 (d, J=8.2 Hz, 2H), 7.64-7.56 (m, 4H), 7.54-7.48 (m, 1H), 7.45-7.37 (m, 2H), 6.92 (s, 1H), 5.65 (s, 2H), 2.77-2.59 (m, 4H), 2.30-2.14 (m, 1H), 1.99-1.82 (m, 1H).

Example 50

3-[4-(1-Amino-cyclobutyl)-phenyl]-7-methoxy-4-oxo-2-phenyl-4H-chromene-8-carboxylic acid amide hydrochloride

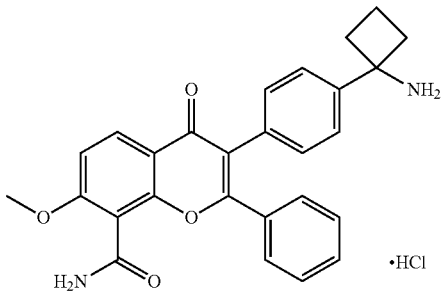 [SMILES: COc1ccc2c(=O)c(-c3ccc(C4(N)CCC4)cc3)c(-c3ccccc3)oc2c1C(N)=O ; Cl]

Step 1: 3-[4-(1-Amino-cyclobutyl)-phenyl]-7-methoxy-4-oxo-2-phenyl-4H-chromene-8-carboxylic acid amide hydrochloride: {1-[4-(8-Cyano-7-methoxy-4-oxo-2-phenyl-4H-chromen-3-yl)-phenyl]-cyclobutyl}-carbamic acid tert-butyl ester (17 mg, 0.03 mmol) was dissolved in concentrated sulfuric acid (2 mL) and stirred at 100° C. for 1 h. The reaction mixture was allowed to cool to RT and was basified to pH 10 by addition of 10 M NaOH (aq). The resulting mixture was extracted using DCM (2×2 mL), dried ($Na_2SO_4$), filtered and concentrated in vacuo. The compound was dissolved in DCM and loaded onto an SCX-2 cartridge. The cartridge was washed repeatedly with MeOH:DCM (1:1) before eluting with 2 M ammonia in methanol solution:DCM (1:1). The eluent was collected and concentrated in vacuo. The resulting residue was subjected to flash chromatography ($SiO_2$, gradient 0-20% MeOH in DCM). The resultant residue was dissolved in a mixture of MeOH (3 mL), water (3 mL) and 1 M HCl (0.6 mL) and chromatographed on a 2 g C18 cartridge {gradient 10 to 100% MeOH in water+1 M HCl (60 µL in each 10 mL of eluent)} to give the title compound as a white solid (2.4 mg, 17%). $^1$H NMR (400 MHz, DMSO-d6): δ 8.62 (bs, 3H), 8.05 (d, J=8.9 Hz, 1H), 7.93 (bs, 1H), 7.68 (bs, 1H), 7.44 (d, J=8.5 Hz, 2H), 7.40-7.26 (m, 6H), 7.23 (d, J=8.3 Hz, 2H), 3.91 (s, 3H), 2.59-2.47 (m, 4H), 2.20-2.07 (m, 1H), 1.83-1.70 (m, 1H). LCMS (Method E): $R_T$=2.65 min, $[M+H]^+$=441.

Example 51

3-[4-(1-Amino-cyclobutyl)-phenyl]-8-bromo-2-phenyl-chromen-4-one

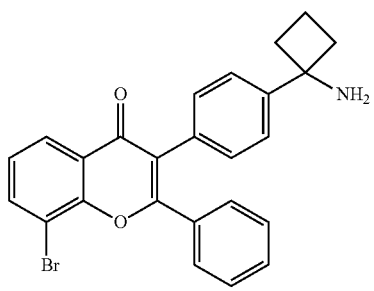 [SMILES: NC1(c2ccc(-c3c(-c4ccccc4)oc4c(Br)cccc4c3=O)cc2)CCC1]

Step 1: 3-Bromo-2-methoxy-benzaldehyde: To a solution of 3-bromo-2-hydroxy-benzaldehyde (2.72 g, 13.53 mmol) in DMF (70 mL) were added potassium carbonate (5.61 g, 40.59 mmol) and iodomethane (1.01 mL, 16.24 mmol). The reaction mixture was stirred at RT. After 18 h, the mixture was acidified with cooling using 1 M HCl (aq), extracted with EtOAc. The organic extract was dried ($Na_2SO_4$), filtered and concentrated in vacuo to afford the title compound as an oil (2.73 g, 94%). $^1$H NMR (300 MHz, $CDCl_3$): δ 10.36 (s, 1H), 7.85-7.79 (m, 2H), 7.15 (dt, J=7.7 and 0.7 Hz, 1H), 4.00 (s, 3H).

Step 2: 1-(3-Bromo-2-methoxy-phenyl)-3-phenyl-prop-2-yn-1-ol: Following the procedure used to prepare 1-(5-fluoro-2-methoxy-phenyl)-3-phenyl-prop-2-yn-1-ol, 3-bromo-2-methoxy-benzaldehyde was reacted to give the title compound as an oil (3.70 g, 92%).

$^1$H NMR (400 MHz, $CDCl_3$): δ 7.61 (dd, J=7.7 and 1.5 Hz, 1H), 7.55 (dd, J=8.1 and 1.7 Hz, 1H), 7.47-7.43 (m, 2H), 7.34-7.28 (m, 3H), 7.05 (t, J=7.8 Hz, 1H), 5.90 (s, 1H), 4.03 (s, 3H), 2.91 (bs, 1H).

Step 3: 1-(3-Bromo-2-methoxy-phenyl)-3-phenyl-propynone: Following the procedure used to prepare 1-(5-fluoro-2-methoxy-phenyl)-3-phenyl-propynone, 1-(3-bromo-2-methoxy-phenyl)-3-phenyl-prop-2-yn-1-ol was reacted to give the title compound as a gummy solid (3.59 g, 98%). $^1$H NMR (400 MHz, $CDCl_3$): δ 8.00 (dd, J=8.0 and 2.0 Hz, 1H), 7.79 (dd, J=7.8 and 1.2 Hz, 1H), 7.68-7.65 (m, 2H), 7.51-7.39 (m, 3H), 7.13 (t, J=7.8 Hz, 1H), 4.00 (s, 3H).

Step 4: 8-Bromo-3-iodo-2-phenyl-chromen-4-one: Following the procedure used to prepare 6-fluoro-3-iodo-2-phenyl-chromen-4-one, 1-(3-bromo-2-methoxy-phenyl)-3-phenyl-propynone was reacted to give the title compound as an off-white solid (1.70 g, 84%). $^1$H NMR (400 MHz, $CDCl_3$): δ 8.24 (dd, J=8.2 and 1.6 Hz, 1H), 7.97-7.90 (m, 3H), 7.61-7.52 (m, 3H), 7.34 (t, J=7.8 Hz, 1H).

Step 5: {1-[4-(8-Bromo-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 8-bromo-3-iodo-2-phenyl-chromen-4-one was reacted to give the title compound (73 mg, 67%). $^1$H NMR (400 MHz, $CDCl_3$): δ 8.24 (dd, J=7.9 and 1.6 Hz, 1H), 7.94 (dd, J=7.7 and 1.5 Hz, 1H), 7.50 (d, J=7.0 Hz, 2H), 7.39 (d, J=8.2 Hz, 2H), 7.36-7.19 (m, 6H), 5.06 (s, 1H), 2.60-2.47 (m, 4H), 2.14-2.01 (m, 1H), 1.91-1.77 (m, 1H), 1.37 (bs, 9H).

Step 6: 3-[4-(1-Amino-cyclobutyl)-phenyl]-8-bromo-2-phenyl-chromen-4-one: Following the procedure used to prepare 3-[4-(1-amino-cyclobutyl)-phenyl]-6-fluoro-2-phenyl-chromen-4-one, {1-[4-(8-bromo-4-oxo-2-phenyl-4H-chromen-3-yl)-phenyl]-cyclobutyl}-carbamic acid tert-butyl ester was reacted to give the title compound as a white solid (25 mg, 86%). $^1$H NMR (400 MHz, $CDCl_3$): δ 8.20 (dd, J=7.9 and 1.5 Hz, 1H), 7.91 (dd, J=7.6 and 1.5 Hz, 1H), 7.50-7.45 (m, 2H), 7.38-7.16 (m, 8H), 2.59-2.49 (m, 2H), 2.23-1.97 (m, 3H), 1.80-1.68 (m, 1H). LCMS (Method E): $R_T$=3.91 min, $[M+H]^+$=446/448.

Example 52

3-[4-(1-Amino-cyclobutyl)-phenyl]-2-phenyl-8-(1H-pyrazol-4-yl)-chromen-4-one hydrochloride

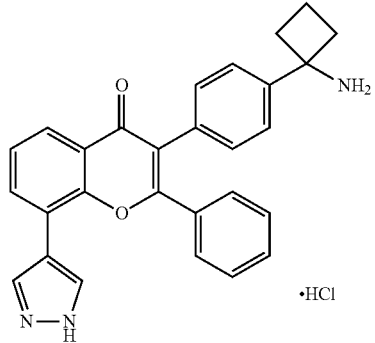 [SMILES: NC1(c2ccc(-c3c(-c4ccccc4)oc4c(-c5cn[nH]c5)cccc4c3=O)cc2)CCC1 ; Cl]

Step 1: (1-{4-[4-oxo-2-phenyl-8-(1H-pyrazol-4-yl)-4H-chromen-3-yl]-phenyl}-cyclobutyl)-carbamic acid tert-butyl ester: Following the procedure used to prepare (1-{4-[4-oxo-2-phenyl-7-(2H-pyrazol-3-yl)-4H-chromen-3-yl]-phenyl}-cyclobutyl)-carbamic acid tert-butyl ester, {1-[4-(8-bromo-4-oxo-2-phenyl-4H-chromen-3-yl)-phenyl]-cyclobutyl}-carbamic acid tert-butyl ester was reacted with 4-pyrazoleboronic acid pinacol ester to give the title compound as a colourless oil (108 mg, 74%). LCMS (Method G): $R_T$=3.86 min, $[M+H]^+$=534.

Step 2: 3-[4-(1-Amino-cyclobutyl)-phenyl]-2-phenyl-8-(1H-pyrazol-4-yl)-chromen-4-one Hydrochloride: Following the procedure used to prepare 3-[4-(1-amino-cyclobutyl)-phenyl]-6-fluoro-2-phenyl-chromen-4-one, (1-{4-[4-oxo-2-phenyl-8-(1H-pyrazol-4-yl)-4H-chromen-3-yl]-phenyl}-cyclobutyl)-carbamic acid tert-butyl ester was treated with TFA. The resultant free base was dissolved in a mixture of MeOH (7 mL), water (7 mL) and 1 M HCl (0.6 mL) and chromatographed on a 20 g C18 cartridge {gradient 10 to 60% MeOH in water+1 M HCl (60 μL in each 10 mL of eluent)} to give the title compound as a white solid (73 mg, 83%). $^1$H NMR (400 MHz, DMSO-d6): δ 8.59 (s, 3H), 8.14-8.08 (m, 3H), 7.95 (dd, J=7.9 and 1.8 Hz, 1H), 7.53-7.32 (m, 8H), 7.25 (d, J=8.3 Hz, 2H), 3.83 (bs, 1H), 2.57-2.43 (m, 4H), 2.19-2.06 (m, 1H), 1.82-1.69 (m, 1H). LCMS (Method E): $R_T$=3.03 min, [M+H]$^+$=434.

Example 53

3-[4-(1-Amino-cyclobutyl)-phenyl]-2-phenyl-8-(1H-pyrazol-3-14)-chromen-4-one hydrochloride

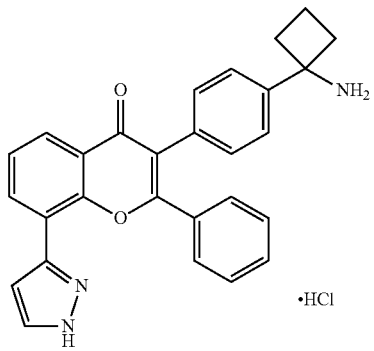 [SMILES: NC1(c2ccc(-c3c(-c4ccccc4)oc4c(-c5cc[nH]n5)cccc4c3=O)cc2)CCC1 ; Cl]

Step 1: 1-(4-{4-oxo-2-phenyl-8-[1-(tetrahydro-pyran-2-yl)-1H-pyrazol-3-yl]-4H-chromen-3-yl}-phenyl)-cyclobutyl]-carbamic acid tert-butyl ester: Following the procedure used to prepare (1-{-4-[4-oxo-2-phenyl-7-(2H-pyrazol-3-yl)-4H-chromen-3-yl]-phenyl}-cyclobutyl)-carbamic acid tert-butyl ester, {1-[4-(8-bromo-4-oxo-2-phenyl-4H-chromen-3-yl)-phenyl]-cyclobutyl}-carbamic acid tert-butyl ester was reacted with 1-(tetrahydro-pyran-2-yl)-3-(4,4,5,5-tetramethyl-[1,3,2]dioxaborolan-2-yl)-1H-pyrazole to give the title compound as a white foam (113 mg, 100%). LCMS (Method A): $R_T$=4.84 min, M+H$^+$=618.

Step 2: 3-[4-(1-Amino-cyclobutyl)-phenyl]-2-phenyl-8-(1H-pyrazol-3-yl)-chromen-4-one Hydrochloride: Following the procedure used to prepare 3-[4-(1-amino-cyclobutyl)-phenyl]-6-fluoro-2-phenyl-chromen-4-one, 1-(4-{4-oxo-2-phenyl-8-[1-(tetrahydro-pyran-2-yl)-1H-pyrazol-3-yl]-4H-chromen-3-yl}-phenyl)-cyclobutyl]-carbamic acid tert-butyl ester was treated with TFA. The resultant free base was dissolved in a mixture of MeOH (7 mL), water (7 mL) and 1 M HCl (0.6 mL) and chromatographed on a 5 g C18 cartridge {gradient 10 to 90% MeOH in water+1 M HCl (60 μL in each 10 mL of eluent)} to give the title compound as a white solid (34 mg, 43%). $^1$H NMR (300 MHz, DMSO-d6): δ 8.71 (s, 3H), 8.36 (dd, J=7.8 and 1.6 Hz, 1H), 8.11 (dd, J=7.8 and 1.8 Hz, 1H), 7.84 (d, J=1.8 Hz, 1H), 7.60 (t, J=7.8 Hz, 1H), 7.53-7.28 (m, 9H), 6.82 (d, J=2.3 Hz, 1H), 4.47 (bs, 1H), 2.61-2.48 (m, 4H), 2.24-2.11 (m, 1H), 1.89-1.71 (m, 1H). LCMS (Method E): $R_T$=3.14 min, [M+H]$^+$=434.

Example 54

3-[4-(1-Amino-cyclobutyl)-phenyl]-8-cyclopropyl-2-phenyl-chromen-4-one hydrochloride

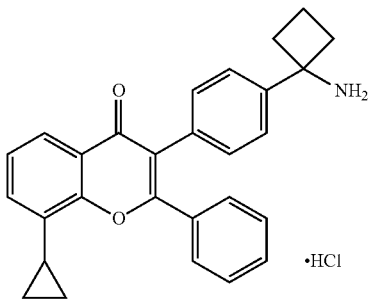 [SMILES: NC1(c2ccc(-c3c(-c4ccccc4)oc4c(C5CC5)cccc4c3=O)cc2)CCC1 ; Cl]

Step 1: {1-[4-(8-Cyclopropyl-4-oxo-2-phenyl-4H-chromen-3-yl)-phenyl]-cyclobutyl}-carbamic acid tert-butyl ester: Following the procedure used to prepare (1-{-4-[4-oxo-2-phenyl-7-(2H-pyrazol-3-yl)-4H-chromen-3-yl]-phenyl}-cyclobutyl)-carbamic acid tert-butyl ester, {1-[4-(8-bromo-4-oxo-2-phenyl-4H-chromen-3-yl)-phenyl]-cyclobutyl}-carbamic acid tert-butyl ester was reacted with cyclopropyl boronic acid pinacol ester to give the title compound in a mixture containing 30% {1-[4-(8-bromo-4-oxo-2-phenyl-4H-chromen-3-yl)-phenyl]-cyclobutyl}-carbamic acid tert-butyl ester (65 mg). LCMS (Method A): $R_T$=5.04 min, [M+H]$^+$=508.

Step 2: 3-[4-(1-Amino-cyclobutyl)-phenyl]-8-cyclopropyl-2-phenyl-chromen-4-one Hydrochloride: Following the procedure used to prepare 3-[4-(1-amino-cyclobutyl)-phenyl]-6-fluoro-2-phenyl-chromen-4-one, a mixture containing 70% {1-[4-(8-cyclopropyl-4-oxo-2-phenyl-4H-chromen-3-yl)-phenyl]-cyclobutyl}-carbamic acid tert-butyl ester and 30% {1-[4-(8-bromo-4-oxo-2-phenyl-4H-chromen-3-yl)-phenyl]-cyclobutyl}-carbamic acid tert-butyl ester was treated with TFA. The resultant free base was reacted with 1-methylpyrazole-4-boronic acid pinacol ester following the procedure of (1-{4-[4-oxo-2-phenyl-7-(2H-pyrazol-3-yl)-4H-chromen-3-yl]-phenyl}-cyclobutyl)-carbamic acid tert-butyl ester. The combined products were dissolved in a mixture of MeOH (7 mL), water (7 mL) and 1 M HCl (0.6 mL) and chromatographed on a 5 g C18 cartridge {gradient 10 to 90% MeOH in water+1 M HCl (60 μL in each 10 mL of eluent)} to give the title compound as a white solid (11 mg). $^1$H NMR (300 MHz, DMSO-d6): δ 8.60 (s, 3H), 7.91 (dd, J=7.1 and 2.4 Hz, 1H), 7.52-7.27 (m, 11H), 2.65-2.47 (m, 4H), 2.45-2.34 (m, 1H), 2.26-2.09 (m, 1H), 1.88-1.73 (m, 1H), 1.14-1.04 (m, 2H), 0.90-0.82 (m, 2H). LCMS (Method E): $R_T$=4.01 min, [M+H]$^+$=408. 3-[4-(1-amino-cyclobutyl)-phenyl]-8-(1-methyl-1H-pyrazol-4-yl)-2-phenyl-chromen-4-one hydrochloride was also isolated.

Example 55

3-[4-(1-Amino-cyclobutyl)-phenyl]-8-(1-methyl-1H-pyrazol-4-yl)-2-phenyl-chromen-4-one hydrochloride

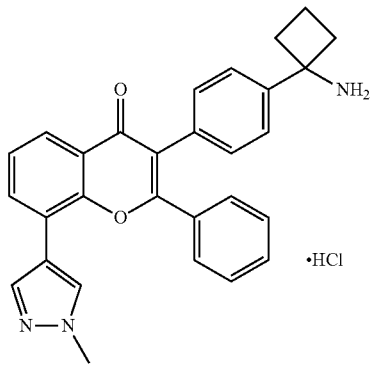 [SMILES: Cn1cc(-c2cccc3c(=O)c(-c4ccc(C5(N)CCC5)cc4)c(-c4ccccc4)oc23)cn1 ; Cl]

Step 1: 3-[4-(1-Amino-cyclobutyl)-phenyl]-8-(1-methyl-1H-pyrazol-4-yl)-2-phenyl-chromen-4-one hydrochloride: Following the procedure used to prepare 3-[4-(1-amino-cyclobutyl)-phenyl]-8-cyclopropyl-2-phenyl-chromen-4-one, a mixture containing 30% 3-[4-(1-amino-cyclobutyl)-phenyl]-8-(1-methyl-1H-pyrazol-4-yl)-2-phenyl-chromen-4-one and 70% 3-[4-(1-amino-cyclobutyl)-phenyl]-8-cyclopropyl-2-phenyl-chromen-4-one was dissolved in a mixture of MeOH (7 mL), water (7 mL) and 1 M HCl (0.6 mL) and chromatographed on a 5 g C18 cartridge {gradient 10 to 90% MeOH in water+1 M HCl (60 μL in each 10 mL of eluent)} to give the title compound as a white solid (5 mg). $^1$H NMR (300 MHz, DMSO-d6): δ 8.77 (s, 3H), 8.23 (s, 1H), 8.09 (dd, J=7.9 and 2.0 Hz, 1H), 8.02-7.97 (m, 2H), 7.70-7.34 (m, 8H), 7.29 (d, J=8.7 Hz, 2H), 3.88 (s, 3H), 2.62-2.48 (m, 4H), 2.29-2.11 (m, 1H), 1.88-1.71 (m, 1H). LCMS (Method E): $R_T$=3.34 min, [M+H]$^+$=448, and 3-[4-(1-amino-cyclobutyl)-phenyl]-8-cyclopropyl-2-phenyl-chromen-4-one hydrochloride.

Example 56

3-[4-(1-Amino-cyclobutyl)-phenyl]-2-phenyl-8-pyridin-3-yl-chromen-4-one

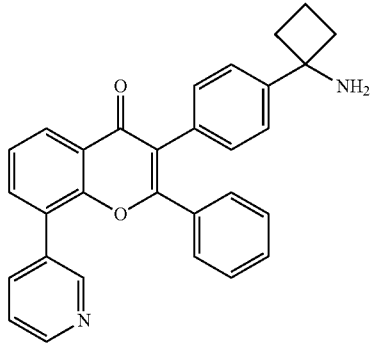 [SMILES: NC1(c2ccc(-c3c(-c4ccccc4)oc4c(-c5cccnc5)cccc4c3=O)cc2)CCC1]

Step 1: {1-[4-(4-oxo-2-phenyl-8-pyridin-3-yl-4H-chromen-3-yl)-phenyl]-cyclobutyl}-carbamic acid tert-butyl ester: Following the procedure used to prepare (1-{4-[4-oxo-2-phenyl-7-(2H-pyrazol-3-yl)-4H-chromen-3-yl]-phenyl}-cyclobutyl)-carbamic acid tert-butyl ester, {1-[4-(8-bromo-4-oxo-2-phenyl-4H-chromen-3-yl)-phenyl]-cyclobutyl}-carbamic acid tert-butyl ester was reacted with pyridine-3-boronic acid to give a crude residue which was insoluble in the EtOAc/aqueous work-up mixture. The solid was collected by filtration and air dried to give the title compound as a tan solid (44 mg, 59%). LCMS (Method B): $R_T$=4.74 min, [M+H]$^+$=545.

Step 2: 3-[4-(1-Amino-cyclobutyl)-phenyl]-2-phenyl-8-pyridin-3-yl-chromen-4-one: Following the procedure used to prepare 3-[4-(1-amino-cyclobutyl)-phenyl]-6-fluoro-2-phenyl-chromen-4-one, {1-[4-(4-oxo-2-phenyl-8-pyridin-3-yl-4H-chromen-3-yl)-phenyl]-cyclobutyl}-carbamic acid tert-butyl ester was reacted to give the title compound as a white solid (4 mg, 11%). $^1$H NMR (400 MHz, DMSO-d6): δ 8.90 (d, J=2.1 Hz, 1H), 8.59 (dd, J=4.8 and 1.6 Hz, 1H), 8.17-8.12 (m, 2H), 7.91 (dd, J=7.5 and 1.8 Hz, 1H), 7.60 (t, J=8.0 Hz, 1H), 7.52-7.48 (m, 1H), 7.36 (d, J=8.6 Hz, 2H), 7.31-7.20 (m, 5H), 7.13 (d, J=8.4 Hz, 2H), 4.05 (d, J=3.8 Hz, 2H), 2.41-2.32 (m, 2H), 2.17-2.08 (m, 2H), 2.03-1.91 (m, 1H), 1.69-1.57 (m, 1H). LCMS (Method E): $R_T$=3.06 min, [M+H]$^+$=445.

Example 57

7-[4-(1-Amino-cyclobutyl)-phenyl]-8-phenyl-1H-9-oxa-1,2-diaza-cyclopenta[a]naphthalen-6-one

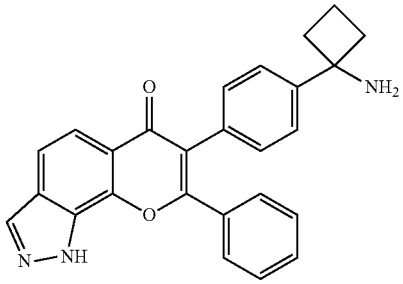 [SMILES: NC1(c2ccc(-c3c(-c4ccccc4)oc4c(ccc5cn[nH]c54)c3=O)cc2)CCC1]

Step 1: 1-Dimethylsulfamoyl-7-methoxy-1H-indazole-6-carboxylic acid methyl ester: Sodium hydride (60% dispersion in mineral oil, 1.27 g, 31.66 mmol) was added to anhydrous THF (100 mL) with stirring under an atmosphere of nitrogen. After 5 min, a solution of 7-methoxy-1H-indazole-6-carboxylic acid methyl ester (5.44 g, 26.38 mmol, prepared as described in *J. Med. Chem.* 2006, 49, 4762-4766) in anhydrous THF (50 mL) was added dropwise over 15 min. After stirring for 30 min, a solution of dimethylsulfamoyl chloride (3.68 mL, 34.3 mmol) in anhydrous THF (20 mL) was added dropwise over 10 min. After stirring for 2 h, the reaction mixture was quenched by addition of water (50 mL) and transferred to a separating funnel using EtOAc. The organic layer was washed with water. The aqueous layers were combined and extracted using EtOAc. The combined organic extracts were dried (Na$_2$SO$_4$), filtered and concentrated in vacuo. The resultant residue was subjected to flash chromatography (SiO$_2$, gradient 0 to 20% EtOAc in DCM) to afford the title compound as a yellow solid (6.23 g, 75%). $^1$H NMR (400 MHz, DMSO-d6): δ 8.98 (s, 1H), 7.47 (d, J=8.8 Hz, 1H), 7.33 (d, J=8.8 Hz, 1H), 4.29 (s, 3H), 3.85 (s, 3H), 2.97 (s, 6H).

Step 2: 6-Hydroxymethyl-7-methoxy-indazole-1-sulfonic acid dimethylamide: To a solution of 1-dimethylsulfamoyl-7-methoxy-1H-indazole-6-carboxylic acid methyl ester (6.23 g, 19.9 mmol) in anhydrous THF (100 mL) at 0° C. under an atmosphere of nitrogen was added lithium borohydride solution (2 M in THF, 39.8 mL, 79.5 mmol) and the mixture was allowed to reach RT with stirring. After 68 h, the mixture was quenched with saturated aqueous ammonium chloride solution (40 mL) and water (80 mL) and extracted with EtOAc (50 mL). The organic phase was washed with brine, dried (Na$_2$SO$_4$), filtered, and concentrated in vacuo to afford the title compound as an oil (5.58 g, 98%). LCMS (Method G): R$_T$=2.73 min, [M+H]$^+$=286.

Step 3: 6-Formyl-7-methoxy-indazole-1-sulfonic acid dimethylamide To a solution of 6-hydroxymethyl-7-methoxy-indazole-1-sulfonic acid dimethylamide (5.58 g, 19.6 mmol) in DCM (250 mL) was added manganese dioxide (17 g, 196 mmol) and the reaction stirred at RT. After 90 h, the mixture was filtered through Celite® and the eluent concentrated in vacuo to afford the title compound (5.14 g, 93%). LCMS (Method G): R$_T$=3.39 min, [M+H]$^+$=284.

Step 4: 6-(1-Hydroxy-3-phenyl-prop-2-ynyl)-7-methoxy-indazole-1-sulfonic acid dimethylamide Following the procedure used to prepare 1-(5-fluoro-2-methoxy-phenyl)-3-phenyl-prop-2-yn-1-ol, 6-formyl-7-methoxy-indazole-1-sulfonic acid dimethylamide was reacted to give the title compound as an oil (187 mg, 74%). $^1$H NMR (300 MHz, CDCl$_3$): δ 8.48 (s, 1H), 7.49-7.43 (m, 2H), 7.40 (d, J=2.8 Hz, 2H), 7.33-7.27 (m, 3H), 6.08 (d, J=5.9 Hz, 1H), 4.43 (s, 3H), 2.02 (s, 6H), 2.95 (d, J=5.9 Hz, 1H).

Step 5: 7-Methoxy-6-(3-phenyl-propynoyl)-indazole-1-sulfonic acid dimethylamide: Following the procedure used to prepare 1-(5-fluoro-2-methoxy-phenyl)-3-phenyl-propynone, 6-(1-hydroxy-3-phenyl-prop-2-ynyl)-7-methoxy-indazole-1-sulfonic acid dimethylamide was reacted to give the title compound as a yellow solid (186 mg, 88%).
$^1$H NMR (400 MHz, CDCl$_3$): δ 8.48 (s, 1H), 7.69-7.65 (m, 3H), 7.49-7.38 (m, 3H), 7.32 (d, J=9.0 Hz, 1H), 4.57 (s, 3H), 3.06 (s, 6H).

Step 6: 7-Iodo-6-oxo-8-phenyl-6H-9-oxa-1,2-diaza-cyclopenta[a]naphthalene-1-sulfonic acid dimethylamide Following the procedure used to prepare 6-fluoro-3-iodo-2-phenyl-chromen-4-one, 7-methoxy-6-(3-phenyl-propynoyl)-indazole-1-sulfonic acid dimethylamide was reacted to give the title compound as a tan solid (173 mg, 82%). LCMS (Method B): R$_T$=4.42 min, [M+H]$^+$=496.

Step 7: {1-[4-(1-Dimethylsulfamoyl-6-oxo-8-phenyl-1,6-dihydro-9-oxa-1,2-diaza-cyclopenta[a]naphthalen-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-iodo-6-oxo-8-phenyl-6H-9-oxa-1,2-diaza-cyclopenta[a]naphthalene-1-sulfonic acid dimethylamide was reacted to give the title compound as a gummy solid (65 mg, 87%). LCMS (Method A): R$_T$=4.81 min, [M+H]$^+$=615.

Step 8: 7-[4-(1-Amino-cyclobutyl)-phenyl]-8-phenyl-1H-9-oxa-1,2-diaza-cyclopenta[a]naphthalen-6-one: Following the procedure used to prepare 3-[4-(1-amino-cyclobutyl)-phenyl]-6-fluoro-2-phenyl-chromen-4-one, {1-[4-(1-dimethylsulfamoyl-6-oxo-8-phenyl-1,6-dihydro-9-oxa-1,2-diaza-cyclopenta[a]naphthalen-7-yl)-phenyl]-cyclobutyl}-carbamic acid tert-butyl ester was reacted to give the title compound as a white solid (31 mg, 71%). $^1$H NMR (400 MHz, DMSO-d6): δ 14.26 (bs, 1H), 8.32 (s, 1H), 7.77 (d, J=8.5 Hz, 1H), 7.68 (d, J=8.5 Hz, 1H), 7.53-7.49 (m, 2H), 7.41-7.30 (m, 5H), 7.14 (d, J=8.5 Hz, 2H), 3.28 (bs, 2H), 2.40-2.32 (m, 2H), 2.12-2.03 (m, 2H), 2.02-1.91 (m, 1H), 1.68-1.57 (m, 1H). LCMS (Method E): R$_T$=3.05 min, [M+H]$^+$=408.

Example 58

7-[4-(1-Amino-cyclobutyl)-phenyl]-1-methyl-8-phenyl-1H-9-oxa-1,2-diaza-cyclopenta[a]naphthalen-6-one

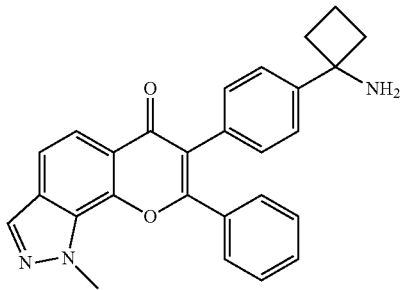 [SMILES: Cn1ncc2ccc3c(=O)c(-c4ccc(C5(N)CCC5)cc4)c(-c4ccccc4)oc3c21]

Step 1: 7-Iodo-8-phenyl-1H-9-oxa-1,2-diaza-cyclopenta[a]naphthalen-6-one: To a solution of 7-iodo-6-oxo-8-phenyl-6H-9-oxa-1,2-diaza-cyclopenta[a]naphthalene-1-sulfonic acid dimethylamide (82 mg, 0.166 mmol) in DCM (2 mL) was added TFA (0.5 mL) at RT. After 3 h, the reaction mixture was concentrated in vacuo to afford the title compound as a white solid (64 mg, 100%). LCMS (Method A): R$_T$=4.23 min, [M+H]$^+$=389.

Step 2: 7-Iodo-1-methyl-8-phenyl-1H-9-oxa-1,2-diaza-cyclopenta[a]naphthalen-6-one: To a solution of 7-iodo-8-phenyl-1H-9-oxa-1,2-diaza-cyclopenta[a]naphthalen-6-one (100 mg, 0.26 mmol) in DMF (5 mL) was added sodium hydride (60% dispersion in oil, 30 mg, 0.77 mmol) and the reaction stirred at RT. After 5 min, iodomethane (0.06 mL, 0.90 mmol) was added and the reaction stirred at RT for 6 h. The reaction mixture was quenched by addition of water (3 mL) and extracted with EtOAc (×2). The combined organic extracts were washed with brine, dried (Na$_2$SO$_4$), filtered, and concentrated in vacuo. The resultant residue was subjected to flash chromatography (SiO$_2$, gradient 0 to 100% EtOAc in cyclohexane) to afford the title compound (55 mg, 55%), LCMS (Method B): R$_T$=3.87 min, [M+H]$^+$=403. 7-iodo-2-methyl-8-phenyl-2H-9-oxa-1,2-diaza-cyclopenta[a]naphthalen-6-one was also isolated.

Step 3: {1-[4-(1-Methyl-6-oxo-8-phenyl-1,6-dihydro-9-oxa-1,2-diaza-cyclopenta[a]naphthalen-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-iodo-1-methyl-8-phenyl-1H-9-oxa-1,2-diaza-cyclopenta[a]naphthalen-6-one was reacted to give the title compound as a gummy solid (70 mg, 98%). LCMS (Method B): R$_T$=4.44 min, [M+H]$^+$=522.

Step 4: 7-[4-(1-Amino-cyclobutyl)-phenyl]-1-methyl-8-phenyl-1H-9-oxa-1,2-diaza-cyclopenta[a]naphthalen-6-one: Following the procedure used to prepare 3-[4-(1-amino-cyclobutyl)-phenyl]-6-fluoro-2-phenyl-chromen-4-one, {1-[4-(1-methyl-6-oxo-8-phenyl-1,6-dihydro-9-oxa-1,2-diaza-cyclopenta[a]naphthalen-7-yl)-phenyl]-cyclobutyl}-carbamic acid tert-butyl ester was reacted to give the title compound as a white solid (38 mg, 67%). $^1$H NMR (400 MHz, DMSO-d6): δ 8.22 (s, 1H), 7.75 (d, J=8.4 Hz, 1H), 7.69 (d, J=8.4 Hz, 1H), 7.52-7.48 (m, 2H), 7.42-7.31 (m, 5H), 7.14 (d, J=8.4 Hz, 2H), 4.37 (s, 3H), 3.27 (bs, 2H), 2.40-2.28 (m, 2H), 2.14-2.04 (m, 2H), 2.02-1.91 (m, 1H), 1.69-1.57 (m, 1H). LCMS (Method E): $R_T$=3.42 min, [M+H]$^+$=422.

Example 59

7-[4-(1-Amino-cyclobutyl)-phenyl]-2-methyl-8-phenyl-2H-9-oxa-1,2-diaza-cyclopenta[a]naphthalen-6-one

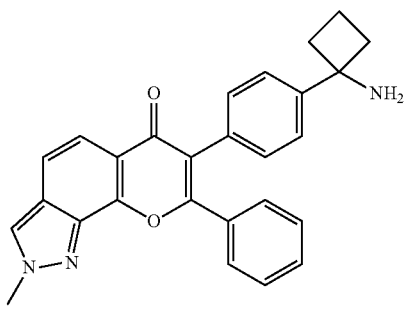 [SMILES: Cn1cc2ccc3c(=O)c(-c4ccc(C5(N)CCC5)cc4)c(-c4ccccc4)oc3c2n1]

Step 1: 7-Iodo-2-methyl-8-phenyl-2H-9-oxa-1,2-diaza-cyclopenta[a]naphthalen-6-one: To a solution of 7-iodo-8-phenyl-1H-9-oxa-1,2-diaza-cyclopenta[a]naphthalen-6-one (100 mg, 0.26 mmol) in DMF (5 mL) was added sodium hydride (60% dispersion in oil, 30 mg, 0.77 mmol) and the reaction stirred at RT. After 5 min, iodomethane (0.06 mL, 0.90 mmol) was added and the reaction stirred at RT for 6 h. The reaction was quenched by addition of water (3 mL) and extracted with EtOAc (×2). The combined organic extracts were washed with brine, dried (Na$_2$SO$_4$), filtered and concentrated in vacuo. The resultant residue was subjected to flash chromatography (SiO$_2$, gradient 0 to 100% EtOAc in cyclohexane) to afford the title compound (20 mg, 20%). LCMS (Method B) $R_T$=3.70 min, [M+H]$^+$=403. 7-iodo-1-methyl-8-phenyl-1H-9-oxa-1,2-diaza-cyclopenta[a]naphthalen-6-one was also isolated.

Step 2: {1-[4-(2-Methyl-6-oxo-8-phenyl-2,6-dihydro-9-oxa-1,2-diaza-cyclopenta[a]naphthalen-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-iodo-2-methyl-8-phenyl-2H-9-oxa-1,2-diaza-cyclopenta[a]naphthalen-6-one was reacted to give the title compound as a gummy solid (24 mg, 92%). LCMS (Method B): $R_T$=4.69 min, [M+H]$^+$=522.

Step 3: 7-[4-(1-Amino-cyclobutyl)-phenyl]-2-methyl-8-phenyl-2H-9-oxa-1,2-diaza-cyclopenta[a]naphthalen-6-one: Following the procedure of 3-[4-(1-amino-cyclobutyl)-phenyl]-6-fluoro-2-phenyl-chromen-4-one, {1-[4-(2-methyl-6-oxo-8-phenyl-2,6-dihydro-9-oxa-1,2-diaza-cyclopenta[a]naphthalen-7-yl)-phenyl]-cyclobutyl}-carbamic acid tert-butyl ester was reacted to give the title compound as a white solid (16 mg, 83%). $^1$H NMR (400 MHz, DMSO-d6): δ 8.55 (s, 1H), 7.69 (d, J=8.7 Hz, 1H), 7.58 (d, J=8.7 Hz, 1H), 7.45-7.31 (m, 7H), 7.18 (d, J=7.7 Hz, 2H), 4.89 (bs, 2H), 4.24 (s, 3H), 2.48-2.35 (m, 2H), 2.22-2.12 (m, 2H), 2.05-1.94 (m, 1H), 1.72-1.59 (m, 1H). LCMS (Method E): $R_T$=3.16 min, [M+H]$^+$=422.

Example 60

3-[4-(1-Amino-cyclobutyl)-phenyl]-7-methyl-2-phenyl-7H-pyrano[2,3-e]indazol-4-one

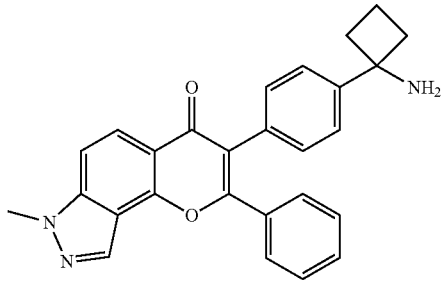 [SMILES: Cn1ncc2c3oc(-c4ccccc4)c(-c4ccc(C5(N)CCC5)cc4)c(=O)c3ccc21]

Step 1: {1-[4-(7-Methyl-4-oxo-2-phenyl-4,7-dihydro-pyrano[2,3-e]indazol-3-yl)-phenyl]-cyclobutyl}-carbamic acid tert-butyl ester: To a solution of {1-[4-(4-oxo-2-phenyl-4,7-dihydro-pyrano[2,3-e]indazol-3-yl)-phenyl]-cyclobutyl}-carbamic acid tert-butyl ester (65 mg, 0.13 mmol) in DMF (3 mL) at 0° C. under an atmosphere of N$_2$ was added sodium hydride (60% in mineral oil, 6 mg, 0.15 mmol). After 5 min, methyl iodide (10 µL, 0.16 mmol) was added and the mixture stirred for a further 2 hours. The reaction was quenched with H$_2$O, partitioned between EtOAc and H$_2$O and the phases separated. The organic extracts were washed with brine, dried (Na$_2$SO$_4$), filtered, and concentrated in vacuo. The resultant residue was subjected to flash chromatography (SiO$_2$, gradient 50 to 70% ethyl acetate in cyclohexane) to afford the title compound as an oil (41 mg, 60%). LCMS (Method B): $R_T$=4.42 min, [M+H]$^+$=522. Also obtained was {1-[4-(8-Methyl-4-oxo-2-phenyl-4,8-dihydro-pyrano[2,3-e]indazol-3-yl)-phenyl]-cyclobutyl}-carbamic acid tert-butyl ester as a white solid (22 mg, 32%). LCMS (Method B): $R_T$=4.26 min, [M+H]$^+$=522.

Step 2: 3-[4-(1-Amino-cyclobutyl)-phenyl]-7-methyl-2-phenyl-7H-pyrano[2,3-e]indazol-4-one: Following the procedure used to prepare 3-[4-(1-amino-cyclobutyl)-phenyl]-6-fluoro-2-phenyl-chromen-4-one, {1-[4-(7-methyl-4-oxo-2-phenyl-4,7-dihydro-pyrano[2,3-e]indazol-3-yl)-phenyl]-cyclobutyl}-carbamic acid tert-butyl ester was reacted to give the title compound as a white solid (28 mg, 84%). $^1$H NMR (400 MHz, DMSO-d6): δ 8.51 (d, J=1.0 Hz, 1H), 8.02 (d, J=8.8 Hz, 1H), 7.76 (dd, J=1.0 and 8.8 Hz, 1H), 7.52-7.48 (m, 2H), 7.45-7.34 (m, 5H), 7.20-7.16 (m, 2H), 4.17 (s, 3H), 2.45-2.36 (m, 2H), 2.20-2.11 (m, 2H), 2.07-1.96 (m, 1H), 1.73-1.61 (m, 1H). LCMS (Method E): $R_T$=3.33 min, [M+H]$^+$=422.

Example 61

3-[4-(1-Amino-cyclobutyl)-phenyl]-8-methyl-2-phenyl-8H-pyrano[2,3-e]indazol-4-one

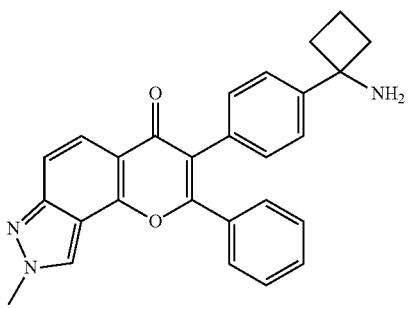

Step 1: {1-[4-(8-Methyl-4-oxo-2-phenyl-4,8-dihydro-pyrano[2,3-e]indazol-3-yl)-phenyl]-cyclobutyl}-carbamic acid tert-butyl ester: To a solution of {1-[4-(4-oxo-2-phenyl-4,7-dihydro-pyrano[2,3-e]indazol-3-yl)-phenyl]-cyclobutyl}-carbamic acid tert-butyl ester (65 mg, 0.13 mmol) in DMF (3 mL) at 0° C. under an atmosphere of $N_2$ was added sodium hydride (60% in mineral oil, 6 mg, 0.15 mmol). After 5 min, methyl iodide (10 μL, 0.16 mmol) was added. After a further 2 hours, the reaction was quenched with $H_2O$, partitioned between EtOAc and $H_2O$ and the phases were separated. The organic extracts were washed with brine, dried ($Na_2SO_4$), filtered, and concentrated in vacuo. The resultant residue was subjected to flash chromatography ($SiO_2$, gradient 50 to 70% ethyl acetate in cyclohexane) to afford the title compound as a white solid (22 mg, 32%). LCMS (Method B): $R_T$=4.26 min, $[M+H]^+$=522. Also obtained was {1-[4-(7-methyl-4-oxo-2-phenyl-4,7-dihydro-pyrano[2,3-e]indazol-3-yl)-phenyl]-cyclobutyl}-carbamic acid tert-butyl ester as an oil (41 mg, 60%). LCMS (Method B): $R_T$=4.42 min, $[M+H]^+$=522.

Step 2: 3-[4-(1-Amino-cyclobutyl)-phenyl]-8-methyl-2-phenyl-8H-pyrano[2,3-e]indazol-4-one: Following the procedure used to prepare 3-[4-(1-amino-cyclobutyl)-phenyl]-6-fluoro-2-phenyl-chromen-4-one, {1-[4-(8-methyl-4-oxo-2-phenyl-4,8-dihydro-pyrano[2,3-e]indazol-3-yl)-phenyl]-cyclobutyl}-carbamic acid tert-butyl ester was reacted to give the title compound as a white solid (15 mg, 89%). $^1$H NMR (400 MHz, DMSO-d6): δ 8.96 (s, 1H), 7.82 (d, J=9.4 Hz, 1H), 7.62 (d, J=9.4 Hz, 1H), 7.49-7.40 (m, 5H), 7.39-7.33 (m, 2H), 7.25-7.21 (m, 2H), 4.23 (s, 3H), 2.51-2.42 (m, 2H), 2.37-2.28 (m, 2H), 2.13-2.03 (m, 1H), 1.77-1.64 (m, 1H). LCMS (Method E): $R_T$=3.13 min, $[M+H]^+$=422.

Example 62

7-[4-(1-Amino-cyclobutyl)-phenyl]-4-chloro-3-methyl-8-phenyl-3H-chromeno[7,8-d]imidazol-6-one hydrochloride

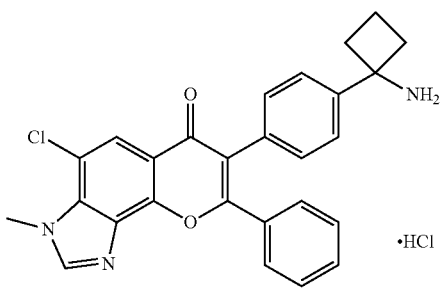 [SMILES: Cn1cnc2c3oc(-c4ccccc4)c(-c4ccc(C5(N)CCC5)cc4)c(=O)c3cc(Cl)c21 ; Cl]

Step 1: 4-Chloro-7-iodo-8-phenyl-1H-chromeno[7,8-d]imidazol-6-one: To a solution of 4-chloro-7-iodo-8-phenyl-1-(2-trimethylsilanyl-ethoxymethyl)-1H-chromeno[7,8-d]imidazol-6-one and 4-chloro-7-iodo-8-phenyl-3-(2-trimethylsilanyl-ethoxymethyl)-3H-chromeno[7,8-d]imidazol-6-one (80 mg, 0.14 mmol) in DCM (4 mL) was added TFA (1.0 mL) at RT. After 18 h, the reaction mixture was evaporated to dryness. The crude residue was triturated with DCM and concentrated in vacuo to afford the title compound as a white solid (59 mg, 100%). LCMS (Method A): $R_T$=4.38 min, $[M+H]^+$=423/425.

Step 2: 4-Chloro-7-iodo-3-methyl-8-phenyl-3H-chromeno[7,8-d]imidazol-6-one and 4-chloro-7-iodo-1-methyl-8-phenyl-1H-chromeno[7,8-d]imidazol-6-one: To a stirred solution of 4-chloro-7-iodo-8-phenyl-1H-chromeno[7,8-d]imidazol-6-one (59 mg, 0.14 mmol) in DMF (1.0 mL) was added potassium carbonate (157 mg, 1.13 mmol) and iodomethane (0.06 mL, 0.95 mmol) at RT. After 2 h, the reaction mixture was poured into water and extracted with EtOAc (×2). The combined organic extracts were washed with brine, dried ($Na_2SO_4$), filtered and concentrated in vacuo to afford a mixture of the title compounds as an off-white solid (48 mg, 80%). LCMS (Method A): $R_T$=4.25 min, $[M+H]^+$=437/439 and $R_T$=4.44 min, $[M+H]^+$=437/439.

Step 3: {1-[4-(4-Chloro-3-methyl-6-oxo-8-phenyl-3,6-dihydro-chromeno[7,8-d]imidazol-7-yl)-phenyl]-cyclobutyl}-carbamic acid tert-butyl ester and {1-[4-(4-chloro-1-methyl-6-oxo-8-phenyl-1,6-dihydro-chromeno[7,8-d]imidazol-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, a mixture of 4-chloro-7-iodo-3-methyl-8-phenyl-3H-chromeno[7,8-d]imidazol-6-one and 4-chloro-7-iodo-1-methyl-8-phenyl-1H-chromeno[7,8-d]imidazol-6-one were reacted to give a mixture of the title compounds as a glass (43 mg, 69%). LCMS (Method A): $R_T$=4.76 min, $[M+H]^+$=556/558 and $R_T$=4.85 min, $[M+H]^+$=556/558.

Step 4: 7-[4-(1-Amino-cyclobutyl)-phenyl]-4-chloro-3-methyl-8-phenyl-3H-chromeno[7,8-d]imidazol-6-one hydrochloride: To a stirred solution of {1-[4-(4-chloro-3-methyl-6-oxo-8-phenyl-3,6-dihydro-chromeno[7,8-d]imidazol-7-yl)-phenyl]-cyclobutyl}-carbamic acid tea-butyl ester and {1-[4-(4-chloro-1-methyl-6-oxo-8-phenyl-1,6-dihydro-chromeno[7,8-d]imidazol-7-yl)-phenyl]-cyclobutyl}-carbamic acid tert-butyl ester (43 mg, 0.08 mmol) in DCM (1.5 mL) was added TFA (0.5 mL) at RT. After 1 h, the reaction mixture was concentrated in vacuo. The resultant residue was subjected to flash chromatography ($SiO_2$, gradient 0 to 20% MeOH in DCM) to yield a white solid. This crude residue was dissolved in a mixture of MeOH (0.5 mL), water (1.5 mL) and 1 M HCl (0.1 mL) and chromatographed on a 10 g C18 cartridge {30 to 60% MeOH in water+1 M HCl (60 μL in each 10 mL of eluent)} to give the title compound as a white solid (4.0 mg). LCMS (Method E): $R_T$=3.27 min, $[M+H]^+$=456/458. $^1$H NMR (300 MHz, $CD_3OD$): δ 8.40 (s, 1H), 7.99 (s, 1H), 7.60-7.49 (m, 4H), 7.47-7.30 (m, 5H), 4.29 (s, 3H), 2.86-2.58 (m, 4H), 2.36-2.22 (m, 1H), 2.06-1.92 (m, 1H).

Example 63

7-[4-(1-Amino-cyclobutyl)-phenyl]-8-phenyl-2H-9-oxa-1,2,3a-triaza-cyclopenta[a]naphthalene-3,6-dione hydrochloride

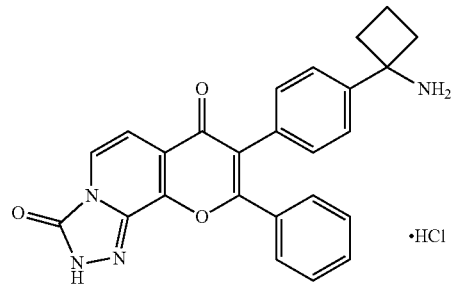 [SMILES: NC1(c2ccc(-c3c(-c4ccccc4)oc4c(ccn5c(=O)[nH]nc45)c3=O)cc2)CCC1 ; Cl]

Step 1: 2-Chloro-3-methoxypyridine: To a stirred solution of 2-chloro-3-hydroxypyridine (25.4 g, 196 mmol) in dry DMF (250 mL), at 0° C., was added sodium methoxide (11.5 g, 213 mmol). After 5 min, the reaction mixture was allowed to warm to RT. After 1 hour, the mixture was cooled to 0° C. and iodomethane (24 mL, 386 mmol) was added. The reaction mixture was stirred at 0° C. for 5 minutes, before allowing to warm to RT. After 2 hours, the reaction mixture was concentrated under reduced pressure. The resultant residue was partitioned between diethyl ether and water. The aqueous phase was isolated and extracted twice with diethyl ether. The combined organic extracts were washed with water, brine, dried ($Na_2SO_4$), filtered and concentrated in vacuo to give the title compound (22.2 g, 79%) as an orange solid. LCMS (Method A): $R_T$=2.76 min, $[M+H]^+$=144/146.

Step 2: (3-Methoxypyridin-2-yl)hydrazine: A stirred solution of 2-chloro-3-methoxypyridine (4.86 g, 33.8 mmol) in hydrazine hydrate (40 mL) was heated under reflux for 1.5 hours. After cooling to RT, the reaction mixture was evaporated to dryness. The resulting residue was partitioned between 10% MeOH in $CHCl_3$ and 40% w/v aqueous potassium carbonate. The aqueous phase was isolated and extracted twice with 10% MeOH in $CHCl_3$. The combined organic extracts were dried ($Na_2SO_4$), filtered and concentrated in vacuo to give the title compound (2.7 g, 57%) as a buff solid. $^1H$ NMR (300 MHz, DMSO-d6): δ 7.65 (dd, J=5.1 and 1.3 Hz, 1H), 6.99 (dd, J=7.7 and 1.3 Hz, 1H) overlapped with 6.98 (br s, 1H), 6.56 (dd, J=7.6 and 5.1 Hz, 1H), 4.05 (br s, 2H), 3.76 (s, 3H). LCMS (Method A): $R_T$=0.34 min, $[M+H]^+$=140.

Step 3: 8-Methoxy-2H-[1,2,4]triazolo[4,3-a]pyridin-3-one: To a stirred solution of (3-methoxypyridin-2-yl)hydrazine (2.7 g, 19.4 mmol) in THF (70 mL) was added 1,1'-carbonyldiimidazole (15.75 g, 90.1 mmol) at RT. After 16 hours, the resultant solid was collected by filtration and washed with THF. The solid was dissolved in a mixture of MeOH (120 mL) and water (20 mL) and stirred at RT for 10 minutes before evaporating to dryness. The resultant residue was subjected to flash chromatography ($SiO_2$, gradient 3 to 5% MeOH in $CHCl_3$) to afford the title compound (2.81 g, 88%) as a white solid. LCMS (Method A): $R_T$=2.08 min, $[M+H]^+$=166.

Step 4: 7-Bromo-8-methoxy-2H-[1,2,4]triazolo[4,3-a]pyridin-3-one and 7-bromo-8-hydroxy-2H-[1,2,4]triazolo[4,3-a]pyridin-3-one: A stirred solution of bromine (5.42 g, 34 mmol) in acetic acid (10 mL) was added to a solution of 8-methoxy-2H-[1,2,4]triazolo[4,3-a]pyridin-3-one (2.80 g, 17.0 mmol) in acetic acid (50 mL) at 10° C. The resulting reaction mixture was stirred at RT for 40 hours before evaporating to dryness to give a mixture of the title compounds (1:1.4) as a yellow solid that was used in the next step without further purification. LCMS (Method A): $R_T$=2.57 min, $[M+H]^+$=230/232 and $R_T$=3.08 min, $[M+H]^+$=244/246.

Step 5: 7-Bromo-8-methoxy-2-(2-trimethylsilanyl-ethoxymethyl)-2H-[1,2,4]triazolo[4,3-a]pyridin-3-one: To a stirred suspension of the mixture of 7-bromo-8-methoxy-2H-[1,2,4]triazolo[4,3-a]pyridin-3-one and 7-bromo-8-hydroxy-2H-[1,2,4]triazolo[4,3-a]pyridin-3-one (from step 4) in DCM (120 mL) at 0° C. was added DIPEA (35 mL, 0.2 mol). After 5 min, (2-chloromethoxy-ethyl)-trimethylsilane (11.9 mL, 67.2 mmol) was added. The mixture was stirred at 0° C. for 1 hour and at RT for a further 2 hours. The resulting mixture was diluted with DCM (200 mL) and washed successively with 0.5 M HCl (aq) (400 mL) and water, dried ($Na_2SO_4$), filtered, and concentrated in vacuo. The resultant residue was subjected to flash chromatography ($SiO_2$, gradient 15 to 30% ethyl acetate in cyclohexane) to afford the title compound (1.30 g, 20%) as a yellow solid. Fractions containing 7-bromo-8-(2-trimethylsilanyl-ethoxymethoxy)-2-(2-trimethylsilanyl-ethoxymethyl)-2H-[1,2,4]triazolo[4,3-a]pyridin-3-one were evaporated and the resultant residue was dissolved in MeOH (120 mL). The solution was stirred for 8 days at RT before evaporating to dryness. The resultant residue was dissolved in DMF (25 mL), cooled to 0° C., and cesium carbonate (13 g, 40 mmol) and iodomethane (3.11 mL, 50 mmol) were added. The reaction mixture was stirred at RT for 16 hours. EtOAc and water were added, the aqueous phase was isolated and extracted twice with EtOAc. The combined organic extracts were washed with water and brine, dried ($Na_2SO_4$), filtered, and concentrated in vacuo. The resultant residue was subjected to flash chromatography ($SiO_2$, gradient 15 to 30% EtOAc in cyclohexane) to afford a further quantity of the title compound (3.26 g, 51%) as a yellow solid. LCMS (Method A): $R_T$=4.70 min, $[M+H]^+$=396/398.

Step 6: 8-Methoxy-3-oxo-2-(2-trimethylsilanyl-ethoxymethyl)-2,3-dihydro-[1,2,4]triazolo[4,3-a]pyridine-7-carboxylic acid methyl ester: A mixture of 7-bromo-8-methoxy-2-(2-trimethylsilanyl-ethoxymethyl)-2H-[1,2,4]triazolo[4,3-a]pyridin-3-one (1.79 g, 4.78 mmol), [1,1'-bis(diphenylphosphino)ferrocene]dichloropalladium(II) (0.94 g, 1.27 mmol), triethylamine (3.6 mL, 25.5 mmol) and MeOH (120 mL) was stirred at 50° C. under a balloon of carbon monoxide for 16 hours. The reaction mixture was allowed to cool to RT and concentrated under reduced pressure. The resultant residue was partitioned between EtOAc and 1 M HCl (aq). The mixture was filtered through a Celite® and the isolated aqueous phase was extracted with EtOAc. The combined organic extracts were washed with water and brine, dried ($Na_2SO_4$), filtered, and concentrated in vacuo. The resultant residue was subjected to flash chromatography ($SiO_2$, gradient 25 to 40% EtOAc in cyclohexane) to afford the title compound (1.52 g, 90%) as a brown solid. LCMS (Method A): $R_T$=4.45 min, $[M+H]^+$=354.

Step 7: 7-Hydroxymethyl-8-methoxy-2-(2-trimethylsilanyl-ethoxymethyl)-2H-[1,2,4]triazolo[4,3-a]pyridin-3-one: To a stirred solution of 8-methoxy-3-oxo-2-(2-trimethylsilanyl-ethoxymethyl)-2,3-dihydro-[1,2,4]triazolo[4,3-a]pyridine-7-carboxylic acid methyl ester (1.51 g, 4.27 mmol) in dry DCM (50 mL), cooled to −78° C., was added 1 M DIBAL in DCM (8.54 mL, 8.54 mmol) over 3 minutes. The reaction mixture was allowed to warm to −50° C. over 45 minutes, followed by cooling to −78° C. and addition of MeOH (5 mL) to quench the reaction. The reaction mixture was allowed to warm to 0° C. and was diluted with DCM. An aqueous solution of Rochelle salt (200 mL, 10% w/v) was added and the mixture was stirred vigorously for 30 minutes. The aqueous phase was isolated and extracted with DCM. The combined organic phases were washed with water, dried ($Na_2SO_4$), filtered, and concentrated in vacuo. The resultant residue was subjected to flash chromatography ($SiO_2$, gradient 50 to 100% EtOAc in cyclohexane) to afford the title compound (1.23 g, 89%) as a pale yellow solid. LCMS (Method A): $R_T$=4.18 min, $[M+H]^+$=326.

Step 8: 8-Methoxy-3-oxo-2-(2-trimethylsilanyl-ethoxymethyl)-2,3-dihydro-[1,2,4]triazolo[4,3-a]pyridine-7-carbaldehyde: To a stirred solution of 7-hydroxymethyl-8-methoxy-2-(2-trimethylsilanyl-ethoxymethyl)-2H-[1,2,4]triazolo[4,3-a]pyridin-3-one (1.23 g, 3.78 mmol) in DCM (100 mL) was added manganese dioxide (3.30 g, 37.8 mmol). After 16 hours, the reaction mixture was filtered through Celite®. The filtrate was evaporated to dryness to afford the title compound (1.15 g, 94%) as a pale yellow solid. LCMS (Method A): $R_T$=4.52 min, $[M+Na]^+$=346.

Step 9: 7-(1-Hydroxy-3-phenyl-prop-2-ynyl)-8-methoxy-2-(2-trimethylsilanyl-ethoxymethyl)-2H-[1,2,4]triazolo[4,3-a]pyridin-3-one: Following the procedure used to prepare 1-(2,6-dimethoxy-pyridin-3-yl)-3-phenyl-prop-2-yn-1-ol, 8-methoxy-3-oxo-2-(2-trimethylsilanyl-ethoxymethyl)-2,3-dihydro-[1,2,4]triazolo[4,3-a]pyridine-7-carbaldehyde was reacted to give the title compound (1.05 g, 100%) as a pale yellow gum. LCMS (Method A): $R_T$=4.75 min, $[M+H]^+$=426.

Step 10: 8-Methoxy-7-(3-phenyl-propynoyl)-2-(2-trimethylsilanyl-ethoxymethyl)-2H-[1,2,4]triazolo[4,3-a]pyridin-3-one: Following the procedure used to prepare 1-(5-fluoro-2-methoxy-phenyl)-3-phenyl-propynone, 7-(1-hydroxy-3-phenyl-prop-2-ynyl)-8-methoxy-2-(2- trimethylsilanyl-ethoxymethyl)-2H-[1,2,4]triazolo[4,3-a]pyridin-3-one was reacted to give the title compound as a yellow solid (933 mg, 89%). LCMS (Method A): $R_T$=4.91 min, [M+H]$^+$=424.

Step 11: 7-Iodo-8-phenyl-2-(2-trimethylsilanyl-ethoxymethyl)-2H-9-oxa-1,2,3a-triaza-cyclopenta[a]naphthalene-3,6-dione: Following the procedure used to prepare 6-fluoro-3-iodo-2-phenyl-chromen-4-one, 8-methoxy-7-(3-phenyl-propynoyl)-2-(2-trimethylsilanyl-ethoxymethyl)-2H-[1,2,4]triazolo[4,3-a]pyridin-3-one was reacted to give the title compound as a cream solid (958 mg, 81%). LCMS (Method A): $R_T$=4.80 min, [M+H]$^+$=536.

Step 12: {1-(4-[3,6-Dioxo-8-phenyl-2-(2-trimethylsilanyl-ethoxymethyl)-2,6-dihydro-3H-9-oxa-1,2,3a-triaza-cyclopenta[a]naphthalen-7-yl]-phenyl}-cyclobutyl)-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-iodo-8-phenyl-2-(2-trimethylsilanyl-ethoxymethyl)-2H-9-oxa-1,2,3a-triaza-cyclopenta[a]naphthalene-3,6-dione was reacted to give the title compound as a pale yellow gum (24 mg, 78%). LCMS (Method A): $R_T$=5.02 min, [M+H]$^+$=655.

Step 13: 7-[4-(1-Amino-cyclobutyl)-phenyl]-8-phenyl-2H-9-oxa-1,2,3a-triaza-cyclopenta[a]naphthalene-3,6-dione hydrochloride: Following the procedure used to prepare 3-[4-(1-amino-cyclobutyl)-phenyl]-6-fluoro-2-phenyl-chromen-4-one, {1-[4-(4-oxo-2-phenyl-4H-pyrano[2,3-b]pyridin-3-yl)-phenyl]-cyclobutyl}-carbamic acid tert-butyl ester was treated with 50% TFA in DCM. The resultant free base was dissolved in a mixture of MeOH (2 mL), water (6 mL) and 1 M HCl (0.1 mL) and chromatographed on a 5 g C18 cartridge {40% MeOH in water+1 M HCl (60 μL in each 10 mL of eluent)} to give the title compound as a pale cream solid (11.1 mg, 66%). $^1$H NMR (400 MHz, DMSO-d6): δ 13.07 (br s, 1H), 8.64 (br s, 3H), 7.82 (d, J=7.2 Hz, 1H), 7.49 (d, J=8.3 Hz, 2H), 7.46-7.36 (m, 5H), 7.30 (d, J=8.3 Hz, 2H), 6.96 (d, J=7.2 Hz, 1H), 2.61-2.50 (m, 4H), 2.23-2.12 (m, 1H), 1.85-1.74 (m, 1H). LCMS (Method E): $R_T$=2.92 min, [M−H]$^+$=423.

Example 64

7-[4-(1-Amino-cyclobutyl)-phenyl]-2-methyl-8-phenyl-2H-9-oxa-1,2,3a-triaza-cyclopenta[a]naphthalene-3,6-dione hydrochloride

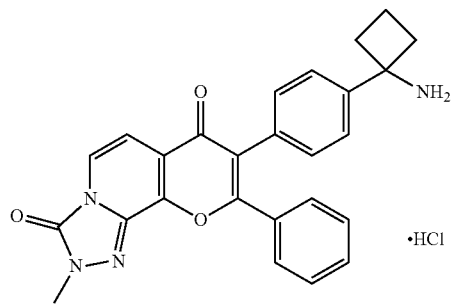 [SMILES: Cn1nc2c3oc(-c4ccccc4)c(-c4ccc(C5(N)CCC5)cc4)c(=O)c3ccn2c1=O ; Cl]

Step 1: 7-Iodo-8-phenyl-2H-9-oxa-1,2,3a-triaza-cyclopenta[a]naphthalene-3,6-dione: To a stirred ice-cooled solution of 7-iodo-8-phenyl-2-(2-trimethylsilanyl-ethoxymethyl)-2H-9-oxa-1,2,3a-triaza-cyclopenta[a]naphthalene-3,6-dione (60 mg, 0.112 mmol) in DCM (2 mL) was added TFA (2 mL). The reaction mixture was allowed to warm to RT. After 16 hours, the solvents were removed in vacuo, the residue was dissolved in THF (2 mL) and benzyltrimethylammonium hydroxide (40% in MeOH, 0.05 mL) was added. The reaction mixture was stirred at RT for 1 hour. EtOAc was added and the mixture was washed with water and brine, dried (Na$_2$SO$_4$), filtered, and concentrated in vacuo to give the title compound (50.4 mg) as a buff solid. LCMS (Method B): $R_T$=3.84 min, [M+H]$^+$=406.

Step 2: 7-Iodo-2-methyl-8-phenyl-2H-9-oxa-1,2,3a-triaza-cyclopenta[a]naphthalene-3,6-dione: To an ice-cooled solution of 7-iodo-8-phenyl-2H-9-oxa-1,2,3a-triaza-cyclopenta[a]naphthalene-3,6-dione in DMF (2 mL) was added cesium carbonate (73 mg, 0.224 mmol) and iodomethane (0.021 mL, 0.336 mmol). The mixture was allowed to warm to RT and stirred for 1.5 hours. The reaction mixture was partitioned between EtOAc and water. The aqueous phase was isolated and extracted twice with EtOAc. The combined organic extracts were washed with water and brine, dried (Na$_2$SO$_4$), filtered, and concentrated in vacuo to give the title compound (25.5 mg, 51%, over 2 steps) as a yellow solid. LCMS (Method A): $R_T$=3.98 min, [M+H]$^+$=420.

Step 3: {1-[4-(2-Methyl-3,6-dioxo-8-phenyl-2,6-dihydro-3H-9-oxa-1,2,3a-triaza-cyclopenta[a]naphthalen-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-iodo-2-methyl-8-phenyl-2H-9-oxa-1,2,3a-triaza-cyclopenta[a]naphthalene-3,6-dione was reacted to give the title compound as a colourless gum (19.9 mg, 61%). LCMS (Method A): $R_T$=4.63 min, [M+H]$^+$=539.

Step 4: 7-[4-(1-Amino-cyclobutyl)-phenyl]-2-methyl-8-phenyl-2H-9-oxa-1,2,3a-triaza-cyclopenta[a]naphthalene-3,6-dione hydrochloride: Following the procedure used to prepare 3-[4-(1-amino-cyclobutyl)-phenyl]-6-fluoro-2-phenyl-chromen-4-one, {1-[4-(2-methyl-3,6-dioxo-8-phenyl-2,6-dihydro-3H-9-oxa-1,2,3a-triaza-cyclopenta[a]naphthalen-7-yl)-phenyl]-cyclobutyl}-carbamic acid tert-butyl ester was treated with TFA. The resultant free base was dissolved in a mixture of MeOH (1.5 mL), water (3.5 mL) and 1 M HCl (0.1 mL) and chromatographed on a 5 g C18 cartridge {30 to 70% MeOH in water+1 M HCl (60 μL in each 10 mL of eluent)} to give the title compound as a white solid (13.5 mg, 77%). $^1$H NMR (400 MHz, DMSO-d6): δ 8.62 (br s, 3H), 7.86 (d, J=7.2 Hz, 1H), 7.50 (d, J=8.3 Hz, 2H), 7.47-7.37 (m, 5H), 7.30 (d, J=8.3 Hz, 2H), 7.00 (d, J=7.2 Hz, 1H), 3.65 (s, 3H), 2.61-2.49 (m, 4H), 2.23-2.12 (m, 1H), 1.85-1.74 (m, 1H). LCMS (Method E): $R_T$=2.95 min, [M+H]$^+$=439.

Example 65

3-[4-(1-Amino-cyclobutyl)-phenyl]-2-phenyl-chromene-4-thione hydrochloride

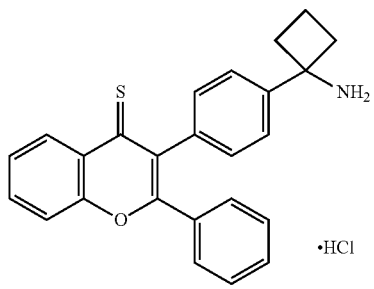 [SMILES: NC1(c2ccc(-c3c(-c4ccccc4)oc4ccccc4c3=S)cc2)CCC1 ; Cl]

Step 1: {1-[4-(2-Phenyl-4-thioxo-4H-chromen-3-yl)-phenyl]-cyclobutyl}-carbamic acid tert-butyl ester: To a solution of {1-[4-(4-oxo-2-phenyl-4H-chromen-3-yl)-phenyl]-cyclobutyl}-carbamic acid tert-butyl ester (30 mg, 0.0642 mmol) in toluene (3 mL) was added Lawesson's reagent (2,4-bis-(4-methoxy-phenyl)-[1,3,2,4]dithiadiphosphetane 2,4-disulfide) (15.6 mg, 0.039 mmol). The reaction mixture was heated at reflux for 3 hours. The cooled mixture was subjected to flash chromatography ($SiO_2$, 20% EtOAc in cyclohexane). A second chromatography ($SiO_2$, 3% EtOAc in toluene) afforded the title compound (35 mg). LCMS (Method A): $R_T$=5.08 min, $[M+H]^+$=484.

Step 2: 3-[4-(1-Amino-cyclobutyl)-phenyl]-2-phenyl-chromene-4-thione hydrochloride: Following the procedure used to prepare 3-[4-(1-amino-cyclobutyl)-phenyl]-6-fluoro-2-phenyl-chromen-4-one, {1-[4-(2-phenyl-4-thioxo-4H-chromen-3-yl)-phenyl]-cyclobutyl}-carbamic acid tert-butyl ester was treated with TFA. The resultant free base was dissolved in a mixture of MeOH (2 mL), water (3 mL) and 1 M HCl (0.1 mL) and then chromatographed on a 5 g C18 cartridge {40 to 80% MeOH in water+1 M HCl (60 μL in each 10 mL of eluent)} to give the title compound as a grey-green solid (17.2 mg, 64% over 2 steps). $^1$H NMR (400 MHz, DMSO-d6): δ 8.63 (br s, 3H), 8.53 (dd, J=8.3 and 1.4 Hz, 1H), 7.95-7.91 (m, 1H), 7.81 (d, J=8.5 Hz, 1H), 7.61-7.57 (m, 1H), 7.48-7.39 (m, 5H), 7.34-7.26 (m, 4H), 2.57-2.49 (m, 4H), 2.23-2.13 (m, 1H), 1.85-1.74 (m, 1H). LCMS (Method E): $R_T$=3.92 min, $[M+H]^+$=384.

Example 66

3-[4-(1-Amino-cyclobutyl)-phenyl]-2-phenyl-chromen-4-one O-methyl-oxime

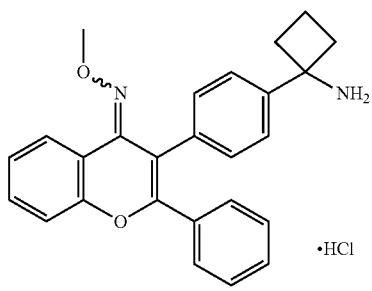 [SMILES: CON=c1c(-c2ccc(C3(N)CCC3)cc2)c(-c2ccccc2)oc2ccccc12 ; Cl]

Step 1: {1-[4-(4-Hydroxyimino-2-phenyl-4H-chromen-3-yl)-phenyl]-cyclobutyl}-carbamic acid tert-butyl ester: A mixture of {1-[4-(2-phenyl-4-thioxo-4H-chromen-3-yl)-phenyl]-cyclobutyl}-carbamic acid tert-butyl ester (33.4 mg, 0.069 mmol), hydroxylamine hydrochloride (14.4 mg, 0.207 mmol) and sodium acetate (17 mg, 0.207 mmol) in IMS (5 mL) was stirred at 80° C. for 16 hours. The cooled reaction mixture was partitioned between DCM and water. The aqueous phase was isolated and extracted with DCM. The combined organic extracts were evaporated to dryness. The resultant residue was subjected to flash chromatography ($SiO_2$, 2% MeOH in DCM) to afford the title compound (27.2 mg, 82%) as a pale yellow solid. LCMS (Method A): $R_T$=4.96 min, $[M+H]^+$=483.

Step 2: {1-[4-(4-Methoxyimino-2-phenyl-4H-chromen-3-yl)-phenyl]-cyclobutyl}-carbamic acid tert-butyl ester: To a stirred solution of {1-[4-(4-hydroxyimino-2-phenyl-4H-chromen-3-yl)-phenyl]-cyclobutyl}-carbamic acid tert-butyl ester (27 mg, 0.056 mmol) in DMF (2 mL) was added potassium carbonate (15.5 mg, 0.112 mmol) and iodomethane (0.011 mL, 0.168 mmol) at RT. After 2 hours, cesium carbonate (36.5 mg, 0.112 mmol) and iodomethane (0.021 mL, 0.336 mmol) were added and the mixture stirred for a further 1.5 hours. The reaction mixture was partitioned between EtOAc and water. The aqueous phase was isolated and extracted with EtOAc. The combined organic extracts were washed with water and brine, dried ($Na_2SO_4$), filtered, and concentrated in vacuo. The resultant residue was subjected to flash chromatography ($SiO_2$, gradient 15 to 25% EtOAc in cyclohexane) to afford the title compound (25.1 mg, 90%) as a colourless gum. LCMS (Method A): $R_T$=5.20 min, $[M+H]^+$=497.

Step 3: 3-[4-(1-Amino-cyclobutyl)-phenyl]-2-phenyl-chromen-4-one O-methyl-oxime hydrochloride: Following the procedure used to prepare 3-[4-(1-amino-cyclobutyl)-phenyl]-6-fluoro-2-phenyl-chromen-4-one, {1-[4-(4-methoxyimino-2-phenyl-4H-chromen-3-yl)-phenyl]-cyclobutyl}-carbamic acid tert-butyl ester was treated with TFA. The resultant free base was dissolved in a mixture of MeOH (2 mL), water (6 mL) and 1 M HCl (0.1 mL) and chromatographed on a 5 g C18 cartridge {35 to 80% MeOH in water+1 M HCl (60 μL in each 10 mL of eluent)} to give the title compound as a white solid (13.3 mg, 69%). $^1$H NMR (400 MHz, $CD_3OD$): δ 8.89 (dd, J=8.4 and 1.4 Hz, 1H), 7.54-7.50 (m, 1H), 7.39 (d, J=8.4 Hz, 2H), 7.33-7.16 (m, 9H), 3.77 (s, 3H), 2.80-2.73 (m, 2H), 2.60-2.52 (m, 2H), 2.28-2.17 (m, 1H), 2.01-1.90 (m, 1H). LCMS (Method E): $R_T$=4.10 min, $[M+H]^+$=397.

Example 67

3-[4-(3-Amino-oxetan-3-yl)-phenyl]-8-bromo-2-phenyl-chromen-4-one

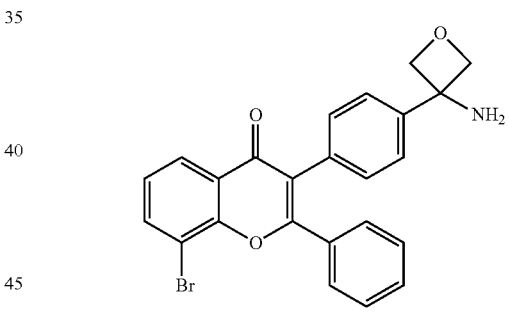

Step 1: 2-Methyl-propane-2-sulfinic acid {3-[4-(4,4,5,5-tetramethyl[1,3,2]dioxaborolan-2-yl)-phenyl]-oxetan-3-yl}-amide: A solution of 2-methyl-propane-2-sulfinic acid [3-(4-bromo-phenyl)-oxetan-3-yl]-amide (200 mg, 0.57 mmol), bis (pinacolato)diboron (146 mg, 0.57 mmol), [1,1'-bis (diphenylphosphino)-ferrocene]dischloropalladium(II), complex with dichloromethane (47 mg, 0.06 mmol) and potassium acetate (169 mg, 1.72 mmol) in DMSO (5 mL) was degassed using argon. The system was sealed and heated at 85° C. for 18 h. The reaction mixture was allowed to cool to RT, diluted using EtOAc, washed with water, brine (×3), dried ($Na_2SO_4$), filtered and concentrated in vacuo. The resultant residue was dissolved in diethyl ether and the solids remaining were removed by filtration. The eluent was concentrated in vacuo to afford the title compound (203 mg, 89%). LCMS (Method B): $R_T$=3.85 min, $[M+H]^+$=380.

Step 2: 2-Methyl-propane-2-sulfinic acid {3-[4-(8-bromo-4-oxo-2-phenyl-4H-chromen-3-yl)-phenyl]-oxetan-3-yl}-amide: Following the procedure used to prepare {1-[4-(6-fluoro-4-oxo-2-phenyl-4H-chromen-3-yl)-phenyl]- cyclobutyl}-carbamic acid tert-butyl ester, 8-bromo-3-iodo-2-phenyl-chromen-4-one and 2-methyl-propane-2-sulfinic acid {3-[4-(4,4,5,5-tetramethyl[1,3,2]dioxaborolan-2-yl)-phenyl]-oxetan-3-yl}-amide were reacted to give the title compound as a tan solid (59 mg, 55%). LCMS (Method B): $R_T$=5.02 min, [M+H]$^+$=552/554.

Step 3: 3-[4-(3-Amino-oxetan-3-yl)-phenyl]-8-bromo-2-phenyl-chromen-4-one: Following the procedure used to prepare 3-[4-(1-amino-cyclobutyl)-phenyl]-6-fluoro-2-phenyl-chromen-4-one, 2-methyl-propane-2-sulfinic acid {3-[4-(8-bromo-4-oxo-2-phenyl-4H-chromen-3-yl)-phenyl]-oxetan-3-yl}-amide was reacted to give the title compound as a white solid (16 mg, 34%). $^1$H NMR (400 MHz, DMSO-d6): δ 8.18 (dd, J=7.8 and 1.6 Hz, 1H), 8.11 (dd, J=8.2 and 1.9 Hz, 1H), 7.54 (d, J=8.7 Hz, 2H), 7.50-7.34 (m, 6H), 7.23 (d, J=8.5, 2H), 4.71 (d, J=6.1 Hz, 2H), 4.67 (d, J=6.1 Hz, 2H), 3.32 (s, 2H). LCMS (Method E): $R_T$=3.67 min, [M+H]$^+$=448/450.

Example 68

7-[4-(3-Amino-oxetan-3-yl)-phenyl]-8-phenyl-2H-9-oxa-1,2,3a-triaza-cyclopenta[a]naphthalene-3,6-dione

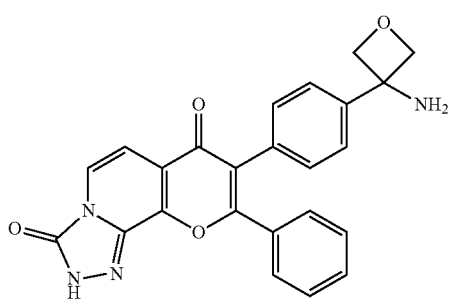 [SMILES: NC1(c2ccc(-c3c(-c4ccccc4)oc4c(ccn5c(=O)[nH]nc45)c3=O)cc2)COC1]

Step 1: 2-Methyl-propane-2-sulfinic acid (3-{-4-[3,6-dioxo-8-phenyl-2-(2-trimethylsilanyl-ethoxymethyl)-2,6-dihydro-3H-9-oxa-1,2,3a-triaza-cyclopenta[a]naphthalen-7-yl]-phenyl}-oxetan-3-yl)-amide: A mixture of 7-iodo-8-phenyl-2-(2-trimethylsilanyl-ethoxymethyl)-2H-9-oxa-1,2,3a-triaza-cyclopenta[a]naphthalene-3,6-dione (53.5 mg, 0.10 mmol), 2-methyl-propane-2-sulfinic acid {3-[4-(4,4,5,5-tetramethyl[1,3,2]dioxaborolan-2-yl)-phenyl]-oxetan-3-yl}-amide (57 mg, 0.15 mmol), [1,1'-bis(diphenylphosphino)-ferrocene]dichloropalladium(II), complex with dichloromethane (4 mg, 0.005 mmol), sodium carbonate solution (2 M in water, 0.3 mL, 0.6 mmol) and DME (2 mL) was purged using nitrogen and heated in a microwave reactor at 125° C. for 1 h. The reaction mixture was allowed to cool to RT and was partitioned between EtOAc and water. The aqueous phase was extracted with EtOAc and the combined organic extracts were washed with water and brine, dried (Na$_2$SO$_4$), filtered, and concentrated in vacuo. The resultant residue was subjected to flash chromatography (SiO$_2$, gradient 0 to 5 (% MeOH in EtOAc) to afford the title compound (46 mg, 70%) as a yellow gum. LCMS (Method H): $R_T$=3.95 min, [M+H]$^+$=661.

Step 2: 7-[4-(3-Amino-oxetan-3-yl)-phenyl]-8-phenyl-2H-9-oxa-1,2,3a-triaza-cyclopenta[a]naphthalene-3,6-dione: To a stirred solution of 2-methyl-propane-2-sulfinic acid (3-{-4-[3,6-dioxo-8-phenyl-2-(2-trimethylsilanyl-ethoxymethyl)-2,6-dihydro-3H-9-oxa-1,2,3a-triaza-cyclopenta[a]naphthalen-7-yl]-phenyl}-oxetan-3-yl)-amide (46 mg, 0.07 mmol) in MeOH (6 mL) was added a solution of HCl in dioxane (4 M, 0.14 mL, 0.56 mmol) at RT. After 1 h, the reaction mixture was evaporated to dryness. The residue was suspended in DCM (5 mL), cooled in an ice bath, and TFA (1 mL) was added. The mixture was stirred at RT for 1 h before evaporating to dryness. The residue was dissolved in MeOH and loaded on to a 2 g SCX-2 cartridge. The cartridge was washed with MeOH before eluting with 2 M NH$_3$ in MeOH solution. The eluent was collected and evaporated. The resulting residue was subjected to flash chromatography (SiO$_2$, gradient 10 to 30% 2 M NH$_3$/MeOH in DCM) to afford the title compound (15 mg, 52%) as a pale yellow solid. $^1$H NMR (400 MHz, DMSO-d6): δ 7.81 (d, J=7.2 Hz, 1H), 7.54 (d, J=8.3 Hz, 2H), 7.44-7.36 (m, 5H), 7.22 (d, J=8.2 Hz, 2H), 6.97 (d, J=7.2 Hz, 1H), 4.70 (d, J=6.1 Hz, 2H), 4.66 (d, J=6.1 Hz, 2H). LCMS (Method E): $R_T$=2.35 min, [M+H]$^+$=427.

Example 69

7-[6-(1-Amino-cyclobutyl)-pyridin-3-yl]-8-phenyl-2H-9-oxa-1,2,3a-triaza-cyclopenta[a]naphthalene-3,6-dione

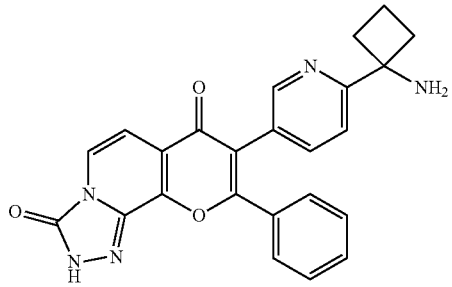 [SMILES: NC1(c2ccc(-c3c(-c4ccccc4)oc4c(ccn5c(=O)[nH]nc45)c3=O)cn2)CCC1]

Step 1: 2-Methyl-propane-2-sulfinic acid (1-{5-[3,6-dioxo-8-phenyl-2-(2-trimethylsilanyl-ethoxymethyl)-2,6-dihydro-3H-9-oxa-1,2,3a-triaza-cyclopenta[a]naphthalen-7-yl]-pyridin-2-yl}-cyclobutyl)-amide: To a microwave vial were added 2-methyl-propane-2-sulfinic acid [1-(5-bromo-pyridin-2-yl)-cyclobutyl]-amide (33 mg, 0.10 mmol), bis(pinacolato)diboron (30.5 mg, 0.12 mmol, [1,1'-bis(diphenylphosphino)-ferrocene]dichloropalladium(II), complex with DCM (2.5 mg, 0.003 mmol), potassium acetate (29.4 mg, 0.30 mmol) and DME (1 mL). The reaction mixture was purged using nitrogen and heated in a microwave reactor at 100° C. for 2 h. The reaction mixture was allowed to cool to RT and 7-iodo-8-phenyl-2-(2-trimethylsilanyl-ethoxymethyl)-2H-9-oxa-1,2,3a-triaza-cyclopenta[a]naphthalene-3,6-dione (53.5 mg, 0.10 mmol), [1,1'-bis(diphenylphosphino)-ferrocene]dischloropalladium(II), complex with dichloromethane (2.5 mg, 0.003 mmol), sodium carbonate solution (2 M in water, 0.2 mL, 0.4 mmol) and DME (0.5 mL) were added. The reaction mixture was purged using nitrogen and heated in a microwave reactor at 125° C. for 1 h. The reaction mixture was allowed to cool to RT, partitioned between EtOAc and water, and was filtered through a Celite® pad. The aqueous phase was extracted with EtOAc and the combined organic extracts were washed with water and brine, dried (Na$_2$SO$_4$), filtered, and concentrated in vacuo. The resultant residue was subjected to flash chromatography (SiO$_2$, gradient 0 to 10% MeOH in EtOAc) to afford the title compound (54 mg, 82%). LCMS (Method B): $R_T$=4.90 min, [M+H]$^+$=660.

Step 2: 7-[6-(1-Amino-cyclobutyl)-pyridin-3-yl]-8-phenyl-2H-9-oxa-1,2,3a-triaza-cyclopenta[a]naphthalene-3,6-dione: To a stirred solution of 2-methyl-propane-2-sulfinic acid (1-{5-[3,6-dioxo-8-phenyl-2-(2-trimethylsilanyl-ethoxymethyl)-2,6-dihydro-3H-9-oxa-1,2,3a-triaza-cyclopenta[a]naphthalen-7-yl]-pyridin-2-yl}-cyclobutyl)-amide (40 mg, 0.061 mmol) in MeOH (3 mL) was added a solution of HCl in dioxane (4 M, 0.3 mL, 1.2 mmol) at RT. After 1 h, the reaction mixture was evaporated to dryness. The residue was dissolved in DCM (2 mL), cooled in an ice bath, and TFA (2 mL) was added. The mixture was stirred at RT for 2 h before evaporating to dryness. The residue was dissolved in MeOH and loaded on to a 5 g SCX-2 cartridge. The cartridge was washed with MeOH before eluting with 2 M $NH_3$ in MeOH solution. The eluent was collected and evaporated. The resulting residue was dissolved in a mixture of MeOH (1.5 mL), water (8.5 mL) and 1 M HCl (0.2 mL) and then chromatographed on a 5 g C18 cartridge {gradient 15 to 45% MeOH in water+1 M HCl (60 µL in each 10 mL of eluent)}. The purified hydrochloride salt was dissolved in MeOH and loaded on to a 5 g SCX-2 cartridge. The cartridge was washed with MeOH before eluting with 2 M $NH_3$ in MeOH solution. The eluent was collected and evaporated to dryness to give the title compound as a white solid. $^1$H NMR (400 MHz, DMSO-d6): δ 8.28 (d, J=1.9 Hz, 1H), 7.81 (d, J=7.2 Hz, 1H), 7.63 (dd, J=8.2 and 2.2 Hz, 1H), 7.57 (dd, J=8.0 and 1.0 Hz, 1H), 7.49-7.39 (m, 5H), 6.96 (d, J=7.1 Hz, 1H), 6.10 (br s, 3H), 2.53-2.45 (m, 2H), 2.08-1.93 (m, 3H), 1.77-1.68 (m, 1H). LCMS (Method E): $R_T$=2.49 min, [M+H]$^+$=426.

Example 70

2-[4-(3,6-Dioxo-8-phenyl-2,6-dihydro-3H-9-oxa-1,2,3a-triaza-cyclopenta[a]naphthalen-7-yl)-phenyl]-2-methyl-propionitrile

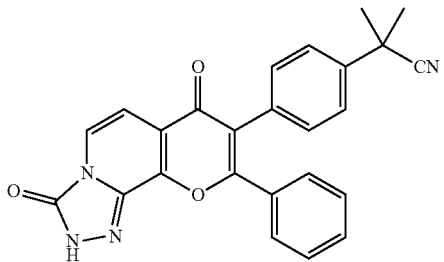 [SMILES: CC(C)(C#N)c1ccc(-c2c(-c3ccccc3)oc3c(ccn4c(=O)[nH]nc34)c2=O)cc1]

Step 1: 2-{-4-[3,6-Dioxo-8-phenyl-2-(2-trimethylsilanyl-ethoxymethyl)-2,6-dihydro-3H-9-oxa-1,2,3a-triaza-cyclopenta[a]naphthalen-7-yl]-phenyl}-2-methyl-propionitrile: Following the procedure used to prepare 2-methyl-propane-2-sulfinic acid (1-{5-[3,6-dioxo-8-phenyl-2-(2-trimethylsilanyl-ethoxymethyl)-2,6-dihydro-3H-9-oxa-1,2,3a-triaza-cyclopenta[a]naphthalen-7-yl]-pyridin-2-yl}-cyclobutyl)-amide, 2-(4-bromo-phenyl)-2-methyl-propionitrile was reacted to give the title compound (55 mg, 99%). LCMS (Method A): $R_T$=4.83 min, [M+H]$^+$=553.

Step 2: 2-[4-(3,6-Dioxo-8-phenyl-2,6-dihydro-3H-9-oxa-1,2,3a-triaza-cyclopenta[a]naphthalen-7-yl)-phenyl]-2-methyl-propionitrile: To a stirred solution of 2-{4-[3,6-dioxo-8-phenyl-2-(2-trimethylsilanyl-ethoxymethyl)-2,6-dihydro-3H-9-oxa-1,2,3a-triaza-cyclopenta[a]naphthalen-7-yl]-phenyl}-2-methyl-propionitrile (55 mg, 0.1 mmol) in DCM (2 mL), cooled in an ice bath, was added TFA (1.5 mL) at RT. After 16 h, the reaction mixture was evaporated to dryness, the resultant residue was dissolved in THF (3 mL) and benzyltrimethylammonium hydroxide solution (0.06 mL, 40% in MeOH) was added. The reaction mixture was stirred at RT for 1.5 h. EtOAc and water were added and the mixture was acidified by the addition of 1 M HCl (1 mL). The aqueous layer was extracted with EtOAc and the combined organic extracts were washed with brine, dried ($Na_2SO_4$), filtered and concentrated in vacuo. The resultant residue was subjected to flash chromatography ($SiO_2$, EtOAc) to afford the title compound (20 mg, 47%) as a white solid. $^1$H NMR (400 MHz, CDCl$_3$): δ 10.05 (s, 1H), 7.72 (d, J=7.3 Hz, 1H), 7.46-7.38 (m, 5H), 7.33-7.22 (m, 5H), 1.73 (s, 6H). LCMS (Method E): $R_T$=4.22 min, [M+H]$^+$=423.

Example 71

7-[6-(1-Amino-cyclobutyl)-pyridin-3-yl]-1-methyl-8-phenyl-1H-9-oxa-1,2-diaza-cyclopenta[a]naphthalen-6-one hydrochloride

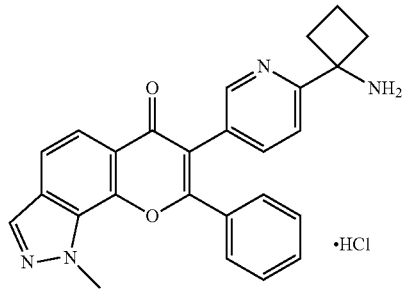 [SMILES: Cn1ncc2ccc3c(=O)c(-c4ccc(C5(N)CCC5)nc4)c(-c4ccccc4)oc3c21 ; Cl]

Step 1: 2-Methyl-propane-2-sulfinic acid {1-[5-(1-methyl-6-oxo-8-phenyl-1,6-dihydro-9-oxa-1,2-diaza-cyclopenta[a]naphthalen-7-yl)-pyridin-2-yl]-cyclobutyl}-amide: Following the procedure used to prepare 2-methyl-propane-2-sulfinic acid (1-{5-[3,6-dioxo-8-phenyl-2-(2-trimethylsilanyl-ethoxymethyl)-2,6-dihydro-3H-9-oxa-1,2,3a-triaza-cyclopenta[a]naphthalen-7-yl]-pyridin-2-yl}-cyclobutyl)-amide, 7-iodo-1-methyl-8-phenyl-1H-9-oxa-1,2-diaza-cyclopenta[a]naphthalen-6-one was reacted to give the title compound (34 mg, 81%) as a pale orange gum. LCMS (Method H): $R_T$=3.41 min, [M+H]$^+$=527.

Step 2: 7-[6-(1-Amino-cyclobutyl)-pyridin-3-yl]-1-methyl-8-phenyl-1H-9-oxa-1,2-diaza-cyclopenta[a]naphthalen-6-one hydrochloride: To a solution of 2-methyl-propane-2-sulfinic acid {1-[5-(1-methyl-6-oxo-8-phenyl-1,6-dihydro-9-oxa-1,2-diaza-cyclopenta[a]naphthalen-7-yl)-pyridin-2-yl]-cyclobutyl}-amide (34 mg, 0.0645 mmol) in MeOH (6 mL) was added a solution of HCl in dioxane (4 M, 0.32 mL, 1.28 mmol). The reaction mixture was stirred at RT for 30 min before evaporating to dryness. The resulting residue was dissolved in a mixture of MeOH (1 mL), water (4 mL) and then chromatographed on a 5 g C18 cartridge {gradient 20 to 60% MeOH in water+1 M HCl (60 µL in each 10 mL of eluent)} to give the title compound (24.3 mg, 82%) as an off-white solid. $^1$H NMR (400 MHz, DMSO-d6): δ 8.78 (br s, 3H), 8.41 (dd, J=2.2 and 0.8 Hz, 1H), 8.29 (s, 1H), 7.89-7.81 (m, 3H), 7.75 (d, J=8.3 Hz, 1H), 7.59-7.57 (m, 2H), 7.51-7.41 (m, 3H), 4.41 (s, 3H), 2.60-2.55 (m, 4H), 2.26-2.15 (m, 1H), 2.05-1.94 (m, 1H). LCMS (Method E): =3.22 min, [M+H]$^+$=423.

Example 72

3-[4-(1-Amino-cyclobutyl)-phenyl]-8-morpholin-4-yl-2-phenyl-chromen-4-one hydrochloride

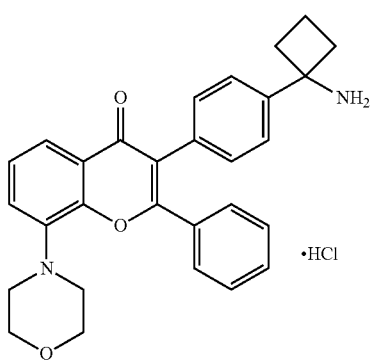 [SMILES: NC1(c2ccc(-c3c(-c4ccccc4)oc4c(N5CCOCC5)cccc4c3=O)cc2)CCC1 ; Cl]

Step 1: {1-[4-(8-Morpholin-4-yl-4-oxo-2-phenyl-4H-chromen-3-yl)-phenyl]-cyclobutyl}-carbamic acid tert-butyl ester: {1-[4-(8-bromo-4-oxo-2-phenyl-4H-chromen-3-yl)-phenyl]-cyclobutyl}-carbamic acid tert-butyl ester (50 mg, 0.091 mmol), morpholine (10 μL, 0.11 mmol), tris(dibenzylideneacetone)dipalladium(0) (5 mg, 0.005 mmol), (S)-BINAP (9 mg, 0.015 mmol) and cesium carbonate (42 mg, 0.127 mmol) were suspended in toluene (1 mL) in a microwave vial. The vial was sealed, evacuated and flushed twice with nitrogen. The reaction mixture was heated in a microwave at 150° C. for 1 h. Further morpholine (10 μL, 0.11 mmol), tris(dibenzylideneacetone)dipalladium(0) (5 mg, 0.005 mmol), (S)-BINAP (9 mg, 0.015 mmol) and cesium carbonate (42 mg, 0.127 mmol) were added to the vial and the resultant mixture was heated in a microwave at 150° C. for 1.5 h. Further morpholine (10 μL, 0.11 mmol), tris(dibenzylideneacetone)dipalladium(0) (5 mg, 0.005 mmol), (S)-BINAP (9 mg, 0.015 mmol) and cesium carbonate (42 mg, 0.127 mmol) were added to the vial and the resultant mixture was heated in a microwave at 150° C. for 1 h. The reaction mixture was diluted with EtOAc, washed with water, dried (Na$_2$SO$_4$), filtered and concentrated in vacuo. The resultant residue was subjected to flash chromatography (SiO$_2$, gradient 0 to 100% ethyl acetate in DCM) to afford the title compound as a pale yellow solid (35 mg, 70%). LCMS (Method G): R$_T$=4.33 min, [M+H]$^+$=553.

Step 2: 3-[4-(1-Amino-cyclobutyl)-phenyl]-8-morpholin-4-yl-2-phenyl-chromen-4-one hydrochloride: Following the procedure of 3-[4-(1-amino-cyclobutyl)-phenyl]-6-fluoro-2-phenyl-chromen-4-one, {1-[4-(8-morpholin-4-yl-4-oxo-2-phenyl-4H-chromen-3-yl)-phenyl]-cyclobutyl}-carbamic acid tert-butyl ester was treated with TFA. The resultant free base was dissolved in a mixture of MeOH (7 mL), water (7 mL) and 1 M HCl (0.6 mL) and chromatographed on a 5 g C18 cartridge {gradient 10 to 50% MeOH in water+1 M HCl (60 μL in each 10 mL of eluent)} to give the title compound as a white solid (23 mg, 75%). $^1$H NMR (400 MHz, DMSO-d6): δ 8.47 (bs, 3H), 7.67 (dd, J=7.5 and 2.1 Hz, 1H), 7.45-7.29 (m, 9H), 7.25 (d, J=8.3 Hz, 2H), 3.74 (t, J=4.1 Hz, 4H), 3.13 (t, J=3.6 Hz, 4H), 2.58-2.44 (m, 4H), 2.19-2.06 (m, 1H), 1.82-1.70 (m, 1H). LCMS (Method E): R$_T$=3.44 min, [M+H]$^+$=453.

Example 73

3-[4-(1-Amino-cyclobutyl)-phenyl]-8-(3-methyl-1H-pyrazol-4-yl)-2-phenyl-chromen-4-one hydrochloride

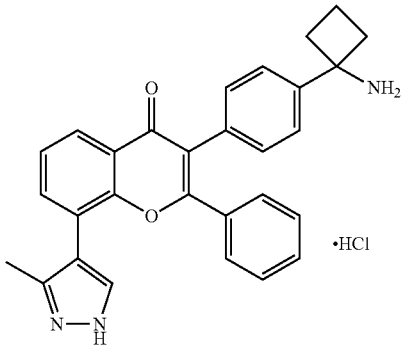 [SMILES: Cc1n[nH]cc1-c1cccc2c(=O)c(-c3ccc(C4(N)CCC4)cc3)c(-c3ccccc3)oc12 ; Cl]

Step 1: (1-{4-[8-(3-Methyl-1H-pyrazol-4-yl)-4-oxo-2-phenyl-4H-chromen-3-yl]-phenyl}-cyclobutyl)-carbamic acid tert-butyl ester: Following the procedure of (1-{4-[4-oxo-2-phenyl-7-(2H-pyrazol-3-yl)-4H-chromen-3-yl]-phenyl]-cyclobutyl}-carbamic acid tert-butyl ester, {1-[4-(8-bromo-4-oxo-2-phenyl-4H-chromen-3-yl)-phenyl]-cyclobutyl}-carbamic acid tert-butyl ester was reacted with 3-methyl-1H-pyrazole-4-boronic acid pinacol ester to give the title compound as a gum (35 mg, 70%). LCMS (Method G): R$_T$=3.81 min, [M+H]$^+$=548.

Step 2: 3-[4-(1-Amino-cyclobutyl)-phenyl]-8-(3-methyl-1H-pyrazol-4-yl)-2-phenyl-chromen-4-one hydrochloride: Following the procedure of 3-[4-(1-amino-cyclobutyl)-phenyl]-6-fluoro-2-phenyl-chromen-4-one, (1-{4-[8-(3-methyl-1H-pyrazol-4-yl)-4-oxo-2-phenyl-4H-chromen-3-yl]-phenyl}-cyclobutyl)-carbamic acid tert-butyl ester was treated with TFA. The resultant free base was dissolved in a mixture of MeOH (7 mL), water (7 mL) and 1 M HCl (0.6 mL) and chromatographed on a 5 g C18 cartridge {gradient 10 to 50% MeOH in water+1 M HCl (60 μL in each 10 mL of eluent)} to give the title compound as a white solid (23 mg, 74%). $^1$H NMR (400 MHz, DMSO-d6): δ 8.61 (s, 3H), 8.00 (dd, J=8.0 and 1.5 Hz, 1H), 7.84 (s, 1H), 7.77 (dd, J=7.4 and 1.7 Hz, 1H), 7.52 (t, J=7.8 Hz, 1H), 7.42 (d, J=8.4 Hz, 2H), 7.38-7.22 (m, 7H), 3.96 (bs, 1H), 2.57-2.43 (m, 4H), 2.21 (s, 3H), 2.19-2.07 (m, 1H), 1.82-1.69 (m, 1H). LCMS (Method E): R$_T$=3.02 min, [M+H]$^+$=448.

Example 74

3-[4-(1-Amino-cyclobutyl)-phenyl]-8-imidazol-1-yl-2-phenyl-chromen-4-one hydrochloride

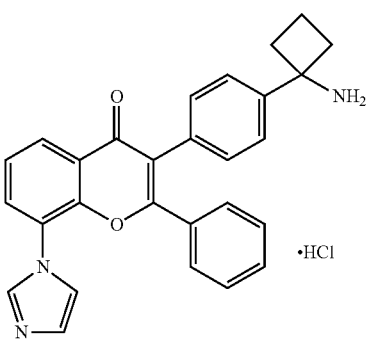 [SMILES: NC1(c2ccc(-c3c(-c4ccccc4)oc4c(-n5ccnc5)cccc4c3=O)cc2)CCC1 ; Cl]

Step 1: 3-[4-(1-Amino-cyclobutyl)-phenyl]-8-imidazol-1-yl-2-phenyl-chromen-4-one hydrochloride: {1-[4-(8-Bromo-4-oxo-2-phenyl-4H-chromen-3-yl)-phenyl]-cyclobutyl}-carbamic acid tert-butyl ester (63 mg, 0.115 mmol), imidazole (11 mg, 0.161 mmol), cesium carbonate (75 mg, 0.23 mmol) and copper (II) iodide (5 mg, 0.023 mmol) were dissolved in DMF (1 mL) in a microwave vial. The vial was sealed, evacuated and flushed twice with nitrogen. The reaction mixture was heated conventionally at 120° C. for 72 h and was allowed to cool to RT. The resultant mixture was diluted with EtOAc, washed with water, dried (Na$_2$SO$_4$), filtered and concentrated in vacuo. The resultant residue was subjected to flash chromatography (SiO$_2$, gradient 0 to 10% MeOH in DCM), dissolved in methanol and loaded onto an SCX-2 cartridge. The cartridge was washed repeatedly with methanol before eluting with 2 M ammonia in methanol solution. The eluent was collected and concentrated in vacuo. The resulting residue was dissolved in a mixture of MeOH (7 mL), water (7 mL and 1 M HCl (0.6 mL) and chromatographed on a 5 g C18 cartridge {gradient 10 to 50% MeOH in water+1 M HCl (60 μL in each 10 mL of eluent)} to give the title compound as a white solid (21 mg, 39%). $^1$H NMR (400 MHz, DMSO-d6): δ 9.38 (bs, 1H), 8.71 (s, 3H), 8.26 (d, J=8.3 Hz, 1H), 8.20-8.12 (m, 2H), 7.77 (s, 1H), 7.71 (t, J=8.3 Hz, 1H), 7.47 (d, J=8.3 Hz, 2H), 7.39-7.17 (m, 7H), 2.52 (t, J=7.9 Hz, 4H), 2.21-2.08 (m, 1H), 1.81-1.68 (m, 1H). LCMS (Method E): R$_T$=2.35 min, [M+H]$^+$=434.

Example 75

3-[4-(1-Amino-cyclobutyl)-phenyl]-8-(1,5-dimethyl-1H-pyrazol-4-yl)-2-phenyl-chromen-4-one hydrochloride

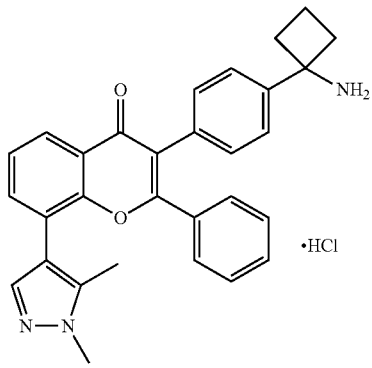 [SMILES: Cc1c(-c2cccc3c(=O)c(-c4ccc(C5(N)CCC5)cc4)c(-c4ccccc4)oc23)cnn1C ; Cl]

Step 1: (1-{4-[8-(1,5-Dimethyl-1H-pyrazol-4-yl)-4-oxo-2-phenyl-4H-chromen-3-yl]-phenyl}-cyclobutyl)-carbamic acid tert-butyl ester: Following the procedure of (1-{4-[4-oxo-2-phenyl-7-(2H-pyrazol-3-yl)-4H-chromen-3-yl]-phenyl}-cyclobutyl)-carbamic acid tert-butyl ester, {1-[4-(8-bromo-4-oxo-2-phenyl-4H-chromen-3-yl)-phenyl]-cyclobutyl}-carbamic acid tert-butyl ester was reacted with 1,5-dimethyl-1H-pyrazole-4-boronic acid pinacol ester to give the title compound (40 mg, 78%). LCMS (Method G): R$_T$=4.12 min, [M+H]$^+$=562.

Step 2: 3-[4-(1-Amino-cyclobutyl)-phenyl]-8-(1,5-dimethyl-1H-pyrazol-4-yl)-2-phenyl-chromen-4-one hydrochloride: Following the procedure of 3-[4-(1-amino-cyclobutyl)-phenyl]-6-fluoro-2-phenyl-chromen-4-one, (1-{4-[8-(1,5-dimethyl-1H-pyrazol-4-yl)-4-oxo-2-phenyl-4H-chromen-3-yl]-phenyl}-cyclobutyl)-carbamic acid tert-butyl ester was treated with TFA. The resultant free base was dissolved in a mixture of MeOH (7 mL), water (7 mL) and 1 M HCl (0.6 mL) and chromatographed on a 5 g C18 cartridge {gradient 10 to 50% MeOH in water+1 M HCl (60 μL in each 10 mL of eluent)} to give the title compound as a white solid (23 mg, 65%). $^1$H NMR (400 MHz, DMSO-d6): δ 8.61 (s, 3H), 8.01 (dd, J=7.9 and 1.7 Hz, 1H), 7.71 (dd, J=7.3 and 1.6 Hz, 1H), 7.67 (s, 1H), 7.53 (t, J=7.6 Hz, 1H), 7.42 (d, J=8.4 Hz, 2H), 7.37-7.22 (m, 7H), 3.74 (s, 3H), 2.57-2.43 (m, 4H), 2.22 (s, 3H), 2.19-2.05 (m, 1H), 1.81-1.69 (m, 1H). LCMS (Method E): R$_T$=3.29 min, [M+H]$^+$=462.

Example 76

3-[4-(1-Amino-cyclobutyl)-phenyl]-2-phenyl-8-(3-trifluoromethyl-1H-pyrazol-4-yl)-chromen-4-one

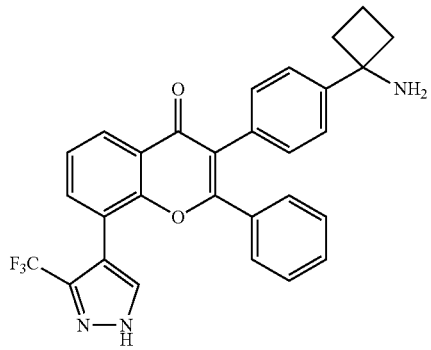 [SMILES: NC1(c2ccc(-c3c(-c4ccccc4)oc4c(-c5c[nH]nc5C(F)(F)F)cccc4c3=O)cc2)CCC1]

Step 1: (1-{-4-[4-oxo-2-phenyl-8-(3-trifluoromethyl-1H-pyrazol-4-yl)-4H-chromen-3-yl]-phenyl}-cyclobutyl)-carbamic acid tert-butyl ester: Following the procedure of (1-{4-[4-oxo-2-phenyl-7-(2H-pyrazol-3-yl)-4H-chromen-3-yl]-phenyl}-cyclobutyl)-carbamic acid tert-butyl ester, {1-[4-(8-bromo-4-oxo-2-phenyl-4H-chromen-3-yl)-phenyl]-cyclobutyl}-carbamic acid tert-butyl ester was reacted with 3-(trifluoromethyl)-1H-pyrazole-4-boronic acid pinacol ester to give the title compound as a white solid (35 mg, 64%). LCMS (Method G): R$_T$=4.15 min, [M+H]$^+$=602.

Step 2: 3-[4-(1-Amino-cyclobutyl)-phenyl]-2-phenyl-8-(3-trifluoromethyl-1H-pyrazol-4-yl)-chromen-4-one: Following the procedure of 3-[4-(1-amino-cyclobutyl)-phenyl]-6-fluoro-2-phenyl-chromen-4-one, (1-{4-[4-oxo-2-phenyl-8-(3-trifluoromethyl-1H-pyrazol-4-yl)-4H-chromen-3-yl]-phenyl}-cyclobutyl)-carbamic acid tert-butyl ester was reacted to give the title compound as a white solid (8 mg, 28%). $^1$H NMR (400 MHz, CDCl$_3$): δ 8.31 (s, 1H), 8.11 (dd, J=8.1 and 1.8 Hz, 1H), 7.74 (dd, J=7.4 and 1.6 Hz, 1H), 7.54 (t, J=7.9 Hz, 1H), 7.36-7.27 (m, 3H), 7.26-7.18 (m, 4H), 7.08 (d, J=8.4 Hz, 2H), 3.27 (bs, 3H), 2.36-2.26 (m, 2H), 2.08-1.87 (m, 3H), 1.65-1.53 (m, 1H). LCMS (Method E): R$_T$=3.41 min, [M+H]$^+$=502.

Example 77

4-{3-[4-(1-Amino-cyclobutyl)-phenyl]-4-oxo-2-phenyl-4H-chromen-8-yl}-piperazin-2-one

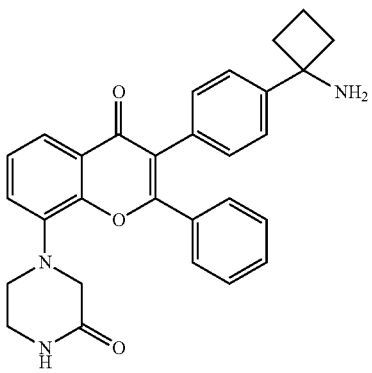 [SMILES: NC1(c2ccc(-c3c(-c4ccccc4)oc4c(N5CCNC(=O)C5)cccc4c3=O)cc2)CCC1]

Step 1: (1-{4-[4-oxo-8-(3-oxo-piperazin-1-yl)-2-phenyl-4H-chromen-3-yl]-phenyl}-cyclobutyl)-carbamic acid tert-butyl ester: Following the procedure of {1-[4-(8-morpholin-4-yl-4-oxo-2-phenyl-4H-chromen-3-yl)-phenyl]-cyclobutyl}-carbamic acid tert-butyl ester, {1-[4-(8-bromo-4-oxo-2-phenyl-4H-chromen-3-yl)-phenyl]-cyclobutyl}-carbamic acid tert-butyl ester was reacted with 2-oxopiperazine to give the title compound as a white solid (35 mg, 64%). LCMS (Method G): $R_T$=3.45 min, $[M+H]^+$= 566.

Step 2: 4-{3-[4-(1-Amino-cyclobutyl)-phenyl]-4-oxo-2-phenyl-4H-chromen-8-yl}-piperazin-2-one: Following the procedure of 3-[4-(1-amino-cyclobutyl)-phenyl]-6-fluoro-2-phenyl-chromen-4-one, (1-{-4-[4-oxo-8-(3-oxo-piperazin-1-yl)-2-phenyl-4H-chromen-3-yl]-phenyl}-cyclobutyl)-carbamic acid tert-butyl ester was reacted to give the title compound as a white solid (8 mg, 28%). $^1$H NMR (400 MHz, CDCl$_3$): δ 7.92 (s, 1H), 7.69 (dd, J=7.4, 1.7 Hz, 1H), 7.41-7.26 (m, 9H), 7.09 (d, J=8.0 Hz, 2H), 3.71 (s, 2H), 3.40 (t, J=5.4 Hz, 2H), 3.35-2.99 (m, 4H), 2.36-2.27 (m, 2H), 2.07-1.87 (m, 3H), 1.65-1.53 (m, 1H). LCMS (Method E): $R_T$=2.79 min, $[M+H]^+$=466.

Example 78

3-[4-(1-Amino-cyclobutyl)-phenyl]-8-(3,5-dimethyl-isoxazol-4-yl)-2-phenyl-chromen-4-one

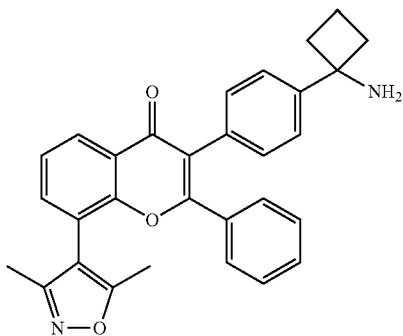 [SMILES: Cc1noc(C)c1-c1cccc2c(=O)c(-c3ccc(C4(N)CCC4)cc3)c(-c3ccccc3)oc12]

Step 1: (1-{4-[8-(3,5-Dimethyl-isoxazol-4-yl)-4-oxo-2-phenyl-4H-chromen-3-yl]-phenyl}-cyclobutyl)-carbamic acid tert-butyl ester: Following the procedure of (1-{-4-[4-oxo-2-phenyl-7-(2H-pyrazol-3-yl)-4H-chromen-3-yl]phenyl}cyclobutyl)-carbamic acid tert-butyl ester, {1-[4-(8-bromo-4-oxo-2-phenyl-4H-chromen-3-yl)-phenyl]-cyclobutyl}-carbamic acid tert-butyl ester was reacted with 3,5-dimethylisoxazole-4-boronic acid to give the title compound (16 mg, 31%). LCMS (Method G): $R_T$=4.34 min, $[M+H]^+$=563.

Step 2: 3-[4-(1-Amino-cyclobutyl)-phenyl]-8-(3-methyl-1H-pyrazol-4-yl)-2-phenyl-chromen-4-one hydrochloride: Following the procedure of 3-[4-(1-amino-cyclobutyl)-phenyl]-6-fluoro-2-phenyl-chromen-4-one, (1-{4-[8-(3,5-dimethyl-isoxazol-4-yl)-4-oxo-2-phenyl-4H-chromen-3-yl]-phenyl}-cyclobutyl)-carbamic acid tert-butyl ester was reacted to give the title compound as a white solid (6 mg, 46%). $^1$H NMR (400 MHz, CDCl$_3$): δ 8.14 (dd, J=7.9 and 1.7 Hz, 1H), 7.79 (dd, J=7.4 and 1.7 Hz, 1H), 7.57 (t, J=7.7 Hz, 1H), 7.36-7.20 (m, 7H), 7.09 (d, J=8.5 Hz, 2H), 2.36-2.27 (m, 2H), 2.26 (s, 3H), 2.15 (bs, 2H), 2.07 (s, 3H), 2.05-1.87 (m, 3H), 1.64-1.53 (m, 1H). LCMS (Method E): $R_T$=3.55 min, $[M+H]^+$=463.

Example 79

3-[4-(1-Amino-cyclobutyl)-phenyl]-7-methoxy-2-phenyl-8-(1H-pyrazol-4-yl)-chromen-4-one

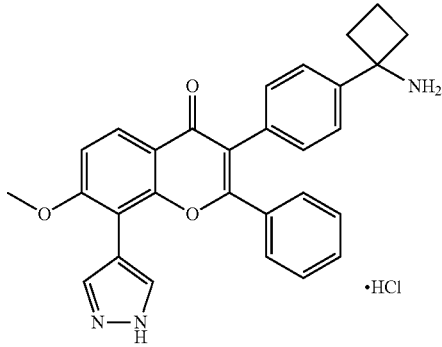 [SMILES: COc1ccc2c(=O)c(-c3ccc(C4(N)CCC4)cc3)c(-c3ccccc3)oc2c1-c1cn[nH]c1 ; Cl]

Step 1: (1-{4-[7-Methoxy-4-oxo-2-phenyl-8-(1H-pyrazol-4-yl)-4H-chromen-3-yl]-phenyl}-cyclobutyl)-carbamic acid tert-butyl ester: Following the procedure used to prepare (1-{4-[4-oxo-2-phenyl-7-(2H-pyrazol-3-yl)-4H-chromen-3-yl]-phenyl}-cyclobutyl)-carbamic acid tert-butyl ester, {1-[4-(8-bromo-7-methoxy-4-oxo-2-phenyl-4H-chromen-3-yl)-phenyl]-cyclobutyl}-carbamic acid tert-butyl ester (100 mg, 0.173 mmol) was reacted with 4-(4,4,5,5-tetramethyl-[1,3,2]dioxaborolan-2-yl)-1H-pyrazole to give the title compound (51 mg, 52%). LCMS (Method H): $R_T$=3.77 min, $[M+H]^+$=564.

Step 2: 3-[4-(1-Amino-cyclobutyl)-phenyl]-7-methoxy-2-phenyl-8-(1H-pyrazol-4-yl)-chromen-4-one: Following the procedure used to prepare 3-[4-(1-amino-cyclobutyl)-phenyl]-6-fluoro-2-phenyl-chromen-4-one, (1-{4-[7-methoxy-4-oxo-2-phenyl-8-(1H-pyrazol-4-yl)-4H-chromen-3-yl]-phenyl}-cyclobutyl)-carbamic acid tert-butyl ester (50 mg, 0.088 mmol) was treated with TFA. The resultant free base was dissolved in a mixture of MeOH (7 mL), water (7 mL) and 1 M HCl (0.6 mL) and chromatographed on a 20 g C18 cartridge {gradient 30 to 80% MeOH in water+1 M HCl (60 μL in each 10 mL of eluent)} to yield the title compound as a white solid (14 mg, 32%). $^1$H NMR (300 MHz, DMSO-d6): δ 8.75 (s, 3H), 8.12-8.01 (m, 3H), 7.50-7.24 (m, 9H), 7.11 (s, 1H), 4.01 (s, 3H), 2.62-2.48 (m, 4H), 2.27-2.10 (m, 1H), 1.87-1.72 (m, 1H). LCMS (Method E): $R_T$=2.99 min, $[M+H]^+$=464.

Example 80

3-[4-(1-Amino-cyclobutyl)-phenyl]-2-phenyl-8-(1H-pyrazol-4-yl)-pyrano[2,3-c]pyridin-4-one hydrochloride

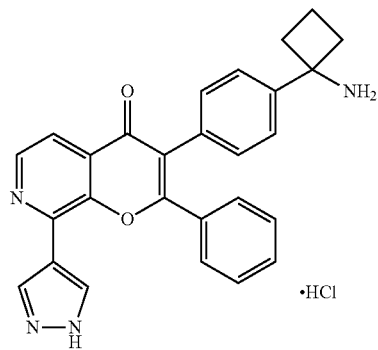 [SMILES: NC1(c2ccc(-c3c(-c4ccccc4)oc4c(-c5cn[nH]c5)nccc4c3=O)cc2)CCC1 ; Cl]

Step 1: (1-{-4-[4-oxo-2-phenyl-8-(1H-pyrazol-4-yl)-4H-pyrano[2,3-c]pyridin-3-yl]-phenyl}-cyclobutyl)-carbamic acid tert-butyl ester: Following the procedure used to prepare (1-{4-[4-oxo-2-phenyl-7-(2H-pyrazol-3-yl)-4H-chromen-3-yl]-phenyl}-cyclobutyl)-carbamic acid tert-butyl ester, {1-[4-(8-chloro-4-oxo-2-phenyl-4H-pyrano[2,3-c]pyridin-3-yl)-phenyl]-cyclobutyl}-carbamic acid tert-butyl ester was reacted with 4-(4,4,5,5-tetramethyl-[1,3,2]dioxaborolan-2-yl)-1H-pyrazole to give the title compound contaminated with some triphenylphosphine oxide (27 mg). LCMS (Method H): $R_T$=3.73 min, $[M+H]^+$=535.

Step 2: 3-[4-(1-Amino-cyclobutyl)-phenyl]-2-phenyl-8-(1H-pyrazol-4-yl)-pyrano[2,3-c]pyridin-4-one hydrochloride: Following the procedure used to prepare 3-[4-(1-amino-cyclobutyl)-phenyl]-6-fluoro-2-phenyl-chromen-4-one, (1-{4-[4-oxo-2-phenyl-8-(1H-pyrazol-4-yl)-4H-pyrano[2,3-c]pyridin-3-yl]-phenyl}-cyclobutyl)-carbamic acid tert-butyl ester was treated with TFA. The resultant free base was dissolved in a mixture of MeOH (0.75 mL), water (4.25 mL) and 1 M HCl (0.1 mL) and then chromatographed on a 2 g C18 cartridge {gradient 15 to 50% MeOH in water+1 M HCl (60 µL in each 5 mL of eluent)} to give the title compound as a white solid (12.1 mg, 81%, 2 steps). $^1$H NMR (400 MHz, DMSO-d6): δ 8.66 (d+br s, J=5.1 Hz, 4H), 8.29 (s, 2H), 7.80 (d, J=5.0 Hz, 1H), 7.55-7.41 (m, 7H), 7.30 (d, J=8.2 Hz, 2H), 2.59-2.51 (m, 4H), 2.23-2.12 (m, 1H), 1.85-1.74 (m, 1H). LCMS (Method E): $R_T$=2.79 min, $[M+H]^+$=435.

Example 81

7-[4-(1-Amino-cyclobutyl)-phenyl]-1-ethyl-8-phenyl-1H-9-oxa-1,2-diaza-cyclopenta[a]naphthalen-6-one hydrochloride

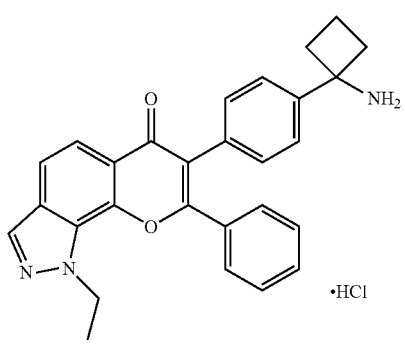 [SMILES: CCn1ncc2ccc3c(=O)c(-c4ccc(C5(N)CCC5)cc4)c(-c4ccccc4)oc3c21 ; Cl]

Step 1: 1-Ethyl-7-iodo-8-phenyl-1H-9-oxa-1,2-diaza-cyclopenta[a]naphthalen-6-one and 2-ethyl-7-iodo-8-phenyl-2H-9-oxa-1,2-diaza-cyclopenta[a]naphthalen-6-one: To a solution of 7-iodo-8-phenyl-1H-9-oxa-1,2-diaza-cyclopenta[a]naphthalen-6-one (100 mg, 0.26 mmol) in DMF (5 mL) was added cesium carbonate (168 mg, 0.515 mmol) and the reaction stirred at RT. After 5 min, iodoethane (0.062 mL, 0.774 mmol) was added and the reaction stirred at RT for 66 h. The reaction mixture was partitioned between EtOAc and water. The organic phase was extracted with more EtOAc and the combined organic extracts were washed with water and brine, dried (Na$_2$SO$_4$), filtered, and concentrated in vacuo. The resultant residue was subjected to flash chromatography (SiO$_2$, gradient 20 to 60% EtOAc in cyclohexane) to afford 1-ethyl-7-iodo-8-phenyl-1H-9-oxa-1,2-diaza-cyclopenta[a]naphthalen-6-one (69.6 mg, 65%), LCMS (Method H): $R_T$=3.88 min, $[M+H]^+$=417, as the earlier eluted compound and 2-ethyl-7-iodo-8-phenyl-2H-9-oxa-1,2-diaza-cyclopenta[a]naphthalen-6-one one (37.9 mg, 35%), LCMS (Method H): $R_T$=3.65 min, $[M+H]^+$=417, as the later eluted compound.

Step 2: {1-[4-(1-Ethyl-6-oxo-8-phenyl-1,6-dihydro-9-oxa-1,2-diaza-cyclopenta[a]naphthalen-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 1-ethyl-7-iodo-8-phenyl-1H-9-oxa-1,2-diaza-cyclopenta[a]naphthalen-6-one was reacted to give the title compound as a colourless solid (44.4 mg, 84%). LCMS (Method H): $R_T$=4.50 min, $[M+H]^+$=536.

Step 3: 7-[4-(1-Amino-cyclobutyl)-phenyl]-1-ethyl-8-phenyl-1H-9-oxa-1,2-diaza-cyclopenta[a]naphthalen-6-one hydrochloride: Following the procedure used to prepare 3-[4-(1-amino-cyclobutyl)-phenyl]-6-fluoro-2-phenyl-chromen-4-one, {1-[4-(1-ethyl-6-oxo-8-phenyl-1,6-dihydro-9-oxa-1,2-diaza-cyclopenta[a]naphthalen-7-yl)-phenyl]-cyclobutyl}-carbamic acid tert-butyl ester was treated with TFA. The resultant free base was dissolved in a mixture of MeOH (1.5 mL), water (3.5 mL) and 1 M HCl (0.2 mL) and chromatographed on a 5 g C18 cartridge {gradient 30 to 70% MeOH in water+1 M HCl (60 µL in each 10 mL of eluent)} to give the title compound (33 mg, 85%) as a white solid. $^1$H NMR (400 MHz, DMSO-d6): δ 8.46 (br s, 3H), 8.30 (s, 1H), 7.82 (d, J=8.6 Hz, 1H), 7.75 (d, J=8.5 Hz, 1H), 7.54-7.38 (m, 7H), 7.32 (d, J=8.3 Hz, 2H), 4.77 (q, J=7.2 Hz, 2H), 2.62-2.49 (m, 4H), 2.23-2.12 (m, 1H), 1.86-1.75 (m, 1H), 1.47 (t, J=7.2 Hz, 3H). LCMS (Method E): $R_T$=3.58 min, $[M+H]^+$=436.

Example 82

7-[4-(1-Amino-cyclobutyl)-phenyl]-2-ethyl-8-phenyl-2H-9-oxa-1,2-diaza-cyclopenta[a]naphthalen-6-one hydrochloride

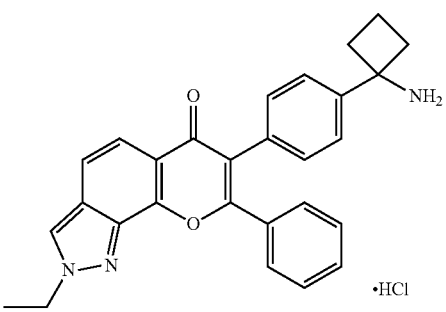 [SMILES: CCn1cc2ccc3c(=O)c(-c4ccc(C5(N)CCC5)cc4)c(-c4ccccc4)oc3c2n1 ; Cl]

Step 1: {1-[4-(2-Ethyl-6-oxo-8-phenyl-2,6-dihydro-9-oxa-1,2-diaza-cyclopenta[a]naphthalen-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 2-ethyl-7-iodo-8-phenyl-2H-9-oxa-1,2-diaza-cyclopenta[a]naphthalen-6-one was reacted to give the title compound as a colourless gum (43.2 mg, 89%). LCMS (Method H): $R_T$=4.24 min, $[M+H]^+$=536.

Step 2: 7-[4-(1-Amino-cyclobutyl)-phenyl]-2-ethyl-8-phenyl-2H-9-oxa-1,2-diaza-cyclopenta[a]naphthalen-6-one hydrochloride: Following the procedure used to prepare 3-[4-(1-amino-cyclobutyl)-phenyl]-6-fluoro-2-phenyl-chromen-4-one, {1-[4-(2-ethyl-6-oxo-8-phenyl-2,6-dihydro-9-oxa-1,2-diaza-cyclopenta[a]naphthalen-7-yl)-phenyl]-cyclobutyl}-carbamic acid tert-butyl ester was treated with TFA. The resultant free base was dissolved in a mixture of MeOH (1.5 mL), water (3.5 mL) and 1 M HCl (0.2 mL) and chromatographed on a 5 g C18 cartridge {gradient 30 to 70% MeOH in water+1 M HCl (60 µL in each 10 mL of eluent)} to give the title compound (30.3 mg, 81%) as a white solid. $^1$H NMR (400 MHz, DMSO-d6): δ 8.66 (s, 1H), 8.53 (br s, 3H), 7.74 (d, J=8.8 Hz, 1H), 7.63 (d, J=8.8 Hz, 1H), 7.49-7.38 (m, 7H), 7.32 (d, J=8.1 Hz, 2H), 4.58 (q, J=7.3 Hz, 2H), 2.62-2.49 (m, 4H), 2.23-2.13 (m, 1H), 1.86-1.75 (m, 1H), 1.55 (t, J=7.3 Hz, 3H). LCMS (Method E): $R_T$=3.36 min, $[M+H]^+$=436.

Example 83

7-[4-(1-Amino-cyclobutyl)-phenyl]-1-isopropyl-8-phenyl-1H-9-oxa-1,2-diaza-cyclopenta[a]naphthalen-6-one hydrochloride

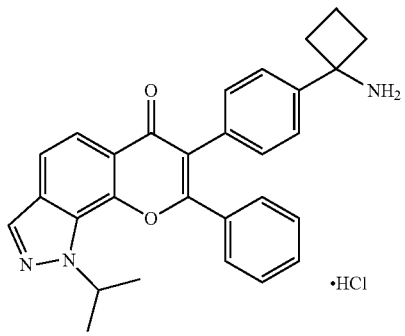 [SMILES: CC(C)n1ncc2ccc3c(=O)c(-c4ccc(C5(N)CCC5)cc4)c(-c4ccccc4)oc3c21 ; Cl]

Step 1: 7-Iodo-1-isopropyl-8-phenyl-1H-9-oxa-1,2-diaza-cyclopenta[a]naphthalen-6-one and 7-Iodo-2-isopropyl-8-phenyl-2H-9-oxa-1,2-diaza-cyclopenta[a]naphthalen-6-one: Following the procedure used to prepare 1-ethyl-7-iodo-8-phenyl-1H-9-oxa-1,2-diaza-cyclopenta[a]naphthalen-6-one and 2-ethyl-7-iodo-8-phenyl-2H-9-oxa-1,2-diaza-cyclopenta[a]naphthalen-6-one, 7-iodo-8-phenyl-1H-9-oxa-1,2-diaza-cyclopenta[a]naphthalen-6-one was reacted with 2-iodopropane to afford 7-iodo-1-isopropyl-8-phenyl-1H-9-oxa-1,2-diaza-cyclopenta[a]naphthalen-6-one (56 mg, 50%), LCMS (Method H): $R_T$=4.11 min, $[M+H]^+$=431, as the earlier eluted compound and 7-iodo-2-isopropyl-8-phenyl-2H-9-oxa-1,2-diaza-cyclopenta[a]naphthalen-6-one (44.8 mg, 40%), LCMS (Method H): $R_T$=3.86 min, $[M+H]^+$=431, as the later eluted compound.

Step 2: {1-[4-(1-Isopropyl-6-oxo-8-phenyl-1,6-dihydro-9-oxa-1,2-diaza-cyclopenta[a]naphthalen-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-iodo-1-isopropyl-8-phenyl-1H-9-oxa-1,2-diaza-cyclopenta[a]naphthalen-6-one was reacted to give the title compound as a white solid (37.3 mg, 81%). LCMS (Method H): $R_T$=4.70 min, $[M+H]^+$=550.

Step 3: 7-[4-(1-Amino-cyclobutyl)-phenyl]-1-isopropyl-8-phenyl-1H-9-oxa-1,2-diaza-cyclopenta[a]naphthalen-6-one hydrochloride: Following the procedure used to prepare 3-[4-(1-amino-cyclobutyl)-phenyl]-6-fluoro-2-phenyl-chromen-4-one, {1-[4-(1-isopropyl-6-oxo-8-phenyl-1,6-dihydro-9-oxa-1,2-diaza-cyclopenta[a]naphthalen-7-yl)-phenyl]-cyclobutyl}-carbamic acid tert-butyl ester was treated with TFA. The resultant free base was dissolved in a mixture of MeOH (3 mL), water (7 mL) and 1 M HCl (0.2 mL) and chromatographed on a 5 g C18 cartridge {gradient 30 to 70% MeOH in water+1 M HCl (60 µL in each 10 mL of eluent)} to give the title compound (26.5 mg, 81%) as a white solid. $^1$H NMR (400 MHz, DMSO-d6): δ 8.55 (br s, 3H), 8.33 (s, 1H), 7.82 (d, J=8.5 Hz, 1H), 7.76 (d, J=8.5 Hz, 1H), 7.53-7.39 (m, 7H), 7.32 (d, J=8.2 Hz, 2H), 5.46 (septet, J=6.6 Hz, 1H), 2.62-2.49 (m, 4H), 2.23-2.13 (m, 1H), 1.86-1.74 (m, 1H), 1.59 (d, J=6.6 Hz, 6H). LCMS (Method E): $R_T$=3.81 min, $[M+H]^+$=450.

Example 84

7-[4-(1-Amino-cyclobutyl)-phenyl]-2-isopropyl-8-phenyl-2H-9-oxa-1,2-diaza-cyclopenta[a]naphthalen-6-one hydrochloride

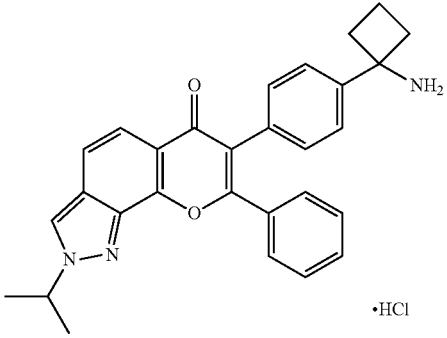 [SMILES: CC(C)n1cc2ccc3c(=O)c(-c4ccc(C5(N)CCC5)cc4)c(-c4ccccc4)oc3c2n1 ; Cl]

Step 1: {1-[4-(2-Isopropyl-6-oxo-8-phenyl-2,6-dihydro-9-oxa-1,2-diaza-cyclopenta[a]naphthalen-7-yl)-phenyl]-cyclobutyl}-carbamic acid tert-butyl ester:
Following the procedure used to prepare {1-[4-(6-fluoro-4-oxo-2-phenyl-4H-chromen-3-yl)-phenyl]-cyclobutyl}-carbamic acid tert-butyl ester, 7-iodo-2-isopropyl-8-phenyl-2H-9-oxa-1,2-diaza-cyclopenta[a]naphthalen-6-one was reacted to give the title compound as a colourless gum (48.3 mg, 85%). LCMS (Method H): $R_T$=4.42 min, $[M+H]^+$=550.

Step 2: 7-[4-(1-Amino-cyclobutyl)-phenyl]-2-isopropyl-8-phenyl-2H-9-oxa-1,2-diaza-cyclopenta[a]naphthalen-6-one hydrochloride: Following the procedure used to prepare 3-[4-(1-amino-cyclobutyl)-phenyl]-6-fluoro-2-phenyl-chromen-4-one, {1-[4-(2-isopropyl-6-oxo-8-phenyl-2,6-dihydro-9-oxa-1,2-diaza-cyclopenta[a]naphthalen-7-yl)-phenyl]-cyclobutyl}-carbamic acid tert-butyl ester was treated with TFA. The resultant free base was dissolved in a mixture of MeOH (3 mL), water (7 mL) and 1 M HCl (0.2 mL) and chromatographed on a 5 g C18 cartridge {gradient 30 to 70% MeOH in water+1 M HCl (60 µL in each 10 mL of eluent)} to give the title compound (30.2 mg, 71%) as a white solid. $^1$H NMR (400 MHz, DMSO-d6): δ 8.70 (s, 1H), 8.54 (br s, 3H), 7.74 (d, J=8.8 Hz, 1H), 7.63 (d, J=8.8 Hz, 1H), 7.50-7.38 (m, 7H), 7.32 (d, J=8.3 Hz, 2H), 4.96 (septet, J=6.7 Hz, 1H), 2.61-2.49 (m, 4H), 2.23-2.12 (m, 1H), 1.86-1.75 (m, 1H), 1.60 (d, J=6.7 Hz, 6H). LCMS (Method E): $R_T$=3.58 min, $[M+H]^+$=450.

Example 85

7-[4-(1-Amino-cyclobutyl)-phenyl]-1-(2-hydroxy-ethyl)-8-phenyl-1H-9-oxa-1,2-diaza-cyclopenta[a]naphthalen-6-one hydrochloride

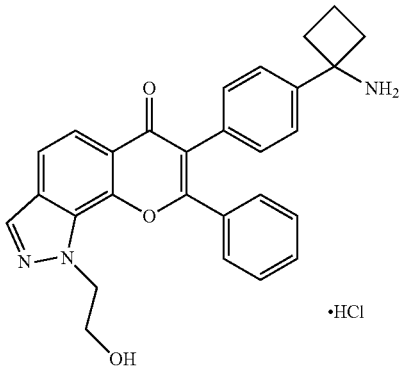 [SMILES: NC1(c2ccc(-c3c(-c4ccccc4)oc4c(ccc5cnn(CCO)c54)c3=O)cc2)CCC1 ; Cl]

Step 1: 1-(2-Hydroxy-ethyl)-7-iodo-8-phenyl-1H-9-oxa-1,2-diaza-cyclopenta[a]naphthalen-6-one and 2-(2-Hydroxy-ethyl)-7-iodo-8-phenyl-2H-9-oxa-1,2-diaza-cyclopenta[a]naphthalen-6-one: Following the procedure used to prepare 1-ethyl-7-iodo-8-phenyl-1H-9-oxa-1,2-diaza-cyclopenta[a]naphthalen-6-one and 2-ethyl-7-iodo-8-phenyl-2H-9-oxa-1,2-diaza-cyclopenta[a]naphthalen-6-one, 7-iodo-8-phenyl-1H-9-oxa-1,2-diaza-cyclopenta[a]naphthalen-6-one was reacted with 2-bromoethanol to afford an inseparable mixture of the title compounds. LCMS (Method H): $R_T$=3.06 and 3.18 min, [M+H]⁺=433.

Step 2: (1-{4-[1-(2-Hydroxy-ethyl)-6-oxo-8-phenyl-1,6-dihydro-9-oxa-1,2-diaza-cyclopenta[a]naphthalen-7-yl]-phenyl}-cyclobutyl)-carbamic acid tert-butyl ester and (1-{4-[2-(2-hydroxy-ethyl)-6-oxo-8-phenyl-2,6-dihydro-9-oxa-1,2-diaza-cyclopenta[a]naphthalen-7-yl]-phenyl}-cyclobutyl)-carbamic acid tert-butyl ester:

Following the procedure used to prepare {1-[4-(6-fluoro-4-oxo-2-phenyl-4H-chromen-3-yl)-phenyl]-cyclobutyl}-carbamic acid tert-butyl ester, the crude mixture of 1-(2-hydroxy-ethyl)-7-iodo-8-phenyl-1H-9-oxa-1,2-diaza-cyclopenta[a]naphthalen-6-one and 2-(2-hydroxy-ethyl)-7-iodo-8-phenyl-2H-9-oxa-1,2-diaza-cyclopenta[a]naphthalen-6-one was reacted to give (1-{4-[1-(2-hydroxy-ethyl)-6-oxo-8-phenyl-1,6-dihydro-9-oxa-1,2-diaza-cyclopenta[a]naphthalen-7-yl]-phenyl}-cyclobutyl)-carbamic acid tert-butyl ester (53.3 mg, 37%), LCMS (Method H): $R_T$=3.86 min, [M+H]⁺=552, as the earlier eluted compound and (1-{4-[2-(2-hydroxy-ethyl)-6-oxo-8-phenyl-2,6-dihydro-9-oxa-1,2-diaza-cyclopenta[a]naphthalen-7-yl]-phenyl}-cyclobutyl)-carbamic acid tert-butyl ester (57.1 mg, 40%), LCMS (Method H): $R_T$=3.68 min, [M+H]⁺=552, as the later eluted compound.

Step 3: 7-[4-(1-Amino-cyclobutyl)-phenyl]-1-(2-hydroxy-ethyl)-8-phenyl-1H-9-oxa-1,2-diaza-cyclopenta[a]naphthalen-6-one hydrochloride: Following the procedure used to prepare 3-[4-(1-amino-cyclobutyl)-phenyl]-6-fluoro-2-phenyl-chromen-4-one, (1-{4-[1-(2-hydroxy-ethyl)-6-oxo-8-phenyl-1,6-dihydro-9-oxa-1,2-diaza-cyclopenta[a]naphthalen-7-yl]-phenyl}-cyclobutyl)-carbamic acid tert-butyl ester was treated with TFA. The resultant free base was dissolved in a mixture of MeOH (2 mL), water (8 mL) and 1 M HCl (0.2 mL) and chromatographed on a 5 g C18 cartridge {gradient 20 to 60% MeOH in water+1 M HCl (60 µL in each 10 mL of eluent)} to give the title compound (33.5 mg, 74%) as a white solid. ¹H NMR (400 MHz, DMSO-d6): δ 8.60 (br s, 3H), 8.33 (s, 1H), 7.81 (d, J=8.6 Hz, 1H), 7.75 (d, J=8.5 Hz, 1H), 7.57-7.55 (m, 2H), 7.51-7.37 (m, 5H), 7.32 (d, J=8.4 Hz, 2H), 4.95 (t, J=5.1 Hz, 1H), 4.80 (t, J=5.6 Hz, 2H), 3.89 (q, J=5.5 Hz, 2H), 2.63-2.52 (m, 4H), 2.24-2.13 (m, 1H), 1.87-1.76 (m, 1H). LCMS (Method E): $R_T$=3.00 min, [M+H]⁺=452.

Example 86

7-[4-(1-Amino-cyclobutyl)-phenyl]-2-(2-hydroxy-ethyl)-8-phenyl-2H-9-oxa-1,2-diaza-cyclopenta[a]naphthalen-6-one hydrochloride

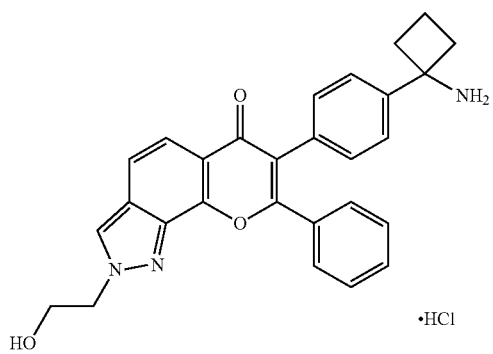 [SMILES: NC1(c2ccc(-c3c(-c4ccccc4)oc4c(ccc5cn(CCO)nc54)c3=O)cc2)CCC1 ; Cl]

Following the procedure used to prepare 3-[4-(1-amino-cyclobutyl)-phenyl]-6-fluoro-2-phenyl-chromen-4-one,
(1-{4-[2-(2-hydroxy-ethyl)-6-oxo-8-phenyl-2,6-dihydro-9-oxa-1,2-diaza-cyclopenta[a]naphthalen-7-yl]-phenyl}-cyclobutyl)-carbamic acid tert-butyl ester was treated with TFA. The resultant free base was dissolved in methanol and loaded onto an SCX-2 cartridge. The cartridge was washed with methanol before eluting with 2 M ammonia in methanol solution. The eluent was collected and concentrated in vacuo. The resulting residue was dissolved in a mixture of MeOH (2 mL), water (8 mL) and 1 M HCl (0.2 mL) and chromatographed on a 5 g C18 cartridge {gradient 20 to 60% MeOH in water+1 M HCl (60 µL in each 10 mL of eluent)} to give the title compound (19.6 mg, 40%) as a white solid. ¹H NMR (400 MHz, DMSO-d6): δ 8.62 (s, 1H), 8.57 (br s, 3H), 7.76 (d, J=8.8 Hz, 1H), 7.62 (d, J=8.8 Hz, 1H), 7.49-7.37 (m, 7H), 7.33 (d, J=8.3 Hz, 2H), 5.05 (t, J=5.3 Hz, 1H), 4.58 (t, J=5.3 Hz, 2H), 3.91 (q, J=5.3 Hz, 2H), 2.62-2.50 (m, 4H), 2.23-2.12 (m, 1H), 1.86-1.75 (m, 1H). LCMS (Method E): $R_T$=2.85 min, [M+H]⁺=452.

Example 87

7-[4-(1-Amino-cyclobutyl)-phenyl]-8-phenyl-1,3-dihydro-chromeno[7,8-d]imidazole-2,6-dione

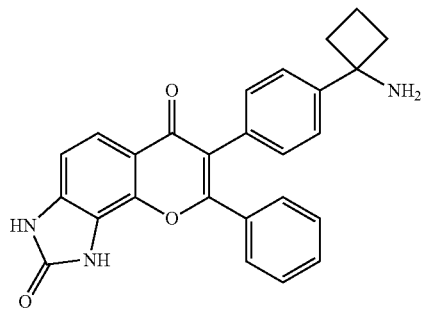 [SMILES: NC1(c2ccc(-c3c(-c4ccccc4)oc4c(ccc5[nH]c(=O)[nH]c54)c3=O)cc2)CCC1]

Step 1: 2,3-Dimethoxy-4-nitro-benzaldehyde: To a solution of 2-hydroxy-3-methoxy-4-nitro-benzaldehyde (10.4 g, 52.8 mmol, prepared as described in: J. Heterocyclic Chem., 1996, 33, 1171-78) in DMF (100 ml) was added potassium carbonate (11.04 g, 80 mmol), followed by methyl iodide (4 mL, 64 mmol) and the mixture stirred at 90° C. for 1 hour. The mixture was partitioned between ethyl acetate and water, separated, the organic phase was washed with brine, dried (Na₂SO₄), filtered, and the solvents were removed in vacuo. The resulting residue was subjected to flash chromatography (SiO₂, 20% ethyl acetate in cyclohexane) to give the title compound as a yellow oil (8.2 g, 74%). LCMS (Method B): $R_T$=3.76 min, [M+H]⁺=212.

Step 2: 1-(2,3-Dimethoxy-4-nitro-phenyl)-3-phenyl-prop-2-yn-1-ol: Following the procedure used to prepare 1-(5-fluoro-2-methoxy-phenyl)-3-phenyl-prop-2-yn-1-ol, 2,3-dimethoxy-4-nitro-benzaldehyde was reacted to give the title compound as a colourless oil (1.42 g, 91%). LCMS (Method G): $R_T$=3.66 min, [M−OH+H]⁺=297.

Step 3: 1-(2,3-Dimethoxy-4-nitro-phenyl)-3-phenyl-propynone: Following the procedure used to prepare 1-(5-fluoro-2-methoxy-phenyl)-3-phenyl-propynone, 1-(2,3-dimethoxy-4-nitro-phenyl)-3-phenyl-prop-2-yn-1-ol was reacted to give the title compound as a yellow solid (1.31 g, 94%). ¹H NMR (400 MHz, CDCl₃): δ 7.77 (d, J=8.8 Hz, 1H), 7.67-7.64 (m, 2H), 7.54 (d, J=8.8 Hz, 1H), 7.53-7.48 (m, 1H), 7.45-7.40 (m, 2H), 4.07 (s, 3H), 4.05 (s, 3H).

Step 4: 3-Iodo-8-methoxy-7-nitro-2-phenyl-chromen-4-one: Following the procedure used to prepare 6-fluoro-3- iodo-2-phenyl-chromen-4-one, 1-(2,3-dimethoxy-4-nitrophenyl)-3-phenyl-propynone was reacted to give the title compound as a white solid (1.58 g, 93%). LCMS (Method G): $R_T$=3.89 min, [M+H]$^+$=424.

Step 5: {1-[4-(8-Methoxy-7-nitro-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-iodo-8-methoxy-7-nitro-2-phenyl-chromen-4-one was reacted to give the title compound as a yellow solid (390 mg, 72%). LCMS (Method G): $R_T$=4.47 min, [M+H]$^+$=543.

Step 6: {1-[4-(8-Amino-7-nitro-4-oxo-2-phenyl-4H-chromen-3-yl)-phenyl]-cyclobutyl}-carbamic acid tert-butyl ester: {1-[4-(8-Methoxy-7-nitro-4-oxo-2-phenyl-4H-chromen-3-yl)-phenyl]-cyclobutyl}-carbamic acid tert-butyl ester (477 mg, 0.88 mmol) was dissolved in a solution of 2 M ammonia in propan-2-ol (12 mL) and heated in a microwave at 155° C. for 1 hour. The solvent was removed and the residue azeotroped with methanol to give the title compound as a yellow solid (420 mg, 91%). LCMS (Method G): $R_T$=4.28 min, [M+H]$^+$=528.

Step 7: 1-[4-(7,8-Diamino-4-oxo-2-phenyl-4H-chromen-3-yl)-phenyl]-cyclobutyl}-carbamic acid tert-butyl ester: To a solution of {1-[4-(8-amino-7-nitro-4-oxo-2-phenyl-4H-chromen-3-yl)-phenyl]-cyclobutyl}-carbamic acid tert-butyl ester (420 mg, 0.8 mmol) in NMP (10 mL) and IMS (3 mL) was added 10% palladium on carbon (350 mg) under a nitrogen atmosphere. The nitrogen was evacuated and replaced with hydrogen (1 atm). The mixture was stirred at RT for 18 hours. The hydrogen atmosphere was evacuated and replaced with nitrogen and the mixture was filtered through a pad of Celite®, eluting with ethyl acetate. The solvent volume was reduced in vacuo and the resultant mixture was poured onto water and extracted with ethyl acetate (3×100 mL). The combined organic extracts were washed with brine, dried ($Na_2SO_4$), filtered, and the solvents were removed in vacuo. The resulting residue was subjected to flash chromatography ($SiO_2$, gradient 60-70% ethyl acetate in cyclohexane) and the resulting residue triturated with water, filtered and the solid collected to give the title compound as a yellow solid (280 mg, 70%). LCMS (Method H): $R_T$=3.66 min, [M+H]$^+$=498.

Step 8: {1-[4-(2,6-Dioxo-8-phenyl-1,2,3,6-tetrahydro-chromeno[7,8-d]imidazol-7-yl)-phenyl]-cyclobutyl}-carbamic acid tert-butyl ester: To a suspension of 1-[4-(7,8-diamino-4-oxo-2-phenyl-4H-chromen-3-yl)-phenyl]-cyclobutyl}-carbamic acid tert-butyl ester (80 mg, 0.16 mmol) in THF (3 mL) was added carbonyl diimidazole (29 mg, 0.18 mmol) and the mixture stirred at RT for 18 hours. Further carbonyl diimidazole (29 mg, 0.18 mmol) was added and the mixture heated to 70° C. and stirred for a further 18 hours. The reaction mixture was allowed to warm to RT, the solvent removed in vacuo and the resulting residue was triturated with ethyl acetate, filtered, and the solid collected to give the title compound as a pale green solid (71 mg, 85%). LCMS (Method H): $R_T$=3.48 min, [M+H]$^+$=524.

Step 9: 7-[4-(1-Amino-cyclobutyl)-phenyl]-8-phenyl-1,3-dihydro-chromeno[7,8-d]imidazole-2,6-dione: Following the procedure used to prepare 3-[4-(1-amino-cyclobutyl)-phenyl]-2-phenyl-7H-pyrano[2,3-e]indazol-4-one, {1-[4-(2,6-dioxo-8-phenyl-1,2,3,6-tetrahydro-chromeno[7,8-d]imidazol-7-yl)-phenyl]-cyclobutyl}-carbamic acid tert-butyl ester was reacted to give the title compound as a yellow solid (41 mg, 75%). $^1$H NMR (400 MHz, DMSO-d6): δ 7.71 (d, J=8.3 Hz, 1H), 7.63 (s, 1H), 7.53-7.49 (m, 2H), 7.44-7.38 (m, 3H), 7.35-7.30 (m, 2H), 7.22-7.19 (m, 2H), 7.14 (d, J=8.3 Hz, 1H), 7.01 (s, 1H), 2.50-2.43 (m, 2H), 2.32-2.22 (m, 2H), 2.12-2.01, (m, 1H), 1.78-1.68 (m, 1H). LCMS (Method E): $R_T$=2.63 min, [M+H]$^+$=424.

Example 88

7-[4-(1-Amino-cyclobutyl)-phenyl]-8-phenyl-1H-9-oxa-1,2,3-triaza-cyclopenta[a]naphthalen-6-one

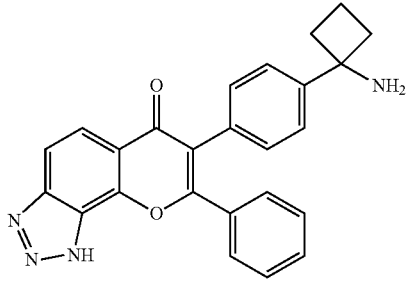 [SMILES: NC1(c2ccc(-c3c(-c4ccccc4)oc4c(ccc5nn[nH]c54)c3=O)cc2)CCC1]

Step 1: {1-[4-(6-oxo-8-phenyl-1,6-dihydro-9-oxa-1,2,3-triaza-cyclopenta[a]naphthalen-7-yl)-phenyl]-cyclobutyl}-carbamic acid tert-butyl ester: To a suspension of {1-[4-(7,8-diamino-4-oxo-2-phenyl-4H-chromen-3-yl)-phenyl]-cyclobutyl}-carbamic acid tert-butyl ester (80 mg, 0.16 mmol) in glacial acetic acid (2 mL) and water (1 mL) at 0° C. was added $NaNO_2$ (14 mg, 0.20 mmol). The resulting mixture was stirred at 0° C. for 30 mins, before allowing to warm to RT. After 16 hours, further $NaNO_2$ (14 mg, 0.20 mmol) was added and the reaction mixture stirred at RT for a further 3 hours. The resultant mixture was poured onto water and the aqueous mixture was extracted with ethyl acetate (2×50 mL). The combined organic extracts were washed with $NaHCO_3$ (2×30 mL), brine, dried ($NaSO_4$), filtered, and the solvent removed in vacuo to give the title compound as a brown solid (51 mg, 63%). LCMS (Method G): $R_T$=3.76 min, [M+H]$^+$=509.

Step 2: 7-[4-(1-Amino-cyclobutyl)-phenyl]-8-phenyl-1H-9-oxa-1,2,3-triaza-cyclopenta[a]naphthalen-6-one: Following the procedure used to prepare 3-[4-(1-amino-cyclobutyl)-phenyl]-2-phenyl-7H-pyrano[2,3-e]indazol-4-one, {1-[4-(6-oxo-8-phenyl-1,6-dihydro-9-oxa-1,2,3-triaza-cyclopenta[a]naphthalen-7-yl)-phenyl]-cyclobutyl}-carbamic acid tert-butyl ester was reacted to give the title compound as a yellow solid (9 mg, 22%). $^1$H NMR (400 MHz, DMSO-d6): δ 7.75-7.70 (m, 2H), 7.53-7.49 (m, 2H), 7.47-7.37 (m, 5H), 7.34-7.31 (m, 2H), 2.61-2.54 (m, 2H), 2.49-2.39 (m, 2H), 2.19-2.08 (m, 1H), 1.86-1.75 (m, 1H). LCMS (Method E): $R_T$=2.93 min, [M+H]$^+$=409.

Example 89

7-[4-(1-Amino-cyclobutyl)-phenyl]-2-methyl-8-phenyl-1H-chromeno[7,8-d]imidazol-6-one

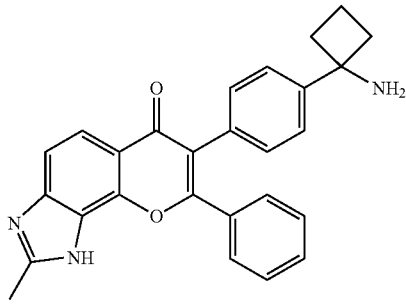 [SMILES: Cc1nc2ccc3c(=O)c(-c4ccc(C5(N)CCC5)cc4)c(-c4ccccc4)oc3c2[nH]1]

Step 1: {1-[4-(2-Methyl-6-oxo-8-phenyl-1,6-dihydro-chromeno[7,8-d]imidazol-7-yl)-phenyl]-cyclobutyl}-carbamic acid tert-butyl ester: To a solution of {1-[4-(7,8-diamino-4-oxo-2-phenyl-4H-chromen-3-yl)-phenyl]- cyclobutyl}-carbamic acid tert-butyl ester (80 mg, 0.16 mmol) in CH$_3$CN (8 mL) was added trimethylorthoacetate (25 μL, 0.20 mmol) and iodine (4 mg, 0.016 mmol) and the reaction mixture was stirred at RT for 2.5 hours. Further trimethylorthoacetate (50 μL, 0.40 mmol) and iodine (24 mg, 0.096 mmol) were added and the reaction stirred for 1 hour. The reaction was quenched with aqueous Na$_2$S$_2$O$_3$, diluted with ethyl acetate and the phases separated. The organic extracts were washed with brine, dried (NaSO$_4$), filtered and the solvents were removed in vacuo. The resulting residue was subjected to flash chromatography (SiO$_2$, ethyl acetate) to give the title compound as a brown solid (35 mg, 42%). LCMS (Method G): R$_T$=3.18 min, [M+H]$^+$=522.

Step 2: 7-[4-(1-Amino-cyclobutyl)-phenyl]-2-methyl-8-phenyl-1H-chromeno[7,8-d]imidazol-6-one: Following the procedure used to prepare 3-[4-(1-amino-cyclobutyl)-phenyl]-2-phenyl-7H-pyrano[2,3-e]indazol-4-one, {1-[4-(2-methyl-6-oxo-8-phenyl-1,6-dihydro-chromeno[7,8-d]imidazol-7-yl)-phenyl]-cyclobutyl}-carbamic acid tert-butyl ester was reacted to give the title compound as a beige solid (20 mg, 71%). $^1$H NMR (400 MHz, DMSO-d6): δ 7.85 (d, J=8.9 Hz, 1H), 7.57 (d, J=8.9 Hz, 1H), 7.50-7.45 (m, 2H), 7.44-7.34 (m, 5H), 7.17-7.13 (m, 2H), 2.59 (s, 3H), 2.40-2.32 (m, 2H), 2.11-2.02 (m, 2H), 2.02-1.93 (m, 1H), 1.70-1.60 (m, 1H). LCMS (Method E): R$_T$=2.62 min, [M+H]$^+$=422.

Example 90

7-[4-(1-Amino-cyclobutyl)-phenyl]-1,2-dimethyl-8-phenyl-1H-chromeno[7,8-d]imidazol-6-one

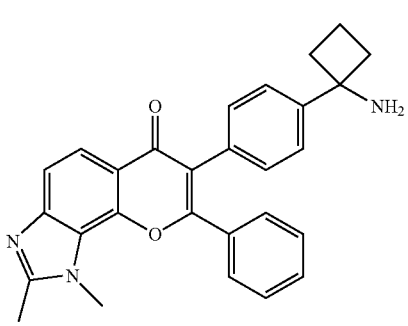 [SMILES: Cc1nc2ccc3c(=O)c(-c4ccc(C5(N)CCC5)cc4)c(-c4ccccc4)oc3c2n1C]

Step 1: {1-[4-(8-Methylamino-7-nitro-4-oxo-2-phenyl-4H-chromen-3-yl)-phenyl]-cyclobutyl}-carbamic acid tert-butyl ester: To a suspension of {1-[4-(8-methoxy-7-nitro-4-oxo-2-phenyl-4H-chromen-3-yl)-phenyl]-cyclobutyl}-carbamic acid tert-butyl ester (477 mg, 0.88 mmol) in propan-2-ol (12 mL) was bubbled gaseous methylamine for 5 minutes. The mixture was heated in a microwave at 155° C. for 1 hour and the solvent removed in vacuo. The resulting residue was subjected to flash chromatography (SiO$_2$, gradient 20-30% ethyl acetate in cyclohexane) to give the title compound as a very bright orange solid (112 mg, 24%). LCMS (Method G): R$_T$=4.47 min, [M+H]$^+$=542.

Step 2: {1-[4-(7-Amino-8-methylamino-4-oxo-2-phenyl-4H-chromen-3-yl)-phenyl]-cyclobutyl}-carbamic acid tert-butyl ester: Following the procedure used to prepare 1-[4-(7,8-diamino-4-oxo-2-phenyl-4H-chromen-3-yl)-phenyl]-cyclobutyl}-carbamic acid tert-butyl ester, {1-[4-(8-methylamino-7-nitro-4-oxo-2-phenyl-4H-chromen-3-yl)-phenyl]-cyclobutyl}-carbamic acid tert-butyl ester was reacted to give the title compound as a yellow oil (95 mg, 89%). LCMS (Method H): R$_T$=3.69 min, [M+H]$^+$=512.

Step 3: {1-[4-(1,2-Dimethyl-6-oxo-8-phenyl-1,6-dihydro-chromeno[7,8-d]imidazol-7-yl)-phenyl]-cyclobutyl}-carbamic acid tert-butyl ester: Following the procedure used to prepare {1-[4-(2-methyl-6-oxo-8-phenyl-1,6-dihydro-chromeno[7,8-d]imidazol-7-yl)-phenyl]-cyclobutyl}-carbamic acid tert-butyl ester, {1-[4-(7-amino-8-methylamino-4-oxo-2-phenyl-4H-chromen-3-yl)-phenyl]-cyclobutyl}-carbamic acid tert-butyl ester was reacted to give the title compound as a white solid (40 mg, 39%). LCMS (Method H): R$_T$=3.34 min, [M+H]$^+$=536.

Step 4: 7-[4-(1-Amino-cyclobutyl)-phenyl]-1,2-dimethyl-8-phenyl-1H-chromeno[7,8-d]imidazol-6-one: Following the procedure used to prepare 3-[4-(1-amino-cyclobutyl)-phenyl]-2-phenyl-7H-pyrano[2,3-e]indazol-4-one, {1-[4-(1,2-dimethyl-6-oxo-8-phenyl-1,6-dihydro-chromeno[7,8-d]imidazol-7-yl)-phenyl]-cyclobutyl}-carbamic acid tert-butyl ester was reacted to give the title compound as a white solid (26 mg, 80%). $^1$H NMR (400 MHz, DMSO-d6): δ 7.84 (d, J=8.4 Hz, 1H), 7.61 (d, J=8.4 Hz, 1H), 7.52-7.49 (m, 2H), 7.44-7.34 (m, 5H), 7.16-7.13 (m, 2H), 4.09 (s, 3H), 2.61 (s, 3H), 2.41-2.33 (m, 2H), 2.12-2.03 (m, 2H), 2.03-1.93 (m, 1H), 1.70-1.61 (m, 1H). LCMS (Method E): R$_T$=2.71 min, [M+H]$^+$=436.

Example 91

7-[4-(1-Amino-cyclobutyl)-phenyl]-8-phenyl-3H-chromeno[7,8-d]oxazole-2,6-dione

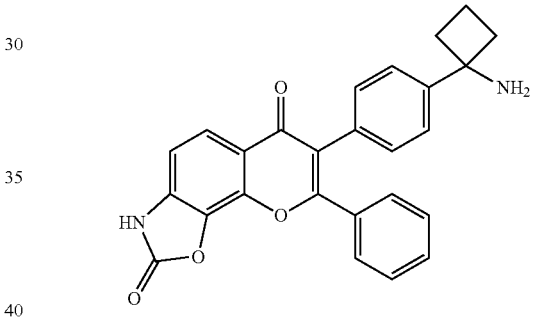

Step 1: 7-Amino-3-iodo-8-methoxy-2-phenyl-chromen-4-one: To a suspension of 3-iodo-8-methoxy-7-nitro-2-phenyl-chromen-4-one (903 mg, 2.1 mmol) in ethyl acetate (7 mL) and IMS (7 mL) was added SnCl$_2$ (2.37 g, 10.5 mmol). The reaction mixture was stirred at 80° C. for 1.5 hours before cooling to cool to RT. The resultant mixture was partitioned between ethyl acetate and water and the phases separated. The aqueous layer was extracted with ethyl acetate and the combined organic extracts were washed with brine, dried (NaSO$_4$), filtered, and the solvent removed in vacuo. The resulting residue was subjected to flash chromatography (SiO$_2$, gradient 40-50% ethyl acetate in cyclohexane) to give the title compound as a yellow solid (752 mg, 91%). LCMS (Method G): R$_T$=3.35 min, [M+H]$^+$=394.

Step 2: 7-Amino-8-hydroxy-3-iodo-2-phenyl-chromen-4-one: To a solution of 7-amino-3-iodo-8-methoxy-2-phenyl-chromen-4-one (494 mg, 1.26 mmol) in DCM (25 mL) under a nitrogen atmosphere at −78° C. was added a solution of BBr$_3$ (1 M in DCM, 8 mL, 8 mmol) dropwise over 15 mins. The mixture was stirred at −78° C. for 1 hour before allowing to warm to RT and stirred for a further 18 hours. The reaction mixture was quenched with the slow addition of saturated aqueous NaHCO$_3$. DCM was added and the resulting biphasic mixture was separated. The aqueous layer was extracted with DCM (2×50 mL) and the combined organic phase was washed with brine, dried (NaSO$_4$), filtered, and the solvent removed to give the title compound as a brown solid (405 mg, 85%). LCMS (Method G): $R_T$=3.04 min, [M+H]$^+$=380.

Step 3: 7-Iodo-8-phenyl-3H-chromeno[7,8-d]oxazole-2,6-dione: Following the procedure used to {1-[4-(2,6-dioxo-8-phenyl-1,2,3,6-tetrahydro-chromeno[7,8-d]imidazol-7-yl)-phenyl]-cyclobutyl}-carbamic acid tert-butyl ester, 7-amino-8-hydroxy-3-iodo-2-phenyl-chromen-4-one was reacted to give the title compound as a yellow solid (105 mg, 100%). LCMS (Method G): $R_T$=3.27, [M+H]$^+$=406.

Step 4: {1-[4-(2,6-Dioxo-8-phenyl-3,6-dihydro-2H-chromeno[7,8-d]oxazol-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-iodo-8-phenyl-3H-chromeno[7,8-d]oxazole-2,6-dione was reacted to give the title compound as a yellow oil (66 mg, 48%). LCMS (Method G): $R_T$=3.95, [M+H]$^+$=525.

Step 5: 7-[4-(1-Amino-cyclobutyl)-phenyl]-8-phenyl-3H-chromeno[7,8-d]oxazole-2,6-dione: Following the procedure used to prepare 3-[4-(1-amino-cyclobutyl)-phenyl]-2-phenyl-7H-pyrano[2,3-e]indazol-4-one, {1-[4-(2,6-dioxo-8-phenyl-3,6-dihydro-2H-chromeno[7,8-d]oxazol-7-yl)-phenyl]-cyclobutyl}-carbamic acid tert-butyl ester was reacted to give the title compound as a white solid (31 mg, 58%). $^1$H NMR (400 MHz, DMSO-d6): δ 7.64 (d, J=8.2 Hz, 1H), 7.43-7.38 (m, 5H), 7.37-7.31 (m, 2H), 7.26-7.22 (m, 2H), 7.02 (d, J=8.2 Hz, 1H), 2.58-2.49 (m, 2H), 2.42-2.32 (m, 2H), 2.16-2.05 (m, 1H), 1.82-1.71 (m, 1H). LCMS (Method E): $R_T$=3.08 min, [M+H]$^+$=425.

Example 92

7-[4-(1-Amino-cyclobutyl)-phenyl]-6-phenyl-1H-4,5-dioxa-1-aza-phenanthrene-2,8-dione

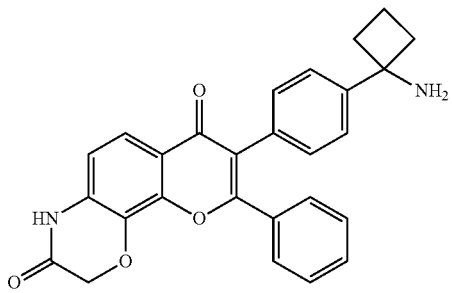 [SMILES: NC1(c2ccc(-c3c(-c4ccccc4)oc4c5c(ccc4c3=O)NC(=O)CO5)cc2)CCC1]

Step 1: 7-Iodo-6-phenyl-1H-4,5-dioxa-1-aza-phenanthrene-2,8-dione: To a solution of 7-amino-8-hydroxy-3-iodo-2-phenyl-chromen-4-one (150 mg, 0.40 mmol), benzyltriethylammonium chloride (91 mg, 0.40 mmol) and NaHCO$_3$ (168 mg, 2 mmol) in CHCl$_3$ (5 mL) at 0° C. was added a solution of chloroacetyl chloride (35 μL, 0.44 mmol) in CHCl$_3$ (1 mL) dropwise over 30 mins. The reaction mixture was stirred at 0° C. for 2 hours before heating at 50° C. for 18 hours. The resultant mixture was cooled to RT and was partitioned between DCM and water. The aqueous phase was filtered and the solid collected and azeotroped with methanol to give the title compound as a beige solid (167 mg, 99%). LCMS (Method G): $R_T$=3.18 min, [M+H]$^+$=420.

Step 2: {1-[4-(2,8-Dioxo-6-phenyl-1,2,3,8-tetrahydro-4,5-dioxa-1-aza-phenanthren-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-iodo-6-phenyl-1H-4,5-dioxa-1-aza-phenanthrene-2,8-dione was reacted to give the title compound as a yellow oil (92 mg, 44%). LCMS (Method H): $R_T$=4.71 min, [M+H]$^+$=539.

Step 3: 7-[4-(1-Amino-cyclobutyl)-phenyl]-6-phenyl-1H-4,5-dioxa-1-aza-phenanthrene-2,8-dione: Following the procedure used to prepare 3-[4-(1-amino-cyclobutyl)-phenyl]-2-phenyl-7H-pyrano[2,3-e]indazol-4-one, {1-[4-(2,8-dioxo-6-phenyl-1,2,3,8-tetrahydro-4,5-dioxa-1-aza-phenanthren-7-yl)-phenyl]-cyclobutyl}-carbamic acid tert-butyl ester was reacted to give the title compound as a white solid (31 mg, 58%). $^1$H NMR (400 MHz, DMSO-d6): δ 7.69 (d, J=8.8 Hz, 1H), 7.42-7.30 (m, 7H), 7.12-7.09 (m, 2H), 7.04 (d, J=8.8 Hz, 1H), 4.80 (s, 2H), 2.39-2.31 (m, 2H), 2.10-2.01 (m, 2H), 2.01-1.93 (m, 1H), 1.69-1.57 (m, 1H). LCMS (Method E): $R_T$=3.03 min, [M+H]$^+$=439.

Example 93

7-Amino-3-[4-(1-amino-cyclobutyl)-phenyl]-8-hydroxy-2-phenyl-chromen-4-one

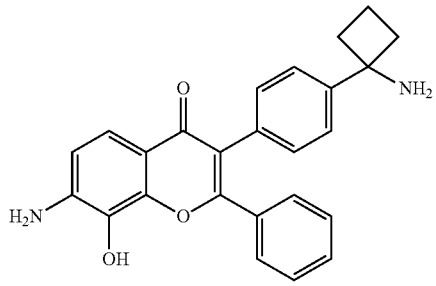 [SMILES: Nc1ccc2c(=O)c(-c3ccc(C4(N)CCC4)cc3)c(-c3ccccc3)oc2c1O]

Step 1: 7-Iodo-8-phenyl-chromeno[7,8-d]oxazol-6-one: To a solution of 7-amino-8-hydroxy-3-iodo-2-phenyl-chromen-4-one (151 mg, 0.4 mmol) in trimethylorthoformate (3 mL) was added p-toluenesulfonic acid (2 mg, 0.01 mmol). The reaction mixture was stirred at 100° C. for 2 hours, allowed to RT and the solvent removed. The resulting residue was subjected to flash chromatography (SiO$_2$, gradient 20-100% ethyl acetate in cyclohexane) to give the title compound as a beige solid (136 mg, 87%). LCMS (Method G): $R_T$=3.52 min, [M+H]$^+$=389.

Step 2: {1-[4-(7-Amino-8-hydroxy-4-oxo-2-phenyl-4H-chromen-3-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 7-iodo-8-phenyl-chromeno[7,8-d]oxazol-6-one was reacted to give the title compound as a yellow oil (25 mg, 14%). LCMS (Method G): $R_T$=3.75 min, [M+H]$^+$=499.

Step 3: 7-Amino-3-[4-(1-amino-cyclobutyl)-phenyl]-8-hydroxy-2-phenyl-chromen-4-one: Following the procedure used to prepare 3-[4-(1-amino-cyclobutyl)-phenyl]-2-phenyl-7H-pyrano[2,3-e]indazol-4-one, {1-[4-(7-amino-8-hydroxy-4-oxo-2-phenyl-4H-chromen-3-yl)-phenyl]-cyclobutyl}-carbamic acid tert-butyl ester was reacted to give the title compound as a yellow solid (9 mg, 45%). $^1$H NMR (400 MHz, DMSO-d6): δ 7.48 (m, 2H), 7.39 (d, J=8.6 Hz, 1H), 7.37-7.27 (m, 5H), 7.09-7.05 (m, 2H), 6.78 (d, J=8.6 Hz, 1H), 5.76-5.69 (br s, 2H), 2.39-2.32 (m, 2H), 2.10-2.02 (m, 2H), 2.02-1.93 (m, 1H), 1.68-1.60 (m, 1H). LCMS (Method E): $R_T$=2.81 min, [M+H]$^+$=399.

Example 94

7-[4-(1-Amino-cyclobutyl)-phenyl]-8-Phenyl-2-trifluoromethyl-1H-chromeno[7,8-d]imidazol-6-one

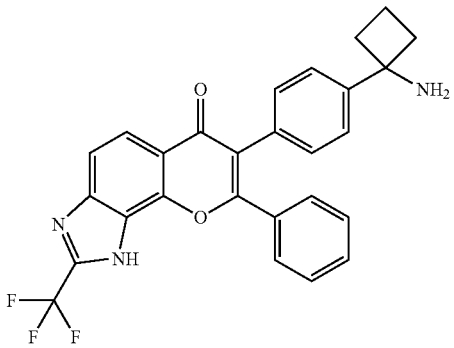 [SMILES: NC1(c2ccc(-c3c(-c4ccccc4)oc4c(ccc5nc(C(F)(F)F)[nH]c54)c3=O)cc2)CCC1]

Step 1: {1-[4-(6-oxo-8-phenyl-2-trifluoromethyl-1,6-dihydro-chromeno[7,8-d]imidazol-7-yl)-phenyl]-cyclobutyl}-carbamic acid tert-butyl ester: To a stirred solution of triphenylphosphine (126 mg, 0.48 mmol) in CCl$_4$ (2 mL) at 0° C. was added triethylamine (67 µL, 0.48 mmol) and TFA (13 µL, 0.18 mmol). After 10 min, {1-[4-(7,8-diamino-4-oxo-2-phenyl-4H-chromen-3-yl)-phenyl]-cyclobutyl}-carbamic acid tert-butyl ester (80 mg, 0.16 mmol) was added and the temperature raised to 80° C. After 2 hours, 1,2-dichloroethane (1 mL) was added to aid solubility. The reaction mixture was stirred for a further 1 hour before cooling to RT. The solution was directly subjected to flash chromatography (SiO$_2$, 40% ethyl acetate in cyclohexane) to give the title compound as an off-white solid (38 mg, 41%). LCMS (Method H): R$_T$=4.20 min, [M+H]$^+$=576.

Step 2: 7-[4-(1-Amino-cyclobutyl)-phenyl]-8-phenyl-2-trifluoromethyl-1H-chromeno[7,8-d]imidazol-6-one: Following the procedure used to prepare 3-[4-(1-amino-cyclobutyl)-phenyl]-2-phenyl-7H-pyrano[2,3-e]indazol-4-one, {1-[4-(6-oxo-8-phenyl-2-trifluoromethyl-1,6-dihydro-chromeno[7,8-d]imidazol-7-yl)-phenyl]-cyclobutyl}-carbamic acid tert-butyl ester was reacted to give the title compound as a yellow solid (25 mg, 80%). $^1$H NMR (400 MHz, DMSO-d6): δ 7.65 (d, J=9.0 Hz, 1H), 7.56 (d, J=9.0 Hz, 1H), 7.50-7.47 (m, 2H), 7.45-7.31 (m, 7H), 2.65-2.56 (m, 2H), 2.53-2.44 (m, 2H), 2.21-2.09 (m, 1H), 1.88-1.76 (m, 1H). LCMS (Method E): R$_T$=3.43 min, [M+H]$^+$=476.

Example 95

7-[4-(1-Amino-cyclobutyl)-phenyl]-2-difluoromethyl-8-phenyl-1H-chromeno[7,8-d]imidazol-6-one

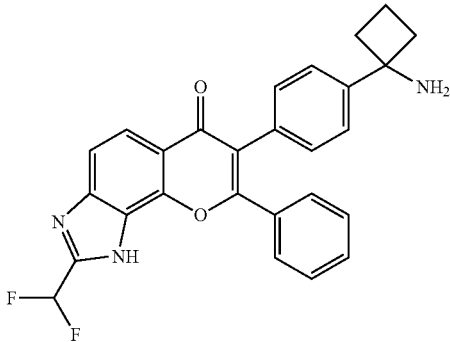 [SMILES: NC1(c2ccc(-c3c(-c4ccccc4)oc4c(ccc5nc(C(F)F)[nH]c54)c3=O)cc2)CCC1]

Step 1: {1-[4-(2-Difluoromethyl-6-oxo-8-phenyl-1,6-dihydro-chromeno[7,8-d]imidazol-7-yl)-phenyl]-cyclobutyl}-carbamic acid tert-butyl ester: To a stirred solution of triphenylphosphine (126 mg, 0.48 mmol) in CCl$_4$ (1 mL) at 0° C. was added triethylamine (67 µL, 0.48 mmol) and difluoroacetic acid (11 µL, 0.18 mmol). After 10 min, {1-[4-(7,8-diamino-4-oxo-2-phenyl-4H-chromen-3-yl)-phenyl]-cyclobutyl}-carbamic acid tert-butyl ester (80 mg, 0.16 mmol) in 1,2-dichloroethane (1 mL) was added, the temperature raised to 80° C. After 2.5 hours, the reaction mixture was allowed to cool to RT and the solution was directly subjected to flash chromatography (SiO$_2$, 40% ethyl acetate in cyclohexane) to give the title compound as a pale yellow solid (64 mg, 72%). LCMS (Method G): R$_T$=3.93 min, [M+H]$^+$=558.

Step 2: 7-[4-(1-Amino-cyclobutyl)-phenyl]-2-difluoromethyl-8-phenyl-1H-chromeno[7,8-d]imidazol-6-one: Following the procedure used to prepare 3-[4-(1-amino-cyclobutyl)-phenyl]-2-phenyl-7H-pyrano[2,3-e]indazol-4-one, {1-[4-(2-difluoromethyl-6-oxo-8-phenyl-1,6-dihydro-chromeno[7,8-d]imidazol-7-yl)-phenyl]-cyclobutyl}-carbamic acid tert-butyl ester was reacted to give the title compound as a white solid (29 mg, 58%). $^1$H NMR (400 MHz, DMSO-d6): δ 7.78 (d, J=8.7 Hz, 1H), 7.59 (d, J=8.7 Hz, 1H), 7.50-7.46 (m, 2H), 7.45-7.34 (m, 5H), 7.27-7.23 (m, 2H), 7.12 (t, J=53.8 Hz, 1H), 2.55-2.46 (m, 2H), 2.34-2.25 (m, 2H), 2.13-2.03 (m, 1H), 1.80-1.70 (m, 1H). LCMS (Method E): R$_T$=3.14 min, [M+H]$^+$=458.

Example 96

7-[4-(1-Amino-cyclobutyl)-phenyl]-1-methyl-8-phenyl-1H-chromeno[7,8-d]imidazol-6-one

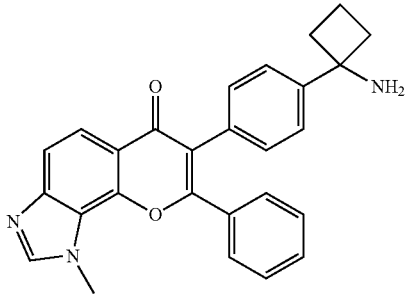 [SMILES: Cn1cnc2ccc3c(=O)c(-c4ccc(C5(N)CCC5)cc4)c(-c4ccccc4)oc3c21]

Step 1: {1-[4-(1-Methyl-6-oxo-8-phenyl-1,6-dihydro-chromeno[7,8-d]imidazol-7-yl)-phenyl]-cyclobutyl}-carbamic acid tert-butyl ester: To a stirred solution of {1-[4-(7-amino-8-methylamino-4-oxo-2-phenyl-4H-chromen-3-yl)-phenyl]-cyclobutyl}-carbamic acid tert-butyl ester (95 mg, 0.19 mmol) in acetonitrile (3 mL) was added trimethylorthoformate (24 µL, 0.22 mmol) and iodine (5 mg, 0.02 mmol) at RT. After 1 hour, the reaction mixture was quenched with Na$_2$S$_2$O$_3$. The resulting mixture was extracted with ethyl acetate (2×30 mL) and the combined organics washed with brine, dried (Na$_2$SO$_4$) and the solvents were removed in vacuo. The resulting residue was subjected to flash chromatography (SiO$_2$, ethyl acetate) to give the title compound as a white solid (67 mg, 68%). LCMS (Method G): R$_T$=3.63 min, [M+H]$^+$=522.

Step 2: 7-[4-(1-Amino-cyclobutyl)-phenyl]-1-methyl-8-phenyl-1H-chromeno[7,8-d]imidazol-6-one: Following the procedure used to prepare 3-[4-(1-amino-cyclobutyl)-phenyl]-2-phenyl-7H-pyrano[2,3-e]indazol-4-one, {1-[4-(1-methyl-6-oxo-8-phenyl-1,6-dihydro-chromeno[7,8-d]imidazol-7-yl)-phenyl]-cyclobutyl}-carbamic acid tert-butyl ester was reacted to give the title compound as a white solid (43 mg, 85%). $^1$H NMR (400 MHz, DMSO-d6): δ 8.44 (s, 1H), 7.88 (d, J=9.2 Hz, 1H), 7.73 (d, J=9.2 Hz, 1H), 7.54-7.50 (m, 2H), 7.44-7.34 (m, 5H), 7.18-7.13 (m, 2H), 4.21 (s, 3H), 2.42-2.34 (m, 2H), 2.12-2.04 (m, 2H), 2.04-1.94 (m, 1H), 1.70-1.59 (m, 1H). LCMS (Method E): $R_T$=2.86 min, $[M+H]^+$=422.

Example 97

7-[4-(1-Amino-cyclobutyl)-phenyl]-3-iodo-8-phenyl-1H-9-oxa-1,2-diaza-cyclopenta[a]naphthalen-6-one hydrochloride

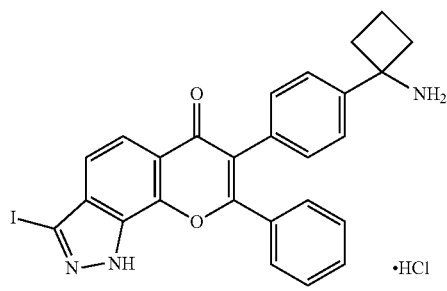 [SMILES: NC1(c2ccc(-c3c(-c4ccccc4)oc4c(ccc5c(I)n[nH]c54)c3=O)cc2)CCC1 ; Cl]

Step 1: {1-[4-(6-oxo-8-phenyl-1,6-dihydro-9-oxa-1,2-diaza-cyclopenta[a]naphthalen-7-yl)-phenyl]-cyclobutyl}-carbamic acid tert-butyl ester: To a microwave vial were added 7-iodo-8-phenyl-1H-9-oxa-1,2-diaza-cyclopenta[a]naphthalen-6-one (100 mg, 0.257 mmol), {1-[4-(4,4,5,5-tetramethyl-[1,3,2]dioxaborolan-2-yl)-phenyl]-cyclobutyl}-carbamic acid tert-butyl ester (115 mg, 0.308 mmol), sodium carbonate solution (2 M in water, 1 mL), tetrakis(triphenylphosphine)palladium(0) (44.5 mg, 0.039 mmol) and DME (3 mL). The reaction mixture was purged using nitrogen and heated in a microwave reactor at 125° C. for 1 hour. Further portions of {1-[4-(4,4,5,5-tetramethyl-[1,3,2]dioxaborolan-2-yl)-phenyl]-cyclobutyl}-carbamic acid tert-butyl ester (50 mg, 0.134 mmol) and tetrakis(triphenylphosphine)palladium(0) (20 mg, 0.017 mmol) were added and the mixture was heated in a microwave reactor at 125° C. for a further 1 hour. The reaction mixture was partitioned between EtOAc and water and the resulting biphasic mixture was separated. The aqueous phase was extracted with EtOAc and the combined organic phase was washed with water and brine, dried ($Na_2SO_4$), filtered, and concentrated in vacuo. The resultant residue was subjected to flash chromatography ($SiO_2$, gradient 30 to 70% EtOAc in cyclohexane) to afford the title compound (55.1 mg, 42%) as a yellow gum. LCMS (Method H): $R_T$=3.95 min, $[M+H]^+$=508.

Step 2: {1-[4-(3-Iodo-6-oxo-8-phenyl-1,6-dihydro-9-oxa-1,2-diaza-cyclopenta[a]naphthalen-7-yl)-phenyl]-cyclobutyl}-carbamic acid tert-butyl ester: To a stirred ice-cooled solution of {1-[4-(6-oxo-8-phenyl-1,6-dihydro-9-oxa-1,2-diaza-cyclopenta[a]naphthalen-7-yl)-phenyl]-cyclobutyl}-carbamic acid tert-butyl ester (52 mg, 0.10 mmol) in DMF (0.5 mL), was added powdered potassium hydroxide (45 mg, 0.80 mmol). After 3 min, a solution of iodine (102 mg, 0.40 mmol) in DMF (0.5 mL) was added. The resulting mixture was stirred at RT for 16 hours. Aqueous sodium thiosulfate was added and the mixture was extracted twice with EtOAc. The combined organic extracts were washed with water and brine, dried ($Na_2SO_4$), filtered and concentrated in vacuo. The resultant residue was subjected to flash chromatography ($SiO_2$, gradient 30 to 75% EtOAc in cyclohexane) to afford the title compound (4.2 mg, 7%) as a white solid. LCMS (Method H): $R_T$=4.39 min, $[M+H]^+$=634.

Step 3: 7-[4-(1-Amino-cyclobutyl)-phenyl]-3-iodo-8-phenyl-1H-9-oxa-1,2-diaza-cyclopenta[a]naphthalen-6-one hydrochloride: Following the procedure used to prepare 3-[4-(1-amino-cyclobutyl)-phenyl]-6-fluoro-2-phenyl-chromen-4-one, {1-[4-(3-iodo-6-oxo-8-phenyl-1,6-dihydro-9-oxa-1,2-diaza-cyclopenta[a]naphthalen-7-yl)-phenyl]cyclobutyl}-carbamic acid tert-butyl ester was treated with TFA. The resultant free base was dissolved in a mixture of MeOH (2 mL), water (3 mL) and 1 M HCl (0.1 mL) and chromatographed on a 2 g C18 cartridge {gradient 40 to 80% MeOH in water+1 M HCl (60 µL in each 5 mL of eluent)} to give the title compound (2.1 mg, 56%) as a white solid.

$^1$H NMR (400 MHz, $CD_3OD$): δ 7.93 (d, J=8.7 Hz, 1H), 7.58-7.48 (m, 5H), 7.45-7.33 (m, 5H), 2.83-2.76 (m, 2H), 2.63-2.56 (m, 2H), 2.30-2.19 (m, 1H), 2.03-1.92 (m, 1H). LCMS (Method E): $R_T$=3.56 min, $[M+H]^+$=534.

Example 98

7-[4-(1-Amino-cyclobutyl)-phenyl]-3-ethyl-1-methyl-8-phenyl-1H-9-oxa-1,2-diaza-cyclopenta[a]naphthalen-6-one hydrochloride

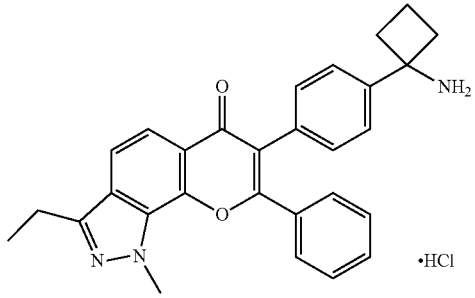 [SMILES: CCc1nn(C)c2c1ccc1c(=O)c(-c3ccc(C4(N)CCC4)cc3)c(-c3ccccc3)oc12 ; Cl]

Step 1: {1-[4-(3-Iodo-1-methyl-6-oxo-8-phenyl-1,6-dihydro-9-oxa-1,2-diaza-cyclopenta[a]naphthalen-7-yl)-phenyl]-cyclobutyl}-carbamic acid tert-butyl ester: To a stirred ice-cooled solution of {1-[4-(6-oxo-8-phenyl-1,6-dihydro-9-oxa-1,2-diaza-cyclopenta[a]naphthalen-7-yl)-phenyl]-cyclobutyl}-carbamic acid tert-butyl ester (69 mg, 0.136 mmol) in DMF (1 mL), was added powdered potassium hydroxide (50 mg, 0.89 mmol). After 2 min, a solution of iodine (112 mg, 0.44 mmol) in DMF (0.5 mL) was added. After a further 10 minutes, iodomethane (0.1 mL, 1.6 mmol) was added. After 15 minutes, ethyl acetate and aqueous sodium thiosulfate were added. The resulting biphasic mixture was separated. The aqueous phase was extracted twice with EtOAc, the combined organic extracts were washed with water and brine, dried ($Na_2SO_4$), filtered, and concentrated in vacuo. The resultant residue was subjected to flash chromatography ($SiO_2$, gradient 20 to 50% EtOAc in cyclohexane) to afford the title compound (55.5 mg, 63%) as a white solid. LCMS (Method H): $R_T$=4.79 min, $[M+H]^+$=648.

Step 2: {1-[4-(1-Methyl-6-oxo-8-phenyl-3-vinyl-1,6-dihydro-9-oxa-1,2-diaza-cyclopenta[a]naphthalen-7-yl)-phenyl]-cyclobutyl}-carbamic acid tert-butyl ester: A mixture of {1-[4-(3-iodo-1-methyl-6-oxo-8-phenyl-1,6-dihydro-9-oxa-1,2-diaza-cyclopenta[a]naphthalen-7-yl)-phenyl]-cyclobutyl}-carbamic acid tert-butyl ester (27 mg, 0.0417 mmol), tetrakis(triphenylphosphine)palladium(0) (4.8 mg, 0.004 mmol) and vinyltributylin (0.0183 mL, 0.063 mmol) in toluene (2 mL) was stirred at 90° C. under nitrogen. After 3 hours, reaction mixture cooled to RT and was subjected to flash chromatography (SiO$_2$, gradient 20 to 40% EtOAc in cyclohexane) to afford the title compound (23.4 mg) as a yellow gum. LCMS (Method H): R$_T$=4.67 min, [M+H]$^+$=548.

Step 3: {1-[4-(3-Ethyl-1-methyl-6-oxo-8-phenyl-1,6-dihydro-9-oxa-1,2-diaza-cyclopenta[a]naphthalen-7-yl)-phenyl]-cyclobutyl}-carbamic acid tert-butyl ester: A solution of {1-[4-(1-methyl-6-oxo-8-phenyl-3-vinyl-1,6-dihydro-9-oxa-1,2-diaza-cyclopenta[a]naphthalen-7-0)-phenyl]-cyclobutyl}-carbamic acid tert-butyl ester (23.4 mg), in IMS (5 mL) was hydrogenated over 10% Pd/C (10 mg) for 16 hours at RT and 1 atmosphere of hydrogen. A further portion of 10% Pd/C (10 mg) was added and the hydrogenation continued for a further 5 hours. The reaction mixture was filtered through Celite® and the filtrate was evaporated to dryness to afford the title compound. LCMS (Method H): R$_T$=4.68 min, [M+H]$^+$=550.

Step 4: 7-[4-(1-Amino-cyclobutyl)-phenyl]-3-ethyl-1-methyl-8-phenyl-1H-9-oxa-1,2-diaza-cyclopenta[a]naphthalen-6-one hydrochloride: Following the procedure used to prepare 3-[4-(1-amino-cyclobutyl)-phenyl]-6-fluoro-2-phenyl-chromen-4-one, {1-[4-(3-ethyl-1-methyl-6-oxo-8-phenyl-1,6-dihydro-9-oxa-1,2-diaza-cyclopenta[a]naphthalen-7-yl)-phenyl]-cyclobutyl}-carbamic acid tert-butyl ester was treated with TFA. The resultant free base was dissolved in a mixture of MeOH (2 mL), water (3 mL) and 1 M HCl (0.1 mL) and chromatographed on a 2 g C18 cartridge {gradient 40 to 65% MeOH in water+1 M HCl (60 μL in each 5 mL of eluent)} to give the title compound (9 mg, 43%, 3 steps) as a white solid. $^1$H NMR (400 MHz, DMSO-d6): δ 8.38 (br s, 3H), 7.80 (d, J=8.6 Hz, 1H), 7.70 (d, J=8.6 Hz, 1H), 7.55-7.53 (m, 2H), 7.50-7.43 (m, 3H), 7.41-7.37 (m, 2H), 7.32 (d, J=8.3 Hz, 2H), 4.34 (s, 3H), 2.99 (q, J=7.6 Hz, 2H), 2.63-2.52 (m, 4H), 2.22-2.11 (m, 1H), 1.87-1.76 (m, 1H), 1.35 (t, J=7.6 Hz, 3H). LCMS (Method E): R$_T$=3.79 min, [M+H]$^+$=450.

Example 99

7-[4-(1-Amino-cyclobutyl)-phenyl]-3-chloro-8-phenyl-1H-9-oxa-1,2-diaza-cyclopenta[a]naphthalen-6-one hydrochloride

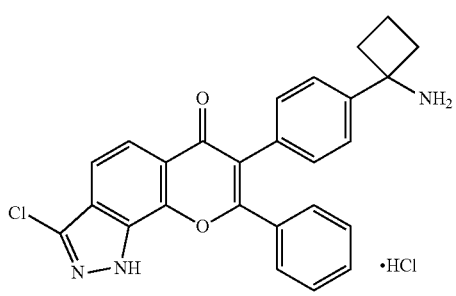 [SMILES: NC1(c2ccc(-c3c(-c4ccccc4)oc4c(ccc5c(Cl)n[nH]c54)c3=O)cc2)CCC1 ; Cl]

Step 1: {1-[4-(3-Chloro-6-oxo-8-phenyl-1,6-dihydro-9-oxa-1,2-diaza-cyclopenta[a]naphthalen-7-yl)-phenyl]-cyclobutyl}-carbamic acid tert-butyl ester: To a stirred solution of {1-[4-(6-oxo-8-phenyl-1,6-dihydro-9-oxa-1,2-diaza-cyclopenta[a]naphthalen-7-yl)-phenyl]-cyclobutyl}-carbamic acid tert-butyl ester (5 mg, 0.01 mmol) in EtOH (1 mL), was added sodium hypochlorite (10% aqueous solution, 0.4 mL) at RT. After 2 h, EtOAc and water were added. The resulting biphasic mixture was separated. The aqueous phase was extracted with EtOAc. The combined organic extracts were washed with water and brine, dried (Na$_2$SO$_4$), filtered, and concentrated in vacuo. The reaction was repeated with {1-[4-(6-oxo-8-phenyl-1,6-dihydro-9-oxa-1,2-diaza-cyclopenta[a]naphthalen-7-yl)-phenyl]-cyclobutyl}-carbamic acid tert-butyl ester (20 mg, 0.039 mmol) and aqueous sodium hypochlorite (2 mL) in EtOH (3 mL) with initial cooling in a cold water bath. After workup, the resultant residues were combined and subjected to flash chromatography (SiO$_2$, gradient 20 to 40% EtOAc in cyclohexane) to afford the title compound (16 mg, 60%) as a white solid. LCMS (Method H): R$_T$=4.39 min, [M+H]$^+$=542/544.

Step 2: 7-[4-(1-Amino-cyclobutyl)-phenyl]-3-chloro-8-phenyl-1H-9-oxa-1,2-diaza-cyclopenta[a]naphthalen-6-one hydrochloride: Following the procedure used to prepare 3-[4-(1-amino-cyclobutyl)-phenyl]-6-fluoro-2-phenyl-chromen-4-one, {1-[4-(3-chloro-6-oxo-8-phenyl-1,6-dihydro-9-oxa-1,2-diaza-cyclopenta[a]naphthalen-7-yl)-phenyl]-cyclobutyl}-carbamic acid tert-butyl ester was treated with TFA. The resultant free base was dissolved in a mixture of MeOH (1.25 mL), water (3.75 mL) and 1 M HCl (0.15 mL) and chromatographed on a 2 g C18 cartridge {gradient 25 to 60% MeOH in water+1 M HCl (60 μL in each 5 mL of eluent)} to give the title compound (10.2 mg, 72%) as a white solid. $^1$H NMR (400 MHz, DMSO-d6): δ 8.54 (br s, 3H), 7.82 (d, J=8.6 Hz, 1H), 7.72 (d, J=8.6 Hz, 1H), 7.57-7.55 (m, 2H), 7.51-7.44 (m, 3H), 7.41-7.37 (m, 2H), 7.34 (d, J=8.3 Hz, 2H), 2.63-2.49 (m, 4H), 2.23-2.12 (m, 1H), 1.87-1.76 (m, 1H). LCMS (Method E): R$_T$=3.51 min, [M+H]$^+$=442/444.

Example 100

7-[4-(1-Amino-cyclobutyl)-phenyl]-3-chloro-1-methyl-8-phenyl-1H-9-oxa-1,2-diaza-cyclopenta[a] naphthalen-6-one hydrochloride

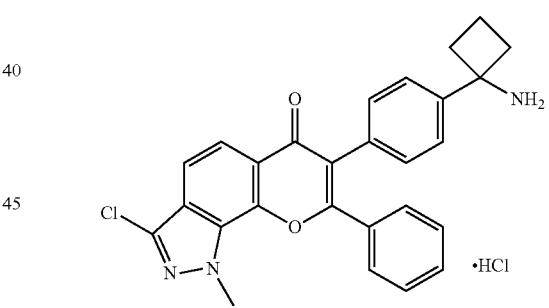

Step 1: 3-Chloro-7-iodo-8-phenyl-1H-9-oxa-1,2-diaza-cyclopenta[a]naphthalen-6-one: To a stirred solution of 7-iodo-8-phenyl-1H-9-oxa-1,2-diaza-cyclopenta[a]naphthalen-6-one (73 mg, 0.188 mmol) in EtOH (10 mL), with cooling in a 10° C. water bath, was added sodium hypochlorite (10% aqueous solution, 9 mL). After 15 minutes, the temperature was allowed to increase to RT. After a further 30 minutes, the reaction mixture was concentrated in vacuo and the remaining reside was partitioned between EtOAc and water. The resulting biphasic mixture was separated, the aqueous phase was further extracted with EtOAc, the combined organic extracts were washed with water and brine, dried (Na$_2$SO$_4$), filtered, and evaporated in vacuo to afford the title compound (44 mg, 55%) as a cream solid. LCMS (Method H): R$_T$=3.75 min, [M+H]$^+$=423/425.

Step 2: 3-Chloro-7-iodo-1-methyl-8-phenyl-1H-9-oxa-1,2-diaza-cyclopenta[a]naphthalen-6-one: To a stirred ice-cooled solution of 3-chloro-7-iodo-8-phenyl-1H-9-oxa-1,2-diaza-cyclopenta[a]naphthalen-6-one (42 mg, 0.10 mmol) in DMF (2 mL), was added cesium carbonate (65 mg, 0.2 mmol). After 5 min, iodomethane (0.0185 mL, 0.3 mmol) was added. After a further 5 min, the reaction mixture was allowed to warm to RT. After a further 15 min, the resulting mixture was partitioned between EtOAc and water. The resulting biphasic mixture was separated, the organic phase was further extracted with EtOAc and the combined organic extracts were washed with water and brine, dried (Na$_2$SO$_4$), filtered, and concentrated in vacuo. The resultant residue was subjected to flash chromatography (SiO$_2$, gradient 30 to 50% EtOAc in cyclohexane) to afford the title compound as a white solid (25 mg, 58%), LCMS (Method H): R$_T$=4.19 min, [M+H]$^+$=437/439.

Step 3: {1-[4-(3-Chloro-1-methyl-6-oxo-8-phenyl-1,6-dihydro-9-oxa-1,2-diaza-cyclopenta[a]naphthalen-7-yl)-phenyl]-cyclobutyl}-carbamic acid tert-butyl ester: Following the procedure used to prepare {1-[4-(6-fluoro-4-oxo-2-phenyl-4H-chromen-3-yl)-phenyl]-cyclobutyl}-carbamic acid tert-butyl ester, 3-chloro-7-iodo-1-methyl-8-phenyl-1H-9-oxa-1,2-diaza-cyclopenta[a]naphthalen-6-one was reacted to give the title compound as a pale yellow gum (34 mg). LCMS (Method H): R$_T$=4.76 min, [M+H]$^+$=556/558.

Step 4: 7-[4-(1-Amino-cyclobutyl)-phenyl]-3-chloro-1-methyl-8-phenyl-1H-9-oxa-1,2-diaza-cyclopenta[a]naphthalen-6-one hydrochloride: Following the procedure used to prepare 3-[4-(1-amino-cyclobutyl)-phenyl]-6-fluoro-2-phenyl-chromen-4-one, {1-[4-(3-chloro-1-methyl-6-oxo-8-phenyl-1,6-dihydro-9-oxa-1,2-diaza-cyclopenta[a]naphthalen-7-yl)-phenyl]-cyclobutyl}-carbamic acid tert-butyl ester was treated with TFA. The resultant free base was dissolved in a mixture of MeOH (1.5 mL), water (3.5 mL) and 1 M HCl (0.15 mL) and chromatographed on a 2 g C18 cartridge {gradient 30 to 65% MeOH in water+1 M HCl (60 µL in each 5 mL of eluent)} to give the title compound (10 mg, 36%, 2 steps) as a white solid. $^1$H NMR (400 MHz, DMSO-d6): δ 8.38 (br s, 3H), 7.82 (d, J=8.6 Hz, 1H), 7.70 (d, J=8.6 Hz, 1H), 7.56-7.53 (m, 2H), 7.51-7.44 (m, 3H), 7.41-7.37 (m, 2H), 7.31 (d, J=8.2 Hz, 2H), 4.38 (s, 3H), 2.62-2.49 (m, 4H), 2.22-2.12 (m, 1H), 1.86-1.75 (m, 1H). LCMS (Method E): R$_T$=3.51 min, [M+H]$^+$=456/458.

Example 101

3-[4-(1-Amino-cyclobutyl)-phenyl]-8-(1-methyl-1H-pyrazol-4-yl)-2-phenyl-pyrano[2,3-c]pyridin-4-one hydrochloride

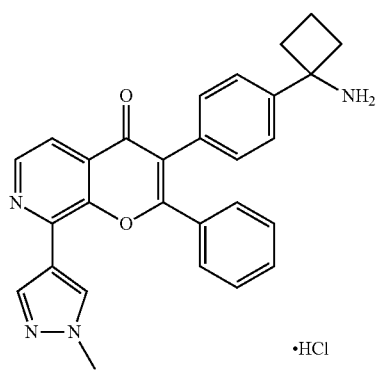 [SMILES: Cn1cc(-c2nccc3c(=O)c(-c4ccc(C5(N)CCC5)cc4)c(-c4ccccc4)oc23)cn1 ; Cl]

Step 1: (1-{4-[8-(1-Methyl-1H-pyrazol-4-yl)-4-oxo-2-phenyl-4H-pyrano[2,3-c]pyridin-3-yl]-phenyl}-cyclobutyl)-carbamic acid tert-butyl ester: Following the procedure used to prepare (1-{4-[4-oxo-2-phenyl-7-(2H-pyrazol-3-yl)-4H-chromen-3-yl]-phenyl}-cyclobutyl)-carbamic acid tert-butyl ester, {1-[4-(8-chloro-4-oxo-2-phenyl-4H-pyrano[2,3-c]pyridin-3-yl)-phenyl]-cyclobutyl}-carbamic acid tert-butyl ester was reacted with 1-methyl-4-(4,4,5,5-tetramethyl-[1,3,2]dioxaborolan-2-yl)-1H-pyrazole to give the title compound (28.7 mg, 97%). LCMS (Method H): R$_T$=4.04 min, [M+H]$^+$=549.

Step 2: 3-[4-(1-Amino-cyclobutyl)-phenyl]-8-(1-methyl-1H-pyrazol-4-yl)-2-phenyl-pyrano[2,3-a]pyridin-4-one hydrochloride: Following the procedure used to prepare 3-[4-(1-amino-cyclobutyl)-phenyl]-6-fluoro-2-phenyl-chromen-4-one, (1-{4-[8-(1-methyl-1H-pyrazol-4-yl)-4-oxo-2-phenyl-4H-pyrano[2,3-c]pyridin-3-yl]-phenyl}-cyclobutyl)-carbamic acid tert-butyl ester was treated with TFA. After evaporation, the residue was dissolved in MeOH and loaded on to a 2 g SCX-2 cartridge. The cartridge was washed with MeOH before eluting with 2 M NH$_3$ in MeOH solution. The eluent was collected and evaporated. The resulting residue was dissolved in a mixture of MeOH (1.5 mL), water (3.5 mL) and 1 M HCl (0.1 mL) and chromatographed on a 2 g C18 cartridge {gradient 30 to 70% MeOH in water+1 M HCl (60 µL in each 5 mL of eluent)} to give the title compound as a yellow solid (14.9 mg, 59%). $^1$H NMR (400 MHz, DMSO-d6): δ 8.65-8.64 (m, 4H), 8.37 (s, 1H), 8.10 (s, 1H), 7.80 (d, J=5.0 Hz, 1H), 7.54-7.41 (m, 7H), 7.31 (d, J=8.2 Hz, 2H), 3.92 (s, 3H), 2.61-2.50 (m, 4H), 2.23-2.12 (m, 1H), 1.86-1.75 (m, 1H). LCMS (Method E): R$_T$=3.08 min, [M+H]$^+$=449.

Example 102

3-[4-(1-Amino-cyclobutyl)-phenyl]-2-phenyl-8-[1,2,4]triazol-4-yl-pyrano[2,3-c]pyridin-4-one hydrochloride

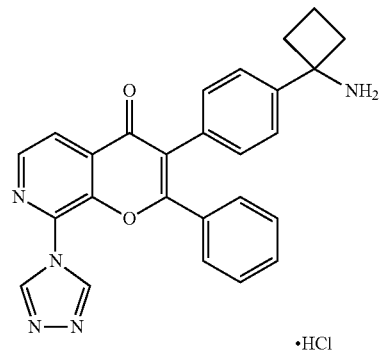 [SMILES: NC1(c2ccc(-c3c(-c4ccccc4)oc4c(-n5cnnc5)nccc4c3=O)cc2)CCC1 ; Cl]

Step 1 {1-[4-(4-oxo-2-phenyl-8-[1,2,4]triazol-4-yl-4H-pyrano[2,3-c]pyridin-3-yl)-phenyl]-cyclobutyl}-carbamic acid tert-butyl ester: To a microwave vial were added {1-[4-(8-chloro-4-oxo-2-phenyl-4H-pyrano[2,3-c]pyridin-3-yl)-phenyl]-cyclobutyl}-carbamic acid tert-butyl ester (6.7 mg, 0.0133 mmol), 1,2,4-triazole (4.6 mg, 0.067 mmol), cesium carbonate (8.7 mg, 0.0266 mmol), copper(I) iodide (0.8 mg, 0.004 mmol) and NMP (0.5 mL). The reaction mixture was heated in a microwave reactor at 150° C. for 30 minutes. The reaction was repeated with {1-[4-(8-chloro-4-oxo-2-phenyl-4H-pyrano[2,3-c]pyridin-3-yl)-phenyl]-cyclobutyl}-carbamic acid tert-butyl ester (20 mg, 0.04 mmol), 1,2,4-triazole (13.8 mg, 0.2 mmol), cesium carbonate (26.1 mg, 0.08 mmol), copper(I) iodide (2.4 mg, 0.012 mmol) and NMP (0.7 mL). The reaction mixtures were combined and partitioned between EtOAc and water. The organic phase was extracted further with EtOAc and the combined organic extracts were washed with water and brine, dried (Na$_2$SO$_4$), filtered, and concentrated in vacuo. The resultant residue was subjected to flash chromatography (SiO$_2$, gradient 50 to 75% EtOAc in cyclohexane) to afford the title compound (13.2 mg, 46%) as a colourless gum. LCMS (Method H): R$_T$=3.84 min, [M+H]$^+$=536.

Step 2: 3-[4-(1-Amino-cyclobutyl)-phenyl]-2-phenyl-8-[1,2,4]triazol-4-yl-pyrano[2,3-c]pyridin-4-one hydrochloride: Following the procedure used to prepare 3-[4-(1-amino-cyclobutyl)-phenyl]-6-fluoro-2-phenyl-chromen-4-one, {1-[4-(4-oxo-2-phenyl-8-[1,2,4]triazol-4-yl-4H-pyrano[2,3-c]pyridin-3-yl)-phenyl]-cyclobutyl}-carbamic acid tert-butyl ester was treated with TFA. After evaporation the residue was dissolved in MeOH and loaded on to a 2 g SCX-2 cartridge. The cartridge was washed with MeOH before eluting with 2 M NH$_3$ in MeOH solution. The eluent was collected and evaporated. The resulting residue was dissolved in a mixture of MeOH (1 mL), water (4 mL) and 1M HCl (0.1 mL) and chromatographed on a 2 g C18 cartridge {gradient 20 to 60% MeOH in water+1 M HCl (60 µL in each 5 mL of eluent)} to give the title compound as a white solid (7 mg, 61%). $^1$H NMR (400 MHz, CD$_3$OD): δ 9.29 (s, 1H), 8.64 (br s, 1H), 8.37 (s, 1H), 8.21 (d, J=4.9 Hz, 1H), 7.54-7.49 (m, 4H), 7.42-7.39 (m, 3H), 7.33-7.29 (m, 2H), 2.83-2.76 (m, 2H), 2.64-2.57 (m, 2H), 2.30-2.20 (m, 1H), 2.04-1.93 (m, 1H). LCMS (Method E): R$_T$=2.88 min, [M−NH$_2$]$^-$=419.

Example 103

3-[1-(1-Amino-cyclobutyl)-phenyl]-2-phenyl-8-(pyridin-2-yloxy)-pyrano[2,3-c]pyridin-4-one hydrochloride

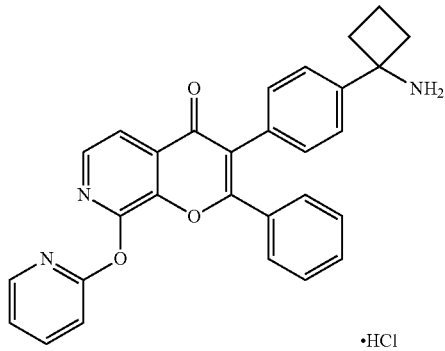 [SMILES: NC1(c2ccc(-c3c(-c4ccccc4)oc4c(Oc5ccccn5)nccc4c3=O)cc2)CCC1 ; Cl]

Step 1 (1-{4-[4-Oxo-2-phenyl-8-(pyridin-2-yloxy)-4H-pyrano[2,3-c]pyridin-3-yl]-phenyl}-cyclobutyl)-carbamic acid tert-butyl ester and (1-{4-[4-oxo-8-(2-oxo-2H-pyridin-1-yl)-2-phenyl-4H-pyrano[2,3-c]pyridin-3-yl]-phenyl]-cyclobutyl}-carbamic acid tert-butyl ester: To a microwave vial were added {1-[4-(8-chloro-4-oxo-2-phenyl-4H-pyrano[2,3-c]pyridin-3-yl)-phenyl]-cyclobutyl}-carbamic acid tert-butyl ester (27 mg, 0.0537 mmol), 2-hydroxypyridine (25.5 mg, 0.268 mmol), cesium carbonate (35 mg, 0.107 mmol), copper (I) iodide (3.2 mg, 0.016 mmol) and NMP (0.8 mL). The reaction mixture was heated in a microwave reactor to 150° C. for 30 minutes. The cooled reaction mixture was partitioned between EtOAc and water. The organic phase was further extracted with EtOAc and the combined organic extracts were washed with water and brine, dried (Na$_2$SO$_4$), filtered, and concentrated in vacuo. The resultant residue was subjected to flash chromatography (SiO$_2$, gradient 30 to 100% EtOAc in cyclohexane) to afford (1-{4-[4-oxo-2-phenyl-8-(pyridin-2-yloxy)-4H-pyrano[2,3-c]pyridin-3-yl]-phenyl}-cyclobutyl)-carbamic acid tert-butyl ester (6.6 mg, 22%) as the earlier eluting isomer: LCMS (Method H): R$_T$=4.25 min, [M+H]$^+$=562, and (1-{4-[4-oxo-8-(2-oxo-2H-pyridin-1-yl)-2-phenyl-4H-pyrano[2,3-c]pyridin-3-yl]-phenyl}-cyclobutyl)-carbamic acid tert-butyl ester (5.4 mg, 18%) as the later eluting isomer: LCMS (Method H): R$_T$=3.78 min, [M+H]$^+$=562.

Step 2: 3-[4-(1-Amino-cyclobutyl)-phenyl]-2-phenyl-8-(pyridin-2-yloxy)-pyrano[2,3-c]pyridin-4-one hydrochloride: Following the procedure used to prepare 3-[4-(1-amino-cyclobutyl)-phenyl]-6-fluoro-2-phenyl-chromen-4-one, (1-{4-[4-oxo-2-phenyl-8-(pyridin-2-yloxy)-4H-pyrano[2,3-c]pyridin-3-yl]-phenyl}-cyclobutyl)-carbamic acid tert-butyl ester was treated with TFA. After evaporation the residue was dissolved in MeOH and loaded on to a 2 g SCX-2 cartridge. The cartridge was washed with MeOH before eluting with 2 M NH$_3$ in MeOH solution. The eluent was collected and evaporated. The resulting residue was dissolved in a mixture of MeOH (1.5 mL), water (3.5 mL) and 1 M HCl (0.1 mL) and chromatographed on a 2 g C18 cartridge {gradient 30 to 60% MeOH in water+1 M HCl (60 µL in each 5 mL of eluent)} to give the title compound as a white solid (2.8 mg, 48%). $^1$H NMR (400 MHz, CD$_3$OD): δ 8.29-8.26 (br m, 2H), 7.98 (dt, J=7.9 and 1.8 Hz, 1H), 7.91 (d, J=5.1 Hz, 1H), 7.48 (d, J=8.4 Hz, 2H), 7.37-7.29 (m, 5H), 7.22-7.15 (m, 4H), 2.82-2.74 (m, 2H), 2.63-2.55 (m, 2H), 2.29-2.18 (m, 1H), 2.03-1.92 (m, 1H). LCMS (Method E): R$_T$=3.43 min, [M−NH$_2$]$^-$=445.

Example 104

3-[4-(1-Amino-cyclobutyl)-phenyl]-8-(2-oxo-2H-pyridin-1-yl)-2-phenyl-pyrano[2,3-c]pyridin-4-one hydrochloride

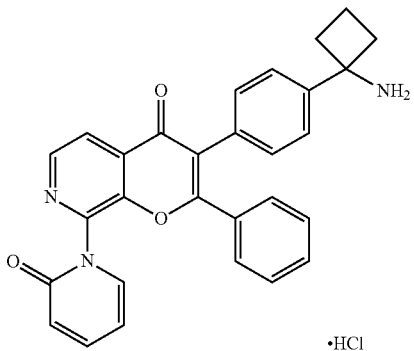 [SMILES: NC1(c2ccc(-c3c(-c4ccccc4)oc4c(-n5ccccc5=O)nccc4c3=O)cc2)CCC1 ; Cl]

Following the procedure used to prepare 3-[4-(1-amino-cyclobutyl)-phenyl]-6-fluoro-2-phenyl-chromen-4-one, (1-{4-[4-oxo-8-(2-oxo-2H-pyridin-1-yl)-2-phenyl-4H-pyrano[2,3-c]pyridin-3-yl]-phenyl}-cyclobutyl)-carbamic acid tert-butyl ester was treated with TFA. After evaporation the residue was dissolved in MeOH and loaded on to a 2 g SCX-2 cartridge. The cartridge was washed with MeOH before eluting with 2 M NH$_3$ in MeOH solution. The eluent was collected and evaporated. The resulting residue was dissolved in a mixture of MeOH (1 mL), water (4 mL) and 1 M HCl (0.1 mL) and chromatographed on a 2 g C18 cartridge {gradient 20 to 60% MeOH in water+1 M HCl (60 µL in each 5 mL of eluent)} to give the title compound as a white solid (3 mg, 63%). $^1$H NMR (400 MHz, CD$_3$OD): δ 8.68 (d, J=5.1 Hz, 1H), 8.22 (d, J=5.1 Hz, 1H), 7.88 (dd, J=6.8 and 1.8 Hz, 1H), 7.73 (ddt, J=9.2, 6.7 and 2.0 Hz, 1H), 7.49 (d, J=8.5 Hz, 2H), 7.38-7.35 (m, 5H), 7.26-7.22 (m, 2H), 6.73 (d, J=9.2 Hz, 1H), 6.58 (dt, J=6.8 and 1.1 Hz, 1H), 2.82-2.75 (m, 2H), 2.63-2.55 (m, 2H), 2.29-2.19 (m, 1H), 2.03-1.92 (m, 1H). LCMS (Method E): $R_T$=2.98 min, [M−NH$_2$]$^-$=445.

Example 105

3-[4-(1-Amino-cyclobutyl)-phenyl]-8-ethynyl-2-phenyl-chromen-4-one

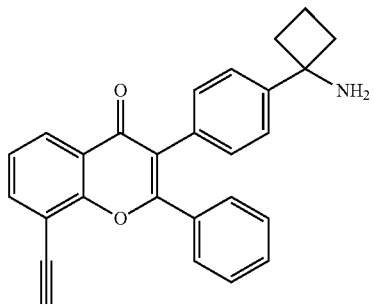 [SMILES: C#Cc1cccc2c(=O)c(-c3ccc(C4(N)CCC4)cc3)c(-c3ccccc3)oc12]

Step 1: {1-[4-(4-oxo-2-phenyl-8-trimethylsilanylethynyl-4H-chromen-3-yl)-phenyl]-cyclobutyl}-carbamic acid tert-butyl ester: Copper(I) iodide (1 mg, 0.005 mmol) and bis(benzonitrile)dichloro palladium(II) (2 mg, 0.005 mmol) were dissolved in toluene (1 mL) with stirring. Tri-tert-butylphosphine (2 mg, 0.01 mmol), diisopropylamine (0.017 ml, 0.118 mmol), {1-[4-(8-bromo-4-oxo-2-phenyl-4H-chromen-3-yl)-phenyl]-cyclobutyl}-carbamic acid tert-butyl ester (50 mg, 0.091 mmol) and (trimethylsilyl)acetylene (0.015 mL, 0.109 mmol) were added, the vial was sealed, and reaction mixture was stirred at RT under an atmosphere of argon for 3 h. The mixture was concentrated in vacuo and the resultant residue subjected to flash chromatography (SiO$_2$, gradient 0 to 10% ethyl acetate in DCM) to afford the title compound as a white solid (51 mg, 100%). LCMS (Method G): $R_T$=5.30 min, [M+H]$^+$=564.

Step 2: {1-[4-(8-Ethynyl-4-oxo-2-phenyl-4H-chromen-3-yl)-phenyl]-cyclobutyl}-carbamic acid tert-butyl ester: A solution of {1-[4-(4-oxo-2-phenyl-8-trimethylsilanylethynyl-4H-chromen-3-yl)-phenyl]-cyclobutyl}-carbamic acid tert-butyl ester (51 mg, 0.091 mmol) in MeOH (2 mL) and DCM (1 mL) was treated with potassium carbonate (15 mg, 0.109 mmol) and the reaction stirred at RT for 3 h. The reaction mixture was quenched with water, diluted with EtOAc, washed with brine, dried (Na$_2$SO$_4$), filtered and concentrated in vacuo to give the title compound as a foamy solid (45 mg, 100%). $^1$H NMR (400 MHz, CDCl$_3$): δ 8.27 (dd, J=7.7 and 1.6 Hz, 1H), 7.86 (dd, J=7.5 and 1.6 Hz, 1H), 7.48 (d, J=7.5 Hz, 2H), 7.41-7.30 (m, 5H), 7.25-7.19 (m, 3H), 5.06 (s, 1H), 3.47 (s, 1H), 2.65-2.27 (m, 4H), 2.14-2.00 (m, 1H), 1.91-1.76 (m, 1H), 1.37 (s, 9H).

Step 3: 3-[4-(1-Amino-cyclobutyl)-phenyl]-8-ethynyl-2-phenyl-chromen-4-one: Following the procedure of 3-[4-(1-amino-cyclobutyl)-phenyl]-6-fluoro-2-phenyl-chromen-4-one, {1-[4-(8-ethynyl-4-oxo-2-phenyl-4H-chromen-3-yl)-phenyl]-cyclobutyl}-carbamic acid tert-butyl ester was treated with TFA. The resultant free base was subjected to flash chromatography (SiO$_2$, gradient 0 to 20% methanolic ammonia in DCM) to afford the title compound as a white solid (8 mg, 100%). $^1$H NMR (400 MHz, DMSO-d6): δ 8.08 (dd, J=7.8, 1.6 Hz, 1H), 7.97 (dd, J=7.6, 1.8 Hz, 1H), 7.48 (t, J=7.4 Hz, 1H), 7.42-7.28 (m, 7H), 7.14 (d, J=8.4 Hz, 2H), 4.65 (s, 1H), 4.01 (bs, 2H), 2.42-2.33 (m, 2H), 2.17-2.07 (m, 2H), 2.03-1.91 (m, 1H), 1.71-1.58 (m, 1H). LCMS (Method E): $R_T$=3.64 min, [M+H]$^+$=392.

Example 106

3-[4-(1-Amino-cyclobutyl)-phenyl]-2-phenyl-8-(1H-[1,2,3]triazol-4-yl)-chromen-4-one

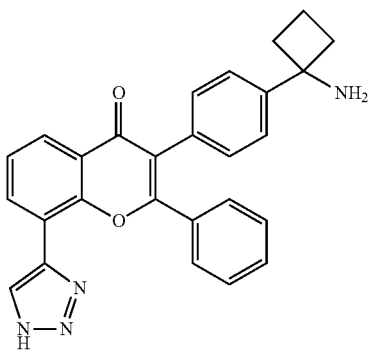 [SMILES: NC1(c2ccc(-c3c(-c4ccccc4)oc4c(-c5c[nH]nn5)cccc4c3=O)cc2)CCC1]

Step 1: (1-{4-[4-oxo-2-phenyl-8-(1H-[1,2,3]triazol-4-yl)-4H-chromen-3-yl]-phenyl}-cyclobutyl)-carbamic acid tert-butyl ester: A solution of {1-[4-(8-Ethynyl-4-oxo-2-phenyl-4H-chromen-3-yl)-phenyl]-cyclobutyl}-carbamic acid tert-butyl ester (34 mg, 0.069 mmol) in MeOH (0.2 mL) and DMF (1.8 mL) was treated with copper(I) iodide (1 mg, 0.003 mmol) and azido trimethylsilane (0.014 ml, 0.104 mmol). The reaction mixture was the stirred at 100° C. for 3.75 h. The resultant mixture was allowed to cool to RT, diluted with EtOAc, washed with brine. The aqueous extracts were further washed with EtOAc (×2). The combined organic extracts were dried (Na$_2$SO$_4$), filtered and concentrated in vacuo. The resultant residue was subjected to flash chromatography (SiO$_2$, gradient 0 to 30% EtOAc in DCM) to give the title compound. LCMS (Method G) $R_T$=3.88 min, [M+H]$^+$=535.

Step 2: 3-[4-(1-Amino-cyclobutyl)-phenyl]-2-phenyl-8-(1H-[1,2,3]triazol-4-yl)-chromen-4-one: Following the procedure of 3-[4-(1-amino-cyclobutyl)-phenyl]-6-fluoro-2-phenyl-chromen-4-one, (1-{4-[4-oxo-2-phenyl-8-(1H-[1,2,3]triazol-4-yl)-4H-chromen-3-yl]-phenyl}-cyclobutyl)-carbamic acid tert-butyl ester was treated with TFA. The resultant free base was subjected to flash chromatography (SiO$_2$, gradient 0 to 20% methanolic ammonia in DCM) to afford the title compound as a white solid (7 mg, 23%, 2 steps). $^1$H NMR (400 MHz, DMSO-d6): δ 8.40 (dd, J=7.6 and 1.8 Hz, 1H), 8.14 (s, 1H), 8.08 (dd, J=7.9 and 1.8 Hz, 1H), 7.58 (t, J=7.8 Hz, 1H), 7.48-7.44 (m, 2H), 7.41-7.31 (m, 5H), 7.11 (d, J=8.6 Hz, 2H), 3.26 (bs, 3H), 2.37-2.27 (m, 2H), 2.08-1.88 (m, 3H), 1.66-1.54 (m, 1H). LCMS (Method E): $R_T$=2.98 min, [M+H]$^+$=435.

Example 107

3-[4-(1-Amino-cyclobutyl)-phenyl]-4-oxo-2-phenyl-4H-chromene-8-carboxylic acid. trifluoro-acetic acid

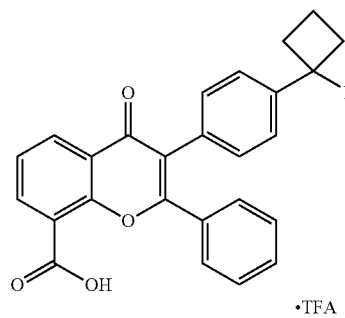

Step 1: 3-[4-(1-tert-Butoxycarbonylamino-cyclobutyl)-phenyl]-4-oxo-2-phenyl-4H-chromene-8-carboxylic acid methyl ester: {1-[4-(8-Bromo-4-oxo-2-phenyl-4H-chromen-3-yl)-phenyl]-cyclobutyl}-carbamic acid tert-butyl ester (200 mg, 0.367 mmol), and [1,1'-bis(diphenylphosphino)-ferrocene]dischloropalladium(II) complex with dichloromethane (60 mg, 0.073 mmol) were loaded into a microwave vial. The vial was sealed and a solution of triethylamine (0.102 mL, 0.732 mmol) in MeOH (4 mL) was added. The vial was evacuated and flushed twice with argon, followed by carbon monoxide. The reaction mixture was heated conventionally at 50° C. under an atmosphere of carbon monoxide for 18 h. The reaction mixture was allowed to cool to RT and was concentrated in vacuo. The resultant residue was subjected to flash chromatography ($SiO_2$, gradient 0 to 10% EtOAc in DCM) to give the title compound as a gum (193 mg, 100%). LCMS (Method G): $R_T$=4.41 min, $[M+H]^+$=526.

Step 2: 3-[4-(1-tert-Butoxycarbonylamino-cyclobutyl)-phenyl]-4-oxo-2-phenyl-4H-chromene-8-carboxylic acid: To a solution of 3-[4-(1-tert-butoxycarbonylamino-cyclobutyl)-phenyl]-4-oxo-2-phenyl-4H-chromene-8-carboxylic acid methyl ester (31 mg, 0.059 mmol) in THF (2 mL) was added a solution of 2 M aqueous lithium hydroxide (2 mL) and the reaction stirred at RT for 18 h. The reaction mixture was diluted with EtOAc, washed with brine, dried ($Na_2SO_4$), filtered, and concentrated in vacuo to give the title compound as an off-white solid (30 mg, 100%). LCMS (Method G): $R_T$=3.81 min, $[M+H]^+$=512.

Step 3: 3-[4-(1-Amino-cyclobutyl)-phenyl]-4-oxo-2-phenyl-4H-chromene-8-carboxylic acid. trifluoro-acetic acid: 3-[4-(1-tert-Butoxycarbonylamino-cyclobutyl)-phenyl]-4-oxo-2-phenyl-4H-chromene-8-carboxylic acid (18 mg, 0.035 mmol) was treated with a solution of 25% TFA in DCM (4 mL) and stirred at RT for 1 h. The reaction mixture was diluted with toluene and concentrated in vacuo. The resultant residue was triturated with diethyl ether and DCM, and concentrated in vacuo to give the title compound as a light tan solid (10 mg, 54%). $^1$H NMR (400 MHz, DMSO-d6): δ 13.44 (bs, 1H), 8.44 (s, 3H), 8.28-8.23 (m, 2H), 7.57 (t, J=7.7 Hz, 1H), 7.48-7.36 (m, 5H), 7.33-7.27 (m, 4H), 2.64-2.53 (m, 2H), 2.51-2.42 (m, 2H), 2.18-2.05 (m, 1H), 1.85-1.73 (m, 1H). LCMS (Method E): $R_T$=2.89 min, $[M+H]^+$=412.

Example 108

3-[4-(1-Amino-cyclobutyl)-phenyl]-8-(3-fluoro-azetidin-1-ylmethyl)-2-phenyl-chromen-4-one

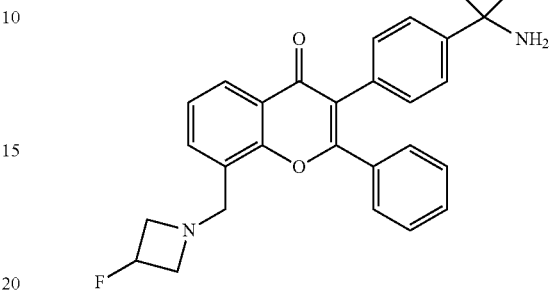

Step 1: {1-[4-(4-Oxo-2-phenyl-8-vinyl-4H-chromen-3-yl)-phenyl]-cyclobutyl}-carbamic acid tert-butyl ester: A solution of {1-[4-(8-bromo-4-oxo-2-phenyl-4H-chromen-3-yl)-phenyl]-cyclobutyl}-carbamic acid tert-butyl ester (100 mg, 0.183 mmol) in anhydrous toluene (3 mL) was degassed using argon. Tetrakis(triphenylphosphine)palladium(0) (21 mg, 0.018 mmol) and tributyl(vinyl)tin (0.080 mL, 0.274 mmol) were added. The reaction vial was degassed using argon and the reaction mixture was stirred at 90° C. for 2 h. The resultant mixture was allowed to cool to RT and subjected to flash chromatography ($SiO_2$, gradient 0 to 40% EtOAc in cyclohexane) to give the title compound as a gummy solid (81 mg, 90%). LCMS (Method G): $R_T$=4.73 min, $[M+H]^+$=494.

Step 2: {1-[4-(8-Formyl-4-oxo-2-phenyl-4H-chromen-3-yl)-phenyl]-cyclobutyl}-carbamic acid tert-butyl ester. A solution of {1-[4-(4-oxo-2-phenyl-8-vinyl-4H-chromen-3-yl)-phenyl]-cyclobutyl}-carbamic acid tert-butyl ester in MeOH (1 mL) and DCM (4 mL) was cooled with stirring to −78° C. Ozone was bubbled through the reaction mixture for 75 min with stirring, followed by air for 5 min with stirring. Dimethylsulfide (0.027 ml, 0.366 mmol) was added and the resultant mixture was allowed to warm to RT and stirred for 2 h. The solvent was removed by bubbling nitrogen through the reaction mixture. The residue was dissolved in EtOAc and washed with brine. The organic extracts were dried ($Na_2SO_4$), filtered and concentrated in vacuo to give the title compound as a gum (81 mg, 90%). LCMS (Method G): $R_T$=4.24 min, $[M+H]^+$=496.

Step 3: (1-{4-[8-(3-Fluoro-azetidin-1-ylmethyl)-4-oxo-2-phenyl-4H-chromen-3-yl]-phenyl}-cyclobutyl)-carbamic acid tert-butyl ester: A solution of {1-[4-(8-formyl-4-oxo-2-phenyl-4H-chromen-3-yl)-phenyl]-cyclobutyl}-carbamic acid tert-butyl ester (81 mg, 0.163 mmol) and 3-fluoroazetidine hydrochloride (23 mg, 0.245 mmol) in dichloroethane (5 mL) was stirred for 10 min. Sodium triacetoxyborohydride (87 mg, 0.409 mmol) was added and the reaction stirred at RT for 18 h. The reaction mixture was quenched with saturated aqueous sodium hydrogen carbonate solution, diluted with DCM, filtered through a phase separation cartridge and concentrated in vacuo. The resultant residue was subjected to flash chromatography ($SiO_2$, gradient 0 to 50% EtOAc in DCM) to give the title compound as a gummy solid. LCMS (Method G): $R_T$=2.71 min, $[M+H]^+$=555.

Step 4: 3-[4-(1-Amino-cyclobutyl)-phenyl]-8-(3-fluoro-azetidin-1-ylmethyl)-2-phenyl-chromen-4-one: Following the procedure of 3-[4-(1-amino-cyclobutyl)-phenyl]-6-fluoro-2-phenyl-chromen-4-one, (1-{4-[8-(3-fluoro-azetidin-1-ylmethyl)-4-oxo-2-phenyl-4H-chromen-3-yl]-phenyl}-cyclobutyl)-carbamic acid tert-butyl ester was treated with TFA. The resultant free base was subjected to flash chromatography (SiO$_2$, gradient 0 to 15% MeOH in DCM) to afford the title compound as a white solid (13 mg, 57%). $^1$H NMR (400 MHz, DMSO-d6): δ 7.97 (dd, J=8.0 and 1.7 Hz, 1H), 7.74 (dd, J=7.1 and 1.4 Hz, 1H), 7.47-7.28 (m, 8H), 7.08 (d, J=8.2 Hz, 2H), 5.27-5.06 (m, 1H), 3.94 (s, 2H), 3.65-3.56 (m, 2H), 3.29-3.16 (m, 2H), 2.36-2.27 (m, 2H), 2.11-1.87 (m, 5H), 1.65-1.54 (m, 1H). LCMS (Method E): R$_T$=2.31 min, [M+H]$^+$=455.

Example 109

8-(4-(1-aminocyclobutyl)phenyl)-9-phenylchromeno[7,8-b][1,4]oxazine-2,7(1H,3H)-dione

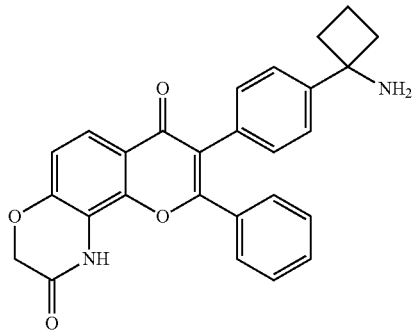 [SMILES: NC1(c2ccc(-c3c(-c4ccccc4)oc4c5c(ccc4c3=O)OCC(=O)N5)cc2)CCC1]

Step 1: tert-butyl 1-(4-(2,7-dioxo-9-phenyl-1,2,3,7-tetrahydro chromeno[7,8-b][1,4]oxazin-8-yl)phenyl)cyclobutylcarbamate: Pd$_2$(dba)$_3$ (1.48 mg, 1.61 μmol), Xantphos (2.80 mg, 4.84 μmol) and cesium carbonate (78.9 mg, 0.242 mmol) were added to a pre-degassed solution of tert-butyl 1-(4-(7-(2-amino-2-oxoethoxy)-8-bromo-4-oxo-2-phenyl-4H-chromen-3-yl)phenyl)cyclobutyl carbamate (50.0 mg, 0.081 mmol) in 1,4-dioxane (1.0 ml)/water (0.1 ml) in a microwave vial. The vessel was sealed and irradiated at 120° C. for 20 minutes (CEM Explorer24/Discover). LCMS (Method J) showed around 30% of starting material remaining. It required further addition of water (0.1 ml) and further microwave irradiation at 120° C. for 20 minutes before almost complete conversion observed. The solvents were removed in vacuo and the remaining residue was partitioned between DCM and water, separated, extracted (2×DCM), dried (Phase Separator), solvents removed in vacuo, and subjected to flash chromatography (SiO$_2$, gradient 0 to 20% EtOAc in cyclohexane) to give the title compound as a pale yellow solid (23.6 mg, 0.044 mmol, 54% yield). LCMS (Method J): R$_T$=1.493 min, [M+Na]$^+$=561 [M–H]$^-$=537.

Step 2: 8-(4-(1-Aminocyclobutyl)phenyl)-9-phenyl-chromeno[7,8-b][1,4]oxazine-2,7(1H,3H)-dione, HCl salt: 4 M HCl in 1,4-dioxane (2.0 ml, 8.00 mmol) was added to a stirred solution of tert-butyl 1-(4-(2,7-dioxo-9-phenyl-1,2,3,7-tetrahydrochromeno[7,8-b][1,4]oxazin-8-yl)phenyl)cyclobutylcarbamate (23.6 mg, 0.044 mmol) in THF (1.0 ml). After 1 hour, analysis by LCMS indicated that there was no residual starting material. Diethyl ether (2.0 ml) was added and the ppt that formed was triturated using diethyl ether (3×1.0 ml), the residual solvents were removed in vacuo and the remaining residue was freeze-dried to the HCl salt of the title compound (13.3 mg, 0.028 mmol, 64% yield) as a pale yellow solid. $^1$H NMR (500 MHz, CDCl$_3$): δ 7.88 (d, 1H), 7.56 (d, 2H), 7.49 (d, 2H), 7.44 (t, 1H), 7.39-7.34 (m, 4H), 7.20 (d, 1H), 4.82 (s, 2H), 2.85-2.77 (m, 2H), 2.65-2.57 (m, 2H), 2.32-2.22 (m, 1H), 2.05-1.95 (m, 1H). LCMS (Method J): R$_T$ 0.774 min, [M–H]$^-$=437.

Example 110

2-(3-(4-(1-aminocyclobutyl)phenyl)-8-bromo-4-oxo-2-phenyl-4H-chromen-7-yloxy)acetonitrile

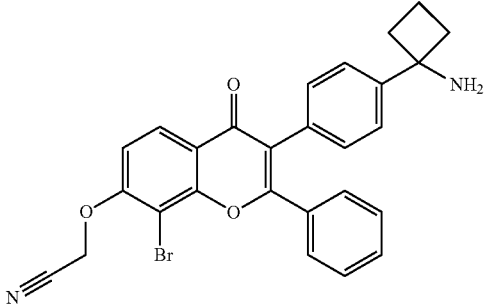 [SMILES: N#CCOc1ccc2c(=O)c(-c3ccc(C4(N)CCC4)cc3)c(-c3ccccc3)oc2c1Br]

2-Chloroacetamide (9.98 mg, 0.107 mmol) was added to a suspension of tert-butyl 1-(4-(8-bromo-7-hydroxy-4-oxo-2-phenyl-4H-chromen-3-yl)phenyl)cyclobutylcarbamate (50.0 mg, 0.089 mmol) and potassium carbonate (24.6 mg, 0.178 mmol) in Acetone (1.0 ml) at 60° C. under an atmosphere of nitrogen. After 16 hours, analysis by LCMS showed no reaction. The temperature was increased to 80° C. After a further 4 hours, analysis by LCMS (Method J) appeared to show no reaction and therefore catalytic TBAI (10 mg) was added and DMF (1.0 ml). The reaction mixture was irradiated at 120° C. for 20 minutes (CEM Explorer/Discover). LCMS showed complete reaction. The reaction mixture was partitioned between EtOAc and 1:1, water/brine, separated, dried (Phase Separator), solvents removed in vacuo and the remaining residue purified by Biotage (20-50% EtOAc in cyclohexane) to give a white solid (36.2 mg, 0.060 mmol, 68% yield) that was dissolved in N-methyl-2-pyrrolidinone (1.0 ml) in a microwave vial. N$_1$,N$_2$-Dimethylethane-1,2-diamine (5.2 mg, 0.058 mmol), copper(I)iodide (11.1 mg, 0.058 mmol) and potassium carbonate (16.6 mg, 0.120 mmol) were added. The vessel was sealed and irradiated at 130° C. for 20 minutes (CEM Explorer/Discover). Analysis by LCMS showed starting material only and therefore the reaction was rerun under microwave conditions at 150° C. for 60 mins. Analysis by LCMS showed that none of the cyclised product was obtained, however, the deprotected nitrile (due to dehydration of the amide) was observed. The reaction mixture was partitioned between ethyl acetate and 1:1 water/brine, separated, dried (Phase Separator), the solvents were removed in vacuo and the remaining residue was subjected to flash chromatography (SiO$_2$, gradient 0 to 5% MeOH in EtOAc) to give the title compound as the free base. The residue was stirred in 2 M HCl in diethyl ether at 0° C. The precipitate that formed was triturated with diethyl ether and freeze dried to give the HCl salt of the compound (5.1 mg, 9.48 μmol, 16%) as a pale yellow solid. $^1$H NMR (500 MHz, CDCl$_3$): δ 7.91 (d, 1H), 7.53-7.47 (m, 4H), 7.41 (t, 1H), 7.37-7.30 (m, 4H), 6.97 (d, 1H), 4.87 (CH$_2$CN o/l with H$_2$O), 2.83-2.75 (m, 2H), 2.62-

2.54 (m, 2H), 2.30-2.20 (m, 1H), 2.03-1.93 (m, 1H). LCMS (Method J): R$_T$=0.933 min, [M−CN−NH$_2$+3H]$^+$=461/463.

Example 111

2-(7-(4-(1-aminocyclobutyl)phenyl)-6-oxo-8-phenylpyrano[3,2-g]indazol-1(6H)-yl)acetonitrile

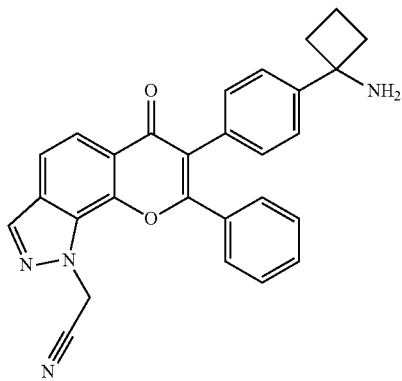 [SMILES: N#CCn1ncc2ccc3c(=O)c(-c4ccc(C5(N)CCC5)cc4)c(-c4ccccc4)oc3c21]

Step 1: 2-(7-iodo-6-oxo-8-phenylpyrano[3,2-g]indazol-1(6H)-yl)acetonitrile: To a solution of 7-iodo-8-phenylpyrano[3,2-g]indazol-6(1H)-one (350 mg, 0.903 mmol) in DMF (10 mL) was added potassium carbonate (415 mg, 3 mmol) and the reaction stirred at RT. After 5 minutes, bromoacetonitrile (162 mg, 1.353 mmol) was added and the reaction stirred at RT for 2 h. The reaction mixture was partitioned between EtOAc and water. The resulting biphasic mixture was separated and the aqueous phase was extracted with EtOAc. The combined organic phase was washed with water and brine, dried (Na$_2$SO$_4$), filtered, and concentrated in vacuo. The resultant residue was subjected to flash chromatography (SiO$_2$, gradient 0 to 70% EtOAc in cyclohexane) to afford the title compound (116 mg, 30%), $^1$H NMR (500 MHz, CDCl$_3$): δ 8.18 (br s, 1H), 8.06 (d, J=8.6 Hz, 1H), 7.90-7.88 (m, 2H), 7.75 (d, J=8.3 Hz, 1H), 7.64-7.60 (m, 3H), 5.52 (s, 2H). LCMS (Method J) R$_T$=1.29 min, [M+H]$^+$=428.

Step 2: tert-butyl (1-(4-(1-(cyanomethyl)-6-oxo-8-phenyl-1,6-dihydropyrano[3,2-g]indazol-7-yl)phenyl)cyclobutyl)carbamate: In a 25 mL round bottom flask were taken 7-iodo-8-phenylpyrano[3,2-g]indazol-6(1H)-one (0.05 g, 0.117 mmol), tert-butyl (1-(4-(4,4,5,5-tetramethyl-1,3,2-dioxaborolan-2-yl)phenyl)cyclobutyl)carbamate (56.0 mg, 0.15 mmol), sodium carbonate (18.61 mg, 0.176 mmol) and PdCl$_2$(dppf) (10.98 mg, 0.015 mmol) in dioxane-water. The reaction mixture was purged using nitrogen and heated conventionally to 70° C. for 2 h. The mixture was partitioned between water and EtOAc. The resulting biphasic mixture was separated and the aqueous phase was extracted with ethyl acetate. The combined organic extracts were washed with brine (10 mL), dried (Na$_2$SO$_4$), filtered, and concentrated in vacuo. The resultant residue was subjected to flash chromatography (SiO$_2$, gradient 0 to 60% ethyl acetate in cyclohexane) to afford the title compound (40 mg, 62%). $^1$H NMR (500 MHz, CDCl$_3$): δ 8.19 (br s, 1H), 8.06 (d, J=8.6 Hz, 1H), 7.71 (d, J=8.3 Hz, 1H), 7.50-7.47 (m, 2H), 7.40-7.30 (m, 5H), 7.25-7.20 (m, 2H), 5.65 (s, 2H) 5.12 (s, 1H, NH) 2.64-2.31 (m, 4H), 2.14-2.00 (m, 1H), 1.89-1.77 (m, 1H), 1.48-1.18 (m, 9H). LCMS (Method J) R$_T$=1.574 min, [M+H]$^+$=491.

Step 3: 2-(7-(4-(1-aminocyclobutyl)phenyl)-6-oxo-8-phenylpyrano[3,2-g]indazol-1(6H)-yl)acetonitrile: tert-Butyl (1-(4-(1-(cyanomethyl)-6-oxo-8-phenyl-1,6-dihydropyrano[3,2-g]indazol-7-yl)phenyl)cyclobutyl)carbamate (20 mg, 0.037 mmol) was loaded in a 1 g SCX-2 cartridge column preconditioned with methanol (2×1 mL). The compound was loaded to the column using 1 mL of methanol. After 1 h the column was washed with 3×1 mL of methanol. The product was eluted with 7 N ammonia in methanol (2×1 mL). The solvent was evaporated to afford the title compound (6 mg, 49%). Residual starting material was recovered from MeOH washed (10 mg). $^1$H NMR (500 MHz, MeOD): δ 8.19 (br s, 1H), 8.06 (d, J=8.6 Hz, 1H), 7.71 (d, J=8.3 Hz, 1H), 7.50-7.47 (m, 2H), 7.40-7.30 (m, 5H), 7.25-7.20 (m, 2H), 5.65 (s, 2H) 5.12 (s, 1H, NH) 2.64-2.56 (m, 4H), 2.30-2.22 (m, 1H), 2.04-1.94 (m, 1H). LCMS (Method J): R$_T$=0.92 min, [M+H]$^+$=448.

Example 112

8-(4-(1-aminocyclobutyl)phenyl)-4-methyl-9-phenylchromeno[8,7-b][1,4]oxazine-3,7(2H,4H)-dione

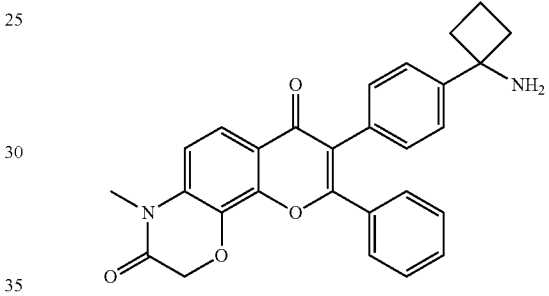

Step 1: {1-[4-(2,8-Dioxo-6-phenyl-1,2,3,8-tetrahydro-4,5-dioxa-1-aza-phenanthren-7-yl)-phenyl]cyclobutyl}-carbamic acid tert-butyl ester: Following the procedure used to prepare tert-butyl (1-(4-(1-(cyanomethyl)-6-oxo-8-phenyl-1,6-dihydropyrano[3,2-g]indazol-7-yl)phenyl)cyclobutyl)carbamate reacted 8-iodo-9-phenylchromeno[8,7-b][1,4]oxazine-3,7(2H,4H)-dione (150 mg, 0.358 mmol), tert-butyl 1-(4-(4,4,5,5-tetramethyl-1,3,2-dioxaborolan-2-yl)phenyl)cyclobutylcarbamate (170 mg, 0.455 mmol) was reacted to give the title compound (100 mg, 52%). LCMS (Method I): R$_T$=6.87 min, [M+H]$^+$=539.

Step 2: tert-butyl (1-(4-(4-methyl-3,7-dioxo-9-phenyl-2,3,4,7-tetrahydrochromeno[8,7-b][1,4]oxazin-8-yl)phenyl)cyclobutyl) carbamate: tert-Butyl 1-(4-(3,7-dioxo-9-phenyl-2,3,4,7-tetrahydro chromeno[8,7-b][1,4]oxazin-8-yl)phenyl)cyclobutylcarbamate (90 mg, 0.167 mmol) was reacted with iodomethane (71.2 mg, 0.501 mmol) and potassium carbonate (69.3 mg, 0.501 mmol) in MeCN (5 ml), at 50° C. for 2 h. The product was extracted with ethyl acetate, washed with water, dried over anhydrous sodium sulphate and evaporated. Purification by column chromatography (SiO$_2$) afforded 40 mg (44%) of the title compound. LCMS (Method J) R$_T$=1.57, M+H 497 (-tBu).

Step 3: 8-(4-(1-aminocyclobutyl)phenyl)-4-methyl-9-phenylchromeno[8,7-b][1,4]oxazine-3,7(2H,4H)-dione: To a solution of tert-butyl 1-(4-(4-methyl-3,7-dioxo-9-phenyl-2,3,4,7-tetrahydro chromeno[8,7-b][1,4]oxazin-8-yl)phenyl) cyclobutylcarbamate (40 mg, 0.072 mmol) in DCM (2 mL) was added 2 M HCl in diethyl ether (2 mL) and stirred at RT for 2 h. The solvents were evaporated and the residue was triturated using DCM. The solid was filtered and washed with DCM (3×1 mL) to give the title compound as the HCl salt.

¹H NMR (500 MHz, CD₃OD): δ 7.89 (d, J=8.8 Hz, 1H), 7.50-7.45 (m, 4H), 7.43-7.40 (m, 1H), 7.37-7.30 (m, 5H), 4.88 (s, 2H), 3.50 (s, 3H), 2.84-2.77 (m, 2H), 2.64-2.57 (m, 2H), 2.31-2.22 (m, 1H), 2.04-1.98 (m, 1H). LCMS (Method J): $R_T$=0.882 min, [M+H]⁺=454.

Example 113

3,8-bis(4-(1-aminocyclobutyl)phenyl)-2-phenyl-4H-pyrano[2,3-c]pyridin-4-one

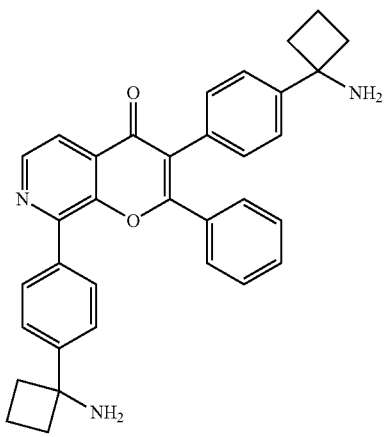 [SMILES: NC1(c2ccc(-c3c(-c4ccccc4)oc4c(-c5ccc(C6(N)CCC6)cc5)nccc4c3=O)cc2)CCC1]

Step 1: di-tert-butyl (((4-oxo-2-phenyl-4H-pyrano[2,3-c]pyridine-3,8-diyl)bis(4,1-phenylene))bis(cyclobutane-1,1-diyl))dicarbamate: Following the procedure used to prepare 3-(4-(1-aminocyclobutyl)phenyl)-8-(1-isobutyl-1H-pyrazol-4-yl)-2-phenyl-4H-pyrano[2,3-c]pyridin-4-one, 8-chloro-3-iodo-2-phenyl-4H-pyrano[2,3-c]pyridin-4-one was reacted with tert-butyl (1-(4-(4,4,5,5-tetramethyl-1,3,2-dioxaborolan-2-yl)phenyl)cyclobutyl)carbamate to give the title compound (60 mg, 6%). LCMS (Method J): $R_T$=1.9 min, [M+H]⁺=658 (-ᵗBu).

Step 2: 3,8-bis(4-(1-aminocyclobutyl)phenyl)-2-phenyl-4H-pyrano[2,3-c]pyridin-4-one: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, di-tert-butyl (((4-oxo-2-phenyl-4H-pyrano[2,3-c]pyridine-3,8-diyl)bis(4,1-phenylene))bis(cyclobutane-1,1-diyl))dicarbamate was reacted with 4 M HCl in 1,4-dioxane to give the title compound as the HCl salt (30 mg, 69%). ¹H NMR (500 MHz, CD₃OD): δ 8.85-8.80 (m, 1H), 8.38-8.32 (m, 1H), 8.25-8.18 (m, 2H), 7.85-7.80 (m, 2H), 7.55-7.52 (m, 2H), 7.45-7.40 (m, 5H), 7.36-7.30 (m, 2H), 2.90-2.62 (m, 8H), 2.38-2.25 (m, 2H), 2.08-1.95 (m, 2H), LCMS (Method J): $R_T$=0.686 min, [M+H]⁺=514.

Example 114

3-(4-(1-aminocyclobutyl)phenyl)-8-(1H-imidazol-1-yl)-2-phenyl-4H-pyrano[2,3-c]pyridin-4-one

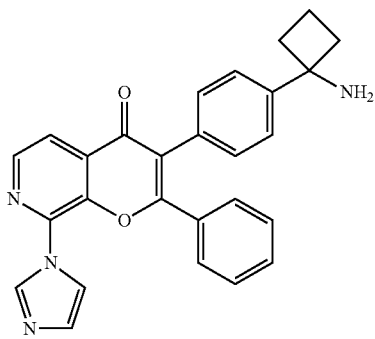 [SMILES: NC1(c2ccc(-c3c(-c4ccccc4)oc4c(-n5ccnc5)nccc4c3=O)cc2)CCC1]

Step 1: tert-butyl (1-(4-(8-(1H-imidazol-1-yl)-4-oxo-2-phenyl-4H-pyrano[2,3-c]pyridin-3-yl)phenyl)cyclobutyl) carbamate: tert-Butyl (1-(4-(8-chloro-4-oxo-2-phenyl-4H-pyrano[2,3-c]pyridin-3-yl)phenyl)cyclobutyl)carbamate (63 mg, 0.115 mmol), imidazole (11 mg, 0.161 mmol), cesium carbonate (75 mg, 0.23 mmol) and copper (II) iodide (5 mg, 0.023 mmol) were dissolved in DMF (1 mL) in a microwave vial. The vial was sealed, evacuated and flushed twice with nitrogen. The reaction mixture was heated conventionally at 120° C. for 72 h. After cooling to RT, the resultant mixture was diluted with EtOAc, washed with water, dried (Na₂SO₄), filtered and concentrated in vacuo. The resultant residue was subjected to flash chromatography (SiO₂, 1:1 ethyl acetate/hexane) to give the title compound (20 mg, 24%). LCMS (Method I): $R_T$=5.89 min, [M+H]⁺=535.

Step 2: 3-(4-(1-aminocyclobutyl)phenyl)-8-(1H-imidazol-1-yl)-2-phenyl-4H-pyrano[2,3-c]pyridin-4-one: tert-Butyl 1-(4-(8-(1H-imidazol-1-yl)-4-oxo-2-phenyl-4H-pyrano[2,3-c]pyridin-3-yl)phenyl)cyclobutylcarbamate (15 mg, 0.028 mmol) was dissolved in DCM (2 mL). 2 M HCl in diethyl ether (2 mL) was added and the reaction mixture was stirred at RT. After 16 hours, the solvent was evaporated. The product was washed several times with DCM and diethyl ether. The product was dissolved in methanol and loaded onto an SCX-2 cartridge. The cartridge was washed repeatedly with methanol before eluting with 2 M ammonia in methanol solution. The eluent was collected and concentrated in vacuo. The resulting residue was dissolved in a mixture of MeOH (7 mL), water (7 mL and 1 M HCl (0.6 mL) and chromatographed on a 5 g C18 cartridge {gradient 10 to 50% MeOH in water+1 M HCl (60 µL in each 10 mL of eluent)} to give the title compound as the HCl salt (5 mg, 41%). ¹H NMR (500 MHz, CD₃OD): δ 9.30 (bs, 1H), 8.68 (d, J=8.3 Hz, 1H), 8.24 (d, J=8.2 Hz, 1H), 7.97 (s, 2H), 7.69-7.37 (m, 9H), 5.5 (s, 2H, NH), 2.85-2.80 (m, 2H), 2.65-2.60 (m, 2H), 2.30-2.25 (m, 1H), 2.05-1.96 (m, 1H). LCMS (Method I): $R_T$=3.34 min, [M+H]⁺=435.

Example 115

3-(4-(1-aminocyclobutyl)phenyl)-2-phenyl-8-(1,3,5-trimethyl-1H-pyrazol-4-yl)-4H-pyrano[2,3-c]pyridin-4-one

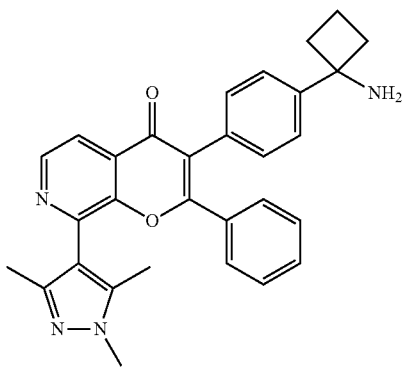 [SMILES: Cc1nn(C)c(C)c1-c1nccc2c(=O)c(-c3ccc(C4(N)CCC4)cc3)c(-c3ccccc3)oc12]

Step 1: tert-Butyl (1-(4-(4-oxo-2-phenyl-8-(1,3,5-trimethyl-1H-pyrazol-4-yl)-4H-pyrano[2,3-c]pyridin-3-yl)phenyl)cyclobutyl)carbamate: In a microwave vial tert-butyl 1-(4-(8-chloro-4-oxo-2-phenyl-4H-pyrano[2,3-c]pyridin-3-yl)phenyl)cyclobutyl carbamate (50.3 mg, 0.100 mmol), sodium carbonate (37.1 mg, 0.35 mmol) and 1,3,5-trimethyl-4-(4,4,5,5-tetramethyl-1,3,2-dioxaborolan-2-yl)-1H-pyrazole (35.4 mg, 0.150 mmol) were dissolved in DME (3 mL) and water (1 mL). The reaction mixture was purged with nitrogen and tetrakis (11.56 mg, 0.01 mmol) was added under nitrogen. The reaction mixture was heated at 140° C. for 1 h in the microwave. The crude product was extracted with ethyl acetate, washed with water, dried over anhydrous sodium sulphate and evaporated. The crude product was purified by column chromatography (SiO$_2$), using 1:1 hex-ethylacetate to 100% ethyl acetate to give the title compound (38 mg, 66%) LCMS (Method I): R$_T$=6.93 min, [M+H]$^+$=577.

Step 2: 3-(4-(1-aminocyclobutyl)phenyl)-2-phenyl-8-(1,3,5-trimethyl-1H-pyrazol-4-yl)-4H-pyrano[2,3-c]pyridin-4-one: Following the procedure used to prepare 3-(4-(1-aminocyclobutyl)phenyl)-8-(1H-imidazol-1-yl)-2-phenyl-4H-pyrano[2,3-c]pyridin-4-one, tert-Butyl 1-(4-(4-oxo-2-phenyl-8-(1,3,5-trimethyl-1H-pyrazol-4-yl)-4H-pyrano[2,3-c]pyridin-3-yl)phenyl)cyclobutylcarbamate (35 mg, 0.061 mmol) was reacted to give the title compound as the HCl salt (14 mg, 46%). $^1$H NMR (500 MHz, CD$_3$OD): δ 8.81 (d, J=8.2 Hz, 1H), 8.35 (d, J=8.3 Hz, 1H), 7.60-7.31 (m, 11H), 3.88 (s, 3H), 2.85-2.80 (m, 2H), 2.65-2.60 (m, 2H), 2.38 (s, 3H), 2.30 (s, 3H), 2.29-2.20 (m, 1H), 1.81-1.69 (m, 1H). LCMS (Method I): R$_T$=4.93 min, [M+H]$^+$=477.

Example 116

3-(4-(1-aminocyclobutyl)phenyl)-8-(1,5-dimethyl-1H-pyrazol-4-yl)-2-phenyl-4H-pyrano[2,3-c]pyridin-4-one

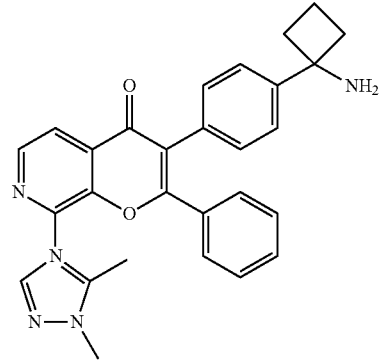

Step 1: tert-butyl (1-(4-(8-(1,5-dimethyl-1H-pyrazol-4-yl)-4-oxo-2-phenyl-4H-pyrano[2,3-c]pyridin-3-yl)phenyl)cyclobutyl)carbamate: Following the procedure used to prepare tert-butyl (1-(4-(4-oxo-2-phenyl-8-(1,3,5-trimethyl-1H-pyrazol-4-yl)-4H-pyrano[2,3-c]pyridin-3-yl)phenyl)cyclobutyl)carbamate, tert-butyl (1-(4-(8-chloro-4-oxo-2-phenyl-4H-pyrano[2,3-c]pyridin-3-yl)phenyl)cyclobutyl)carbamate was reacted with 1,5-dimethyl-4-(4,4,5,5-tetramethyl-1,3,2-dioxaborolan-2-yl)-1H-pyrazole to give the title compound (46 mg, 82%). LCMS (Method I): R$_T$=7.35 min, [M+H]$^+$=563.

Step 2: 3-(4-(1-aminocyclobutyl)phenyl)-8-(1,5-dimethyl-1H-pyrazol-4-yl)-2-phenyl-4H-pyrano[2,3-c]pyridin-4-one hydrochloride: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl 1-(4-(8-(1,5-dimethyl-1H-pyrazol-4-yl)-4-oxo-2-phenyl-4H-pyrano[2,3-c]pyridin-3-yl)phenyl)cyclobutylcarbamate was reacted to give the title compound (15 mg, 46%) as an HCl salt. $^1$H NMR (500 MHz, CD$_3$OD): δ 8.78 (d, J=8.2 Hz, 1H), 8.25 (bs, 1H) 8.15 (d, J=8.3 Hz, 1H), 7.60-7.35 (m, 11H), 3.91 (s, 3H), 2.80-2.78 (m, 2H), 2.65-2.60 (m, 2H), 2.55 (s, 3H), 2.29-2.20 (m, 1H), 2.01-1.91 (m, 1H). LCMS (Method I): R$_T$=4.82 min, [M+F1]$^+$=463.

Example 117

3-(4-(1-aminocyclobutyl)phenyl)-8-(1-isobutyl-1H-pyrazol-4-0)-2-phenyl-4H-pyrano[2,3-c]pyridin-4-one

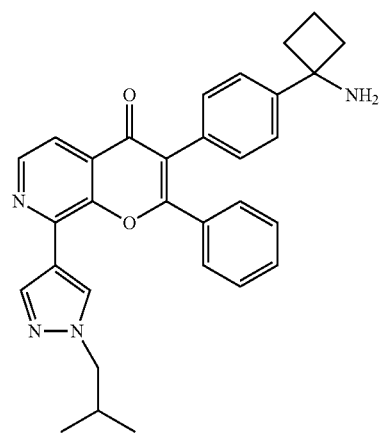 [SMILES: CC(C)Cn1cc(-c2nccc3c(=O)c(-c4ccc(C5(N)CCC5)cc4)c(-c4ccccc4)oc23)cn1]

Step 1: tert-butyl 1-(4-(8-(1-isobutyl-1H-pyrazol-4-yl)-4-oxo-2-phenyl-4H-pyrano[2,3-c]pyridin-3-yl)phenyl)cyclobutylcarbamate: tert-Butyl 1-(4-(8-chloro-4-oxo-2-phenyl-4H-pyrano[2,3-c]pyridin-3-yl)phenyl)cyclobutylcarbamate (0.050 g, 0.1 mmol), sodium carbonate (0.032 g, 0.3 mmol) and 1-isobutyl-4-(4,4,5,5-tetramethyl-1,3,2-dioxaborolan-2-yl)-1H-pyrazole (0.025 g, 0.100 mmol) were dissolved in dioxane (5 mL) and water (1 mL). The reaction mixture was degassed, PdCl$_2$(dppf)-CH$_2$Cl$_2$ adduct (0.012 g, 0.0150 mmol) added and heated at 80° C. After 16 hours, the reaction mixture was filtered through Celite®, washed with ethyl acetate, evaporated and purified by column chromatography using 0-40% ethyl acetate in hexane to give the title compound (40 mg, 68%). LC-MS (Method I): $R_T$=8.27 min, [M+H]$^+$=591.

Step 2: 3-(4-(1-aminocyclobutyl)phenyl)-8-(1-isobutyl-1H-pyrazol-4-yl)-2-phenyl-4H-pyrano[2,3-c]pyridin-4-one: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl 1-(4-(8-(1-isobutyl-1H-pyrazol-4-yl)-4-oxo-2-phenyl-4H-pyrano[2,3-c]pyridin-3-yl)phenyl)cyclobutylcarbamate was reacted to give the title compound as the HCl salt (15 mg, 63%). $^1$H NMR (500 MHz, CD$_3$OD): δ 8.63 (d, J=8.2 Hz, 1H), 8.35 (s, 1H), 8.25 (s, 1H), 7.95 (d, J=8.3 Hz, 1H), 7.55-7.35 (m, 11H), 4.01 (d, 2H), 2.75-2.70 (m, 2H), 2.62-2.55 (m, 2H), 2.28-2.19 (m, 2H), 2.01-1.91 (m, 1H), 0.95 (d, 6H). LCMS (Method I): $R_T$=4.86 min, [M+2]$^+$=492.

Example 118

3-(4-(1-aminocyclobutyl)phenyl)-8-(2-methoxyphenyl)-2-phenyl-4H-pyrano[2,3-c]pyridin-4-one

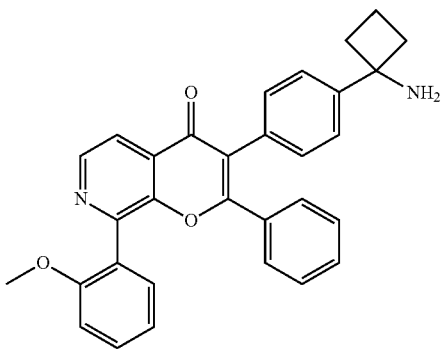 [SMILES: COc1ccccc1-c1nccc2c(=O)c(-c3ccc(C4(N)CCC4)cc3)c(-c3ccccc3)oc12]

Step 1: tert-Butyl 1-(4-(8-(2-methoxyphenyl)-4-oxo-2-phenyl-4H-pyrano[2,3-c]pyridin-3-yl)phenyl)cyclobutylcarbamate: Following the procedure used to prepare 3-(4-(1-aminocyclobutyl)phenyl)-8-(1-isobutyl-1H-pyrazol-4-yl)-2-phenyl-4H-pyrano[2,3-c]pyridin-4-one, tert-butyl 1-(4-(8-chloro-4-oxo-2-phenyl-4H-pyrano[2,3-c]pyridin-3-yl)phenyl)cyclobutyl carbamate was reacted with 2-methoxy phenylboronic acid to give the title compound (40 mg, 70%). LCMS (Method I): $R_T$=7.97 min, [M+H]$^+$=575.

Step 2: 3-(4-(1-aminocyclobutyl)phenyl)-8-(2-methoxyphenyl)-2-phenyl-4H-pyrano[2,3-c]pyridin-4-one: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl 1-(4-(8-(2-methoxyphenyl)-4-oxo-2-phenyl-4H-pyrano[2,3-c]pyridin-3-yl)phenyl)cyclobutylcarbamate was reacted to give the title compound as an HCl salt (15 mg, 62%). $^1$H NMR (500 MHz, CD$_3$OD): δ 8.78 (d, J=8.2 Hz, 1H), 8.32 (d, J=8.3 Hz, 1H), 7.65-7.15 (m, 11H), 3.80 (s, 2H), 3.61 (s, 1H), 2.85-2.75 (m, 2H), 2.62-2.55 (m, 2H), 2.28-2.20 (m, 1H), 2.05-1.91 (m, 1H). LC-MS (Method I): $R_T$=4.68 min, [M+2]$^+$=476.

Example 119

3-(4-(1-aminocyclobutyl)phenyl)-8-(2-(methylsulfonyl)phenyl)-2-phenyl-4H-pyrano[2,3-c]pyridin-4-one

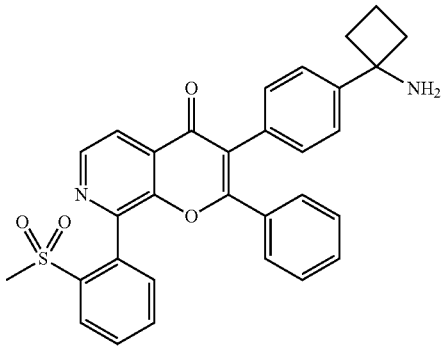 [SMILES: CS(=O)(=O)c1ccccc1-c1nccc2c(=O)c(-c3ccc(C4(N)CCC4)cc3)c(-c3ccccc3)oc12]

Step 1: tert-butyl (1-(4-(8-(2-(methylsulfonyl)phenyl)-4-oxo-2-phenyl-4H-pyrano[2,3-c]pyridin-3-yl)phenyl)cyclobutyl)carbamate: Following the procedure used to prepare 3-(4-(1-aminocyclobutyl)phenyl)-8-(1-isobutyl-1H-pyrazol-4-yl)-2-phenyl-4H-pyrano[2,3-c]pyridin-4-one, tert-butyl (1-(4-(8-chloro-4-oxo-2-phenyl-4H-pyrano[2,3-c]pyridin-3-yl)phenyl)cyclobutyl)carbamate was reacted with (2-(methylsulfonyl)phenyl)boronic acid to give the title compound (40 mg, 62%). LCMS (Method I): $R_T$=7.31 min, [M+2]$^+$=567 (-tBu).

Step 2: 3-(4-(1-aminocyclobutyl)phenyl)-8-(2-(methylsulfonyl)phenyl)-2-phenyl-4H-pyrano[2,3-c]pyridin-4-one: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl 1-(4-(8-(2-(methylsulfonyl)phenyl)-4-oxo-2-phenyl-4H-pyrano[2,3-c]pyridin-3-yl)phenyl)cyclobutylcarbamate was reacted to give the title compound as the HCl salt. (15 mg, 60%). $^1$H NMR (500 MHz, CD$_3$OD): δ 8.72 (d, J=8.2 Hz, 1H), 8.21 (m, 1H), 8.15 (d, J=8.3 Hz, 1H), 7.95 (m, 2H), 7.90-7.78 (m, 1H), 7.70-7.61 (m, 4H), 7.45-7.40 (m, 2H), 7.35-7.30 (m, 2H), 7.15-7.05 (m, 1H), 3.65 (s, 3H), 2.85-2.75 (m, 2H), 2.62-2.55 (m, 2H), 2.25-2.19 (m, 1H), 2.05-1.95 (m, 1H). LC-MS (Method I): $R_T$=0.52 min, [M+2]$^+$=524.

Example 120

3-(4-(1-aminocyclobutyl)phenyl)-8-methyl-2-phenyl-4H-pyrano[2,3c]pyridin-4-one

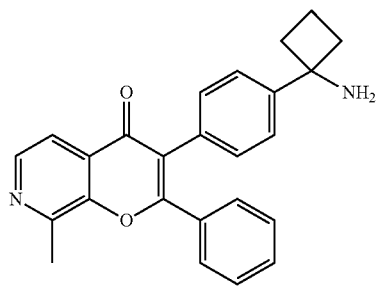 [SMILES: Cc1nccc2c(=O)c(-c3ccc(C4(N)CCC4)cc3)c(-c3ccccc3)oc12]

Step 1: tert-butyl 1-(4-(8-methyl-4-oxo-2-phenyl-4H-pyrano[2,3-c]pyridin-3-yl)phenyl)cyclobutylcarbamate: tert-Butyl 1-(4-(8-chloro-4-oxo-2-phenyl-4H-pyrano[2,3-c]pyridin-3-yl)phenyl)cyclobutylcarbamate (50.3 mg, 0.1 mmol) was dissolved in 1,4-dioxane (5 mL). Methyl boronic acid (8.98 mg, 0.15 mmol) and potassium carbonate (41.5 mg, 0.3 mmol) were added. The solution was degassed, flushing with nitrogen tetrakis (11.56 mg, 0.01 mmol) was added and the solution was refluxed for 24 h. The reaction mixture was filtered, washed with ethyl acetate and evaporated. The crude product was purified by column chromatography using hex and ethyl acetate (0-65%) to give the title compound (20 mg, 42%). LCMS (Method I): $R_T$=7.40 min, [M+H]$^+$=483.

Step 2: 3-(4-(1-aminocyclobutyl)phenyl)-8-methyl-2-phenyl-4H-pyrano[2,3-c]pyridin-4-one: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl 1-(4-(8-methyl-4-oxo-2-phenyl-4H-pyrano[2,3-c]pyridin-3-yl)phenyl)cyclobutylcarbamate was reacted to give the title compound as the HCl salt. (10 mg, 77%). $^1$H NMR (500 MHz, CD$_3$OD): δ 8.65 (d, J=8.2 Hz, 1H), 8.32 (d, J=8.3 Hz, 1H), 7.60-7.32 (m, 11H), 3.05 (s, 3H), 2.85-2.75 (m, 2H), 2.62-2.55 (m, 2H), 2.28-2.21 (m, 1H), 2.05-1.95 (m, 1H). LCMS (Method I): $R_T$=3.52 min, [M+H]$^+$=419.

Example 121

2-(3-(4-(1-aminocyclobutyl)phenyl)-4-oxo-2-phenyl-4H-pyrano[2,3-c]pyridin-8-yl)-6-fluorobenzoic acid

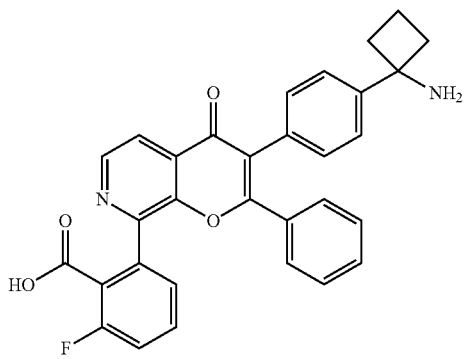 [SMILES: NC1(c2ccc(-c3c(-c4ccccc4)oc4c(-c5cccc(F)c5C(=O)O)nccc4c3=O)cc2)CCC1]

Step 1: tert-butyl (1-(4-(8-(2-cyano-3-fluorophenyl)-4-oxo-2-phenyl-4H-pyrano[2,3-c]pyridin-3-yl)phenyl)cyclobutyl)carbamate: Following the procedure used to prepare 3-(4-(1-aminocyclobutyl)phenyl)-8-(1-isobutyl-1H-pyrazol-4-yl)-2-phenyl-4H-pyrano[2,3-c]pyridin-4-one, tert-butyl 1-(4-(8-chloro-4-oxo-2-phenyl-4H-pyrano[2,3-c]pyridin-3-yl)phenyl)cyclobutylcarbamate was reacted with 2-fluoro-6-(4,4,5,5-tetramethyl-1,3,2-dioxaborolan-2-yl)benzonitrile to give the title compound (40 mg, 44%). LCMS (Method I): $R_T$=7.90 min, [M+H]$^+$=532 (-tBu).

Step 2: 2-(3-(4-(1-aminocyclobutyl)phenyl)-4-oxo-2-phenyl-4H-pyrano[2,3-c]pyridin-8-yl)-6-fluorobenzoic acid: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl (1-(4-(8-(2-cyano-3-fluorophenyl)-4-oxo-2-phenyl-4H-pyrano[2,3-c]pyridin-3-yl)phenyl)cyclobutyl)carbamate was reacted with HCl in dioxane and further heated 5 min with concentrated sulphuric acid (0.1 mL) to give the title compound. (5 mg, 20%). $^1$H NMR (500 MHz, CD$_3$OD): δ 8.65 (d, J=8.2 Hz, 1H), 8.15 (d, J=8.3 Hz, 1H), 7.71-7.65 (m, 1H), 7.58-7.54 (m, 1H), 7.50-7.45 (m, 2H), 7.40-7.25 (m, 6H) 7.20-7.15 (m, 2H), 2.85-2.75 (m, 2H), 2.62-2.55 (m, 2H), 2.28-2.19 (m, 1H), 2.05-1.91 (m, 1H). LCMS (Method I): $R_T$=4.25 min, [M+2]$^+$=508.

Example 122

3-(4-(1-aminocyclobutyl)phenyl)-8-(3-isocyanophenyl)-2-phenyl-4H-pyrano[2,3-c]pyridin-4-one

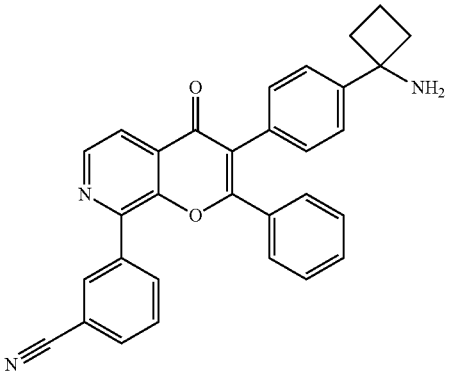 [SMILES: N#Cc1cccc(-c2nccc3c(=O)c(-c4ccc(C5(N)CCC5)cc4)c(-c4ccccc4)oc23)c1]

Step 1: tert-butyl 1-(4-(8-(3-isocyanophenyl)-4-oxo-2-phenyl-4H-pyrano[2,3-c]pyridin-3-yl)phenyl)cyclobutylcarbamate: Following the procedure used to prepare 3-(4-(1-aminocyclobutyl)phenyl)-8-(1-isobutyl-1H-pyrazol-4-yl)-2-phenyl-4H-pyrano[2,3-c]pyridin-4-one, tert-butyl 1-(4-(8-chloro-4-oxo-2-phenyl-4H-pyrano[2,3-c]pyridin-3-yl)phenyl)cyclobutyl carbamate was reacted with 3-cyanophenylboronic acid to give the title compound (40 mg, 70%). LCMS (Method I): $R_T$=8.77 min, [M+H]$^+$=514 (-$^t$Bu).

Step 2: 3-(4-(1-aminocyclobutyl)phenyl)-8-(3-isocyanophenyl)-2-phenyl-4H-pyrano[2,3-c]pyridin-4-one: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl (1-(4-(8-(3-isocyanophenyl)-4-oxo-2-phenyl-4H-pyrano[2,3-c]pyridin-3-yl)phenyl)cyclobutyl)carbamate was reacted with HCl in dioxane. The product was purified by preparative HPLC to give the title compound (5 mg, 15%). $^1$H NMR (500 MHz, CD$_3$OD): δ 8.69 (d, J=8.2 Hz, 1H), 8.41 (s, 1H), 8.32-8.29 (m, 1H), 8.05 (d, J=8.3 Hz, 1H), 7.79-7.75 (m, 1H), 7.65-7.61 (m, 1H), 7.40-7.19 (m, 9H), 2.75-2.65 (m, 2H), 2.45-2.40 (m, 2H), 2.18-2.12 (m, 1H), 1.91-1.82 (m, 1H). LC-MS (Method I): $R_T$=4.68 min, [M+2]$^+$=471.

Example 123

3-(4-(1-aminocyclobutyl)phenyl)-2-phenyl-8-(pyridin-3-yl)-4H-pyrano[2,3-c]pyridin-4-one hydrochloride

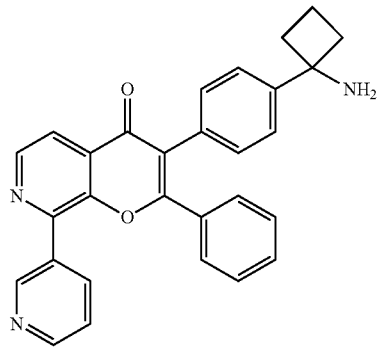 [SMILES: NC1(c2ccc(-c3c(-c4ccccc4)oc4c(-c5cccnc5)nccc4c3=O)cc2)CCC1]

Step 1: tert-Butyl 1-(4-(4-oxo-2-phenyl-8-(pyridin-3-yl)-4H-pyrano[2,3-c]pyridin-3-yl)phenyl)cyclobutylcarbamate:

Following the procedure used to prepare tert-butyl 1-(4-(8-(1-isobutyl-1H-pyrazol-4-yl)-4-oxo-2-phenyl-4H-pyrano[2,3-c]pyridin-3-yl)phenyl)cyclobutyl carbamate, tert-butyl 1-(4-(8-chloro-4-oxo-2-phenyl-4H-pyrano[2,3-c]pyridin-3-yl)phenyl)cyclobutylcarbamate was reacted with pyridine-3-boronic acid to give the title compound (20 mg, 37%). LCMS (Method I): $R_T$=7.45 min, [M+H]$^+$=546.

Step 2: 3-(4-(1-aminocyclobutyl)phenyl)-2-phenyl-8-(pyridin-3-yl)-4H-pyrano[2,3-c]pyridin-4-one hydrochloride: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl 1-(4-(4-oxo-2-phenyl-8-(pyridin-3-yl)-4H-pyrano[2,3-c]pyridin-3-yl)phenyl)cyclobutyl carbamate was reacted with HCl in dioxane to give the title compound as the HCl salt (12 mg, 70%). $^1$H NMR (500 MHz, CD$_3$OD): δ 9.49 (bs, 1H), 9.25-9.20 (m, 1H), 8.90-8.85 (m, 1H), 8.78 (m, 1H), 8.25-8.20 (m, 2H), 8.15 (m, 1H), 7.91-7.80 (m, 2H), 7.41-7.20 (m, 6H), 2.71-2.62 (m, 2H), 2.55-2.45 (m, 2H), 2.20-2.14 (m, 1H), 1.88-1.82 (m, 1H). LCMS (Method I): $R_T$=4.06 min, [M+2]$^+$=447.

Example 124

3-(4-(1-aminocyclobutyl)phenyl)-2,8-diphenyl-4H-pyrano[2,3-c]pyridin-4-one

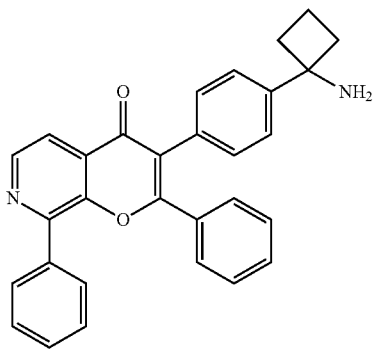 [SMILES: NC1(c2ccc(-c3c(-c4ccccc4)oc4c(-c5ccccc5)nccc4c3=O)cc2)CCC1]

Step 1: tert-Butyl (1-(4-(4-oxo-2,8-diphenyl-4H-pyrano[2,3-c]pyridin-3-yl)phenyl)cyclobutyl)carbamate: Following the procedure used to prepare tert-butyl 1-(4-(8-(1-isobutyl-1H-pyrazol-4-yl)-4-oxo-2-phenyl-4H-pyrano[2,3-c]pyridin-3-yl)phenyl)cyclobutylcarbamate, tert-butyl 1-(4-(8-chloro-4-oxo-2-phenyl-4H-pyrano[2,3-c]pyridin-3-yl)phenyl)cyclobutylcarbamate was reacted with phenylboronic acid to give the title compound (40 mg, 61%). LCMS (Method I): $R_T$=8.96 min, [M+H]$^+$=545.

Step 2: 3-(4-(1-aminocyclobutyl)phenyl)-2,8-diphenyl-4H-pyrano[2,3-c]pyridin-4-one: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl (1-(4-(4-oxo-2,8-diphenyl-4H-pyrano[2,3-c]pyridin-3-yl)phenyl)cyclobutyl)carbamate was reacted give the title compound (5 mg, 15%). $^1$H NMR (500 MHz, CD$_3$OD): δ 8.65 (d, J=5.1 Hz, 1H), 7.96 (d, J=5.1 Hz, 1H), 7.89-7.85 (m, 2H), 7.46-7.15 (m, 12H), 2.69-2.63 (m, 2H), 2.49-2.52 (m, 2H), 2.20-2.11 (m, 1H), 1.92-1.78 (m, 1H). LCMS (Method I): $R_T$=4.67 min, [M+2]$^+$=446.

Example 125

3-(4-(1-aminocyclobutyl)phenyl)-8-(2-hydroxyethoxy)-2-phenyl-4H-pyrano[2,3-c]pyridin-4-one

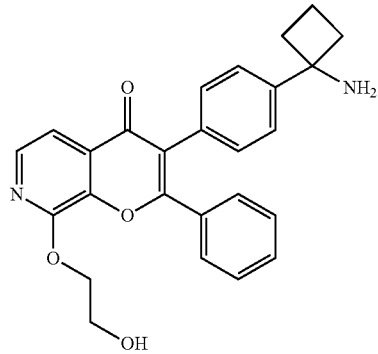 [SMILES: NC1(c2ccc(-c3c(-c4ccccc4)oc4c(OCCO)nccc4c3=O)cc2)CCC1]

Step 1: tert-Butyl 1-(4-(8-(2-hydroxyethoxy)-4-oxo-2-phenyl-4H-pyrano[2,3-c]pyridin-3-yl)phenyl)cyclobutylcarbamate: To a solution of tert-butyl 1-(4-(8-chloro-4-oxo-2-phenyl-4H-pyrano[2,3-c]pyridin-3-yl)phenyl)cyclobutylcarbamate (50 mg, 0.099 mmol) in DMF (1 mL) were added ethane-1,2-diol (30.8 mg, 0.497 mmol) and potassium tert-butoxide (33.5 mg, 0.298 mmol) under nitrogen. The reaction mixture was stirred at RT overnight, followed by heating at 50° C. for 4 h. The product was extracted with ethyl acetate, washed with water, dried, and purified by chromatography to give the title compound (20 mg, 38%). LCMS (Method J): $R_T$=1.493 min, [M+H]$^+$=529.

Step 2: 3-(4-(1-aminocyclobutyl)phenyl)-8-(2-hydroxyethoxy)-2-phenyl-4H-pyrano[2,3-c]pyridin-4-one: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl 1-(4-(8-(2-hydroxyethoxy)-4-oxo-2-phenyl-4H-pyrano[2,3-c]pyridin-3-yl)phenyl)cyclobutylcarbamate was reacted to give the title compound. (10 mg, 62%). $^1$H NMR (400 MHz, CD$_3$OD): δ 8.15 (d, 1H), 7.55 (d, 1H), 7.49-7.31 (m, 9H), 4.68-4.65 (m, 2H), 3.95-4.01 (m, 2H), 2.82-2.75 (m, 2H), 2.63-2.52 (m, 2H), 2.30-2.19 (m, 1H), 2.03-1.92 (m, 1H). LCMS (Method I): $R_T$=3.83 min, [M+2]$^+$=430.

Example 126

3-[4-(1-Amino-cyclobutyl)-phenyl]-8-cyclopropyl-2-phenyl-chromen-4-one hydrochloride

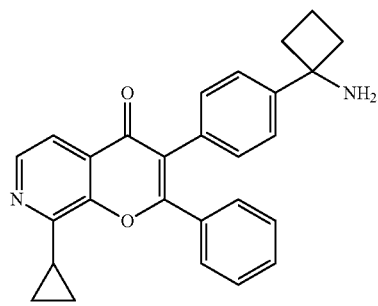 [SMILES: NC1(c2ccc(-c3c(-c4ccccc4)oc4c(C5CC5)nccc4c3=O)cc2)CCC1]

Step 1: tert-Butyl 1-(4-(8-cyclopropyl-4-oxo-2-phenyl-4H-pyrano[2,3-c]pyridin-3-yl)phenyl)cyclobutylcarbamate:

tert-Butyl 1-(4-(8-chloro-4-oxo-2-phenyl-4H-pyrano[2,3-c]pyridin-3-yl)phenyl)cyclobutyl carbamate (50.3 mg, 0.1 mmol), cesium carbonate (98 mg. 0.3 mmol), potassium cyclopropyltrifluoroborate (20 mg, 0.15 mmol) were suspended in α,α,α-trifluorotoluene (1 mL) The reaction mixture was degassed and purged with nitrogen. To that was added di-adamentyl-n-butyl phosphine (10 mg, 0.01 mmol) and the reaction mixture was heated under microwave conditions at 120° C. for 3 h. The resulting mixture was allowed to cool to RT, partitioned between ethyl acetate (40 mL) and water (10 mL). The resulting biphasic mixture was separated, the organic layer was washed with brine (5 mL), the combined organic phase was dried ($Na_2SO_4$), filtered, and concentrated in vacuo. The resulting residue was subjected to flash chromatography ($SiO_2$, 0-50% ethyl acetate in cyclohexane) to give the title compound (30 mg, 60%) LCMS (Method I): $R_T$=5.04 min, $[M+H]^+$=509.

Step 2: 3-(4-(1-aminocyclobutyl)phenyl)-8-cyclopropyl-2-phenyl-4H-pyrano[2,3-c]pyridin-4-one: Following the procedure used to prepare 3-(4-(1-aminocyclobutyl)phenyl)-2-phenyl-8-(1,3,5-trimethyl-1H-pyrazol-4-yl)-4H-pyrano[2,3-c]pyridin-4-one, tert-butyl 1-(4-(8-cyclopropyl-4-oxo-2-phenyl-4H-pyrano[2,3-c]pyridin-3-yl)phenyl)cyclobutyl carbamate was reacted to give the title compound as the HCl salt (10 mg, 46%). $^1$H NMR (500 MHz, $CD_3OD$): δ 8.45 (d, 1H), 8.02 (d, 1H), 7.53-7.31 (m, 9H), 2.65-2.47 (m, 4H), 2.45-2.34 (m, 1H), 2.26-2.09 (m, 1H), 1.88-1.73 (m, 1H), 1.14-1.04 (m, 2H), 0.90-0.82 (m, 2H). LCMS (Method I): $R_T$=4.73 min, $[M+2]^+$=410.

Example 127

3-(4-(1-aminocyclobutyl)phenyl)-4-oxo-2-phenyl-4H-pyrano[2,3-c]pyridine-8-carbonitrile

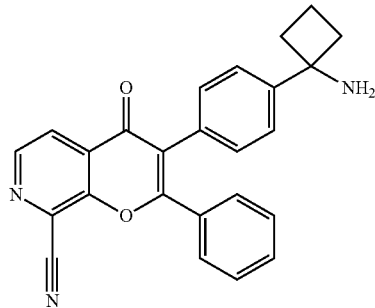 [SMILES: N#Cc1nccc2c(=O)c(-c3ccc(C4(N)CCC4)cc3)c(-c3ccccc3)oc12]

Step 1: tert-Butyl (1-(4-(8-cyano-4-oxo-2-phenyl-4H-pyrano[2,3-c]pyridin-3-yl)phenyl)cyclobutyl)carbamate: tert-Butyl (1-(4-(8-chloro-4-oxo-2-phenyl-4H-pyrano[2,3-c]pyridin-3-yl)phenyl)cyclobutyl)carbamate (50 mg, 0.1 mmol), zinc (II) cyanide (38 mg, 0.058 mmol) and binaphthyl-di-tert-butyl phosphine (4 mg, 0.01 mmol), palladium (II) trifluoroacetate (4 mg, 0.01 mmol), zinc dust (2 mg) were suspended in DMA (1 mL) in a microwave vial. The vial was sealed, evacuated and flushed twice with nitrogen. The reaction mixture was heated at 95° C. for 18 h. The resulting mixture was allowed to cool to RT, partitioned between ethyl acetate (40 mL) and water (20 mL) and the phases were separated. The organic layer was washed with brine (2 mL), dried ($Na_2SO_4$), filtered and concentrated in vacuo. The resulting residue was subjected to flash chromatography ($SiO_2$, 50% ethyl acetate in cyclohexane) to afford the title compound (30 mg, 61%). LCMS (Method I): $R_T$=7.63 min, $[M+H]^+$=438 (-$^t$Bu), $[M+Na]^+$=516.

Step 2: 3-(4-(1-aminocyclobutyl)phenyl)-4-oxo-2-phenyl-4H-pyrano[2,3-c]pyridine-8-carbonitrile hydrochloride: To a solution of tert-butyl 1-(4-(8-cyano-4-oxo-2-phenyl-4H-pyrano[2,3-c]pyridin-3-yl)phenyl)cyclobutylcarbamate (10 mg, 0.020 mmol) in DCM (2 mL) was added 4M HCl in 1,4-dioxane (1.0 ml). The reaction mixture was stirred at RT for overnight. The solvent was evaporated and the crude product was washed several times with DCM and acetonitrile (3×1 ml). The product was dried to give the title compound as the HCl salt (5 mg, 71%). $^1$H NMR (500 MHz, $CD_3OD$): δ 8.55 (d, 1H), 8.15 (d, 1H), 7.48-7.18 (m, 9H), 2.75-2.67 (m, 2H), 2.55-2.42 (m, 2H), 2.18-2.09 (m, 1H), 1.88-1.73 (m, 1H). LCMS (Method I): $R_T$=4.39 min, $[M+2]^+$=395.

Example 128

3-(4-(1-aminocyclobutyl)phenyl)-8-ethyl-2-phenyl-4H-pyrano[2,3-c]pyridin-4-one

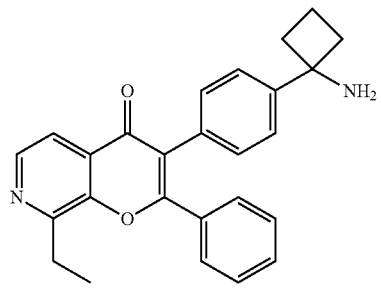 [SMILES: CCc1nccc2c(=O)c(-c3ccc(C4(N)CCC4)cc3)c(-c3ccccc3)oc12]

Step 1: tert-Butyl 1-(4-(4-oxo-2-phenyl-8-vinyl-4H-pyrano[2,3-c]pyridin-3-yl)phenyl)cyclobutylcarbamate: tert-Butyl 1-(4-(8-chloro-4-oxo-2-phenyl-4H-pyrano[2,3-c]pyridin-3-yl)phenyl)cyclobutyl carbamate (50.3 mg, 0.1 mmol), cesium carbonate (98 mg. 0.3 mmol), potassium trifluoro(vinyl)borate (20 mg, 0.15 mmol) were suspended in α,α,α-trifluorotoluene (1 mL). The reaction mixture was degassed and purged with nitrogen. To that was added di-adamentyl-n-butyl phosphine (10 mg, 0.01 mmol) and the reaction mixture was heated under microwave conditions at 120° C. for 3 h. The resulting mixture was allowed to cool to RT, partitioned between ethyl acetate (40 mL) and water (10 mL). The organic layer was washed with brine (5 mL), dried ($Na_2SO_4$), filtered and concentrated in vacuo. The resulting residue was subjected to flash chromatography ($SiO_2$, 0-50% ethyl acetate in cyclohexane) to give the title compound (37 mg, 75%).

Step 2: tert-Butyl 1-(4-(8-ethyl-4-oxo-2-phenyl-4H-pyrano[2,3-c]pyridin-3-yl)phenyl)cyclobutylcarbamate: Following same procedure used to prepare 3-(4-(1-aminocyclobutyl)phenyl)-2-phenyl-5,6,7,8-tetrahydro-4H-pyrano[2,3-c]pyridin-4-one, tert-butyl 1-(4-(4-oxo-2-phenyl-8-vinyl-4H-pyrano[2,3-c]pyridin-3-yl)phenyl)cyclobutyl carbamate (15 mg, 0.03 mmol) was hydrogenated to give the title compound (10 mg, 67%). LCMS (Method I): $R_T$=6.39 min, $[M+1]^+$=497.

Step 3: 3-(4-(1-Aminocyclobutyl)phenyl)-8-ethyl-2-phenyl-4H-pyrano[2,3-c]pyridin-4-one: Following same procedure used to prepare 3-(4-(1-aminocyclobutyl)phenyl)-8-(2-chloroethyl)-2-phenyl-4H-pyrano[2,3-c]pyridin-4-one, tert-butyl 1-(4-(8-ethyl-4-oxo-2-phenyl-4H-pyrano[2,3-c]pyridin-3-yl)phenyl)cyclobutylcarbamate was reacted with 4

M HCl in 1,4-dioxane to give the title compound (5 mg, 62%). $^1$H NMR (500 MHz, CD$_3$OD): δ 8.61 (d, 1H), 7.95 (d, 1H), 7.51-7.30 (m, 9H), 3.42-3.35 (m, 2H), 2.75-2.67 (m, 2H), 2.55-2.42 (m, 2H), 2.28-2.12 (m, 1H), 1.98-1.88 (m, 1H). 1.5 (t, 3H). LCMS (Method I): R$_T$=4.31 min, [M+2]$^+$=398.

Example 129

3-(4-(1-aminocyclobutyl)phenyl)-8-(2-chloroethyl)-2-phenyl-4H-pyrano[2,3-c]pyridin-4-one

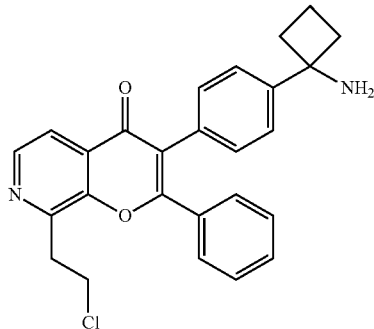 [SMILES: NC1(c2ccc(-c3c(-c4ccccc4)oc4c(CCCl)nccc4c3=O)cc2)CCC1]

To a solution of tert-butyl 1-(4-(4-oxo-2-phenyl-8-vinyl-4H-pyrano[2,3-c]pyridin-3-yl)phenyl)cyclobutylcarbamate (15 mg, 0.030 mmol) in DCM was added 4 M HCl in 1,4-dioxane (0.05 mL, 2 mmol). The reaction mixture was stirred at RT for 4 h. The solvents were removed in vacuo. The product was chromatographed on a 5 g C18 cartridge {gradient 10 to 50% MeOH in water+1 M HCl (60 µL in each 10 mL of eluent)} to give the title compound as an HCl salt (5 mg, 38%). $^1$H NMR (500 MHz, CD$_3$OD): δ 8.61 (d, 1H), 7.95 (d, 1H), 7.51-7.30 (m, 9H), 4.15-4.08 (m, 2H), 3.68-3.60 (m, 2H), 2.75-2.67 (m, 2H), 2.55-2.42 (m, 2H), 2.28-2.12 (m, 1H), 1.98-1.88 (m, 1H). LCMS (Method I): R$_T$=4.49 min, [M+2]$^+$=432.

Phenyl-oxetanyl derivatives are also prepared by, for example, the following method (see also WO2009/068682):

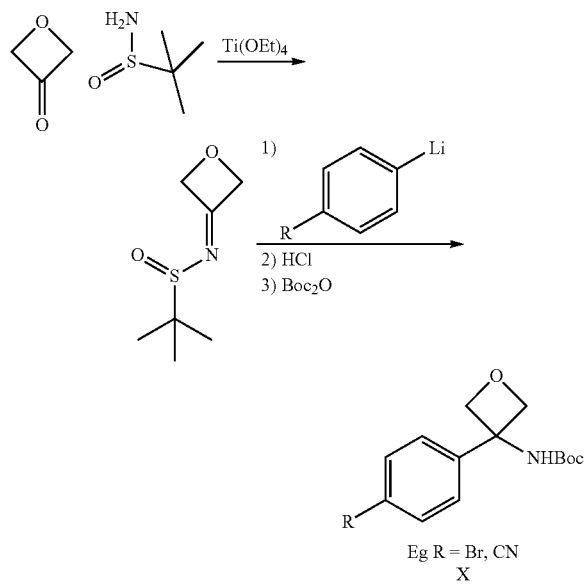

1-(4-bromophenyl)cyclopropanamine is commercially available and may be readily Boc protected using, for example, reaction with Boc$_2$O:

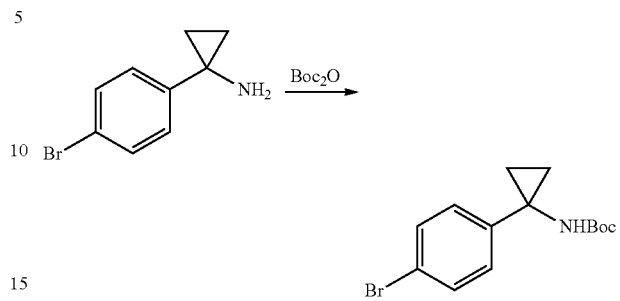

Following conversion into the corresponding boronic ester (for example using bis-pinaolato diboron, Pd(dppf)Cl$_2$ and KOAc), these intermediates may then undergo metal mediated cross-couplings to form analogues where Z=O, CH$_2$ and is a carbon-carbon bond:

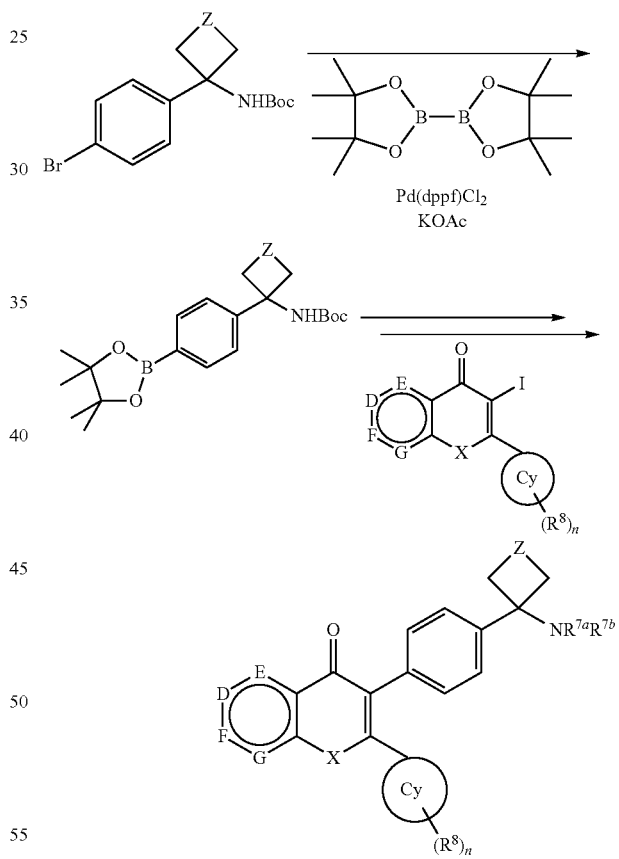

AKT Kinase Assay Testing

Testing of the compounds was performed using an AKT Kinase Assay:

Activated AKT isoforms 1, 2 and 3 were assayed utilising a 5' FAM Crosstide (Seq. GRPRTSSFAEG-OH). The extent of kinase phosphorylation was determined by fluorescent polarisation using IMAP progressive binding reagent, which introduces binding beads which allow the reagent to specifically bind to phosphate residues via covalent co-ordination complex bonds.

iMAP binding solution stops Crosstide/kinase interaction and specifically binds phosphorylated substrates. The degree of phosphorylation is determined by fluorescent polarisation (excitation 485 nm; emission 528 nm) or the reduction in speed of rotation of the excited substrate.

The following materials were used in the assay:
a) Activated AKT isoforms (SignalChem.) dissolved in Complete Reaction buffer at a pre-determined concentration selected so that the assay was carried out in the linear range.
b) AKT substrate peptide: FAM Crosstide (R7110) Molecular Devices, diluted in complete reaction buffer.
c) iMAP Progressive Screening Express Kit (R8127) Molecular Devices
d) Complete Reaction Buffer containing 0.1% BSA, 10 mM Tris-HCl, 10 mM $MgCl_2$, 0.05% $NaN_3$ and 0.01% phosphate free BSA, 1 mM DTT
e) Progressive Binding Solution containing 75% Buffer A, 25% Buffer B and low volume Binding Reagent which contains the binding entity for the assay
f) ATP diluted in complete reaction buffer
g) Black polystyrene 384 well assay plates (Nunc).
h) Biotek Synergy 4 Hybrid Plate reader.

5 µl of test compound was dissolved in DMSO (Sigma Aldrich) and serially diluted in complete reaction buffer to give a fourteen point half log dose response and plated into 384 well black plates. The compound was incubated at room temperature with activated AKT isoform (5 µl) at the pre-determined concentration, for 45 minutes.

2.5 µl of ATP solution mixed with 2.5 µl of AKT substrate peptide (FAM Crosstide (R7110) Molecular Devices) were dispensed into each well and the plate centrifuged at 1000 rpm for 20 seconds to ensure homogenous mixing of reagents. The reaction mix was incubated in the dark for one hour at room temperature.

The kinase reaction was stopped by the addition of Progressive Binding Solution and the mixture allowed to equilibrate for one hour in the dark, at room temperature.

The fluorescent polarisation generated in each well was determined using a Biomek Synergy 4 Hybrid plate reader. In brief, each reaction solution was excited at 485 nm with the emission measured at 528 nm in both the parallel and perpendicular pathway.

The polarisation value generated in each well was calculated by Gen5 software (Biotek) and the % inhibition of kinase activity compared to vehicle control was calculated via GraphPad Prism. $IC_{50}$ values for each compound were calculated by non-linear regression analysis using Prism software.

All plates were internally controlled by two methods. Firstly, by calculating the signal:noise ratio; based on kinase polarisation without inhibitor and polarisation generated by complete reaction buffer in the absence of activated kinase. Secondly by determining IC50 values generated by known inhibitors of the AKT isoforms.

Testing of the compounds was also performed using in vitro cell proliferation assays:

Cell Titre Glo (Promega) is a highly sensitive homogeneous reagent used to determine the viability of cells. The reagent uses a stable form of luciferase to measure ATP as an output of viability. The luminescent values generated in the assay are directly proportional to the number of viable cells in your assay.

The following materials were used: White, clear bottomed 96 well assay plates (Costar); Cell titre Glo reagents; LnCaP (ECACC) cells grown in RPMI medium (Invitrogen) supplemented with 10 mM HEPES (Invitrogen), 1 mM Sodium pyruvate (Invitrogen), 2 mM L-Glutamine (Invitrogen) and 10% Foetal calf serum (Invitrogen); PC3 (ECACC) cells grown in RPMI medium supplemented with 10% Foetal calf serum (Invitrogen); Trypsin (Invitrogen); PBS (Invitrogen); Biotek Synergy 4 Hybrid Plate reader; 96 well plate shaker (Stuart SSL5); Eppendorf 5414 desk-top centrifuge; Beckman Coulter cell counter Z1 single threshold system.

Prostate cell lines, PC3 and LnCaP, were washed, detached and re-suspended in their respective fresh media. The cells were pelleted by centrifugation (Eppendorf 5414) and spent supernatant discarded. The cells were re-suspended by vortex mixing, counted and seeded into clear bottom white 96 well plates at a density of 5000 cells per well. The cells were incubated (Sanyo) overnight at 37° C. (95% $O_2$/5% $CO_2$), and next day treated with increasing concentrations of test compound formulated in fresh medium. The plates were returned to the incubator for 72 hours.

Cell Titre Glo (Promega) was prepared by mixing the supplied reagents as per manufacturer's instructions and left to stand at room temperature. The cell plates were removed from the incubator and 80 µl of the Cell Titre Glo solution added to each well. The plate was shaken for five minutes to ensure homogenous mixing of reagents and cells, then left to stand for ten minutes at room temperature.

The cell viability post compound treatment was determined by the luminescent intensity emitted from the drug treated wells in the plate. In brief, the assay plate was placed in the Biotex Synergy 4 Hybrid plate reader and the luminescence read in each well. The compound treated wells were compared to vehicle treated wells and the % inhibition of cell viability calculated.

The data was analysed using GraphPad Prism, with $IC_{50}$ values generated using non-linear regression of the data set.

Analysis of Compound Effects on AKT Signalling Pathways

Phosphorylation status of various members of the AKT/PI3K pathway were investigated via western blotting.

Materials Required for this Assay: 20× Running buffer (Invitrogen); Rainbow marker ladder (GE Healthcare); Reducing buffer (Invitrogen); 20× Transfer buffer (Invitrogen); 4-12% Bis-Tris Gels (Invitrogen); Filter paper (Whatman); Nitrocellulose (Amersham); ECL plus detection reagents (GE Healthcare); Radiographic film (Kodak); Biorad Protein determination reagent (Biorad); AKT pathway signalling antibodies (Cell Signalling)

LnCaP and PC3 cell lines were washed, detached and re-suspended in fresh medium. They were seeded in 90 $mm^2$ dishes and incubated overnight (95% $O_2$/5% $CO_2$) to allow adherence. When the cells had reached 60% confluence, the medium was removed and replaced with compound or vehicle supplemented medium. The plates were incubated for a range of time points.

The medium was removed and the cells placed on ice and washed in PBS. 300 µl of lysis buffer was added to the dish and left for a few minutes, before the cells were scraped into the solution and pipetted into a centrifuge tube. The tube was placed on ice for 10 minutes and then vortexed to aid cellular lysis. The sample was centrifuged (Eppendorf bench-top ultra-fuge) at 13.2 k rpm for 10 minutes at 4° C. The resultant supernatant was assayed for protein content using the Bradford method (Biorad) and equal quantities of protein calculated and heated in sample reducing buffer to 95° C. for ten minutes.

The samples were run on 4-12% Bis-Tris gels (Invitrogen), transferred onto nitrocellulose membrane (Amersham) and blocked with a 5% non-fat milk solution.

The membranes were used to determine difference in total AKT, pSer473 AKT, pGSK3β and total GSK3β (all sourced from Cell Signalling). The respective primary antibodies were diluted in 1% non-fat milk blocking solution and incubated on the membranes overnight at 4° C. The membranes were washed three times in PBS and incubated with the respective secondary antibodies (Sigma Aldrich) for two hours and the proteins were detected using ECL plus detection reagents (GE Healthcare).

The invention claimed is:

1. A compound according to Formula (I):

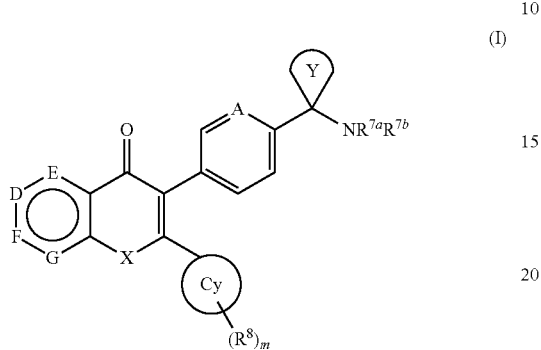

wherein:
0, 1 or 2 of D, E, F and G are independently selected from N, NH and $NR^1$ and the others are independently selected from CH and $CR^2$, wherein each $R^1$ is independently selected from aryl, C1-C10 alkyl, $CONHR^3$, $CONR^{3a}R^{3b}$, $COR^3$ and $CO_2R^3$ and each $R^2$ is independently selected from aryl, C1-C10 alkyl, CN, CHO, $CO_2H$, $CONH_2$, $CONHR^3$, $CONR^{3a}R^{3b}$, $COR^3$, $CO_2R^3$, $NH_2$, $NHR^3$, $NR^{3a}R^{3b}$, oxo, OH, $OR^3$, SH, $SR^3$, $SOR^3$, $SO_2R^3$, $SO_2NHR^3$, $SO_2NR^{3a}R^{3b}$, F, Cl, Br and I, wherein each $R^3$, $R^{3a}$ and $R^{3b}$ is independently selected from optionally substituted C1-C10 alkyl, and optionally substituted C1-C10 aryl, including wherein $R^{3a}$ and $R^{3b}$ are joined to one another to form a heterocycle that includes the nitrogen to which they are attached, wherein A is N or CH;
wherein at least D or G is NH or $NR^1$ if E or F is CO and at least E or F is NH or $NR^1$ if D or G is CO,
wherein separate $R^1$ and/or $R^2$ groups may be joined to one another to form a heterocycle that includes the C and/or N atoms to which they are attached if the separate $R^1$ and/or $R^2$ groups are contained on D and E and/or F and G, or D and F and the separate $R^2$ groups are selected from $OR^3$, $SR^3$, $SOR^3$, $SO_2R^3$, $SO_2NHR^3$, $SO_2NR^{3a}R^{3b}$, $NHR^3$, $NR^{3a}R^{3b}$, $CO_2R^3$, $CONHR^3$ and $CONR^{3a}R^3$, and/or wherein separate $R^1$ and/or $R^2$ groups on F and G may be joined to form the structure:

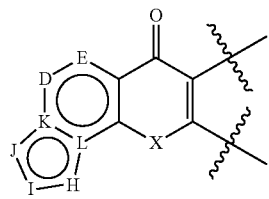

where 0 or 1 of K and L are N and the other(s) is/are C, and wherein H, I and J are independently selected from O, S, NH, $NR^4$, N, CH and $CR^5$, wherein each $R^4$ is independently selected from aryl, C1-C10 alkyl, $CONHR^6$, $CONR^{6a}R^{6b}$, $COR^6$ and $CO_2R^6$ and each $R^5$ is independently selected from aryl, C1-C10 alkyl, CN, CHO, $CO_2H$, $CONH_2$, $CONHR^6$, $CONR^{6a}R^{6b}$, $COR^6$, $CO_2R^6$, oxo, $NH_2$, $NHR^6$, $NR^{6a}R^{6b}$, OH, $OR^6$, SH, $SR^6$, $SOR^6$, $SO_2R^6$, $SO_2NHR^6$, $SO_2NR^{6a}R^{6b}$, F, Cl, Br and I, wherein each $R^6$, $R^{6a}$ and $R^{6b}$ is independently selected from C1-C10 alkyl, including wherein $R^{6a}$ and $R^{6b}$ are joined to one another to form a heterocycle that includes the nitrogen to which they are attached, X is selected from O, S, SO, $SO_2$ or a carbon-carbon bond;
$R^{7a}$ and $R^{7b}$ are independently selected from H and alkyl, including wherein $R^{7a}$ and $R^{7b}$ are joined to one another to form a heterocycle that includes the nitrogen to which they are attached; and

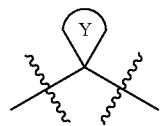

is selected from:

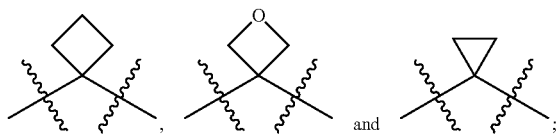 [SMILES: *C1(*)CCC1 ; *C1(*)COC1 ; *C1(*)CC1]

or where the $R^{7a}$ and $R^{7b}$ groups are absent as is the nitrogen to which they are bound and Y is geminal dimethyl so that the moiety bound is

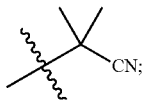 [SMILES: *C(C)(C)C#N]

ring Cy is selected from ($C_3$ to $C_8$)cycloalkyl and aryl, wherein m is 0, 1, 2, 3, 4 or 5, and each $R^8$ is independently selected from alkyl, CN, CHO $CO_2H$, $CONH_2$, $CONHR^9$, $CONR^{9a}R^{9b}$, $COR^9$, $CO_2R^9$, $NH_2$, $NHR^9$, $NR^{9a}R^{9b}$, OH, $OR^9$, SH, $SR^9$, F, Cl, Br and I, wherein each $R^9$, $R^{9a}$ and $R^{9b}$ is independently selected from alkyl, including wherein $R^{9a}$ and $R^{9b}$ form a heterocycle that includes the nitrogen to which they are attached;
or where the ketone carboxyl oxygen opposite X is replaced with a sulphur atom to give a thioketone or with a group comprising nitrogen to give an imine or optionally lower alkyl substituted oxime;
and pharmaceutically acceptable salts, stereoisomers and tautomers thereof.

2. The compound of claim 1, wherein

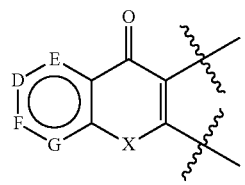

is selected from:
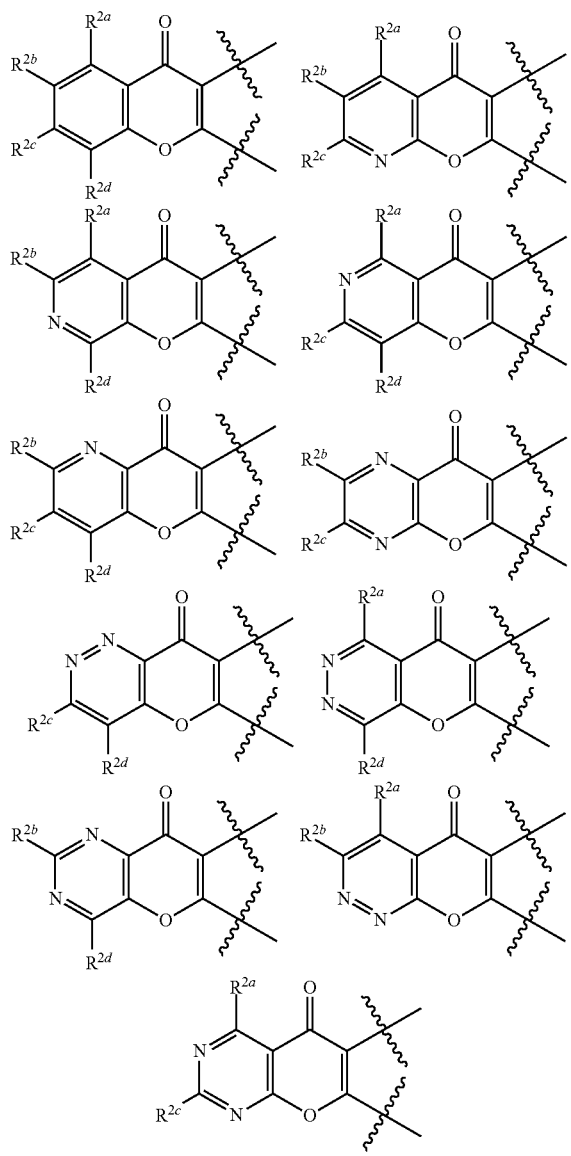
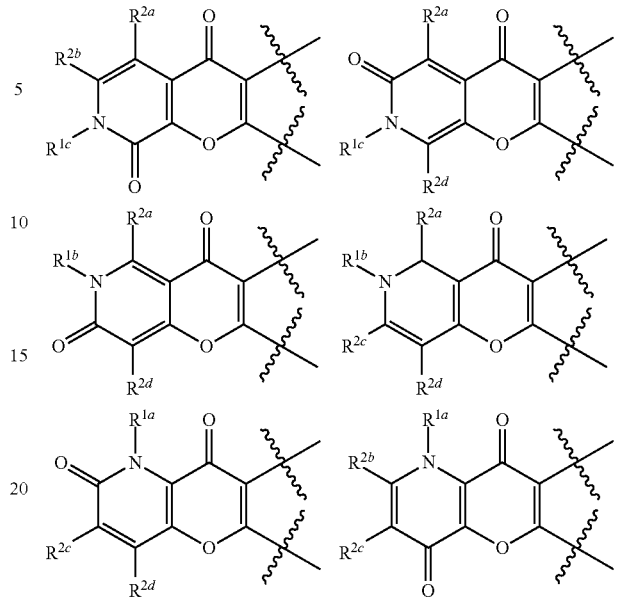
wherein $R^{1a}$, $R^{1b}$, $R^{1c}$ and $R^{1d}$ are independently selected from $R^1$ and H and $R^{2a}$, $R^{2b}$, $R^{2c}$ and $R^{2d}$ are independently selected from $R^2$ and H.
4. The compound of claim 1, wherein
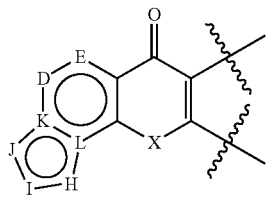
is selected from:
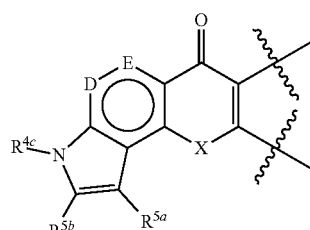
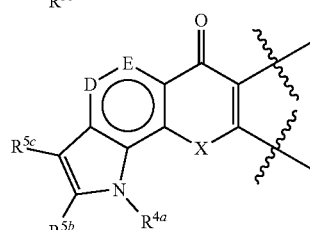
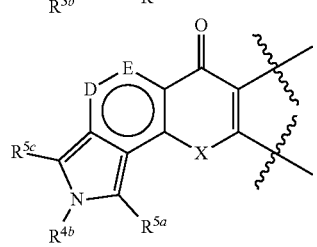
wherein $R^{2a}$, $R^{2b}$, $R^{2c}$ and $R^{2d}$ are independently selected from $R^2$ and H.
3. The compound of claim 1, wherein
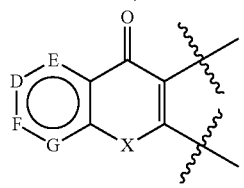
is selected from:
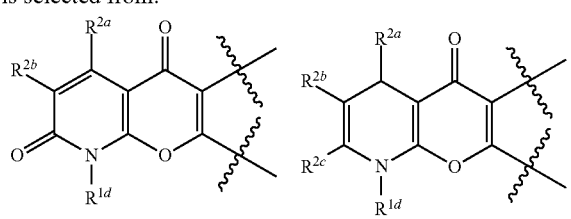

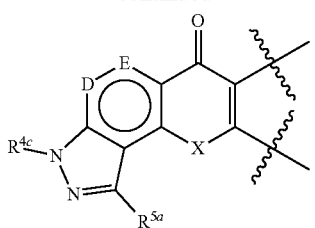
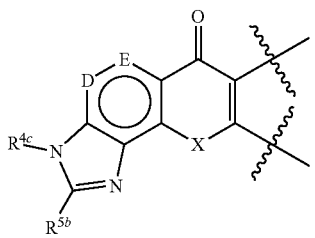
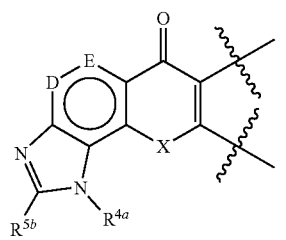
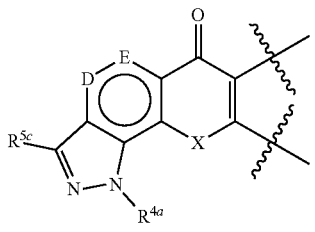
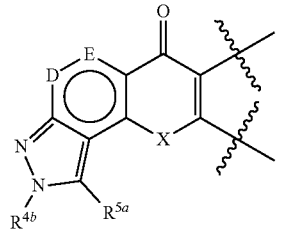
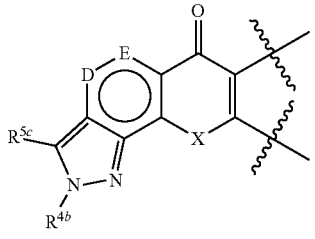
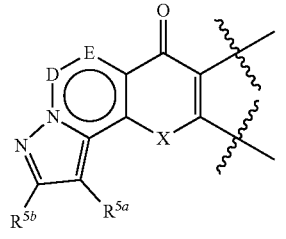
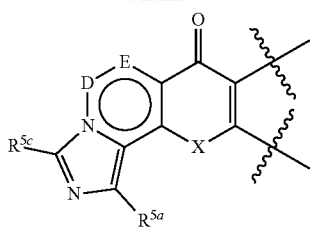
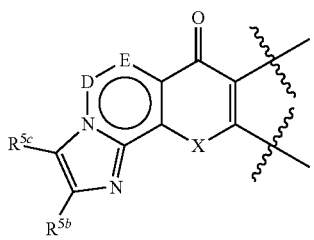
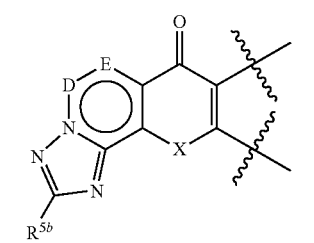
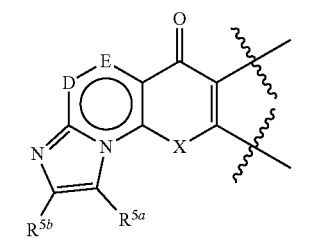
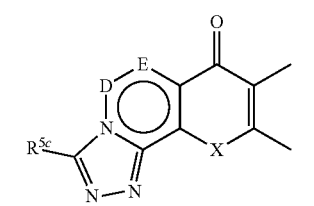
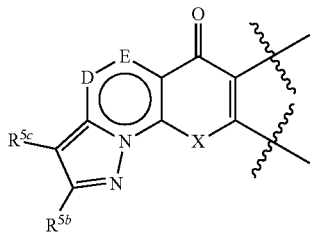
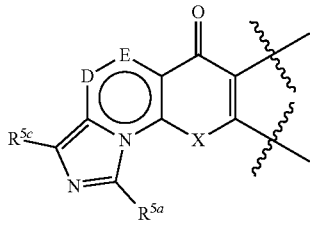

-continued

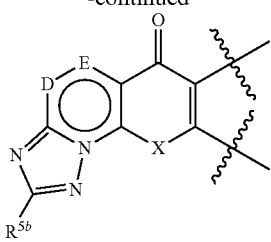

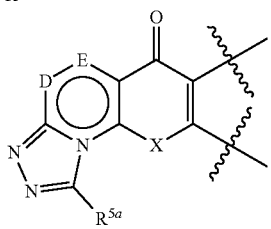

wherein $R^{4a}$, $R^{4b}$ and $R^{4c}$ are independently selected from $R^4$ and H and $R^{5a}$, $R^{5b}$ and $R^{5c}$ are independently selected from $R^5$ and H.

5. The compound of claim 1, wherein D and E are independently selected from N, CH and $CR^2$.

6. The compound of claim 1, wherein Cy is phenyl and m is 0.

7. A compound according to claim 1 and selected from:

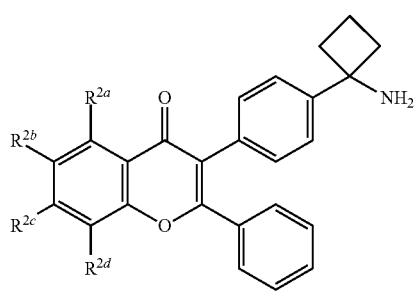

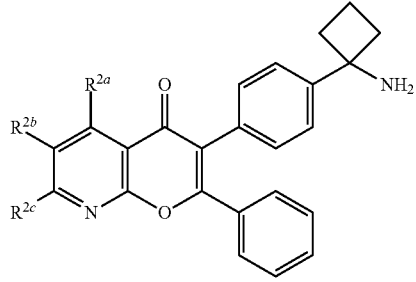

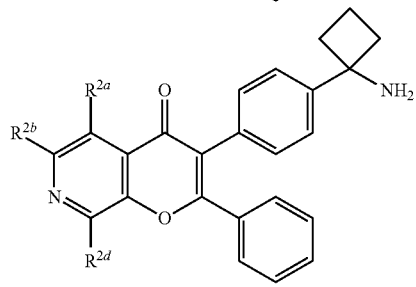

wherein $R^{2a}$, $R^{2b}$, $R^{2c}$ and $R^{2d}$ are independently selected from $R^2$ and H.

8. A compound according to claim 1 and selected from:

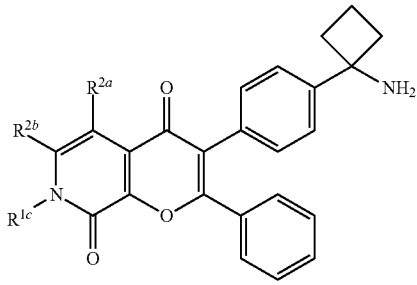

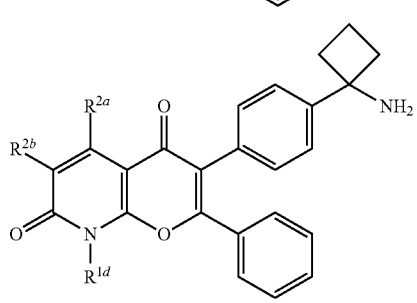

wherein $R^{1a}$, $R^{1b}$, $R^{1c}$ and $R^{1d}$ are independently selected from $R^1$ and H and $R^{2a}$, $R^{2b}$, $R^{2c}$ and $R^{2d}$ are independently selected from $R^2$ and H.

9. A compound according to claim 1 and having the formula:

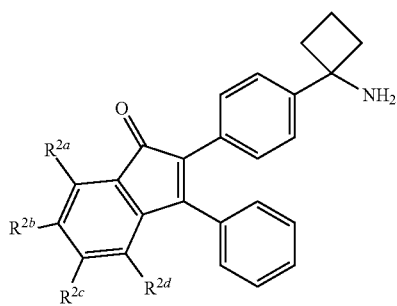

wherein $R^{2a}$, $R^{2b}$, $R^{2c}$ and $R^{2d}$ are independently selected from $R^2$ and H.

10. A compound according to claim 1 and selected from:

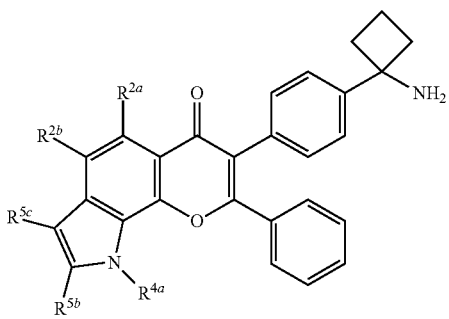

-continued
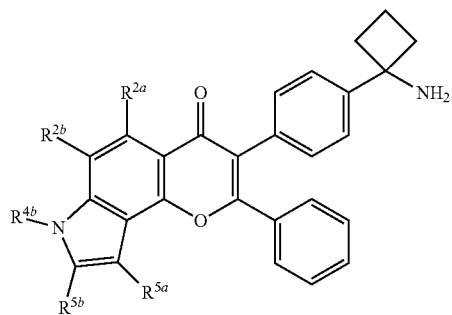
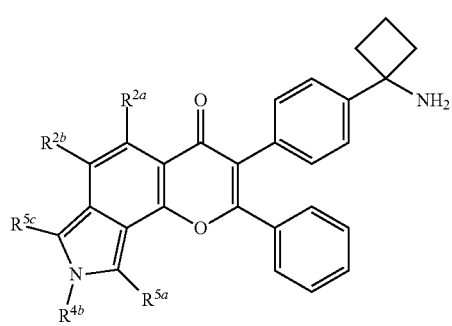
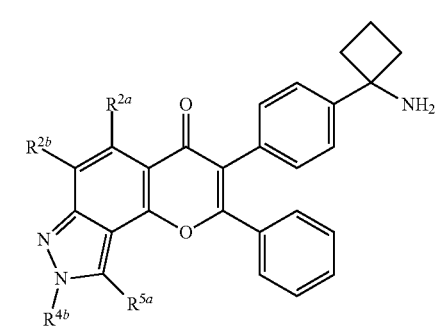
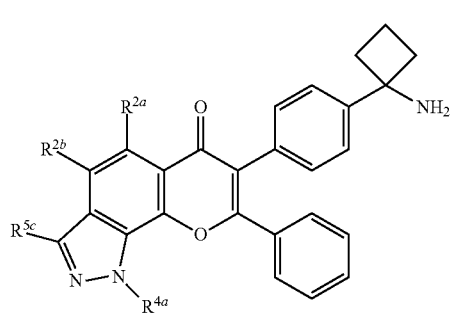
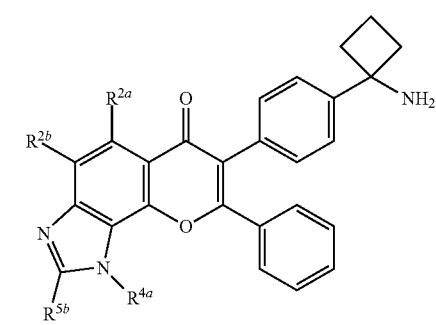
-continued
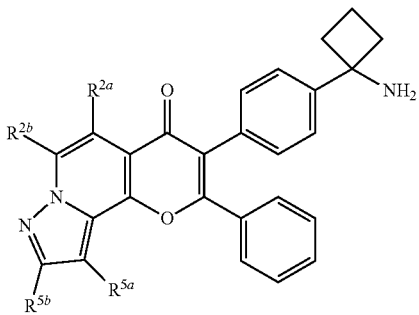
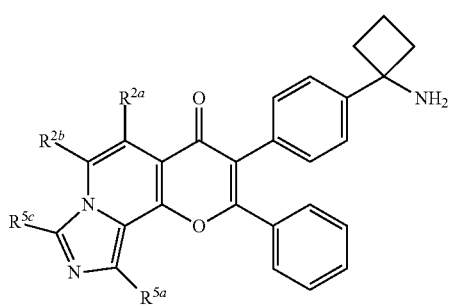
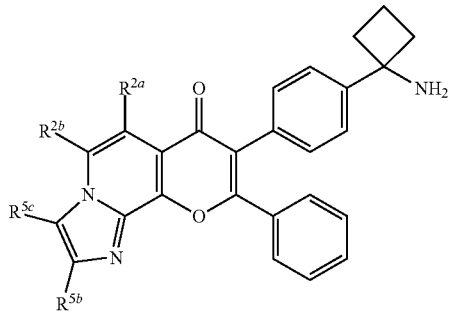
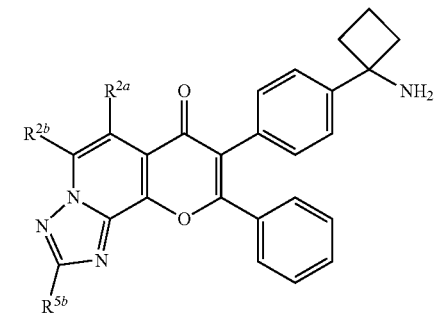
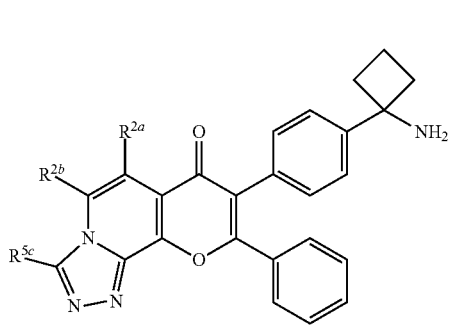

167
-continued

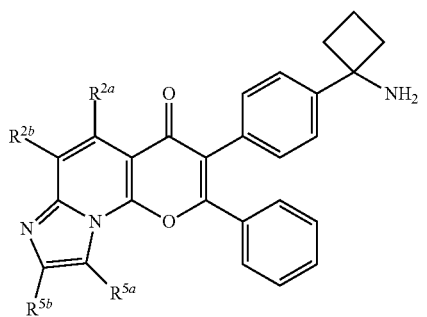

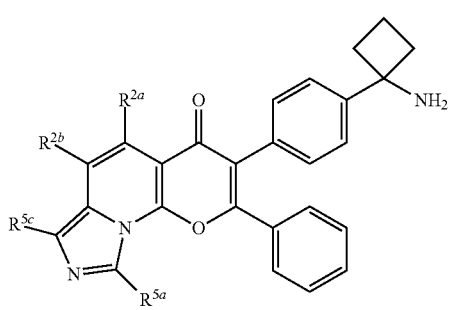

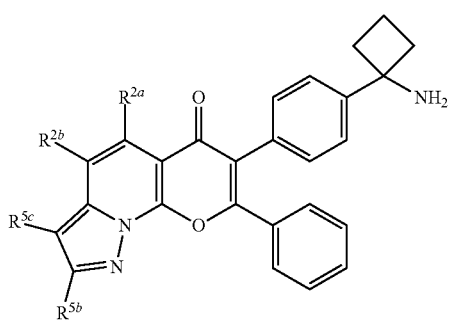

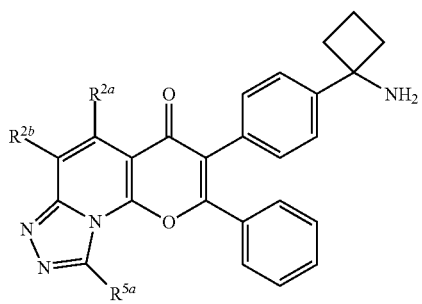

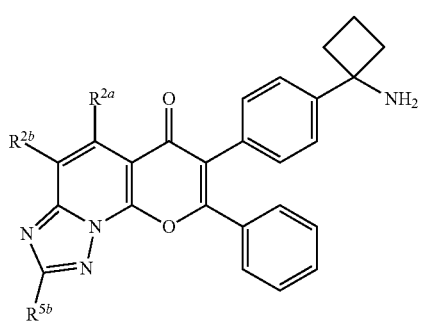

168
-continued

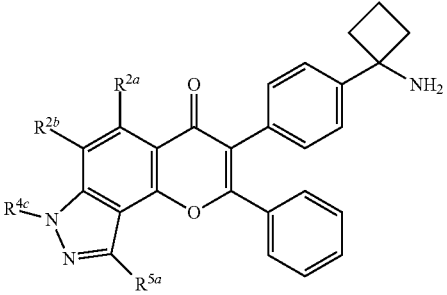

wherein $R^{2a}$ and $R^{2a}$ are independently selected from $R^2$ and H, $R^{4a}$, $R^{4b}$ and $R^{4c}$ are independently selected from $R^4$ and H, and $R^{5a}$, $R^{5b}$ and $R^{5c}$ are independently selected from H and $R^5$.

11. A compound selected from:
3-[4-(1-Amino-cyclobutyl)-phenyl]-6-fluoro-2-phenyl-chromen-4-one,
3-[4-(1-Amino-cyclobutyl)-phenyl]-8-fluoro-2-phenyl-chromen-4-one,
3-[4-(1-Amino-cyclobutyl)-phenyl]-5-fluoro-2-phenyl-chromen-4-one,
3-[4-(1-Amino-cyclobutyl)-phenyl]-7,8-dimethoxy-2-phenyl-chromen-4-one,
3-[4-(1-Amino-cyclobutyl)-phenyl]-6-methoxy-2-phenyl-chromen-4-one,
3-[4-(1-Amino-cyclobutyl)-phenyl]-6-methoxy-7-methyl-2-phenyl-chromen-4-one,
3-[4-(1-Amino-cyclobutyl)-phenyl]-7-methoxy-6-methyl-2-phenyl-chromen-4-one,
7-[4-(1-Amino-cyclobutyl)-phenyl]-6-phenyl-2,3-dihydro-1,4,5-trioxa-anthracen-8-one,
3-[4-(1-Amino-cyclobutyl)-phenyl]-8-bromo-7-methoxy-2-phenyl-chromen-4-one,
3-[4-(1-Amino-cyclobutyl)-phenyl]-7-methoxy-4-oxo-2-phenyl-4H-chromene-6-carboxylic acid amide,
3-[4-(1-Amino-cyclobutyl)-phenyl]-7-methoxy-4-oxo-2-phenyl-4H-chromene-6-carbonitrile,
3-[4-(1-Amino-cyclobutyl)-phenyl]-7-methoxy-4-oxo-2-phenyl-4H-chromene-8-carbonitrile,
3-[4-(1-Amino-cyclobutyl)-phenyl]-2-phenyl-7-bromo-chromen-4-one,
3-[4-(1-Amino-cyclobutyl)-phenyl]-7-methoxy-2-phenyl-chromen-4-one,
3-[4-(1-Amino-cyclobutyl)-phenyl]-6,7-dimethoxy-2-phenyl-chromen-4-one,
3-[4-(1-Amino-cyclobutyl)-phenyl]-8-methoxy-2-phenyl-chromen-4-one,
3-[4-(1-Amino-cyclobutyl)-phenyl]-2-phenyl-7-(2H-pyrazol-3-yl)-chromen-4-one,
3-[4-(1-Amino-cyclobutyl)-phenyl]-4-oxo-2-phenyl-4H-chromene-7-carboxylic acid amide,
3-[4-(1-Amino-cyclobutyl)-phenyl]-6-bromo-2-phenyl-chromen-4-one,
3-[4-(1-Amino-cyclobutyl)-phenyl]-6-(4-methyl-piperazin-1-yl)-2-phenyl-chromen-4-one,
3-[4-(1-Amino-cyclobutyl)-phenyl]-4-oxo-2-phenyl-4H-chromene-6-carbonitrile,
3-[4-(1-Amino-cyclobutyl)-phenyl]-6-imidazol-1-yl-2-phenyl-chromen-4-one,
3-[4-(1-Amino-cyclobutyl)-phenyl]-6,7-difluoro-2-phenyl-chromen-4-one,
3-[4-(1-Amino-cyclobutyl)-phenyl]-2-phenyl-7-trifluoromethoxy-chromen-4-one, 3-[4-(1-Amino-cyclobutyl)-phenyl]-2-phenyl-6-trifluoromethoxy-chromen-4-one,
3-[4-(1-Amino-cyclobutyl)-phenyl]-7-bromo-6-methoxy-2-phenyl-chromen-4-one,
3-[4-(1-Amino-cyclobutyl)-phenyl]-6-bromo-7-methoxy-2-phenyl-chromen-4-one,
3-[4-(1-Amino-cyclobutyl)-phenyl]-6-methoxy-2-phenyl-7-(2H-pyrazol-3-yl)-chromen-4-one,
3-[4-(1-Amino-cyclobutyl)-phenyl]-6-methoxy-4-oxo-2-phenyl-4H-chromene-7-carboxylic acid amide,
3-[4-(1-Amino-cyclobutyl)-phenyl]-6-methoxy-4-oxo-2-phenyl-4H-chromene-7-carbonitrile,
3-[4-(1-Amino-cyclobutyl)-phenyl]-7-(2-methoxy-ethyl)-2-phenyl-7H-pyrano[2,3-c]pyridine-4,8-dione,
3-[4-(1-Amino-cyclobutyl)-phenyl]-8-difluoromethoxy-2-phenyl-pyrano[2,3-c]pyridin-4-one,
3-[4-(1-Amino-cyclobutyl)-phenyl]-2-phenyl-7H-pyrano[2,3-e]indazol-4-one,
3-[4-(1-Amino-cyclobutyl)-phenyl]-2-phenyl-pyrano[2,3-b]pyridin-4-one,
3-[4-(1-Amino-cyclobutyl)-phenyl]-7-methoxy-2-phenyl-pyrano[2,3-b]pyridin-4-one,
3-[4-(1-Amino-cyclobutyl)-phenyl]-2-phenyl-8H-pyrano[2,3-b]pyridine-4,7-dione,
3-[4-(1-Amino-cyclobutyl)-phenyl]-7-fluoro-2-phenyl-chromen-4-one,
3-[4-(1-Amino-cyclobutyl)-phenyl]-7-chloro-2-phenyl-pyrano[2,3-b]pyridin-4-one,
3-[4-(1-Amino-cyclobutyl)-phenyl]-8-methoxy-2-phenyl-pyrano[2,3-c]pyridin-4-one,
3-[4-(1-Amino-cyclobutyl)-phenyl]-2-phenyl-7H-pyrano[2,3-c]pyridine-4,8-dione,
3-[4-(1-Amino-cyclobutyl)-phenyl]-7-methyl-2-phenyl-7H-pyrano[2,3-c]pyridine-4,8-dione,
3-[4-(1-Amino-cyclobutyl)-phenyl]-8-chloro-2-phenyl-pyrano[2,3-c]pyridin-4-one,
3-[4-(1-Amino-cyclobutyl)-phenyl]-7-(2-hydroxy-ethyl)-2-phenyl-7H-pyrano[2,3-c]pyridine-4,8-dione,
7-[4-(1-Amino-cyclobutyl)-phenyl]-4-chloro-8-phenyl-1H-chromeno[7,8-d]imidazol-6-one,
7-[4-(1-Amino-cyclobutyl)-phenyl]-8-phenyl-1H-chromeno[7,8-d]imidazol-6-one,
3-[4-(1-Amino-cyclobutyl)-phenyl]-2-phenyl-1-benzopyran-4-one,
7-Amino-3-[4-(1-amino-cyclobutyl)-phenyl]-2-phenyl-1-benzopyran-4-one, and
2-(4-(1-aminocyclobutyl)phenyl)-3-phenyl-1H-inden-1-one,
7-Amino-3-[4-(1-amino-cyclobutyl)-phenyl]-6-bromo-2-phenyl-chromen-4-one,
3-[4-(1-Amino-cyclobutyl)-phenyl]-7-methoxy-4-oxo-2-phenyl-4H-chromene-8-carboxylic acid amide,
3-[4-(1-Amino-cyclobutyl)-phenyl]-8-bromo-2-phenyl-chromen-4-one,
3-[4-(1-Amino-cyclobutyl)-phenyl]-2-phenyl-8-(1H-pyrazol-4-yl)-chromen-4-one,
3-[4-(1-Amino-cyclobutyl)-phenyl]-2-phenyl-8-(1H-pyrazol-3-yl)-chromen-4-one,
3-[4-(1-Amino-cyclobutyl)-phenyl]-8-cyclopropyl-2-phenyl-chromen-4-one,
3-[4-(1-Amino-cyclobutyl)-phenyl]-8-(1-methyl-1H-pyrazol-4-yl)-2-phenyl-chromen-4-one,
3-[4-(1-Amino-cyclobutyl)-phenyl]-2-phenyl-8-pyridin-3-yl-chromen-4-one,
7-[4-(1-Amino-cyclobutyl)-phenyl]-8-phenyl-1H-9-oxa-1,2-diaza-cyclopenta[a]naphthalen-6-one,
7-[4-(1-Amino-cyclobutyl)-phenyl]-1-methyl-8-phenyl-1H-9-oxa-1,2-diaza-cyclopenta[a]naphthalen-6-one,
7-[4-(1-Amino-cyclobutyl)-phenyl]-2-methyl-8-phenyl-2H-9-oxa-1,2-diaza-cyclopenta[a]naphthalen-6-one,
3-[4-(1-Amino-cyclobutyl)-phenyl]-7-methyl-2-phenyl-7H-pyrano[2,3-e]indazol-4-one,
3-[4-(1-Amino-cyclobutyl)-phenyl]-8-methyl-2-phenyl-8H-pyrano[2,3-e]indazol-4-one,
7-[4-(1-Amino-cyclobutyl)-phenyl]-4-chloro-3-methyl-8-phenyl-3H-chromeno[7,8-d]imidazol-6-one,
7-[4-(1-Amino-cyclobutyl)-phenyl]-8-phenyl-2H-9-oxa-1,2,3a-triaza-cyclopenta[a]naphthalene-3,6-dione,
7-[4-(1-Amino-cyclobutyl)-phenyl]-2-methyl-8-phenyl-2H-9-oxa-1,2,3a-triaza-cyclopenta[a]naphthalene-3,6-dione,
3-[4-(1-Amino-cyclobutyl)-phenyl]-2-phenyl-chromene-4-thione,
3-[4-(1-Amino-cyclobutyl)-phenyl]-2-phenyl-chromen-4-one O-methyl-oxime,
3-[4-(3-Amino-oxetan-3-yl)-phenyl]-8-bromo-2-phenyl-chromen-4-one,
7-[4-(3-Amino-oxetan-3-yl)-phenyl]-8-phenyl-2H-9-oxa-1,2,3a-triaza-cyclopenta[a]naphthalene-3,6-dione,
7-[6-(1-Amino-cyclobutyl)-pyridin-3-yl]-8-phenyl-2H-9-oxa-1,2,3a-triaza-cyclopenta[a]naphthalene-3,6-dione,
2-[4-(3,6-Dioxo-8-phenyl-2,6-dihydro-3H-9-oxa-1,2,3a-triaza-cyclopenta[a]naphthalen-7-yl)-phenyl]-2-methyl-propionitrile,
7-[6-(1-Amino-cyclobutyl)-pyridin-3-yl]-1-methyl-8-phenyl-1H-9-oxa-1,2-diaza-cyclopenta[a]naphthalen-6-one,
3-[4-(1-Amino-cyclobutyl)-phenyl]-8-morpholin-4-yl-2-phenyl-chromen-4-one,
3-[4-(1-Amino-cyclobutyl)-phenyl]-8-(3-methyl-1H-pyrazol-4-yl)-2-phenyl-chromen-4-one,
3-[4-(1-Amino-cyclobutyl)-phenyl]-8-imidazol-1-yl-2-phenyl-chromen-4-one,
3-[4-(1-Amino-cyclobutyl)-phenyl]-8-(1,5-dimethyl-1H-pyrazol-4-yl)-2-phenyl-chromen-4-one,
3-[4-(1-Amino-cyclobutyl)-phenyl]-2-phenyl-8-(3-trifluoromethyl-1H-pyrazol-4-yl)-chromen-4-one,
4-{3-[4-(1-Amino-cyclobutyl)-phenyl]-4-oxo-2-phenyl-4H-chromen-8-yl}-piperazin-2-one,
3-[4-(1-Amino-cyclobutyl)-phenyl]-8-(3,5-dimethyl-isoxazol-4-yl)-2-phenyl-chromen-4-one,
3-[4-(1-Amino-cyclobutyl)-phenyl]-7-methoxy-2-phenyl-8-(1H-pyrazol-4-yl)-chromen-4-one,
3-[4-(1-Amino-cyclobutyl)-phenyl]-2-phenyl-8-(1H-pyrazol-4-yl)-pyrano[2,3-c]pyridin-4-one,
7-[4-(1-Amino-cyclobutyl)-phenyl]-1-ethyl-8-phenyl-1H-9-oxa-1,2-diaza-cyclopenta[a]naphthalen-6-one,
7-[4-(1-Amino-cyclobutyl)-phenyl]-2-ethyl-8-phenyl-2H-9-oxa-1,2-diaza-cyclopenta[a]naphthalen-6-one,
7-[4-(1-Amino-cyclobutyl)-phenyl]-1-isopropyl-8-phenyl-1H-9-oxa-1,2-diaza-cyclopenta[a]naphthalen-6-one,
7-[4-(1-Amino-cyclobutyl)-phenyl]-2-isopropyl-8-phenyl-2H-9-oxa-1,2-diaza-cyclopenta[a]naphthalen-6-one,
7-[4-(1-Amino-cyclobutyl)-phenyl]-1-(2-hydroxy-ethyl)-8-phenyl-1H-9-oxa-1,2-diaza-cyclopenta[a]naphthalen-6-one,
7-[4-(1-Amino-cyclobutyl)-phenyl]-2-(2-hydroxy-ethyl)-8-phenyl-2H-9-oxa-1,2-diaza-cyclopenta[a]naphthalen-6-one,
7-[4-(1-Amino-cyclobutyl)-phenyl]-8-phenyl-1,3-dihydro-chromeno[7,8-d]imidazole-2,6-dione, 7-[4-(1-Amino-cyclobutyl)-phenyl]-8-phenyl-1H-9-oxa-1,2,3-triaza-cyclopenta[a]naphthalen-6-one, 7-[4-(1-Amino-cyclobutyl)-phenyl]-2-methyl-8-phenyl-1H-chromeno[7,8-d]imidazol-6-one, 7-[4-(1-Amino-cyclobutyl)-phenyl]-1,2-dimethyl-8-phenyl-1H-chromeno[7,8-d]imidazol-6-one, 7-[4-(1-Amino-cyclobutyl)-phenyl]-8-phenyl-3H-chromeno[7,8-d]oxazole-2,6-dione, 7-[4-(1-Amino-cyclobutyl)-phenyl]-6-phenyl-1H-4,5-dioxa-1-aza-phenanthrene-2,8-dione, 7-Amino-3-[4-(1-amino-cyclobutyl)-phenyl]-8-hydroxy-2-phenyl-chromen-4-one, 7-[4-(1-Amino-cyclobutyl)-phenyl]-8-phenyl-2-trifluoromethyl-1H-chromeno[7,8-d]imidazol-6-one, 7-[4-(1-Amino-cyclobutyl)-phenyl]-2-difluoromethyl-8-phenyl-1H-chromeno[7,8-d]imidazol-6-one, 7-[4-(1-Amino-cyclobutyl)-phenyl]-1-methyl-8-phenyl-1H-chromeno[7,8-d]imidazol-6-one, 7-[4-(1-Amino-cyclobutyl)-phenyl]-3-iodo-8-phenyl-1H-9-oxa-1,2-diaza-cyclopenta[a]naphthalen-6-one, 7-[4-(1-Amino-cyclobutyl)-phenyl]-3-ethyl-1-methyl-8-phenyl-1H-9-oxa-1,2-diaza-cyclopenta[a]naphthalen-6-one, 7-[4-(1-Amino-cyclobutyl)-phenyl]-3-chloro-8-phenyl-1H-9-oxa-1,2-diaza-cyclopenta[a]naphthalen-6-one, 7-[4-(1-Amino-cyclobutyl)-phenyl]-3-chloro-1-methyl-8-phenyl-1H-9-oxa-1,2-diaza-cyclopenta[a]naphthalen-6-one, 3-[4-(1-Amino-cyclobutyl)-phenyl]-8-(1-methyl-1H-pyrazol-4-yl)-2-phenyl-pyrano[2,3-c]pyridin-4-one, 3-[4-(1-Amino-cyclobutyl)-phenyl]-2-phenyl-8-[1,2,4]triazol-4-yl-pyrano[2,3-c]pyridin-4-one, 3-[4-(1-Amino-cyclobutyl)-phenyl]-2-phenyl-8-(pyridin-2-yloxy)-pyrano[2,3-c]pyridin-4-one, 3-[4-(1-Amino-cyclobutyl)-phenyl]-8-(2-oxo-2H-pyridin-1-yl)-2-phenyl-pyrano[2,3-c]pyridin-4-one, 3-[4-(1-Amino-cyclobutyl)-phenyl]-8-ethynyl-2-phenyl-chromen-4-one, 3-[4-(1-Amino-cyclobutyl)-phenyl]-2-phenyl-8-(1H-[1,2,3]triazol-4-yl)-chromen-4-one, 3-[4-(1-Amino-cyclobutyl)-phenyl]-4-oxo-2-phenyl-4H-chromene-8-carboxylic acid, 3-[4-(1-Amino-cyclobutyl)-phenyl]-8-(3-fluoro-azetidin-1-ylmethyl)-2-phenyl-chromen-4-one, and pharmaceutically acceptable salts, stereoisomers and tautomers thereof.

12. A compound selected from:
7-[4-(1-Amino-cyclobutyl)-phenyl]-8-phenyl-2H-9-oxa-1,2,3a-triaza-cyclopenta[a]naphthalene-3,6-dione hydrochloride;

7-[4-(1-Amino-cyclobutyl)-phenyl]-2-methyl-8-phenyl-2H-9-oxa-1,2,3a-triaza-cyclopenta[a]naphthalene-3,6-dione hydrochloride;

or pharmaceutically acceptable salts, stereoisomers and tautomers thereof.

13. A pharmaceutical composition comprising a pharmaceutical carrier and, dispersed therein, a compound of claim 1.

14. The compound of claim 1, for use in the treatment of cancer.

15. A method of treating cancer comprising administering a compound according to claim 1, to a patient in need thereof.

16. The compound of claim 11 that is 7-[4-(1-Amino-cyclobutyl)-phenyl]-1-(2-hydroxy-ethyl)-8-phenyl-1H-9-oxa-1,2-diaza-cyclopenta[a]naphthalen-6-one; or pharmaceutically acceptable salts, stereoisomers and tautomers thereof.

* * * * *